(12) United States Patent
Rogynskyy et al.

(10) Patent No.: US 11,470,170 B2
(45) Date of Patent: *Oct. 11, 2022

(54) SYSTEMS AND METHODS FOR DETERMINING THE SHAREABILITY OF VALUES OF NODE PROFILES

(71) Applicant: People.ai, Inc., San Francisco, CA (US)

(72) Inventors: Oleg Rogynskyy, Menlo Park, CA (US); Yurii Brunets, Burlingame, CA (US); Devin Rice, San Francisco, CA (US)

(73) Assignee: People.ai, Inc., San Francisco, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/694,253

(22) Filed: Nov. 25, 2019

(65) Prior Publication Data

US 2020/0089681 A1 Mar. 19, 2020

Related U.S. Application Data

(63) Continuation of application No. 16/399,679, filed on Apr. 30, 2019, now Pat. No. 10,489,387.

(Continued)

(51) Int. Cl.
*H04L 67/50* (2022.01)
*G06F 16/9035* (2019.01)
(Continued)

(52) U.S. Cl.
CPC .............. *H04L 67/535* (2022.05); *G06F 7/14* (2013.01); *G06F 11/3024* (2013.01);
(Continued)

(58) Field of Classification Search
CPC .... G06F 16/58; G06F 16/78; G06F 16/24575; G06F 16/284; G06F 16/9535;
(Continued)

(56) References Cited

U.S. PATENT DOCUMENTS 5,504,861 A 4/1996 Crockett et al.
5,873,093 A 2/1999 Williamson et al.
(Continued)

FOREIGN PATENT DOCUMENTS

CN 110365575 A 10/2019
WO WO-2017/050991 A1 3/2017
(Continued)

OTHER PUBLICATIONS

"Node Profile Electronic Activity Account Policy Filtering Parsing Remove Subset" Google Search.
(Continued)

*Primary Examiner* — Angelica Ruiz
(74) *Attorney, Agent, or Firm* — Foley & Lardner LLP

(57) ABSTRACT

The present disclosure relates to determining the shareability of values of node profiles. Record objects and electronic activities of a system of record corresponding to a data source provider may be accessed. Each record object may correspond to a record object type and have one or more object field-value pairs. Node profiles may be maintained. Values of fields corresponding to a predetermined type of field including fewer than a predetermined threshold number of data source providers may be identified. A restriction tag used to restrict populating other node profiles may be generated. Provision of the value with a second data source provider may be restricted.

20 Claims, 31 Drawing Sheets

Related U.S. Application Data

(60) Provisional application No. 62/747,452, filed on Oct. 18, 2018, provisional application No. 62/725,999, filed on Aug. 31, 2018, provisional application No. 62/676,187, filed on May 24, 2018.

(51) Int. Cl.

| | | |
|---|---|---|
| G06F 16/335 | (2019.01) | |
| G06F 16/2455 | (2019.01) | |
| G06F 16/28 | (2019.01) | |
| G06F 16/26 | (2019.01) | |
| G06F 16/901 | (2019.01) | |
| G06F 16/903 | (2019.01) | |
| G16H 50/20 | (2018.01) | |
| G06F 16/27 | (2019.01) | |
| G06F 16/22 | (2019.01) | |
| G06F 16/23 | (2019.01) | |
| G06F 16/245 | (2019.01) | |
| G06F 16/906 | (2019.01) | |
| G06F 16/21 | (2019.01) | |
| G06F 16/11 | (2019.01) | |
| G06F 16/215 | (2019.01) | |
| G06F 16/2458 | (2019.01) | |
| G06F 16/25 | (2019.01) | |
| G06F 16/2457 | (2019.01) | |
| G06F 16/9535 | (2019.01) | |
| G06F 16/178 | (2019.01) | |
| G06F 16/17 | (2019.01) | |
| G06F 16/29 | (2019.01) | |
| G06F 16/35 | (2019.01) | |
| G06F 40/295 | (2020.01) | |
| G06F 7/14 | (2006.01) | |
| G06F 11/30 | (2006.01) | |
| G06F 11/34 | (2006.01) | |
| G06F 21/62 | (2013.01) | |
| G06F 3/08 | (2006.01) | |
| G06N 3/08 | (2006.01) | |
| G06N 5/04 | (2006.01) | |
| G06N 7/02 | (2006.01) | |
| G06Q 10/04 | (2012.01) | |
| G06Q 10/06 | (2012.01) | |
| G06Q 10/10 | (2012.01) | |
| G06Q 50/22 | (2018.01) | |
| H04L 41/14 | (2022.01) | |
| H04L 43/026 | (2022.01) | |
| H04L 43/045 | (2022.01) | |
| H04L 43/062 | (2022.01) | |
| H04L 43/065 | (2022.01) | |
| H04L 43/067 | (2022.01) | |
| H04L 43/0876 | (2022.01) | |
| H04L 43/00 | (2022.01) | |
| H04L 51/046 | (2022.01) | |
| H04L 67/125 | (2022.01) | |
| H04L 67/30 | (2022.01) | |
| H04L 67/306 | (2022.01) | |
| H04M 3/436 | (2006.01) | |
| H04M 15/00 | (2006.01) | |
| G06F 40/237 | (2020.01) | |
| H04L 67/303 | (2022.01) | |
| G06N 5/02 | (2006.01) | |
| G06F 16/31 | (2019.01) | |
| G06F 16/182 | (2019.01) | |
| G06F 40/20 | (2020.01) | |
| H04L 51/42 | (2022.01) | |
| H04L 51/212 | (2022.01) | |
| H04L 51/234 | (2022.01) | |
| H04L 61/45 | (2022.01) | |
| G16H 15/00 | (2018.01) | |
| G16H 50/30 | (2018.01) | |
| G06N 20/00 | (2019.01) | |
| G06F 40/205 | (2020.01) | |
| H04M 3/56 | (2006.01) | |
| H04L 12/14 | (2006.01) | |
| H04L 101/37 | (2022.01) | |

(52) U.S. Cl.
CPC ...... *G06F 11/3452* (2013.01); *G06F 11/3495* (2013.01); *G06F 16/122* (2019.01); *G06F 16/178* (2019.01); *G06F 16/1734* (2019.01); *G06F 16/182* (2019.01); *G06F 16/212* (2019.01); *G06F 16/215* (2019.01); *G06F 16/219* (2019.01); *G06F 16/22* (2019.01); *G06F 16/221* (2019.01); *G06F 16/2228* (2019.01); *G06F 16/2264* (2019.01); *G06F 16/2272* (2019.01); *G06F 16/23* (2019.01); *G06F 16/235* (2019.01); *G06F 16/2365* (2019.01); *G06F 16/2379* (2019.01); *G06F 16/2386* (2019.01); *G06F 16/245* (2019.01); *G06F 16/2457* (2019.01); *G06F 16/2477* (2019.01); *G06F 16/24558* (2019.01); *G06F 16/24564* (2019.01); *G06F 16/24575* (2019.01); *G06F 16/24578* (2019.01); *G06F 16/254* (2019.01); *G06F 16/256* (2019.01); *G06F 16/26* (2019.01); *G06F 16/27* (2019.01); *G06F 16/273* (2019.01); *G06F 16/28* (2019.01); *G06F 16/285* (2019.01); *G06F 16/288* (2019.01); *G06F 16/289* (2019.01); *G06F 16/29* (2019.01); *G06F 16/313* (2019.01); *G06F 16/337* (2019.01); *G06F 16/355* (2019.01); *G06F 16/901* (2019.01); *G06F 16/906* (2019.01); *G06F 16/9024* (2019.01); *G06F 16/9035* (2019.01); *G06F 16/90344* (2019.01); *G06F 16/9535* (2019.01); *G06F 21/6218* (2013.01); *G06F 40/20* (2020.01); *G06F 40/237* (2020.01); *G06F 40/295* (2020.01); *G06N 3/08* (2013.01); *G06N 5/025* (2013.01); *G06N 5/04* (2013.01); *G06N 7/02* (2013.01); *G06Q 10/04* (2013.01); *G06Q 10/06312* (2013.01); *G06Q 10/06393* (2013.01); *G06Q 10/06398* (2013.01); *G06Q 10/063114* (2013.01); *G06Q 10/107* (2013.01); *G06Q 10/1091* (2013.01); *G06Q 10/1095* (2013.01); *G06Q 50/22* (2013.01); *G16H 50/20* (2018.01); *H04L 41/14* (2013.01); *H04L 43/026* (2013.01); *H04L 43/045* (2013.01); *H04L 43/062* (2013.01); *H04L 43/065* (2013.01); *H04L 43/067* (2013.01); *H04L 43/0876* (2013.01); *H04L 43/14* (2013.01); *H04L 51/046* (2013.01); *H04L 51/212* (2022.05); *H04L 51/234* (2022.05); *H04L 51/42* (2022.05); *H04L 61/45* (2022.05); *H04L 67/125* (2013.01); *H04L 67/30* (2013.01); *H04L 67/303* (2013.01); *H04L 67/306* (2013.01); *H04M 3/436* (2013.01); *H04M 15/755* (2013.01); *G06F 40/205* (2020.01); *G06N 20/00* (2019.01); *G06Q 10/10* (2013.01); *G16H 15/00* (2018.01); *G16H 50/30* (2018.01); *H04L 12/1407* (2013.01); *H04L 2101/37* (2022.05); *H04M 3/56* (2013.01)

(58) Field of Classification Search
CPC ......... G06F 21/6218; G06F 2221/2113; G06F 16/20; G06F 16/583
See application file for complete search history.

(56) References Cited

U.S. PATENT DOCUMENTS

| | | | |
|---|---|---|---|
| 5,930,764 A | 7/1999 | Melchione et al. | |
| 6,067,525 A | 5/2000 | Johnson et al. | |
| 7,007,032 B1* | 2/2006 | Chen | G06F 7/22 707/693 |
| 7,043,690 B1 | 5/2006 | Bates et al. | |
| 7,099,855 B1 | 8/2006 | Nelken et al. | |
| 7,162,522 B2 | 1/2007 | Adar et al. | |
| 7,197,502 B2 | 3/2007 | Feinsmith | |
| 7,257,690 B1 | 8/2007 | Baird | |
| 7,318,104 B1 | 1/2008 | Lee et al. | |
| 7,346,610 B2 | 3/2008 | Ruthfield et al. | |
| 7,444,374 B1 | 10/2008 | Baker | |
| 7,499,870 B1 | 3/2009 | Petrossi | |
| 7,743,051 B1 | 6/2010 | Kashyap et al. | |
| 7,822,631 B1 | 10/2010 | Vander Mey et al. | |
| 7,849,103 B2 | 12/2010 | Hyatt et al. | |
| 7,849,141 B1 | 12/2010 | Bellegarda et al. | |
| 7,912,842 B1 | 3/2011 | Bayliss | |
| 7,921,204 B2 | 4/2011 | Wilson et al. | |
| 7,949,578 B2 | 5/2011 | Johnson et al. | |
| 8,032,598 B1 | 10/2011 | He et al. | |
| 8,200,527 B1 | 6/2012 | Thompson et al. | |
| 8,205,264 B1 | 6/2012 | Kailash et al. | |
| 8,296,370 B2 | 10/2012 | Adams et al. | |
| 8,406,745 B1 | 3/2013 | Upadhyay et al. | |
| 8,442,189 B2 | 5/2013 | Michaelis et al. | |
| 8,448,072 B1 | 5/2013 | Lai et al. | |
| 8,468,123 B2 | 6/2013 | Dalvi et al. | |
| 8,478,624 B1 | 7/2013 | Bivens et al. | |
| 8,489,588 B2 | 7/2013 | Figueroa et al. | |
| 8,639,552 B1 | 1/2014 | Chen et al. | |
| 8,732,095 B2 | 5/2014 | Cornford | |
| 8,938,510 B2 | 1/2015 | Pouzin et al. | |
| 8,943,151 B2 | 1/2015 | Smith et al. | |
| 8,948,372 B1 | 2/2015 | Beall et al. | |
| 8,989,053 B1 | 3/2015 | Skaaksrud et al. | |
| 8,996,395 B1 | 3/2015 | Stibel et al. | |
| 9,154,514 B1 | 10/2015 | Prakash | |
| 9,158,782 B2 | 10/2015 | Nucci et al. | |
| 9,208,207 B2 | 12/2015 | Venkataramani et al. | |
| 9,258,423 B1 | 2/2016 | Beall et al. | |
| 9,298,727 B2 | 3/2016 | Hazlewood et al. | |
| 9,305,079 B2 | 4/2016 | Starbuck et al. | |
| 9,317,574 B1 | 4/2016 | Brisebois et al. | |
| 9,326,146 B2* | 4/2016 | Bradley | H04W 12/06 |
| 9,515,973 B2 | 12/2016 | Jones | |
| 9,530,119 B1 | 12/2016 | Grisso et al. | |
| 9,665,885 B1 | 5/2017 | Allouche | |
| 9,686,308 B1 | 6/2017 | Srivastava | |
| 9,690,820 B1 | 6/2017 | Girulat, Jr. | |
| 9,785,764 B2 | 10/2017 | Loughlin-Mchugh et al. | |
| 9,813,363 B1 | 11/2017 | Caldwell et al. | |
| 9,898,743 B2 | 2/2018 | Bessler et al. | |
| 9,923,852 B2 | 3/2018 | Smith et al. | |
| 9,973,483 B2 | 5/2018 | Allrich et al. | |
| 10,013,673 B2 | 7/2018 | Baessler et al. | |
| 10,049,136 B1 | 8/2018 | Barsness et al. | |
| 10,067,987 B1 | 9/2018 | Khanna et al. | |
| 10,235,685 B2 | 3/2019 | Sun et al. | |
| 10,311,042 B1 | 6/2019 | Kumar | |
| 10,318,543 B1 | 6/2019 | Sharifi | |
| 10,425,531 B1 | 9/2019 | Liu | |
| 10,430,239 B2 | 10/2019 | Tang et al. | |
| 10,438,172 B2 | 10/2019 | Rangan | |
| 10,475,054 B1 | 11/2019 | Riazzi et al. | |
| 10,565,229 B2 | 2/2020 | Rogynskyy et al. | |
| 10,607,165 B2 | 3/2020 | Punera et al. | |
| 10,740,771 B2 | 8/2020 | Sun et al. | |
| 10,846,643 B2 | 11/2020 | Xu et al. | |
| 10,936,623 B2 | 3/2021 | Mahalingam et al. | |
| 11,151,486 B1 | 10/2021 | Ross et al. | |
| 2001/0022558 A1 | 9/2001 | Karr et al. | |
| 2002/0059095 A1 | 5/2002 | Cook | |
| 2002/0077998 A1 | 6/2002 | Andrews et al. | |
| 2002/0082882 A1 | 6/2002 | Perry et al. | |
| 2002/0087647 A1 | 7/2002 | Quine et al. | |
| 2002/0116366 A1 | 8/2002 | Magouirk et al. | |
| 2002/0138571 A1 | 9/2002 | Trinon et al. | |
| 2002/0150093 A1 | 10/2002 | Ott et al. | |
| 2003/0018643 A1 | 1/2003 | Mi et al. | |
| 2003/0069780 A1 | 4/2003 | Hailwood et al. | |
| 2003/0182310 A1 | 9/2003 | Charnock et al. | |
| 2003/0208468 A1 | 11/2003 | McNab et al. | |
| 2003/0229529 A1 | 12/2003 | Mui et al. | |
| 2004/0015386 A1 | 1/2004 | Abe et al. | |
| 2004/0039619 A1 | 2/2004 | Zarb | |
| 2004/0039624 A1 | 2/2004 | Ikezawa et al. | |
| 2004/0054646 A1 | 3/2004 | Daniell et al. | |
| 2004/0054737 A1 | 3/2004 | Daniell | |
| 2004/0133645 A1 | 7/2004 | Massanelli et al. | |
| 2004/0158816 A1 | 8/2004 | Pandipati et al. | |
| 2004/0186765 A1 | 9/2004 | Kataoka | |
| 2004/0193515 A1 | 9/2004 | Peterson et al. | |
| 2004/0249650 A1 | 12/2004 | Freedman et al. | |
| 2005/0010470 A1 | 1/2005 | Marino | |
| 2005/0015452 A1 | 1/2005 | Corson | |
| 2005/0021529 A1 | 1/2005 | Hodson et al. | |
| 2005/0038693 A1 | 2/2005 | Janus | |
| 2005/0149479 A1 | 7/2005 | Richardson et al. | |
| 2005/0187862 A1 | 8/2005 | Dheer et al. | |
| 2005/0246221 A1 | 11/2005 | Geritz et al. | |
| 2005/0262209 A1 | 11/2005 | Yu | |
| 2005/0267887 A1 | 12/2005 | Robins | |
| 2006/0026033 A1 | 2/2006 | Brydon et al. | |
| 2006/0036461 A1 | 2/2006 | Chuah et al. | |
| 2006/0067250 A1 | 3/2006 | Boyer et al. | |
| 2006/0069730 A1 | 3/2006 | Azuma | |
| 2006/0085205 A1 | 4/2006 | Kumar | |
| 2006/0085419 A1 | 4/2006 | Rosen | |
| 2006/0106626 A1 | 5/2006 | Jeng et al. | |
| 2006/0122861 A1 | 6/2006 | Scott et al. | |
| 2006/0179114 A1 | 8/2006 | Deeds | |
| 2006/0200432 A1 | 9/2006 | Flinn et al. | |
| 2006/0224437 A1 | 10/2006 | Gupta et al. | |
| 2006/0235831 A1 | 10/2006 | Adinolfi et al. | |
| 2006/0235935 A1 | 10/2006 | Ng | |
| 2006/0242040 A1 | 10/2006 | Rader | |
| 2007/0011144 A1 | 1/2007 | Balan et al. | |
| 2007/0061626 A1 | 3/2007 | Nelson et al. | |
| 2007/0067394 A1 | 3/2007 | Adams et al. | |
| 2007/0073818 A1 | 3/2007 | Gardner et al. | |
| 2007/0150234 A1 | 6/2007 | Wicks | |
| 2007/0162432 A1 | 7/2007 | Armstrong et al. | |
| 2007/0239721 A1 | 10/2007 | Ullman et al. | |
| 2007/0250417 A1 | 10/2007 | Lane et al. | |
| 2007/0260692 A1 | 11/2007 | Burgoyne et al. | |
| 2007/0282673 A1 | 12/2007 | Nagpal et al. | |
| 2007/0288466 A1 | 12/2007 | Bohannon et al. | |
| 2008/0005106 A1 | 1/2008 | Schumacher et al. | |
| 2008/0015880 A1 | 1/2008 | Freedenberg et al. | |
| 2008/0071601 A1 | 3/2008 | Cihla et al. | |
| 2008/0086343 A1 | 4/2008 | Pendergraft et al. | |
| 2008/0096531 A1 | 4/2008 | McQuaide et al. | |
| 2008/0114628 A1 | 5/2008 | Johnson et al. | |
| 2008/0147478 A1 | 6/2008 | Mall et al. | |
| 2008/0162487 A1 | 7/2008 | Richter | |
| 2008/0167930 A1 | 7/2008 | Cao et al. | |
| 2008/0275957 A1 | 11/2008 | Pouzin et al. | |
| 2008/0288405 A1 | 11/2008 | John | |
| 2009/0004321 A1 | 1/2009 | Seki | |
| 2009/0018996 A1 | 1/2009 | Hunt et al. | |
| 2009/0019003 A1 | 1/2009 | Bohannon et al. | |
| 2009/0112678 A1 | 4/2009 | Luzardo | |
| 2009/0132345 A1 | 5/2009 | Meyssami et al. | |
| 2009/0164926 A1 | 6/2009 | Boyle et al. | |
| 2009/0192858 A1 | 7/2009 | Johnson | |
| 2009/0313065 A1 | 12/2009 | George et al. | |
| 2010/0002859 A1 | 1/2010 | Hepworth et al. | |

(56) References Cited

U.S. PATENT DOCUMENTS

| | | |
|---|---|---|
| 2010/0010912 A1 | 1/2010 | Jones et al. |
| 2010/0030610 A1 | 2/2010 | Gomeh |
| 2010/0030858 A1 | 2/2010 | Chasin |
| 2010/0036786 A1 | 2/2010 | Pujara |
| 2010/0046505 A1 | 2/2010 | Saw et al. |
| 2010/0114897 A1 | 5/2010 | Polo-Malouvier et al. |
| 2010/0121684 A1 | 5/2010 | Morio et al. |
| 2010/0125475 A1 | 5/2010 | Twyman |
| 2010/0144318 A1 | 6/2010 | Cable |
| 2010/0169134 A1 | 7/2010 | Cheng et al. |
| 2010/0191728 A1 | 7/2010 | Reilly et al. |
| 2010/0198636 A1 | 8/2010 | Choudhary et al. |
| 2010/0205123 A1 | 8/2010 | Sculley et al. |
| 2010/0211548 A1 | 8/2010 | Ott et al. |
| 2010/0227302 A1 | 9/2010 | McGilvery et al. |
| 2010/0250682 A1 | 9/2010 | Goldberg et al. |
| 2011/0010218 A1 | 1/2011 | Gupta |
| 2011/0035228 A1 | 2/2011 | Li et al. |
| 2011/0055196 A1 | 3/2011 | Sundelin et al. |
| 2011/0066717 A1 | 3/2011 | Ahola |
| 2011/0078150 A1 | 3/2011 | Rashad et al. |
| 2011/0106920 A1 | 5/2011 | Longo |
| 2011/0191693 A1 | 8/2011 | Baggett et al. |
| 2011/0202370 A1 | 8/2011 | Green et al. |
| 2011/0213974 A1 | 9/2011 | Ardon et al. |
| 2011/0276396 A1 | 11/2011 | Rathod |
| 2011/0279458 A1 | 11/2011 | Gnanasambandam et al. |
| 2011/0283205 A1 | 11/2011 | Nie et al. |
| 2011/0289065 A1 | 11/2011 | Wells |
| 2011/0289161 A1 | 11/2011 | Rankin et al. |
| 2011/0302221 A1 | 12/2011 | Tobin et al. |
| 2011/0307397 A1 | 12/2011 | Benmbarek |
| 2012/0030168 A1 | 2/2012 | Weissenberger et al. |
| 2012/0030187 A1 | 2/2012 | Marano et al. |
| 2012/0046992 A1 | 2/2012 | Hu et al. |
| 2012/0047014 A1 | 2/2012 | Smadja et al. |
| 2012/0047143 A1 | 2/2012 | Petersen et al. |
| 2012/0054135 A1 | 3/2012 | Salaka et al. |
| 2012/0059795 A1 | 3/2012 | Hersh et al. |
| 2012/0078906 A1 | 3/2012 | Anand et al. |
| 2012/0084340 A1 | 4/2012 | McCormack et al. |
| 2012/0089432 A1 | 4/2012 | Podgurny et al. |
| 2012/0096041 A1 | 4/2012 | Rao et al. |
| 2012/0110515 A1 | 5/2012 | Abramoff et al. |
| 2012/0117250 A1 | 5/2012 | Santamaria et al. |
| 2012/0131139 A1 | 5/2012 | Siripurapu et al. |
| 2012/0150888 A1 | 6/2012 | Hyatt et al. |
| 2012/0173580 A1 | 7/2012 | Diorio et al. |
| 2012/0185480 A1 | 7/2012 | Ni et al. |
| 2012/0185544 A1 | 7/2012 | Chang et al. |
| 2012/0191570 A1 | 7/2012 | Bennett et al. |
| 2012/0197907 A1 | 8/2012 | Malyshev et al. |
| 2012/0232955 A1 | 9/2012 | Riazzi et al. |
| 2012/0254128 A1 | 10/2012 | Bath et al. |
| 2012/0310763 A1 | 12/2012 | Meehan |
| 2012/0331064 A1 | 12/2012 | Deeter et al. |
| 2013/0006634 A1 | 1/2013 | Grokop et al. |
| 2013/0013667 A1 | 1/2013 | Serena |
| 2013/0031172 A1 | 1/2013 | Olsen et al. |
| 2013/0041961 A1 | 2/2013 | Thrower et al. |
| 2013/0054613 A1 | 2/2013 | Bishop |
| 2013/0073662 A1 | 3/2013 | Meunier et al. |
| 2013/0080212 A1 | 3/2013 | Li et al. |
| 2013/0091042 A1 | 4/2013 | Shah et al. |
| 2013/0110907 A1 | 5/2013 | Sherwin et al. |
| 2013/0117287 A1 | 5/2013 | Jagota et al. |
| 2013/0117289 A1 | 5/2013 | Fischer et al. |
| 2013/0124257 A1 | 5/2013 | Schubert |
| 2013/0124626 A1 | 5/2013 | Cathcart et al. |
| 2013/0179236 A1 | 7/2013 | Hicyilmaz et al. |
| 2013/0179790 A1 | 7/2013 | Nadiadi et al. |
| 2013/0191416 A1 | 7/2013 | Lee et al. |
| 2013/0204663 A1 | 8/2013 | Kahlow |
| 2013/0205215 A1 | 8/2013 | Dunn et al. |
| 2013/0212115 A1 | 8/2013 | Yerli |
| 2013/0212200 A1 | 8/2013 | Dennis et al. |
| 2013/0238375 A1 | 9/2013 | Graupner et al. |
| 2013/0254134 A1 | 9/2013 | Pothineni et al. |
| 2013/0290690 A1 | 10/2013 | Nucci et al. |
| 2013/0311498 A1 | 11/2013 | Lambert et al. |
| 2013/0339105 A1 | 12/2013 | Russell et al. |
| 2013/0339276 A1 | 12/2013 | Lai et al. |
| 2014/0006044 A1 | 1/2014 | Pradhan et al. |
| 2014/0019409 A1 | 1/2014 | Tseng et al. |
| 2014/0025686 A1 | 1/2014 | Wong |
| 2014/0025693 A1 | 1/2014 | Arora et al. |
| 2014/0046711 A1 | 2/2014 | Borodow et al. |
| 2014/0066044 A1 | 3/2014 | Ramnani et al. |
| 2014/0067803 A1 | 3/2014 | Kapadia et al. |
| 2014/0074550 A1 | 3/2014 | Chourey |
| 2014/0074551 A1 | 3/2014 | Setayesh et al. |
| 2014/0081685 A1 | 3/2014 | Thacker et al. |
| 2014/0081690 A1 | 3/2014 | Winters |
| 2014/0129942 A1 | 5/2014 | Rathod |
| 2014/0149560 A1 | 5/2014 | Hakami et al. |
| 2014/0164065 A1 | 6/2014 | Prieto |
| 2014/0172478 A1 | 6/2014 | Vadasz |
| 2014/0172504 A1 | 6/2014 | Duva et al. |
| 2014/0172872 A1 | 6/2014 | Hyatt et al. |
| 2014/0180762 A1 | 6/2014 | Gilbert |
| 2014/0180788 A1 | 6/2014 | George et al. |
| 2014/0181935 A1 | 6/2014 | Beckmann et al. |
| 2014/0195449 A1 | 7/2014 | Komissarchik et al. |
| 2014/0196037 A1 | 7/2014 | Gopalan |
| 2014/0211791 A1 | 7/2014 | Cadiz et al. |
| 2014/0236663 A1 | 8/2014 | Smith et al. |
| 2014/0244300 A1 | 8/2014 | Bess et al. |
| 2014/0244531 A1 | 8/2014 | Baldwin et al. |
| 2014/0278271 A1 | 9/2014 | Stevenson et al. |
| 2014/0278909 A1 | 9/2014 | Potter et al. |
| 2014/0297751 A1 | 10/2014 | Antani et al. |
| 2014/0365509 A1 | 12/2014 | Lester et al. |
| 2014/0372363 A1 | 12/2014 | Chestnut et al. |
| 2015/0019204 A1 | 1/2015 | Simard et al. |
| 2015/0032499 A1 | 1/2015 | Duftler et al. |
| 2015/0032738 A1 | 1/2015 | Nachnani et al. |
| 2015/0032829 A1 | 1/2015 | Barshow et al. |
| 2015/0039380 A1 | 2/2015 | Bellini et al. |
| 2015/0039703 A1 | 2/2015 | Kursun |
| 2015/0046233 A1 | 2/2015 | Srulowitz et al. |
| 2015/0058324 A1 | 2/2015 | Kauwe |
| 2015/0067687 A1 | 3/2015 | Turner |
| 2015/0081396 A1 | 3/2015 | Miller |
| 2015/0100356 A1 | 4/2015 | Bessler et al. |
| 2015/0106260 A1 | 4/2015 | Andrews et al. |
| 2015/0112880 A1 | 4/2015 | Blaylock et al. |
| 2015/0120374 A1 | 4/2015 | Kolegayev et al. |
| 2015/0120714 A1 | 4/2015 | Xu et al. |
| 2015/0127585 A1 | 5/2015 | Pinckney et al. |
| 2015/0128252 A1 | 5/2015 | Konami |
| 2015/0134389 A1 | 5/2015 | Punera et al. |
| 2015/0134431 A1* | 5/2015 | Georgoff ............ G06Q 30/0207 705/14.13 |
| 2015/0135043 A1 | 5/2015 | Apps et al. |
| 2015/0143248 A1 | 5/2015 | Beechuk et al. |
| 2015/0149484 A1 | 5/2015 | Kelley |
| 2015/0170060 A1 | 6/2015 | Blechner et al. |
| 2015/0170091 A1 | 6/2015 | Kovilpattii et al. |
| 2015/0213358 A1 | 7/2015 | Shelton et al. |
| 2015/0228038 A1 | 8/2015 | Stevenson et al. |
| 2015/0242490 A1 | 8/2015 | Czajka et al. |
| 2015/0242753 A1 | 8/2015 | Yarlagadda et al. |
| 2015/0249742 A1 | 9/2015 | Li et al. |
| 2015/0269530 A1 | 9/2015 | Work et al. |
| 2015/0278504 A1 | 10/2015 | Azim et al. |
| 2015/0288744 A1 | 10/2015 | Dwan et al. |
| 2015/0294377 A1 | 10/2015 | Chow |
| 2015/0302436 A1 | 10/2015 | Reynolds |
| 2015/0332319 A1 | 11/2015 | Baizeau et al. |
| 2015/0347591 A1 | 12/2015 | Bax et al. |
| 2015/0347917 A1 | 12/2015 | Hua et al. |
| 2015/0347952 A1 | 12/2015 | Guan et al. |
| 2015/0350144 A1 | 12/2015 | Zeng et al. |
| 2015/0356160 A1 | 12/2015 | Berwick et al. |

(56) References Cited

U.S. PATENT DOCUMENTS

| | | |
|---|---|---|
| 2015/0371172 A1 | 12/2015 | Minter |
| 2015/0379131 A1 | 12/2015 | Gurevich et al. |
| 2016/0006875 A1 | 1/2016 | Burmeister et al. |
| 2016/0012121 A1 | 1/2016 | Skarin et al. |
| 2016/0014151 A1 | 1/2016 | Prakash |
| 2016/0019661 A1 | 1/2016 | Bouganim et al. |
| 2016/0048548 A1 | 2/2016 | Thomas et al. |
| 2016/0048791 A1 | 2/2016 | Kadakia et al. |
| 2016/0048854 A1 | 2/2016 | Kahlow |
| 2016/0057499 A1 | 2/2016 | Foerster et al. |
| 2016/0063118 A1 | 3/2016 | Campbell et al. |
| 2016/0063336 A1 | 3/2016 | Poplavski et al. |
| 2016/0065628 A1 | 3/2016 | Guo et al. |
| 2016/0071152 A1 | 3/2016 | Nicklin et al. |
| 2016/0086190 A1 | 3/2016 | Bohrer et al. |
| 2016/0092040 A1 | 3/2016 | Sherman |
| 2016/0110400 A1 | 4/2016 | Greene et al. |
| 2016/0110826 A1 | 4/2016 | Morimoto et al. |
| 2016/0119289 A1 | 4/2016 | Jain et al. |
| 2016/0125067 A1 | 5/2016 | Alexe et al. |
| 2016/0125471 A1 | 5/2016 | Hsu et al. |
| 2016/0142275 A1 | 5/2016 | Hendry et al. |
| 2016/0171373 A1 | 6/2016 | Allen et al. |
| 2016/0180038 A1 | 6/2016 | Clark et al. |
| 2016/0189082 A1 | 6/2016 | Garrish et al. |
| 2016/0196511 A1 | 7/2016 | Anisingaraju et al. |
| 2016/0196523 A1 | 7/2016 | Pieper |
| 2016/0212266 A1 | 7/2016 | Soundar |
| 2016/0217407 A1 | 7/2016 | Ostanik |
| 2016/0217429 A1 | 7/2016 | Lau |
| 2016/0224939 A1 | 8/2016 | Chen et al. |
| 2016/0226811 A1 | 8/2016 | Kerschhofer et al. |
| 2016/0239774 A1 | 8/2016 | Babar |
| 2016/0241532 A1 | 8/2016 | Loughlin-McHugh et al. |
| 2016/0241579 A1 | 8/2016 | Roosenraad et al. |
| 2016/0255034 A1 | 9/2016 | Yuan |
| 2016/0255139 A1 | 9/2016 | Rathod |
| 2016/0260044 A1 | 9/2016 | Sabet et al. |
| 2016/0306812 A1 | 10/2016 | Mchenry et al. |
| 2016/0308812 A1 | 10/2016 | Johnstone et al. |
| 2016/0314132 A1 | 10/2016 | Lineberger et al. |
| 2016/0321583 A1 | 11/2016 | Jones et al. |
| 2016/0335686 A1 | 11/2016 | Athulurutlrumala et al. |
| 2016/0342968 A1 | 11/2016 | Margalit et al. |
| 2016/0350134 A1 | 12/2016 | Verweyst et al. |
| 2016/0350440 A1 | 12/2016 | Vaishnav et al. |
| 2016/0352530 A1 | 12/2016 | Andrews et al. |
| 2016/0357790 A1 | 12/2016 | Elkington et al. |
| 2016/0364427 A1 | 12/2016 | Wedgeworth, III |
| 2017/0017886 A1 | 1/2017 | Gao et al. |
| 2017/0019487 A1 | 1/2017 | Maheshwari et al. |
| 2017/0024484 A1 | 1/2017 | Qiu |
| 2017/0032042 A1 | 2/2017 | Rykowski et al. |
| 2017/0032186 A1 | 2/2017 | Murata et al. |
| 2017/0039286 A1 | 2/2017 | Walke et al. |
| 2017/0039296 A1 | 2/2017 | Bastide et al. |
| 2017/0039527 A1 | 2/2017 | Rangan |
| 2017/0046651 A1 | 2/2017 | Lin et al. |
| 2017/0048253 A1 | 2/2017 | Anton et al. |
| 2017/0048285 A1 | 2/2017 | Pearl et al. |
| 2017/0053244 A1 | 2/2017 | Khalil |
| 2017/0061552 A1 | 3/2017 | Young et al. |
| 2017/0075894 A1 | 3/2017 | Poornachandran et al. |
| 2017/0076321 A1 | 3/2017 | Reznek et al. |
| 2017/0091270 A1 | 3/2017 | Guo et al. |
| 2017/0091394 A1 | 3/2017 | Gurupur et al. |
| 2017/0093776 A1 | 3/2017 | Dixon |
| 2017/0111462 A1 | 4/2017 | Oberli et al. |
| 2017/0116552 A1 | 4/2017 | Deodhar et al. |
| 2017/0132229 A1 | 5/2017 | Parihar et al. |
| 2017/0132553 A1 | 5/2017 | Theirl et al. |
| 2017/0193420 A1 | 7/2017 | Tiwari |
| 2017/0206276 A1 | 7/2017 | Gill |
| 2017/0206557 A1 | 7/2017 | Abrol et al. |
| 2017/0213272 A1 | 7/2017 | Mowatt et al. |
| 2017/0249466 A1 | 8/2017 | Ben-Yair et al. |
| 2017/0262807 A1 | 9/2017 | Kolls |
| 2017/0264584 A1 | 9/2017 | Chatterjee et al. |
| 2017/0286480 A1 | 10/2017 | Xie et al. |
| 2017/0286526 A1 | 10/2017 | Bar-Or et al. |
| 2017/0295144 A1 | 10/2017 | Song et al. |
| 2017/0308974 A1 | 10/2017 | Adiga et al. |
| 2017/0316080 A1 | 11/2017 | Brisebois et al. |
| 2017/0323233 A1 | 11/2017 | Bencke et al. |
| 2017/0324767 A1 | 11/2017 | Srivastava |
| 2017/0331916 A1 | 11/2017 | Banatwala et al. |
| 2017/0332220 A1 | 11/2017 | Nordstrom et al. |
| 2017/0337199 A1 | 11/2017 | Kogan et al. |
| 2017/0337647 A1 | 11/2017 | Vaynshteyn |
| 2017/0344556 A1 | 11/2017 | Wu et al. |
| 2017/0353423 A1 | 12/2017 | Morrison et al. |
| 2017/0364580 A1 | 12/2017 | Ishitobi |
| 2017/0372268 A1 | 12/2017 | Ilan et al. |
| 2018/0004746 A1 | 1/2018 | Hedinsson et al. |
| 2018/0012139 A1 | 1/2018 | Schmid et al. |
| 2018/0025082 A1 | 1/2018 | Harik et al. |
| 2018/0025303 A1 | 1/2018 | Janz |
| 2018/0033025 A1 | 2/2018 | Sun et al. |
| 2018/0054720 A1 | 2/2018 | Messenger et al. |
| 2018/0060122 A1 | 3/2018 | Tang et al. |
| 2018/0060387 A1 | 3/2018 | Le et al. |
| 2018/0063265 A1 | 3/2018 | Crossley et al. |
| 2018/0082678 A1 | 3/2018 | Olmstead et al. |
| 2018/0091654 A1 | 3/2018 | Miller et al. |
| 2018/0096267 A1 | 4/2018 | Masekera et al. |
| 2018/0096271 A1 | 4/2018 | Raanani et al. |
| 2018/0097844 A1 | 4/2018 | Rao et al. |
| 2018/0101797 A1 | 4/2018 | Mueller et al. |
| 2018/0114177 A1 | 4/2018 | Somech et al. |
| 2018/0121520 A1 | 5/2018 | Degiere et al. |
| 2018/0131667 A1 | 5/2018 | Jain et al. |
| 2018/0150599 A1 | 5/2018 | Valdes et al. |
| 2018/0150783 A1 | 5/2018 | Xu et al. |
| 2018/0157739 A1 | 6/2018 | Khaitan et al. |
| 2018/0158007 A1 | 6/2018 | Frangeti |
| 2018/0165621 A1 | 6/2018 | Guo et al. |
| 2018/0173906 A1 | 6/2018 | Rodriguez et al. |
| 2018/0174085 A1 | 6/2018 | McCoy |
| 2018/0189356 A1 | 7/2018 | Ghafourifar et al. |
| 2018/0219818 A1 | 8/2018 | Kramer et al. |
| 2018/0219830 A1 | 8/2018 | O'Brien et al. |
| 2018/0225051 A1 | 8/2018 | Vansa |
| 2018/0232680 A1 | 8/2018 | Hazime et al. |
| 2018/0246774 A1 | 8/2018 | Byrne |
| 2018/0262617 A1 | 9/2018 | Soundar |
| 2018/0268341 A1 | 9/2018 | Rini et al. |
| 2018/0268416 A1 | 9/2018 | Ponnusamy et al. |
| 2018/0285884 A1 | 10/2018 | Long |
| 2018/0285906 A1 | 10/2018 | Ng et al. |
| 2018/0288060 A1 | 10/2018 | Jackson et al. |
| 2018/0288455 A1 | 10/2018 | Baughman et al. |
| 2018/0300364 A1 | 10/2018 | Xu |
| 2018/0300387 A1 | 10/2018 | Nk |
| 2018/0308057 A1 | 10/2018 | Kenthapadi et al. |
| 2018/0315062 A1 | 11/2018 | Parekh et al. |
| 2018/0322461 A1 | 11/2018 | Subedi et al. |
| 2018/0330334 A1 | 11/2018 | Gowru et al. |
| 2018/0332162 A1 | 11/2018 | Schutter et al. |
| 2018/0349482 A1 | 12/2018 | Oliner et al. |
| 2018/0365309 A1 | 12/2018 | Oliner et al. |
| 2018/0373696 A1 | 12/2018 | Terry et al. |
| 2018/0374171 A1 | 12/2018 | Aizen et al. |
| 2019/0007362 A1 | 1/2019 | Shmunis et al. |
| 2019/0018546 A1 | 1/2019 | Kwizera et al. |
| 2019/0026681 A1 | 1/2019 | Polli et al. |
| 2019/0028492 A1 | 1/2019 | Coleman et al. |
| 2019/0057339 A1 | 2/2019 | Ponnusamy et al. |
| 2019/0066021 A1 | 2/2019 | Tang et al. |
| 2019/0068747 A1 | 2/2019 | Lervik et al. |
| 2019/0079934 A1 | 3/2019 | Liao et al. |
| 2019/0087764 A1 | 3/2019 | Bhushanam et al. |
| 2019/0089701 A1 | 3/2019 | Mercury et al. |
| 2019/0089829 A1 | 3/2019 | Nicholls et al. |
| 2019/0095961 A1 | 3/2019 | Wu et al. |

(56) References Cited

U.S. PATENT DOCUMENTS

| | | | |
|---|---|---|---|
| 2019/0098364 A1 | 3/2019 | Sansom et al. |
| 2019/0108493 A1 | 4/2019 | Nelson et al. |
| 2019/0121998 A1 | 4/2019 | Vanderleest |
| 2019/0122322 A1 | 4/2019 | Perez |
| 2019/0130037 A1 | 5/2019 | Guo et al. |
| 2019/0138635 A1 | 5/2019 | Givon |
| 2019/0140988 A1 | 5/2019 | Snider et al. |
| 2019/0140995 A1 | 5/2019 | Roller et al. |
| 2019/0164179 A1 | 5/2019 | Sun et al. |
| 2019/0171693 A1 | 6/2019 | Dotan-Cohen et al. |
| 2019/0199677 A1 | 6/2019 | Bajaria et al. |
| 2019/0199745 A1 | 6/2019 | Jakobsson et al. |
| 2019/0207876 A1 | 7/2019 | Terry et al. |
| 2019/0228365 A1 | 7/2019 | Kamath |
| 2019/0236199 A1 | 8/2019 | Mahalingam et al. |
| 2019/0236511 A1 | 8/2019 | Xu et al. |
| 2019/0236516 A1 | 8/2019 | Ponnusamy |
| 2019/0364154 A1 | 11/2019 | Hermanek et al. |
| 2020/0125669 A1 | 4/2020 | Subedi |
| 2020/0302116 A1 | 9/2020 | Rogynskyy et al. |
| 2020/0304448 A1 | 9/2020 | Zhang et al. |
| 2020/0349178 A1 | 11/2020 | Raju |
| 2021/0157312 A1 | 5/2021 | Cella et al. |
| 2022/0138191 A1 | 5/2022 | Hermanek et al. |

FOREIGN PATENT DOCUMENTS

| | | |
|---|---|---|
| WO | WO-2018/064662 | 4/2018 |
| WO | WO-2018/081827 A1 | 5/2018 |

OTHER PUBLICATIONS

Aviso. AI-Driven Forecasting and Pipeline Management. Feb. 24, 2018. <https://web.archive.org/web/20180224123501/https://www.aviso.com/>. (6 pages).

DataSelf BI. "5 Analytics for Sales: Demo for Salespeople—DataSelf / Tableau", Dec. 13, 2017. <https://www.youtube.com/watch?v= B01hgTQ_SwM>. (1 page).

DataSelf. Oct. 15, 2017. <https://web.archive.org/web/20171015213907 /https://dataself.com/>. (1 page).

DealSheet. Increase Win Rates, Exceed Quota: Outside In DealSheet and AccountPlan. Feb. 25, 2018. <https://www.youtube.com/ watch?v=krgRrzmViDg>. (1 page).

Final Office Action on U.S. Appl. No. 16/360,892 dated May 19, 2020 (38 pages).

Final Office Action on U.S. Appl. No. 16/371,035 dated Jan. 15, 2020 (20 pages).

Final Office Action on U.S. Appl. No. 16/371,049 dated Mar. 10, 2020 (32 pages).

Final Office Action on U.S. Appl. No. 16/371,050 dated Apr. 13, 2020 (10 pages).

Final Office Action on U.S. Appl. No. 16/398,150 dated Mar. 5, 2020 (22 pages).

Final Office Action on U.S. Appl. No. 16/399,690 dated Jan. 9, 2020 (14 pages).

Final Office Action on U.S. Appl. No. 16/399,768 dated Apr. 15, 2020 (9 pages).

Final Office Action on U.S. Appl. No. 16/418,725 dated Apr. 20, 2020 (27 pages).

Final Office Action on U.S. Appl. No. 16/418,747 dated Mar. 19, 2020 (18 pages).

Final Office Action on U.S. Appl. No. 16/418,807 dated Jan. 3, 2020 (24 pages).

Final Office Action on U.S. Appl. No. 16/418,836 dated Mar. 30, 2020 (17 pages).

Final Office Action on U.S. Appl. No. 16/418,851 dated Mar. 23, 2020 (21 pages).

Final Office Action on U.S. Appl. No. 16/418,867 dated Mar. 12, 2020 (31 pages).

Final Office Action on U.S. Appl. No. 16/418,892 dated Apr. 17, 2020 (34 pages).

Final Office Action on U.S. Appl. No. 16/421,280 dated Feb. 28, 2020 (48 pages).

Garysmithpartnership. "12 Must-Have Salesforce Dashboard Charts | With Video and Examples", May 7, 2017. <https://web.archive.org/web/20170507121801 /http://garysmithpartnership.com:80/salesforce-dashboards>. (27 pages).

https://pages.clari.com/rs/866-BBG-005/images/Clari-SB-AI-Applications-for-Sales-0917.pdf, Feb. 5, 2018. (9 pages).

https://scholar.google.com/scholar?as_q=%28first name%29 and %28last name%29 and %28contact%29 and%28email%29 and %28phone%. dated Dec. 12, 2019 (2 pages).

IEEE Xplore Search Results, dated Jan. 7, 2020 (3 pages).

Insight Squared. 7 Sales Dashboard Examples And Templates. Jul. 5, 2017. <https://web.archive.org/web/20170705225032/https: //www.insightsquared.com/2015/09/7-sales-dashboard-examples-and-templates/>. (10 pages).

International Search Report and Written Opinion of the International Searching Authority on PCT PCT/US2019/034030 dated Sep. 30, 2019 (14 pages).

International Search Report and Written Opinion of the International Searching Authority on PCT PCT/US2019/034033 dated Sep. 30, 2019 (16 pages).

International Search Report and Written Opinion of the International Searching Authority on PCT PCT/US2019/034042 dated Sep. 30, 2019 (14 pages).

International Search Report and Written Opinion of the International Searching Authority on PCT PCT/US2019/034045 dated Sep. 30, 2019 (16 pages).

International Search Report and Written Opinion of the International Searching Authority on PCT PCT/US2019/034046 dated Sep. 30, 2019 (14 pages).

International Search Report and Written Opinion of the International Searching Authority on PCT PCT/US2019/034050 dated Sep. 30, 2019 (15 pages).

International Search Report and Written Opinion of the International Searching Authority on PCT PCT/US2019/034052 dated Sep. 30, 2019 (16 pages).

International Search Report and Written Opinion of the International Searching Authority on PCT PCT/US2019/034062 dated Sep. 30, 2019 (14 pages).

International Search Report and Written Opinion of the International Searching Authority on PCT PCT/US2019/034068 dated Sep. 30, 2019 (14 pages).

International Search Report and Written Opinion of the International Searching Authority on PCT PCT/US2019/034070 dated Sep. 30, 2019 (14 pages).

Klipfolio. Dashboard software for teams who want to continuously monitor the health of their business. May 30, 2017. <https://web.archive.org/web/20170530091735/https ://www. kl ipfolio .com/>. (1 page).

Mahmud, et al.; "Home Location Identification of Twitter users"; arXiv:1403.2345; Dated Mar. 7, 2014.(23 pages).

Nexd. Nexd Rebrands as Olona; Announces General Availability of Industry's First Proactive Enterprise Sales Tool. Sep. 18, 2017. < https ://www.newswire.com/news/nexd-rebrands-as-olono-announces-general-avai lability-of-industrys-19943271 >. (4 pages).

Non-Final Office Action on U.S. Appl. No. 16/237,585 dated Apr. 25, 2019 (12 pages).

Non-Final Office Action on U.S. Appl. No. 16/360,892 dated Aug. 28, 2019 (34 pages).

Non-Final Office Action on U.S. Appl. No. 16/361,009 dated Jul. 11, 2019 (14 pages).

Non-Final Office Action on U.S. Appl. No. 16/361,025 dated Jul. 25, 2019 (19 pages).

Non-Final Office Action on U.S. Appl. No. 16/371,035 dated Jul. 9, 2019 (22 pages).

Non-Final Office Action on U.S. Appl. No. 16/371,048 dated Jul. 8, 2019 (12 pages).

Non-Final Office Action on U.S. Appl. No. 16/371,049 dated Jun. 10, 2019 (27 pages).

(56) References Cited

OTHER PUBLICATIONS

Non-Final Office Action on U.S. Appl. No. 16/371,050 dated Jun. 26, 2019 (8 pages).
Non-Final Office Action on U.S. Appl. No. 16/398,150 dated Jul. 26, 2019 (14 pages).
Non-Final Office Action on U.S. Appl. No. 16/398,220 dated Jul. 25, 2019 (13 pages).
Non-Final Office Action on U.S. Appl. No. 16/399,690 dated Jun. 28, 2019 (13 pages).
Non-Final Office Action on U.S. Appl. No. 16/399,768 dated Jun. 27, 2019 (8 pages).
Non-Final Office Action on U.S. Appl. No. 16/418,539 dated Aug. 22, 2019 (11 pages).
Non-Final Office Action on U.S. Appl. No. 16/418,725 dated Aug. 15, 2019 (24 pages).
Non-Final Office Action on U.S. Appl. No. 16/418,747 dated Aug. 8, 2019 (16 pages).
Non-Final Office Action on U.S. Appl. No. 16/418,807 dated Jul. 25, 2019 (23 pages).
Non-Final Office Action on U.S. Appl. No. 16/418,826 dated Jul. 17, 2019 (9 pages).
Non-Final Office Action on U.S. Appl. No. 16/418,836 dated Jul. 29, 2019 (13 pages).
Non-Final Office Action on U.S. Appl. No. 16/418,846 dated Jun. 28, 2019 (17 pages).
Non-Final Office Action on U.S. Appl. No. 16/418,851 dated Jul. 10, 2019 (17 pages).
Non-Final Office Action on U.S. Appl. No. 16/418,867 dated Aug. 16, 2019 (26 pages).
Non-Final Office Action on U.S. Appl. No. 16/418,892 dated Aug. 28, 2019 (28 pages).
Non-Final Office Action on U.S. Appl. No. 16/420,052 dated Aug. 7, 2019 (11 pages).
Non-Final Office Action on U.S. Appl. No. 16/421,151 dated Aug. 2, 2019 (24 pages).
Non-Final Office Action on U.S. Appl. No. 16/421,280 dated Aug. 19, 2019 (35 pages).
Non-Final Office Action on U.S. Appl. No. 16/421,298 dated Aug. 6, 2019 (7 pages).
Non-Final Office Action on U.S. Appl. No. 16/421,328 dated Jul. 25, 2019 (16 pages).
Non-Final Office Action on U.S. Appl. No. 16/421,370 dated Aug. 23, 2019 (11 pages).
Non-Final Office Action on U.S. Appl. No. 16/695,082 dated Feb. 24, 2020 (18 pages).
Notice of Allowance on U.S. Appl. No. 16/399,679 dated Jun. 26, 2019 (20 pages).
Notice of Allowance on U.S. Appl. No. 16/213,754 dated Aug. 15, 2019 (8 pages).
Notice of Allowance on U.S. Appl. No. 16/213,754 dated Mar. 11, 2019 (33 pages).
Notice of Allowance on U.S. Appl. No. 16/213,754 dated Nov. 14, 2019 (9 pages).
Notice of Allowance on U.S. Appl. No. 16/237,579 dated Apr. 10, 2019 (16 pages).
Notice of Allowance on U.S. Appl. No. 16/237,579 dated Dec. 18, 2019 (12 pages).
Notice of Allowance on U.S. Appl. No. 16/237,579 dated Sep. 26, 2019 (13 pages).
Notice of Allowance on U.S. Appl. No. 16/237,580 dated Apr. 24, 2019 (16 pages).
Notice of Allowance on U.S. Appl. No. 16/237,580 dated Dec. 12, 2019 (11 pages).
Notice of Allowance on U.S. Appl. No. 16/237,580 dated Jul. 25, 2019 (15 pages).
Notice of Allowance on U.S. Appl. No. 16/237,580 dated Jun. 21, 2019 (13 pages).
Notice of Allowance on U.S. Appl. No. 16/237,580 dated Nov. 6, 2019 (11 pages).
Notice of Allowance on U.S. Appl. No. 16/237,582 dated Apr. 2, 2019 (16 pages).
Notice of Allowance on U.S. Appl. No. 16/237,582 dated Aug. 21, 2019 (7 pages).
Notice of Allowance on U.S. Appl. No. 16/237,582 dated Oct. 17, 2019 (2 pages).
Notice of Allowance on U.S. Appl. No. 16/237,585 dated Nov. 13, 2019 (8 pages).
Notice of Allowance on U.S. Appl. No. 16/360,866 dated Aug. 27, 2019 (9 pages).
Notice of Allowance on U.S. Appl. No. 16/360,866 dated Jun. 5, 2019 (17 pages).
Notice of Allowance on U.S. Appl. No. 16/360,866 dated Oct. 25, 2019 (2 pages).
Notice of Allowance on U.S. Appl. No. 16/360,884 dated Aug. 14, 2019 (8 pages).
Notice of Allowance on U.S. Appl. No. 16/360,884 dated Jun. 11, 2019 (12 pages).
Notice of Allowance on U.S. Appl. No. 16/360,884 dated Nov. 18, 2019 (3 pages).
Notice of Allowance on U.S. Appl. No. 16/360,933 dated Aug. 12, 2019 (8 pages).
Notice of Allowance on U.S. Appl. No. 16/360,933 dated Jun. 19, 2019 (17 pages).
Notice of Allowance on U.S. Appl. No. 16/360,933 dated Nov. 22, 2019 (4 pages).
Notice of Allowance on U.S. Appl. No. 16/360,960 dated Aug. 23, 2019 (7 pages).
Notice of Allowance on U.S. Appl. No. 16/360,960 dated May 13, 2019 (9 pages).
Notice of Allowance on U.S. Appl. No. 16/360,997 dated Aug. 9, 2019 (8 pages).
Notice of Allowance on U.S. Appl. No. 16/360,997 dated May 30, 2019 (23 pages).
Notice of Allowance on U.S. Appl. No. 16/361,009 dated Feb. 25, 2020 (10 pages).
Notice of Allowance on U.S. Appl. No. 16/361,009 dated Mar. 27, 2020 (2 pages).
Notice of Allowance on U.S. Appl. No. 16/361,009 dated May 4, 2020 (2 pages).
Notice of Allowance on U.S. Appl. No. 16/361,025 dated Apr. 29, 2020 (7 pages).
Notice of Allowance on U.S. Appl. No. 16/371,035 dated May 4, 2020 (10 pages).
Notice of Allowance on U.S. Appl. No. 16/371,037 dated Aug. 1, 2019 (12 pages).
Notice of Allowance on U.S. Appl. No. 16/371,037 dated Oct. 21, 2019 (7 pages).
Notice of Allowance on U.S. Appl. No. 16/371,039 dated Aug. 21, 2019 (17 pages).
Notice of Allowance on U.S. Appl. No. 16/371,041 dated Jul. 31, 2019 (10 pages).
Notice of Allowance on U.S. Appl. No. 16/371,042 dated Aug. 13, 2019 (19 pages).
Notice of Allowance on U.S. Appl. No. 16/371,044 dated Aug. 7, 2019 (5 pages).
Notice of Allowance on U.S. Appl. No. 16/371,044 dated Jun. 12, 2019 (16 pages).
Notice of Allowance on U.S. Appl. No. 16/371,044 dated Nov. 18, 2019 (5 pages).
Notice of Allowance on U.S. Appl. No. 16/371,048 dated Apr. 16, 2020 (2 pages).
Notice of Allowance on U.S. Appl. No. 16/371,048 dated Jan. 17, 2020 (5 pages).
Notice of Allowance on U.S. Appl. No. 16/371,048 dated Mar. 20, 2020 (2 pages).
Notice of Allowance on U.S. Appl. No. 16/398,153 dated Jul. 17, 2019 (27 pages).
Notice of Allowance on U.S. Appl. No. 16/398,157 dated Aug. 21, 2019 (19 pages).
Notice of Allowance on U.S. Appl. No. 16/398,157 dated Nov. 6, 2019 (2 pages).

(56) References Cited

OTHER PUBLICATIONS

Notice of Allowance on U.S. Appl. No. 16/398,220 dated Dec. 12, 2019 (13 pages).
Notice of Allowance on U.S. Appl. No. 16/398,260 dated Aug. 14, 2019 (17 pages).
Notice of Allowance on U.S. Appl. No. 16/399,679 dated Oct. 15, 2019 (2 pages).
Notice of Allowance on U.S. Appl. No. 16/399,679 dated Oct. 25, 2019 (2 pages).
Notice of Allowance on U.S. Appl. No. 16/399,679 dated Sep. 5, 2019 (2 pages).
Notice of Allowance on U.S. Appl. No. 16/399,690 dated Apr. 22, 2020 (8 pages).
Notice of Allowance on U.S. Appl. No. 16/399,706 dated Jun. 27, 2019 (17 pages).
Notice of Allowance on U.S. Appl. No. 16/399,706 dated Oct. 30, 2019 (2 pages).
Notice of Allowance on U.S. Appl. No. 16/399,787 dated Jul. 25, 2019 (21 pages).
Notice of Allowance on U.S. Appl. No. 16/399,787 dated Oct. 29, 2019 (2 pages).
Notice of Allowance on U.S. Appl. No. 16/400,000 dated Jun. 18, 2019 (17 pages).
Notice of Allowance on U.S. Appl. No. 16/400,000 dated Oct. 24, 2019 (2 pages).
Notice of Allowance on U.S. Appl. No. 16/418,539 dated Apr. 20, 2020 (2 pages).
Notice of Allowance on U.S. Appl. No. 16/418,539 dated Mar. 20, 2020 (10 pages).
Notice of Allowance on U.S. Appl. No. 16/418,539 dated May 5, 2020 (2 pages).
Notice of Allowance on U.S. Appl. No. 16/418,629 dated Aug. 15, 2019 (20 pages).
Notice of Allowance on U.S. Appl. No. 16/418,629 dated Oct. 21, 2019 (2 pages).
Notice of Allowance on U.S. Appl. No. 16/418,769 dated Aug. 16, 2019 (20 pages).
Notice of Allowance on U.S. Appl. No. 16/418,769 dated Oct. 23, 2019 (5 pages).
Notice of Allowance on U.S. Appl. No. 16/418,826 dated Jan. 21, 2020 (6 pages).
Notice of Allowance on U.S. Appl. No. 16/418,846 dated Feb. 6, 2020 (8 pages).
Notice of Allowance on U.S. Appl. No. 16/418,846 dated May 5, 2020 (3 pages).
Notice of Allowance on U.S. Appl. No. 16/418,891 dated Aug. 6, 2019 (10 pages).
Notice of Allowance on U.S. Appl. No. 16/418,891 dated Nov. 1, 2019 (2 pages).
Notice of Allowance on U.S. Appl. No. 16/419,583 dated Feb. 7, 2020 (19 pages).
Notice of Allowance on U.S. Appl. No. 16/420,039 dated Aug. 7, 2019 (10 pages).
Notice of Allowance on U.S. Appl. No. 16/420,039 dated Nov. 26, 2019 (2 pages).
Notice of Allowance on U.S. Appl. No. 16/420,052 dated Apr. 8, 2020 (2 pages).
Notice of Allowance on U.S. Appl. No. 16/420,052 dated Dec. 30, 2019 (5 pages).
Notice of Allowance on U.S. Appl. No. 16/420,052 dated Mar. 26, 2020 (2 pages).
Notice of Allowance on U.S. Appl. No. 16/421,256 dated Sep. 25, 2019 (14 pages).
Notice of Allowance on U.S. Appl. No. 16/421,288 dated Aug. 16, 2019 (19 pages).
Notice of Allowance on U.S. Appl. No. 16/421,288 dated Oct. 30, 2019 (2 pages).
Notice of Allowance on U.S. Appl. No. 16/421,298 dated Aug. 26, 2019 (14 pages).
Notice of Allowance on U.S. Appl. No. 16/421,298 dated Oct. 22, 2019 (3 pages).
Notice of Allowance on U.S. Appl. No. 16/421,298 dated Oct. 28, 2019 (3 pages).
Notice of Allowance on U.S. Appl. No. 16/421,324 dated Aug. 14, 2019 (22 pages).
Notice of Allowance on U.S. Appl. No. 16/421,324 dated Nov. 1, 2019 (2 pages).
Notice of Allowance on U.S. Appl. No. 16/421,328 dated Feb. 5, 2020 (9 pages).
Notice of Allowance on U.S. Appl. No. 16/421,370 dated Apr. 13, 2020 (2 pages).
Notice of Allowance on U.S. Appl. No. 16/421,370 dated Apr. 22, 2020 (2 pages).
Notice of Allowance on U.S. Appl. No. 16/421,370 dated Feb. 10, 2020 (9 pages).
Notice of Allowance on U.S. Appl. No. 16/694,274 dated Feb. 7, 2020 (20 pages).
Notice of Allowance on U.S. Appl. No. 16/694,274 dated May 7, 2020 (2 pages).
Olona. Olono's Sales activity management system to increase average quota attainment. Feb. 18, 2018. <https://www.youtube.com/ watch?v=3OtqtBPIM7M&t=1s>. (1 page).
Final Office Action on U.S. Appl. No. 16/371,049 dated May 2, 2022.
Non-Final Office Action on U.S. Appl. No. 17/102,397 dated May 18, 2022.
Notice of Allowance on U.S. Appl. No. 16/700,484 dated May 31, 2022.
Notice of Allowance on U.S. Appl. No. 16/877,078 dated May 4, 2022.
Notice of Allowance on U.S. Appl. No. 16/895,946 dated May 18, 2022.
Andrews-Todd, Jessica, et al. "Identifying Profiles of Collaborative Problem Solvers in an Online Electronics Environment." International Educational Data Mining Society (2018). (Year: 2018).
Destefano et al., "Improving Data Governance in Large Organizations through Ontology and Linked Data," 2016 IEEE 3rd International Conference on Cyber Security and Cloud Computing (CSCloud) Year: 2016 | Conference Paper | Publisher: IEEE.
Final Office Action on U.S. Appl. No. 16/418,836 dated Nov. 23, 2021.
Final Office Action on U.S. Appl. No. 16/420,059 dated Jan. 19, 2021.
Final Office Action on U.S. Appl. No. 16/695,082 dated Dec. 3, 2020.
Final Office Action on U.S. Appl. No. 16/371,049 dated May 21, 2021.
Foreign Action other than Search Report on PCT PCT/US2019/034033 dated Dec. 3, 2020.
Foreign Action other than Search Report on PCT PCT/US2019/034042 dated Dec. 3, 2020.
Foreign Action other than Search Report on PCT PCT/US2019/034046 dated Dec. 4, 2020.
Foreign Action other than Search Report on PCT PCT/US2019/034062 dated Dec. 3, 2020.
Foreign Action other than Search Report on PCT PCT/US2019/034068 dated Dec. 3, 2020.
Foreign Action other than Search Report on US PCT/US2019/034052 dated Dec. 3, 2020.
Foreign Search Report on PCT PCT/US2019/034045 dated Dec. 3, 2020.
Heng et al., "Integrated analytics system for electric industry asset management," IBM Journal of Research and Development Year: 2016 | vol. 60, Issue: 1 | Journal Article | Publisher: IBM.
http://download.microsoft.com/download/D/1/0/D10ACD6B-0C91-4545-9BD8-2AE431ECF749/Microsoft_Dynamics_CRM_2016_User_Guide.pdf.
https://help.salesforce.com/s/articleView?id=release-notes.salesforce_release_notes.htm&type=5&release=206.
https://help.salesforce.com/s/articleView?id=release-notes.salesforce_release_notes.htm&type=5&release=210.

(56) References Cited

OTHER PUBLICATIONS

Non Final Office Action on U.S. Appl. No. 16/708,247 dated May 21, 2021.
Non-Final Office Action on U.S. Appl. No. 16/418,892 dated Jan. 1, 2021.
Non-Final Office Action on U.S. Appl. No. 16/360,892 dated Feb. 3, 2022.
Non-Final Office Action on U.S. Appl. No. 16/360,892 dated Apr. 21, 2021.
Non-Final Office Action on U.S. Appl. No. 16/360,953 dated Jan. 27, 2021.
Non-Final Office Action on U.S. Appl. No. 16/371,049 dated Sep. 23, 2020.
Non-Final Office Action on U.S. Appl. No. 16/399,768 dated Nov. 20, 2020.
Non-Final Office Action on U.S. Appl. No. 16/418,725 dated Mar. 4, 2021.
Non-Final Office Action on U.S. Appl. No. 16/418,747 dated Jan. 27, 2021.
Non-Final Office Action on U.S. Appl. No. 16/418,747 dated Feb. 25, 2022.
Non-Final Office Action on U.S. Appl. No. 16/418,836 dated Apr. 2, 2021.
Non-Final Office Action on U.S. Appl. No. 16/421,280 dated Oct. 16, 2020.
Non-Final Office Action on U.S. Appl. No. 16/421,280 dated Nov. 9, 2021.
Non-Final Office Action on U.S. Appl. No. 16/700,484 dated Oct. 28, 2021.
Non-Final Office Action on U.S. Appl. No. 16/700,510 dated Feb. 16, 2021.
Non-Final Office Action on U.S. Appl. No. 16/708,257 dated Jul. 12, 2021.
Non-Final Office Action on U.S. Appl. No. 16/716,221 dated Oct. 4, 2021.
Non-Final Office Action on U.S. Appl. No. 16/877,078 dated Jun. 9, 2021.
Non-Final Office Action on U.S. Appl. No. 16/895,946 dated Oct. 14, 2021.
Non-Final Office Action on U.S. Appl. No. 17/157,471 dated Mar. 25, 2022.
Notice of Allowance in regards to U.S. Appl. No. 16/725,705 dated May 26, 2021.
Notice of Allowance on U.S. Appl. No. 16/792,676 dated Dec. 30, 2021.
Notice of Allowance on U.S. Appl. No. 16/360,953 dated Jan. 4, 2022.
Notice of Allowance on U.S. Appl. No. 16/360,953 dated Jul. 28, 2021.
Notice of Allowance on U.S. Appl. No. 16/361,025 dated Feb. 10, 2021.
Notice of Allowance on U.S. Appl. No. 16/371,035 dated Aug. 26, 2020.
Notice of Allowance on U.S. Appl. No. 16/371,035 dated Nov. 9, 2020.
Notice of Allowance on U.S. Appl. No. 16/398,150 dated Jul. 22, 2020.
Notice of Allowance on U.S. Appl. No. 16/398,150 dated Aug. 18, 2020.
Notice of Allowance on U.S. Appl. No. 16/398,150 dated Nov. 18, 2020.
Notice of Allowance on U.S. Appl. No. 16/398,220 dated Aug. 19, 2020.
Notice of Allowance on U.S. Appl. No. 16/398,220 dated Nov. 12, 2020.
Notice of Allowance on U.S. Appl. No. 16/399,690 dated Aug. 12, 2020.
Notice of Allowance on U.S. Appl. No. 16/399,690 dated Nov. 12, 2020.
Notice of Allowance on U.S. Appl. No. 16/418,807 dated Jan. 12, 2021.
Notice of Allowance on U.S. Appl. No. 16/418,807 dated Nov. 20, 2020.
Notice of Allowance on U.S. Appl. No. 16/418,851 dated Jan. 11, 2021.
Notice of Allowance on U.S. Appl. No. 16/418,851 dated Feb. 1, 2021.
Notice of Allowance on U.S. Appl. No. 16/418,867 dated Sep. 23, 2020.
Notice of Allowance on U.S. Appl. No. 16/418,867 dated Nov. 13, 2020.
Notice of Allowance on U.S. Appl. No. 16/418,892 dated Apr. 6, 2022.
Notice of Allowance on U.S. Appl. No. 16/418,892 dated Dec. 13, 2021.
Notice of Allowance on U.S. Appl. No. 16/420,059 dated Jan. 14, 2022.
Notice of Allowance on U.S. Appl. No. 16/420,059 dated Apr. 6, 2021.
Notice of Allowance on U.S. Appl. No. 16/695,082 dated Mar. 26, 2021.
Notice of Allowance on U.S. Appl. No. 16/700,498 dated Mar. 2, 2022.
Notice of Allowance on U.S. Appl. No. 16/700,510 dated Oct. 6, 2021.
Notice of Allowance on U.S. Appl. No. 16/708,247 dated Dec. 16, 2021.
Notice of Allowance on U.S. Appl. No. 16/708,257 dated Mar. 1, 2022.
Notice of Allowance on U.S. Appl. No. 16/773,363 dated Jan. 11, 2022.
Notice of Allowance on U.S. Appl. No. 16/792,676 dated Apr. 27, 2022.
Notice of Allowance on U.S. Appl. No. 16/877,016 dated Oct. 6, 2020.
Notice of Allowance on U.S. Appl. No. 16/877,016 dated Nov. 17, 2020.
Notice of Allowance on U.S. Appl. No. 16/877,078 dated Nov. 24, 2021.
Notice of Allowance re U.S. Appl. No. 16/148,892 dated Aug. 24, 2021.
*People.ai* v *Clari*—complaint ND Cal.
*People.ai* v *Clari*—document 19 Answering brief.
*People.ai* v *Clari*—document 21 first amended complaint.
*People.ai* v *Clari*—document 24 reply brief.
*People.ai* v *Clari*—document 27 answer to amended complaint.
*People.ai* v *Clari*—document 30 answer by plaintiff.
*People.ai* v *Clari*—document 45 statement of co-pending proceedings.
*People.ai* v *Clari*—document 53 Defendant 12c motion.
*People.ai* v *Clari*—document 56 Joint stipulation to extend briefing schedule for Defendant's motion for judgement on the pleadings.
*People.ai* v *Clari*—document 58 Plaintiff's response to Defendant's motion for judgement on the pleadings.
*People.ai* v *Clari*—document 58-01 Exhibit A.
*People.ai* v *Clari*—document 61 Defendant's reply in support of motion for judgement on the pleadings.
*People.ai* v *Clari*—document 64 Plaintiff's motion for leave to file second amended complaint.
*People.ai* v *Clari*—document 64-01 Plaintiff's brief in support of motion for leave to file second amended complaint.
*People.ai* v *Clari*—document 64-02 Declaration of L.Silva in support of Plaintiff's motion for leave to file a second amended complaint.
*People.ai* v *Clari*—document 64-03 Exhibit 1.
*People.ai* v *Clari*—document 64-04 Exhibit 2.
*People.ai* v *Clari*—document 8 Motion to dismiss.
*People.ai* v *Clari*—document 9 opening brief.
*People.ai* v *SetSail*—document 1 complaint ND Cal.
*People.ai* v *SetSail*—document 100 plaintiff's response to defendant's motion for judgement on the pleadings.

(56) References Cited

OTHER PUBLICATIONS

*People.ai* v *SetSail*—document 101-00 Declaration of Lucas Silva in support of plaintiff's opposition to defendant's motion for judgement on the pleadings.
*People.ai* v *SetSail*—document 101-01 Exhibit A.
*People.ai* v *SetSail*—document 102 Defendant's reply supporting its motion for judgement on the pleadings pursuant to FRCP12.
*People.ai* v *SetSail*—document 105 Letter from People.ai to Judge.
*People.ai* v *SetSail*—document 112 Plaintiff's motion to file certain documents under seal.
*People.ai* v *SetSail*—document 112-01 Declaration of L.Silva in support of Plaintiff's motion to file certain documents under seal.
*People.ai* v *SetSail*—document 112-19 Plaintiff's "Patent Showdown" motion for summary judgment.
*People.ai* v *SetSail*—document 114-00 Defendant's motion for partial summary judgement.
*People.ai* v *SetSail*—document 114-01 Declaration of S.Chatterjee in support of Defendant's motion for partial summary judgement.
*People.ai* v *SetSail*—document 114-02 Chatterjee Declaration Exhibit A.
*People.ai* v *SetSail*—document 114-03 Chatterjee Declaration Exhibit B1.
*People.ai* v *SetSail*—document 114-04 Chatterjee Declaration Exhibit B2.
*People.ai* v *SetSail*—document 114-05 Chatterjee Declaration Exhibit B3.
*People.ai* v *SetSail*—document 114-06 Chatterjee Declaration Exhibit C.
*People.ai* v *SetSail*—document 114-08 Chatterjee Declaration Exhibit E.
*People.ai* v *SetSail*—document 114-09 Chatterjee Declaration Exhibit F.
*People.ai* v *SetSail*—document 114-10 Chatterjee Declaration Exhibit G.
*People.ai* v *SetSail*—document 114-11 Chatterjee Declaration Exhibit H.
*People.ai* v *SetSail*—document 114-12 Declaration of B.Lui in support of Defendant's motion of partial summary judgement.
*People.ai* v *SetSail*—document 114-13 Lui Declaration Exhibit A.
*People.ai* v *SetSail*—document 114-14 Declaration of H.Levi in support of Defendant's motion for partial summary judgement.
*People.ai* v *SetSail*—document 117-07 Chatterjee Declaration Exhibit D.
*People.ai* v *SetSail*—document 36 first amended complaint.
*People.ai* v *SetSail*—document 43 Defendant motion to dismiss.
*People.ai* v *SetSail*—document 46 response to motion to dismiss first amended complaint.
*People.ai* v *SetSail*—document 47 reply in support of motion to dismiss first amended complaint.
*People.ai* v *SetSail*—document 50 opposition response.
*People.ai* v *SetSail*—document 59 notice of motion for leave.
*People.ai* v *SetSail*—document 66 opposition response.
*People.ai* v *SetSail*—document 68 reply brief in support of motion for leave.
*People.ai* v *SetSail*—document 73 Order re Judgement on the Pleadings.
*People.ai* v *SetSail*—document 74 second amended complaint.
*People.ai* v *SetSail*—document 79 answer to second amended complaint.
*People.ai* v *SetSail*—document 88 answer to counterclaims.
*People.ai* v *SetSail*—document 90 motion for judgement on the pleadings.
Silverston, Physically Implementing Universal Data Models to Integrate Data Sep. 02, DM Review, http://www.dmreview.com/article_sub_articleId_5675.html.
Talburt et al., Entity Information Lifecycle for Big Data: Master Data Management and Information Integration 2015, Elsevier, 255 pages.
U.S. Notice of Allowance on U.S. Appl. No. 16/418,725 dated Feb. 17, 2022.
U.S. Notice of Allowance on U.S. Appl. No. 16/418,725 dated Sep. 22, 2021.
U.S. Notice of Allowance on U.S. Appl. No. 16/420,059 dated Sep. 7, 2021.
U.S. Notice of Allowance on U.S. Appl. No. 16/695,082 dated Oct. 22, 2021.
U.S. Notice of Allowance on U.S. Appl. No. 16/695,082 dated Jul. 8, 2021.
U.S. Notice of Allowance on U.S. Appl. No. 16/700,498 dated Dec. 15, 2021.
U.S. Notice of Allowance on U.S. Appl. No. 16/700,498 dated Aug. 4, 2021.
U.S. Notice of Allowance on U.S. Appl. No. 16/700,510 dated Feb. 1, 2022.
U.S. Notice of Allowance on U.S. Appl. No. 17/129,213 dated Jan. 14, 2022.
U.S. Office Action dated Aug. 3, 2021 for U.S. Appl. No. 16/418,747.
U.S. Office Action on U.S. Appl. No. 16/421,280 dated Apr. 16, 2021.
U.S. Office Action on U.S. Appl. No. 16/700,510 dated Jul. 20, 2021.
U.S. Office Action on U.S. Appl. No. 16/725,705 dated Feb. 17, 2021.
U.S. Office Action on U.S. Appl. No. 16/792,676 dated Jun. 24, 2021.
U.S. Office Action on U.S. Appl. No. 17/102,379 dated Feb. 15, 2022.
U.S. Office Action on U.S. Appl. No. 17/129,213 dated Jul. 19, 2021.
Final Office Action on U.S. Appl. No. 16/421,280 dated Jul. 21, 2022.
Non-Final Office Action on U.S. Appl. No. 17/014,176 dated Aug. 15, 2022.
Notice of Allowance on U.S. Appl. No. 16/418,892 dated Jul. 20, 2022.
Notice of Allowance on U.S. Appl. No. 16/708,257 dated Jul. 15, 2022.
Notice of Allowance on U.S. Appl. No. 16/716,221 dated Jun. 30, 2022.
Notice of Allowance on U.S. Appl. No. 16/877,078 dated Aug. 24, 2022.
Notice of Allowance on U.S. Appl. No. 16/895,946 dated Aug. 24, 2022.
Notice of Allowance on U.S. Appl. No. 17/102,379 dated Jul. 13, 2022.
Notice of Allowance on U.S. Appl. No. 17/129,213 dated Jul. 5, 2022.

\* cited by examiner

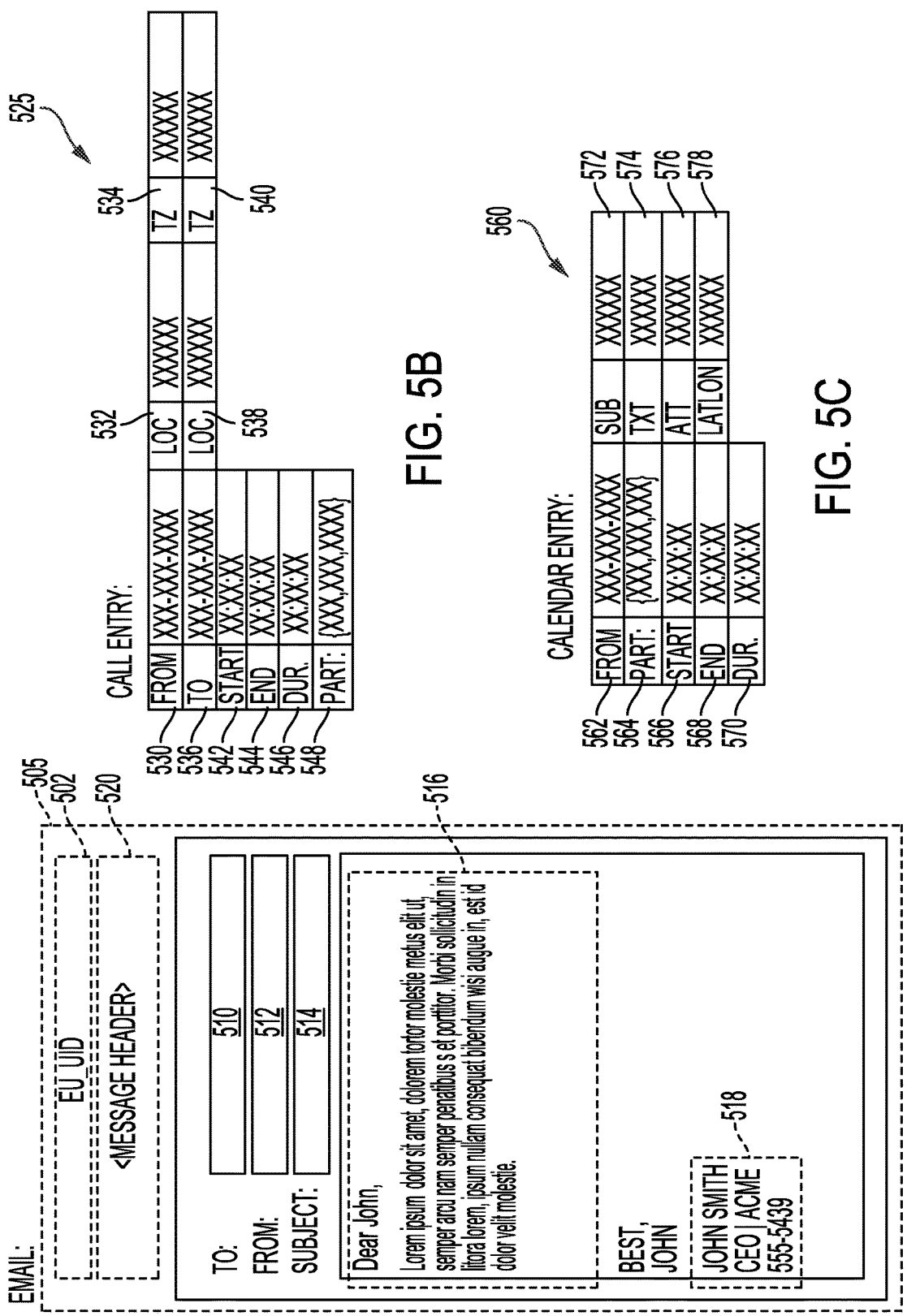

SCORECARD FOR MEASURING ENGAGEMENT

| | SALES ACTIVITY | POINTS |
|---|---|---|
| HIGH | IN-PERSON MEETING | 50 |
| | CONFERENCE CALL | 30 |
| MEDIUM | RECEIVED EMAIL | 10 |
| | SENT EMAIL | 5 |
| | COLD EMAIL | 2 |
| | BLAST EMAIL | 2 |
| LOW | CALL | 1 |

1300

| VOLUME |
|---|
| 2 |
| 5 |
| 87 |
| 165 |
| 5 |
| 2 |
| 5 |

1302

×

| NORMALIZED SENIORITY / TITLE | WEIGHT |
|---|---|
| CxO | 50 |
| SVP | 40 |
| VP | 30 |
| DIRECTOR | 20 |
| MANAGER | 10 |
| ADMIN, IC | 5 |

1304

×

| NORMALIZED DEPARTMENT | WEIGHT |
|---|---|
| SALES | 5 |
| MARKETING | 5 |
| IT / SECURITY | 3 |
| OPS | 2 |

1306

= ENGAGEMENT SCORE

CONFIGURABLE PER YOUR SALES MOTION

FIG. 13

Calendar Event
Block for Acme

Show Feed | Click to add topics:

Edit Layout | Help for this Page

Event Detail

Files [0] | Notes [0] | Attachments [0]

[Edit] [Delete] [Create Follow-Up Task] [Create Follow-Up Event] [Export Event]

▼ Calendar Details

| | | | |
|---|---|---|---|
| Subject | Block for ACME | Assigned To | John Smith |
| Location | | Type | Meeting |
| Meeting Status (People.ai) | Completed | Event Subtype | Event |
| Meeting Changed Time (People.ai) | 5/18/2018 3:02 PM | Show Time As | Busy |
| People.ai Activity Time | 5/18/2018 10:30 AM | Description | Created by People.ai |
| Date Sent | | People.ai Activity Type | Conference Call |
| Start | 5/18/2018 10:30 AM  Check Availability | Call Duration in Minutes (People.ai) | |
| End | 5/18/2018 2:30 PM | | |
| All-day Event | ☐ | | |

▼ Related To

| | | | |
|---|---|---|---|
| Name | Jane Doe | Related To | ACME |

▼ People.ai Info

| | | | |
|---|---|---|---|
| People.ai ExternalId | 44s9htv6c2pn9kolkpnaujbo5s | Participants | jsmith@acme.com |
| | | Email | jane@example.com |

▼ Other Information

| | | | |
|---|---|---|---|
| Human Activity | #Error! | Needs Setup | ☑ |
| Created By People.ai | ☑ | | |

▼ System Information

| | | | |
|---|---|---|---|
| Created By | Sam Smith | Last Modified By | Sam Smith |

Reminder

Reminder ☐

FIG. 14

SYSTEMS AND METHODS FOR DETERMINING THE SHAREABILITY OF VALUES OF NODE PROFILES

CROSS-REFERENCE TO RELATED APPLICATIONS

The present application is a continuation of U.S. application Ser. No. 16/399,679, titled "SYSTEMS AND METHODS FOR DETERMINING THE SHAREABILITY OF VALUES OF NODE PROFILES" filed on Apr. 30, 2019, and now issued as U.S. Pat. No. 10,489,387, which claims the benefit of and priority to U.S. Provisional Patent Application 62/747,452, filed Oct. 18, 2018, U.S. Provisional Patent Application 62/725,999, filed Aug. 31, 2018, and U.S. Provisional Patent Application 62/676,187, filed May 24, 2018, each of which are incorporated herein by reference for all purposes.

BACKGROUND

An organization may attempt to manage or maintain a system of record associated with electronic communications at the organization. The system of record can include information such as contact information, logs, and other data associated with the electronic activities. Data regarding the electronic communications can be transmitted between computing devices associated with one or more organizations using one or more transmission protocols, channels, or formats, and can contain various types of information. For example, the electronic communication can include information about a sender of the electronic communication, a recipient of the electronic communication, and content of the electronic communication. The information regarding the electronic communication can be input into a record being managed or maintained by the organization. However, due to the large volume of heterogeneous electronic communications transmitted between devices and the challenges of manually entering data, inputting the information regarding each electronic communication into a system of record can be challenging, time consuming, and error prone.

SUMMARY

One aspect of the present disclosure relates to a method for determining the shareability of values of node profiles. The method may include accessing, by one or more processors, at least one of i) a plurality of electronic activities transmitted or received via electronic accounts associated with one or more data source providers or ii) a plurality of record objects of one or more systems of record associated with the one or more data source providers. The method may include maintaining, by the one or more processors, a plurality of node profiles, each node profile of the plurality of node profiles including one or more field-value pairs, each field-value pair including a value determined from data of one or more of the plurality of electronic activities or the plurality of record objects. The method may include identifying, by the one or more processors, for a first node profile, a value of a field corresponding to a predetermined type of field that is included in one or more electronic activities or record objects accessed from a set of first data source providers including fewer than a predetermined threshold number of data source providers. The method may include generating, by the one or more processors, a restriction tag used by the one or more processors to restrict populating other node profiles of the plurality of node profiles or systems of record with the value of the node field-value pair of the first node profile. The method may include restricting, by the one or more processors, provision of the value to at least one second system of record of a second data source provider different from any data source provider of the first set of data source providers.

In some implementations, generating the restriction tag may include storing, in one or more data structures, an association between the restriction tag and at least one of the first node profile or the node field-value pair of the first node profile.

In some implementations the predetermined type of the field corresponds to a contact identifier field.

In some implementations, the value of the node field-value pair of the first node profile comprises a value data structure storing at least one entry comprising an identifier identifying an electronic activity or record object that includes the value and a source of the electronic activity or the record object identified by the identifier.

In some implementations, the plurality of electronic activities comprises a plurality of first electronic activities, and wherein generating the restriction tag comprises storing, in one or more data structures, an association between the restriction tag and at least one of the first node profile or the node field-value pair of the first node profile. The method may further include accessing, by the one or more processors, a second electronic activity and extracting, by the one or more processors, an electronic activity field-value pair from the second electronic activity matching the node field-value pair of the first node profile. The method may further include adding, by the one or more processors, a new entry to the value data structure of the value of the node field-value pair, the new entry identifying the second electronic activity and a second source of the second electronic activity, wherein the second source is different from the first source. The method may further include updating, by the one or more processors, the one or more data structures to remove the association between the restriction tag and at least one of the first node profile or the node field-value pair of the first node profile responsive to determining that the second source is different from the first source.

In some implementations, the method may include communicating, by the one or more processors, the value of the node field-value pair to at least one second system of record having a record object that is matched to the node profile including the node field-value pair.

In some implementations, the method may include matching, by the one or more processors, the first node profile to a record object by comparing one or more node field-value pairs of the first node profile to one or more corresponding object field-value pairs of the record object.

In some implementations, the method may include receiving, by the one or more processors, a request to restrict access to a second node field-value pair of the first node profile. The method may include generating, by the one or more processors, a second restriction tag to restrict populating other node profiles of the plurality of node profiles or systems of record with the second value of the second node field-value pair. The method may include storing, by the one or more processors, in one or more data structures, an association between the second restriction tag and the second node field-value pair.

In some implementations, the method may include receiving, by the one or more processors, a second electronic activity of the plurality of electronic activities including one or more activity field-value pairs and matching, by the one or more processors, the second electronic activity to a second node profile. The method may include updating, by the one or more processors, the second node profile to generate a second node field-value pair responsive to determining that the activity field-value pair is not included in the second node profile and determining, by the one or more processors, that the field is of the predetermined type of field. The method may include generating, by the one or more processors, a second restriction tag to restrict populating other node profiles of the plurality of node profiles or systems of record with the value of the second node field-value pair.

Another aspect of the present disclosure relates to a system for determining the shareability of values of node profiles. The system may include one or more hardware processors configured by machine-readable instructions. The one or more hardware processors may be configured to access at least one of i) a plurality of electronic activities transmitted or received via electronic accounts associated with one or more data source providers or ii) a plurality of record objects of one or more systems of record associated with the one or more data source providers and maintain a plurality of node profiles, each node profile of the plurality of node profiles including one or more field-value pairs, each field-value pair including a value determined from data of one or more of the plurality of electronic activities or the plurality of record objects. The one or more hardware processors may be configured to identify, for a first node profile, a value of a field corresponding to a predetermined type of field that is included in one or more electronic activities or record objects accessed from a set of first data source providers including fewer than a predetermined threshold number of data source providers and generate a restriction tag used by the one or more processors to restrict populating other node profiles of the plurality of node profiles or systems of record with the value of the node field-value pair of the first node profile. The one or more hardware processors may be configured to restrict provision of the value to at least one second system of record of a second data source provider different from any data source provider of the first set of data source providers.

In some implementations of the system, the one or more processors may be configured to generate the restriction tag by storing, in one or more data structures, an association between the restriction tag and at least one of the first node profile or the node field-value pair of the first node profile.

In some implementations of the system, the predetermined type of the field may correspond to a contact identifier field.

In some implementations of the system, the value of the node field-value pair of the first node profile may include a value data structure storing at least one entry comprising an identifier identifying an electronic activity or record object that includes the value and a source of the electronic activity or the record object identified by the identifier.

In some implementations of the system, the plurality of electronic activities may include a plurality of first electronic activities. The one or more processors may further be configured to generate the restriction tag by storing, in one or more data structures, an association between the restriction tag and at least one of the first node profile or the node field-value pair of the first node profile and access a second electronic activity. The one or more processors may be configured to extract an electronic activity field-value pair from the second electronic activity matching the node field-value pair of the first node profile. The one or more processors may further be configured to add a new entry to the value data structure of the value of the node field-value pair, the new entry identifying the second electronic activity and a second source of the second electronic activity. The second source is different from the first source and the one or more processors may update the one or more data structures to remove the association between the restriction tag and at least one of the first node profile or the node field-value pair of the first node profile responsive to determining that the second source is different from the first source.

In some implementations of the system, the one or more processors may further be configured to communicate the value of the node field-value pair to at least one second system of record having a record object that is matched to the node profile including the node field-value pair.

In some implementations of the system, the one or more processors may further be configured to match the first node profile to a record object by comparing one or more node field-value pairs of the first node profile to one or more corresponding object field-value pairs of the record object.

In some implementations of the system, the one or more processors further be configured to receive a request to restrict access to a second node field-value pair of the first node profile and generate a second restriction tag to restrict populating other node profiles of the plurality of node profiles or systems of record with the second value of the second node field-value pair. The one or more processors may further be configured to store, in one or more data structures, an association between the second restriction tag and the second node field-value pair.

In some implementations of the system, the one or more processors may further be configured to receive a second electronic activity of the plurality of electronic activities including one or more activity field-value pairs and match the second electronic activity to a second node profile. The one or more processors may further be configured to update the second node profile to generate a second node field-value pair responsive to determining that the activity field-value pair is not included in the second node profile, determine that the field is of the predetermined type of field, and generate a second restriction tag to restrict populating other node profiles of the plurality of node profiles or systems of record with the value of the second node field-value pair.

Yet another aspect of the present disclosure relates to a non-transient computer-readable storage medium having instructions embodied thereon, the instructions being executable by one or more processors to perform a method for determining the shareability of values of node profiles. The method may include accessing at least one of i) a plurality of electronic activities transmitted or received via electronic accounts associated with one or more data source providers or ii) a plurality of record objects of one or more systems of record associated with the one or more data source providers and maintaining a plurality of node profiles, each node profile of the plurality of node profiles including one or more field-value pairs, each field-value pair including a value determined from data of one or more of the plurality of electronic activities or the plurality of record objects. The method may include identifying, for a first node profile, a value of a field corresponding to a predetermined type of field that is included in one or more electronic activities or record objects accessed from a set of first data source providers including fewer than a predetermined threshold number of data source providers and generating a restriction tag used by the one or more processors to restrict populating other node profiles of the plurality of node profiles or systems of record with the value of the node field-value pair of the first node profile. The method may include restricting provision of the value to at least one second system of record of a second data source provider different from any data source provider of the first set of data source providers.

In some implementations, the method may further include generating the restriction tag by storing, in one or more data structures, an association between the restriction tag and at least one of the first node profile or the node field-value pair of the first node profile.

BRIEF DESCRIPTIONS OF THE DRAWINGS

FIGS. 5A-5C illustrate various types of example electronic activities according to embodiments of the present disclosure;

FIG. 13 illustrates an example calculation for calculating the engagement score of an opportunity record object according to embodiments of the present disclosure;

FIG. 14 illustrates an example user interface identifying various pieces of information that can be extracted from an electronic activity according to embodiments of the present disclosure;

DETAILED DESCRIPTION

Figure 1:
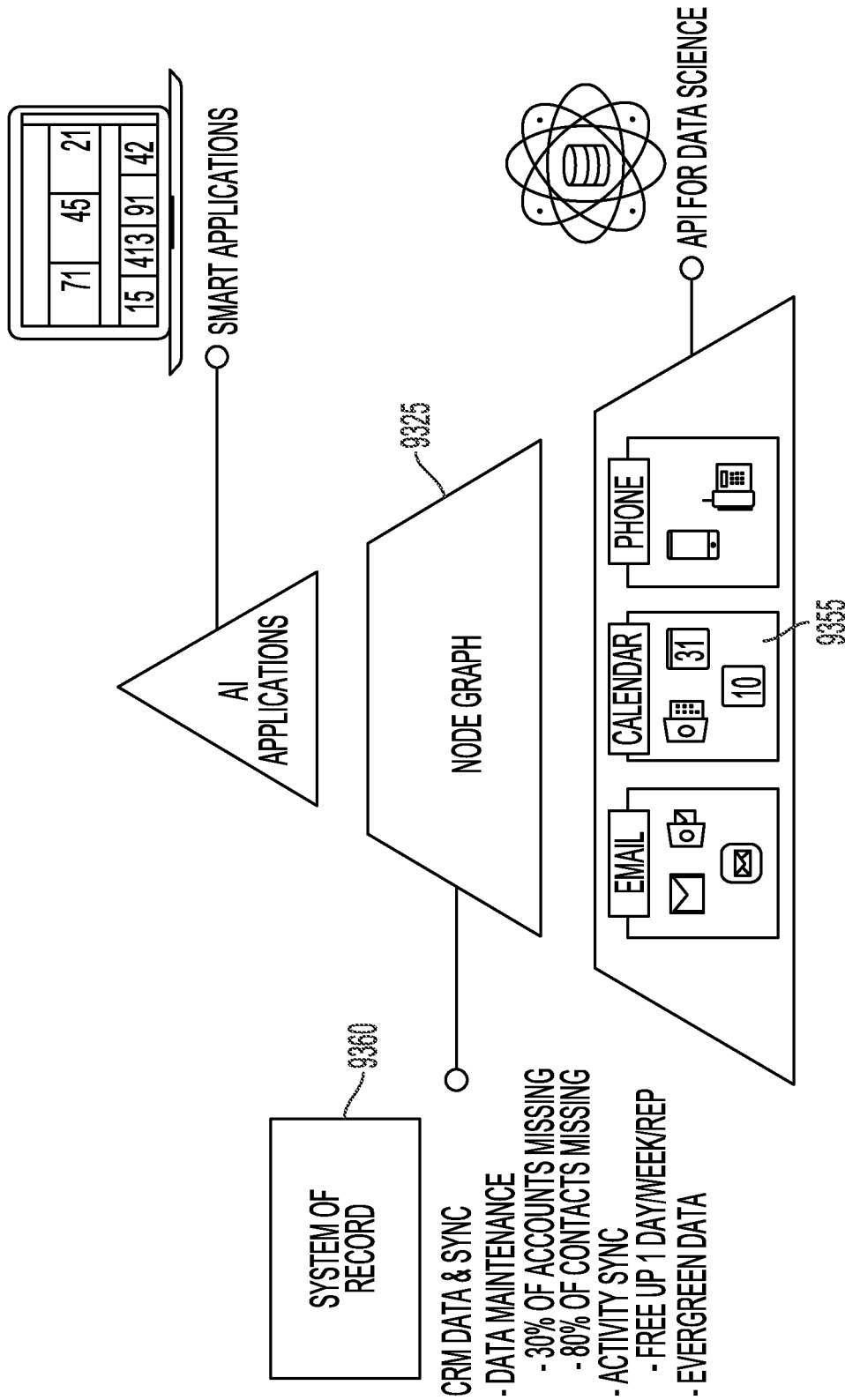
FIG. 1 illustrates a tiered system architecture for aggregating electronic activities and synchronizing the electronic activities to one or more systems of record according to embodiments of the present disclosure.

The present disclosure relates to systems and methods for constructing a node graph based on electronic activity. The node graph can include a plurality of nodes and a plurality of edges between the nodes indicating activity or relationships that are derived from a plurality of data sources that can include one or more types of electronic activities. The plurality of data sources can include email or messaging servers, phone servers, servers storing calendar information, meeting information, among others. The plurality of data sources further includes systems of record, such as customer relationship management systems, enterprise resource planning systems, document management systems, applicant tracking systems or other source of data that may maintain electronic activities, activities or records.

The present disclosure further relates to systems and methods for using the node graph to manage, maintain, improve, or otherwise modify one or more systems of record by linking and or synchronizing electronic activities to one or more record objects of the systems of record. In particular, the systems described herein can be configured to automatically synchronize real-time or near real-time electronic activity to one or more objects of systems of record. The systems can further extract business process information from the systems of record and in combination with the node graph, use the extracted business process information to improve business processes and to provide data driven solutions to improve such business processes.

The present disclosure relates to systems and methods for constructing a node graph based on electronic activity. The node graph can include a plurality of nodes and a plurality of edges between the nodes indicating activity or relationships that are derived from a plurality of data sources that can include one or more types of electronic activities. The present disclosure further relates to systems and methods for using the node graph to manage, maintain, improve, or otherwise modify one or more systems of record by linking and or synchronizing electronic activities to one or more record objects of the systems of record. In particular, the systems described herein can be configured to automatically synchronize real-time or near real-time electronic activity to one or more objects of systems of record. The systems can further extract business process information from the systems of record and in combination with the node graph, use the extracted business process information to improve business processes and to provide data driven solutions to improve such business processes.

At least one aspect of the present disclosure is directed to systems and methods for maintaining an electronic activity derived member node network. For example, a node profile for a member node in a node graph can include information such as first name, last name, company, and job title. However, it may be challenging to accurately and efficiently populate fields in a node profile due to large number of member nodes. Furthermore, permitting self-population of node profiles by member nodes can result in erroneous data values, improper data values, or otherwise undesired data values due in part to human bias. Having erroneous data values in a node profile can cause downstream components or functions that perform processing using the node profiles to malfunction or generate faulty outputs.

Thus, systems and methods of the present technical solution can generate an electronic activity derived member node network that includes node profiles for a member node that is generated based on electronic activity. By generating the member node profile for the member node using electronic activity and a statistical analysis, the system can generate the profile with data fields and values that pass a verification process or statistical analysis using electronic activities.

Referring briefly to FIG. 1, FIG. 1 illustrates a tiered system architecture for aggregating electronic activities and synchronizing the electronic activities to one or more systems of record according to embodiments of the present disclosure. As shown in FIG. 1, at the first tier, the system, such as the data processing system 9300 (shown in FIG. 3), aggregates electronic activities from one or more data source providers. At the second tier, the system extracts information from the aggregated electronic activities and one or more systems of record of one or more data source providers to construct and maintain a node graph including the plurality of nodes and edges indicating the connections between the nodes. At the third tier, the system utilizes the electronic activities, the systems of record, and the node graph to provide data driven insights to improve one or more business processes of the data source providers and to assist various data source providers in extracting data driven insights.

Figure 2:
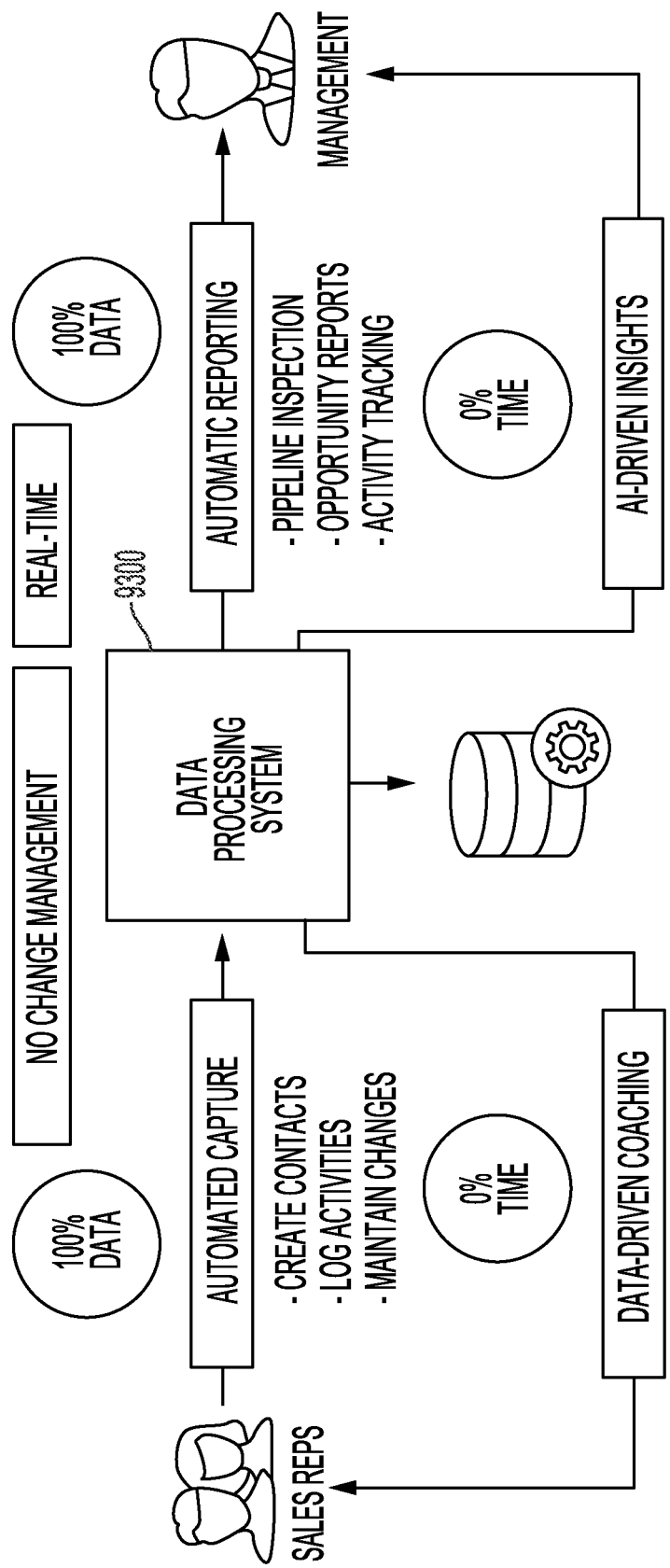
FIG. 2 illustrates a process flow for aggregating electronic activities and synchronizing the electronic activities to one or more systems of record according to embodiments of the present disclosure.

FIG. 2 illustrates a process flow for aggregating electronic activities and synchronizing the electronic activities to one or more systems of record according to embodiments of the present disclosure. The system can be configured to receive and aggregate electronic activities identifying one or more nodes. The system can parse the electronic activities and extract information from the electronic activities to generate node profiles for each node, log activities and maintain changes made to each of the node profiles maintained by the system. The system can further be configured to extract information from the electronic activities of the nodes and determine insights or metrics that can be shared with one or more other nodes and the users of the system. The system can be further configured to synchronize the electronic activities to objects of one or more systems of record.

In a particular use case, sales representatives of an organization may be involved in electronic activities, such as emails, phone calls, meetings, among others that can be tracked and captured by the system via ingestion from one or more data sources of the organization or other organizations. The system can extract information from the electronic activities that may be associated with deals or opportunities the sales representatives are working on. The system can use the information from these electronic activities to generate reports for managers of the organization. These reports are generated based on data derived from electronic activity without requiring the sales representatives to perform any additional activities. Furthermore, the managers also do not need to spend time generating these reports as the system can automatically generate these reports. Furthermore, the system can identify trends and behaviors that may be determined through machine learning techniques otherwise not tracked by the managers, thereby providing reports that may otherwise not be generated by the managers. Further, sales representatives may also no longer be required to spend time synchronizing electronic activities to one or more systems of record. Rather, the system can be configured to automatically synchronize the electronic activities to the appropriate objects of the one or more systems of record. The system can further receive information from the one or more systems and records to determine the results associated with the sales representative's efforts and perform analytics to generate recommendations to assist the sales representatives achieve their goals and eventually improve their performance as sales representatives as well as provide company management with recommendations about improving the performance of the overall business.

Figure 3:
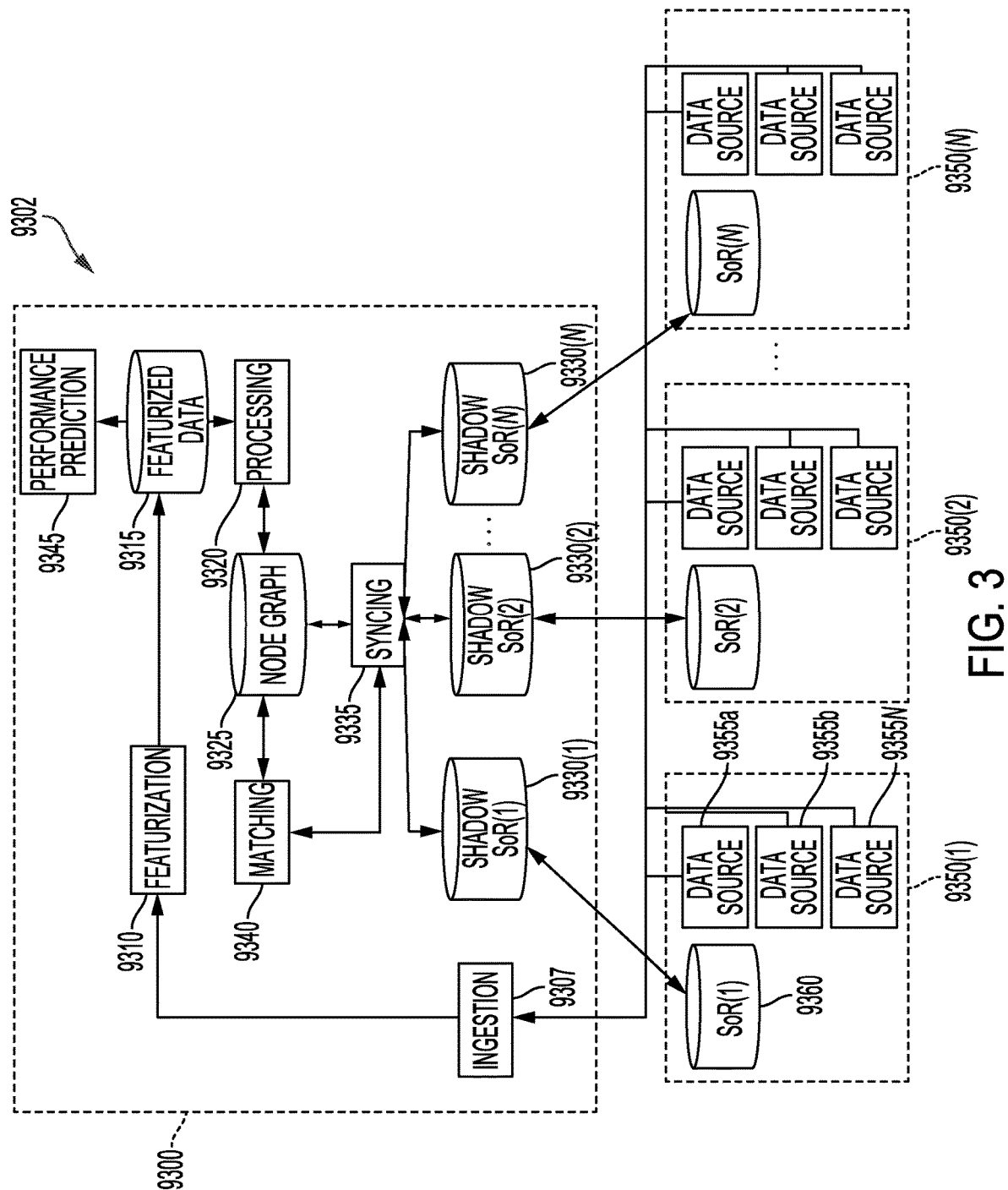
FIG. 3 illustrates a processing flow diagram for aggregating electronic activities and synchronizing the electronic activities to one or more systems of record according to embodiments of the present disclosure.

Referring now to FIG. 3, FIG. 3 illustrates a processing flow diagram for aggregating electronic activities, processing the electronic activities to update node profiles of people and to construct a node graph, and synchronizing the electronic activities to one or more systems of record. The process flow 9302 can be executed by a data processing system 9300 that can receive electronic activity and other data from a plurality of data source providers 9350(1)-9350(N). Each data source provider 9350 can include one or more data sources 9355*a-n* and/or one or more system of record instances 9360. Examples of data sources can include electronic mail servers, telephone log servers, contact servers, other types of servers and end-user applications that may receive or maintain electronic activity data or profile data relating to one or more nodes. The data processing system 9300 can ingest electronic activity (9307). The data processing system 9300 can featurize (9310) and tag the ingested electronic activity (9307) and store the featurized data in a featurized data store (9315). The data processing system 9300 can process the featurized data (9320) to generate a node graph 9325 including a plurality of node profiles. The data processing system 9300 can further maintain a plurality of system of record instances 9330(1)-9330(N) corresponding to system of record instances of the data source providers 9350. The data processing system 9300 can utilize the system of record instances to augment the node profiles of the node graph by synchronizing data stored in the system of record instances maintained by the data processing system (9300). The data processing system 9300 can further match (9340) the ingested electronic activities to one or more record objects maintained in one or more systems of record instances of the data source provider from which the electronic activity was received. The data processing system 9300 can further synchronize the electronic activity matched to record objects to update the system of record instances of the data source provider (9350). Furthermore, the data processing system 9300 can use the featurized data to provide performance predictions (9345) and generate other business process related outputs, insights and recommendations.

As described herein, electronic activity can include any type of electronic communication that can be stored or logged. Examples of electronic activity can include electronic mail messages, telephone calls, calendar invitations, social media messages, mobile application messages, instant messages, cellular messages such as SMS, MMS, among others, as well as electronic records of any other activity, such as digital content, such as files, photographs, screenshots, browser history, internet activity, shared documents, among others.

The electronic activity can be stored on one or more data source servers. The electronic activity can be owned or managed by one or more data source providers, such as companies that utilize the services of the data processing system 9300. The electronic activity can be associated with or otherwise maintained, stored or aggregated by an electronic activity source, such as Google G Suite, Microsoft Office365, Microsoft Exchange, among others. In some embodiments, the electronic activity can be real-time (or near real-time) electronic activity, asynchronous electronic activity (such as emails, text messages, among others) or synchronous electronic activity (such as meetings, phone calls, video calls), or other activity in which two parties are communicating simultaneously.

1. Systems and Methods for Generating a Node Graph Using Electronic Activities

As described above, the present disclosure relates to systems and methods for constructing a node graph based on electronic activity. The node graph can include a plurality of nodes and a plurality of edges between the nodes indicating activity or relationships that are derived from a plurality of data sources that can include one or more types of electronic activities. The plurality of data sources can further include systems of record, such as customer relationship management systems, enterprise resource planning systems, document management systems, applicant tracking systems or other source of data that may maintain electronic activities, activities or records.

Figure 4:
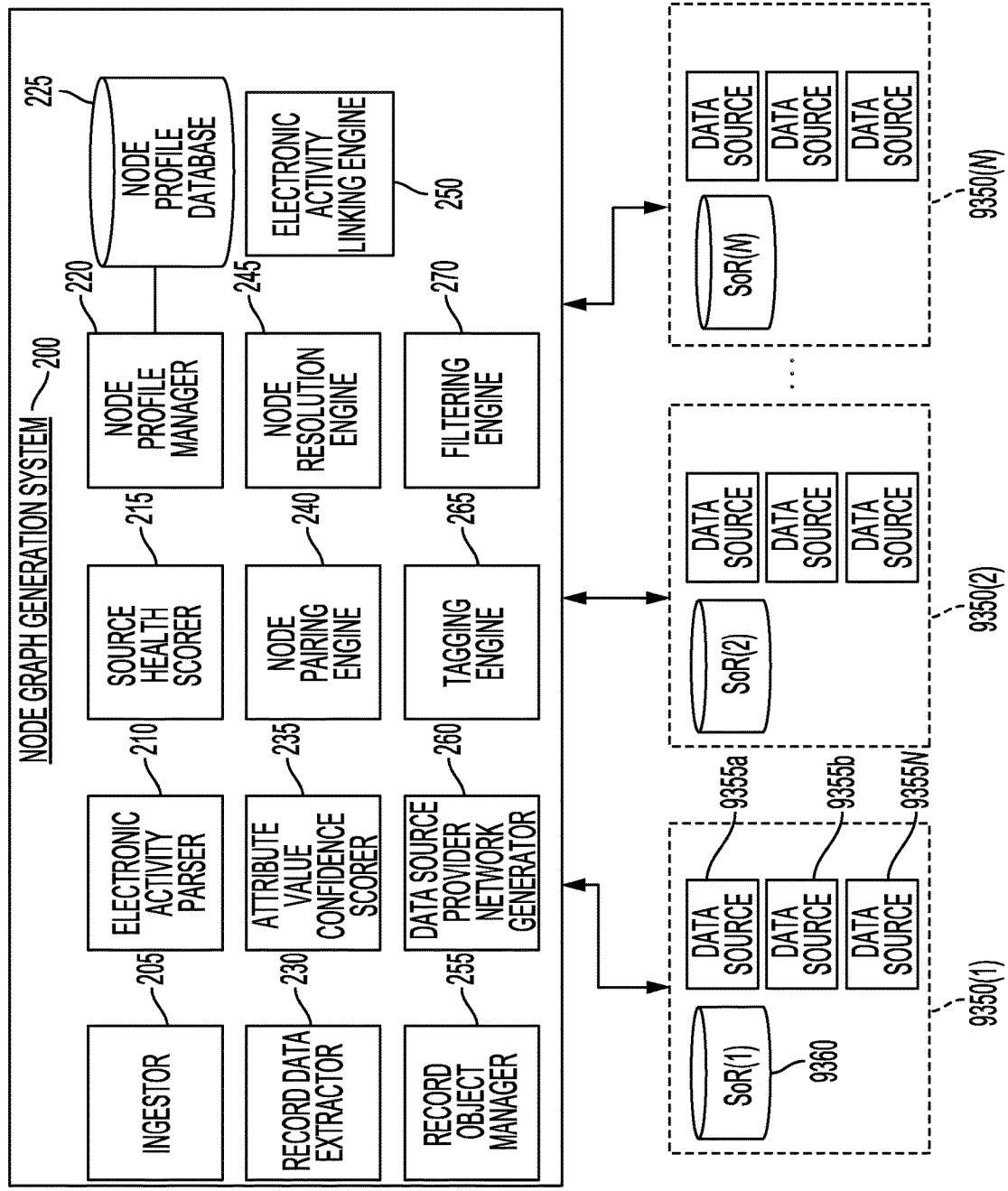
FIG. 4 illustrates a node graph generation system for constructing a node graph based on electronic activity according to embodiments of the present disclosure.

Referring now to FIG. 4, FIG. 4 illustrates a node graph generation system 200 for constructing a node graph based on electronic activity. The node graph generation system 200 can be, include or be part of the data processing system 9300 described in FIG. 3. The node graph generation system 200 can include an electronic activity ingestor 205, an electronic activity parser 210, a source health scorer 215, a node profile manager 220, a node profile database 225, a record data extractor 230, an attribute value confidence scorer 235, a node pairing engine 240, a node resolution engine 245, an electronic activity linking engine 250, a record object manager 255, a data source provider network generator 260, a tagging engine 265 and a filtering engine 270. The node graph generation system 200 can receive electronic activity and systems of record data from one or more data source providers 9350. The data source providers can provide electronic activity or data stored or maintained on a plurality of data sources 355 and one or more systems of record 360.

Referring now to FIG. 5A, FIG. 5A illustrates an example electronic activity or message. The electronic message 505 can identify one or more recipients 510, one or more senders 512, a subject line 514, an email body 516, an email signature 518 and a message header 520. The message header can include additional information relating to the transmission and receipt of the email message, including a time at which the email was sent, a message identifier identifying a message, an IP address associated with the message, a location associated with the message, a time zone associated with the sender, a time at which the message was transmitted, received, and first accessed, among others. The electronic message 505 can include additional data in the electronic message 505 or in the header or metadata of the electronic message 505.

Referring now to FIG. 5B, FIG. 5B illustrates an example call entry representing a phone call or other synchronous communication is shown. The call entry 525 can identify a caller 530, a location 532 of the caller, a time zone 534 of the caller, a receiver 536, a location 538 of the receiver, a time zone 540 of the receiver, a start date and time 542, an end date and time 544, a duration 546 and a list of participants 548. In some embodiments, the times at which each participant joined and left the call can be included. Furthermore, the locations from which each of the callers called can be determined based on determining if the user called from a landline, cell phone, or voice over IP call, among others. The call entry 525 can also include fields for phone number prefixes (e.g., 800, 866, and 877), phone number extensions, and caller ID information.

Referring now to FIG. 5C, FIG. 5C illustrates an example calendar entry 560. The calendar entry 560 can identify a sender 562, 564564564*a* list of participants 564, a start date and time 566 location 532 of the caller, an end date and time 568, a duration 570 of the calendar entry, a subject 572 of the calendar entry, a body 574 of the calendar entry, one or more attachments 576 included in the calendar entry and a location of event 578, described by the calendar entry 560. The calendar entry can include additional data in the calendar entry or in the header or metadata of the calendar entry 560.

In some embodiments, the electronic activities are exchanged between or otherwise involve nodes. In some embodiments, nodes can be representative of people or companies. In some embodiments, nodes can be member nodes or group nodes. A member node may refer to a node representative of a person that is part of a company or other organizational entity. A group node may refer to a node that is representative of the company or other organizational entity and is linked to multiple member nodes. The electronic activity may be exchanged between member nodes in which case the system is configured to identify the member nodes and the one or more group nodes associated with each of the member nodes. Each node can correspond to a node profile. The node profile can include one or more field-value pairs that represent the node.

The data processing system 9300 or the node graph generation system 200 can be configured to assign each electronic activity a unique electronic activity identifier. This unique electronic activity identifier can be used to uniquely identify the electronic activity. Further, each electronic activity can be associated with a source that provides the electronic activity. In some embodiments, the data source can be the company or entity that authorizes the system 9300 or 200 to receive the electronic activity. In some embodiments, the source can correspond to a system of record, an electronic activity server that stores or manages electronic activity, or any other server that stores or manages electronic activity related to a company or entity. As will be described herein, the quality, health or hygiene of the source of the electronic activity may affect the role the electronic activity plays in generating the node graph. The node graph generation system 200 can be configured to determine a time at which the electronic activity occurred. In some embodiments, the time may be based on when the electronic activity was transmitted, received or recorded. As will be described herein, the time associated with the electronic activity can also affect the role the electronic activity plays in generating the node graph.

Referring again to FIG. 4, additional details relating to the functions performed by various components or modules of the node graph generation system 200 are provided herein.

A. Electronic Activity Ingestion

The electronic activity ingestor 205 can be any script, file, program, application, set of instructions, or computer-executable code that is configured to enable a computing device on which the electronic activity ingestor 205 is executed to perform one or more functions of the electronic activity ingestor 205 described herein. The electronic activity ingestor 205 can be configured to ingest electronic activities from the plurality of data source providers. The electronic activities may be received or ingested in real-time or asynchronously as electronic activities are generated, transmitted or stored by the one or more data source providers.

The node graph generation system 200 can ingest electronic activity from a plurality of different source providers. In some embodiments, the node graph generation system 200 can be configured to manage electronic activities and one or more systems of record for one or more enterprises, organizations, companies, businesses, institutions or any other group associated with a plurality of electronic activity accounts. The node graph generation system 200 can ingest electronic activities from one or more servers that hosts, processes, stores or manages electronic activities. In some embodiments, the one or more servers can be electronic mail or messaging servers. The node graph generation system 200 can ingest all or a portion of the electronic activities stored or managed by the one or more servers. In some embodiments, the node graph generation system 200 can ingest the electronic activities stored or managed by the one or more servers once or repeatedly on a periodic basis, such as daily, weekly, monthly or any other frequency.

The node graph generation system 200 can further ingest other data that may be used to generate or update node profiles of one or more nodes maintained by the node graph generation system 200. The other data may also be stored by the one or more servers that hosts, processes, stores or manages electronic activities. This data can include contact data, such as Names, addresses, phone numbers, Company information, titles, among others.

The node graph generation system 200 can further ingest data from one or more systems of record. The systems of record can be hosted, processed, stored or managed by one or more servers of the systems of record. The systems of record can be linked or otherwise associated with the one or more servers that host, process, store or manage electronic activities. In some embodiments, both the servers associated with the electronic activities and the servers maintaining the systems of record may belong to the same organization or company.

The electronic activity ingestor 205 can receive an electronic activity and can assign each electronic activity, an electronic activity unique identifier 502 to enable the node graph generation system 200 to uniquely identify each electronic activity. In some embodiments, the electronic activity unique identifier 502 can be the same identifier as a unique electronic activity identifier included in the electronic activity. In some embodiments, the unique electronic activity is included in the electronic activity by the source of the electronic activity or any other system.

The electronic activity ingestor 205 can be configured to format the electronic activity in a manner that allows the electronic activity to be parsed or processed. In some embodiments, the electronic activity ingestor 205 can identify one or more fields of the electronic activity and apply one or more normalization techniques to normalize the values included in the one or more fields. In some embodiments, the electronic activity ingestor 205 can format the values of the fields to allow content filters to apply one or more policies to identify one or more regex patterns for filtering the content, as described herein.

It should be appreciated that the electronic activity ingestor 205 can be configured to ingest electronic activities in a real-time or near real-time basis for accounts of one or more enterprises, organizations, companies, businesses, institutions or any other group associated with a plurality of electronic activity account with which the node graph generation system 200 has integrated. When an enterprise client subscribes to a service provided by the node graph generation system 200, the enterprise client provides access to electronic activities maintained by the enterprise client by going through an onboarding process. That onboarding process allows the system 200 to access electronic activities owned or maintained by the enterprise client from one or more electronic activities sources. This can include the enterprise client's mail servers, one or more systems of record, one or more phone services or servers of the enterprise client, among other sources of electronic activity. The electronic activities ingested during an onboarding process may include electronic activities that were generated in the past, perhaps many years ago, that were stored on the electronic activities' sources. In addition, in some embodiments, the system 200 can be configured to ingest and re-ingest the same electronic activities from one or more electronic activities sources on a periodic basis, including daily, weekly, monthly, or any reasonable frequency.

The electronic activity ingestor 205 can be configured to receive access to each of the electronic activities from each of these sources of electronic activity including the systems of record of the enterprise client. The electronic activity ingestor 205 can establish one or more listeners, or other mechanisms to receive electronic activities as they are received by the sources of the electronic activities enabling real-time or near real-time integration.

As more and more data is ingested and processed as described herein, the node graph generated by the node graph generation system 200 as well as node profiles of nodes can get richer and richer with more information. The additional information, as will be described herein, can be used to populate missing fields or add new values to existing fields, reinforce field values that have low confidence scores and further increase the confidence score of field values, adjust confidence scores of certain data points, and identify patterns or make deductions based on the values of various fields of node profiles of nodes included in the graph.

As more data is ingested, the node graph generation system 200 can use existing node graph or node profile data to predict missing or ambiguous values in electronic activities such that the more node profiles and data included in the node graph, the better the predictions of the node graph generation system 200, thereby improving the processing of the ingested electronic activities and thereby improving the quality of each node profile of the node graph, which eventually will improve the quality of the overall node graph of the node graph generation system 200.

The node graph generation system 200 can be configured to periodically regenerate or recalculate the node graph. The node graph generation system 200 can do so responsive to additional data being ingested by the system 200. When new electronic activities or data is ingested by the node graph generation system 200, the system 200 can be configured to recalculate the node graph as the confidence scores (as will be described later) can change based on the information included in the new electronic activities. In some embodiments, the ingestor may re-ingest previously ingested data from the one or more electronic activity sources or simply ingest the new electronic activity not previously ingested by the system 200.

B. Electronic Activity Parsing

The electronic activity parser 210 can be any script, file, program, application, set of instructions, or computer-executable code, which is configured to enable a computing device on which the electronic activity parser 210 is executed to perform one or more functions of the electronic activity parser 210 described herein.

The electronic activity parser 210 can be configured to parse the electronic activity to identify one or more values of fields to be used in generating node profiles of one or more nodes and associate the electronic activities between nodes for use in determining the connection and connection strength between nodes. The node profiles can include fields having name-value pairs or field-value pairs. The electronic activity parser 210 can be configured to parse the electronic activity to identify values for as many fields of the node profiles of the nodes with which the electronic activity is associated.

The electronic activity parser 210 can be configured to first identify each of the nodes associated with the electronic activity. In some embodiments, the electronic activity parser 210 can parse the metadata of the electronic activity to identify the nodes. The metadata of the electronic activity can include a To field, a From field, a Subject field, a Body field, a signature within the body and any other information included in the electronic activity header that can be used to identify one or more values of one or more fields of any node profile of nodes associated with the electronic activity. In some embodiments, non-email electronic activity can include meetings or phone calls. The metadata of such non-email electronic activity can include a duration of the meeting or call, one or more participants of the meeting or call, a location of the meeting, locations associated with the initiator and receiver of the phone call, in addition to other information that may be extracted from the metadata of such electronic activity. In some embodiments, nodes are associated with the electronic activity if the node is a sender of the electronic activity, a recipient of the electronic activity, a participant of the electronic node, or identified in the contents of the electronic activity. The node can be identified in the contents of the electronic activity or can be inferred based on information maintained by the node graph generation system 200 and based on the connections of the node and one or more of the sender or recipients of the electronic activity.

The electronic activity parser 210 can be configured to parse the electronic activity to identify attributes, values, or characteristics of the electronic activity. In some embodiments, the electronic activity parser 210 can apply natural language processing techniques to the electronic activity to identify regex patterns, words or phrases, or other types of content that may be used for sentiment analysis, filtering, tagging, classifying, deduplication, effort estimation, and other functions performed by the data processing system 9300.

In some embodiments, the electronic activity parser 210 can be configured to parse an electronic activity to identify values of fields or attributes of one or more nodes. For instance, when an electronic mail message is ingested into the node graph generation system 200, the electronic activity parser 210 can identify a FROM field of the electronic mail message. The FROM field can include a name and an email address. The name can be in the form of a first name and a last name or a last name, first name. The parser can extract the name in the FROM field and the email address in the FROM field to determine whether a node is associated with the sender of the electronic mail message.

C. Signature Parsing

In some embodiments, the electronic activity parser 210 can be configured to identify a signature in a body of an electronic message. The parser 210 can identify the signature by utilizing a signature detection policy that includes logic for identifying patterns of signatures. In some embodiments, a signature can include one or more values of attributes, such as values for attributes including but not limited to a name, a phone number, a company name, a company division, a company address, a job title, one or more social network handles or links, an email address, among others. By parsing the signature, the electronic activity parser 210 can identify each of the values corresponding to the various fields of a node profile associated with the sender of the electronic activity. In addition to information included in the signature, the electronic activity parser can utilize information from the header of the electronic activity (i.e. first and last name) to identify where the signature is located by finding the same first name, last name and email address within a predetermined proximity or distance of each other in a region of the body, for instance, the bottom of the body. Stated in another way, the present disclosure describes methods and systems for utilizing header data of an electronic activity, which in certain embodiments, is verified to make it easier to locate a signature of an email, which may be buried under, around or with other textual content. In some embodiments, one or more of a first name, a last name and an email address extracted from the header of the electronic activity is used to identify text strings that match the extracted first name, last name and the email address. Responsive to determining that text strings matching the first name, last name and the email address are within a predetermined distance of one another, the parser 210 can identify the text strings are portions of the signature of the electronic activity. The information parsed from the signature can be used to determine a confidence score of a value of a field as further described herein with respect to the attribute value confidence scorer 235. The electronic activity parser 210 can also use signature parsing for node selection and in the identification of the node, to which the activity, containing the signature can be associated.

D. Node Profiles

The node profile manager 220 can be any script, file, program, application, set of instructions, or computer-executable code that is configured to enable a computing device on which the node profile manager 220 is executed to perform one or more functions of the node profile manager 220 described herein. The node profile manager is configured to manage node profiles associated with each node. Node profiles of nodes can be used to construct a node graph that includes nodes linked to one another based on relationships between the nodes that can be determined from electronic activities parsed and processed by the node graph generation system 200 as well as other information that may be received from one or more systems of record.

Figure 6A:
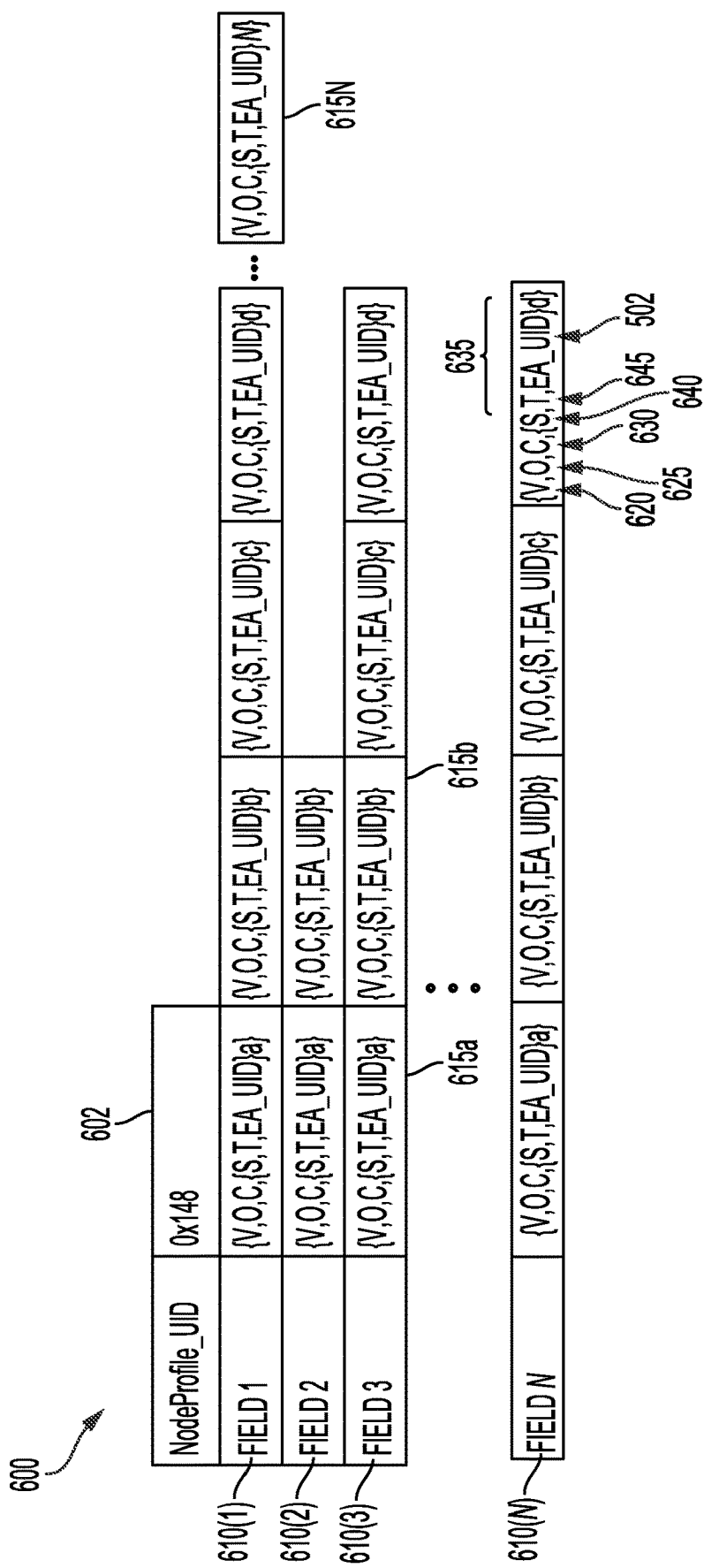
FIG. 6A illustrates a representation of a node profile of a node according to embodiments of the present disclosure.

Referring now to FIG. 6A, FIG. 6A illustrates a representation of a node profile of a node. The node profile 600 can include a unique node profile identifier 602 and one or more fields or attributes 610a-610n. Each field 610 can include one or more value data structures 615. Each value data structure can include a value 620, an occurrence metric 625, a confidence score 630 and one or more entries 635a-n. Each entry 635 can identify a data source 640 from which the value was identified (for instance, a source of a system of record or a source of an electronic activity), a number of occurrences of the value that appear in the electronic activity, a time 645 associated with the electronic activity (for instance, at which time the electronic activity occurred) and an electronic activity unique identifier 502 identifying the electronic activity. In some embodiments, the occurrence metric 625 can identify a number of times that value is confirmed or identified from electronic activities or systems of record. The node profile manager 220 can be configured to update the occurrence metric each time the value is confirmed. In some embodiments, the electronic activity can increase the occurrence metric of a value more than once. For instance, for a field such as name, the electronic activity parser can parse multiple portions of an electronic activity. In some embodiments, parsing multiple portions of the electronic activity can provide multiple confirmations of, for example, the name associated with the electronic activity.

The node profile manager 220 can be configured to maintain a node profile for each node that includes a time series of data points for every value data structure 615 that are generated based on electronic activities identifying the respective node. The node profile manager 220 can maintain, for each field of the node profile, one or more values data structures 615. The node profile manager 220 can maintain a confidence score for each value of the field. As will be described herein the confidence score of the value can be determined using information relating to the electronic activities or systems of record that contribute to the value. The confidence score for each value can also be based on the below-described health score of the data source from which the value was received. Further, the node profile manager 220 can maintain an occurrence metric that identifies a number of times electronic activities or systems of record have contributed to the value. In some embodiments, the occurrence metric is equal to or greater than the number of electronic activities or systems of record that contribute to the value. In some embodiments, the system 200 or the node profile manager 220 can determine that the electronic activity can contribute to the value by generating an activity field-value pair that has a value that matches the value of the value data structure corresponding to the field of the node profile. In some embodiments, the system 200 or the node profile manager 220 can determine that the electronic activity can contribute to the value by parsing the electronic activity to determine an inference that corresponds to the value. The node profile manager 220 further maintains an array including the plurality of entries 635 for each value. As more and more electronic activities and data from more systems of record are ingested by the node graph generation system 200, values of each of the fields of node profiles of nodes will become more enriched thereby further refining the confidence score of each value.

In some embodiments, the node profile can include different types of fields for different types of nodes. Member nodes and group nodes may have some common fields but may also include different fields. Further, member nodes may include fields that get updated more frequently than group nodes. Examples of some fields of member nodes can include i) First name; ii) Last name; iii) Email; iv) job title; v) Phone; vi) Social media handle; vii) LinkedIn URL; viii) website; among others. Each of the fields can be a multidimensional array, such as a 3-dimensional array. In some embodiments, each field corresponds to one or more name value pairs, where each field is a name and each value for that field is a value. Examples of some fields of group nodes can include i) Company or Organization name; ii) Address of Company; iii) Phone; iv) Website; v) Social media handle; vi) LinkedIn handle; among others. Each of the fields can be a multidimensional array, such as a 3-dimensional array. In some embodiments, each field corresponds to one or more name value pairs, where each field is a name and each value for that field is a value.

The node profile manager 220 can maintain, for each field of each node profile, a field data structure that can be stored as a multidimensional array. The multidimensional array can include a dimension relating to data points that identify a number of electronic activities or systems of record that contribute to the field or the value of the field. Another dimension can identify the source, which can have an associated trust score that can be used to determine how much weight to assign to the data point from that source. Another dimension can identify a time at which the data point was generated (for instance, in the case of a data point derived from an electronic activity such as an email, the time the data point was generated can be the time the electronic activity was sent or received). In the case of a data point being derived from a system of record, the time the data point was generated can be the time the data point can be entered into the system of record or the time the data point was last accessed, modified, confirmed, or otherwise validated in or by the system of record. These dimensions are all used to determine a confidence score of the value as will be described herein. In some embodiments, the node profile manager 220 can assign a contribution score to each data point. The contribution score can be indicative of the data point's contribution towards the confidence score of the value. The contribution score of a data point can decay over time as the data point becomes staler. The contribution scores of each of the data points derived from electronic activities and systems of record can be used to compute the confidence score of the value of a field of the node profile.

Figure 6B:
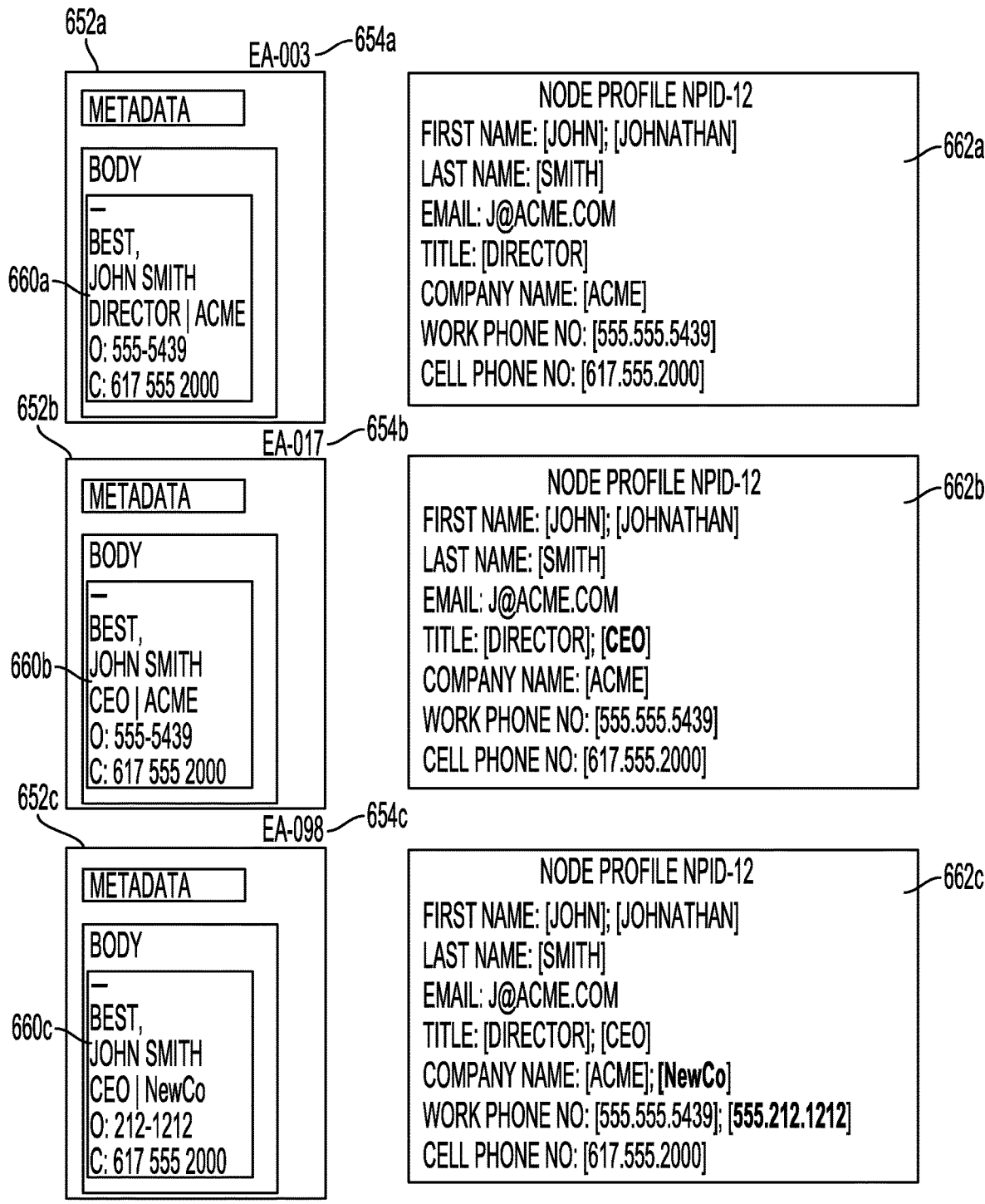
FIG. 6B illustrates representations of three electronic activities and representations of three states of a node profile of a node according to embodiments of the present disclosure.

Referring now to FIG. 6B, FIG. 6B illustrates a representation of three electronic activities and a representation of three states of a node profile of a node according to embodiments of the present disclosure. As shown in FIG. 6B, three electronic activities sent at a first time, a second time and third time are shown. The first electronic activity 652a includes or is associated with a first electronic activity identifier 654a ("EA-003"). The second electronic activity 652b includes or is associated with a second electronic activity identifier 654b ("EA-017"). The third electronic activity 652c includes or is associated with a third electronic activity identifier 654b ("EA-098"). Collectively, the electronic activities can be referred to herein as electronic activities 652 or individually as electronic activity 652. Each electronic activity can include corresponding metadata, as described above, a body, and a respective signature 660a-c included in the body of the respective electronic activity 652. As shown in FIG. 6B, each of the signatures 660a-c is different from the others.

FIG. 6B also includes three different representations of a node profile corresponding to three different times. The node profile corresponds to a node profile of the sender of the electronic activities 652 as determined by the node profile manager 220. The first representation 662a of the node profile was updated after the first electronic activity 652a was ingested by the node graph generation system 200 but before the second and third electronic activities 652b and 652c were ingested by the system 200. The second representation 662b of the node profile was updated after the first and second electronic activities 652a and 652b were ingested by the node graph generation system 200 but before the third electronic activity 652c was ingested by the system 200. The third representation 662c of the node profile was updated after all three electronic activities 652 were ingested by the node graph generation system 200.

Each of the representations 662 of the node profile can include fields and corresponding values. For example, in the first representation 662a, the field "First Name" is associated with 2 different values, John and Johnathan. The first representation 662a also includes the field "Title" which is associated with the value "Director." In contrast, the second representation 662b and the third representation 662c both include an additional value "CEO" for the field "Title." Furthermore, in the third representation 662c, the field "Company Name" is associated with 2 different values, Acme and NewCo in contrast with the first two representations 662a and 662b of the node profile. The values of the field Last Name and Cell Phone Number remain the same in all three representations 662 of the node profile.

Each of the values included in the node profile can be supported by one or more data points. Data points can be pieces of information or evidence that can be used to support the existence of values of fields of node profiles. A data point can be an electronic activity, a record object of a system of record (as will be described herein), or other information that is accessible and processable by the system 200. In some embodiments, a data point can identify an electronic activity, a record object of a system of record (as will be described herein), or other information that is accessible and processable by the system 200 that serves as a basis for supporting a value in a node profile. Each data point can be assigned its own unique identifier. Each data point can be associated with a source of the data point identifying an origin of the data point. The source of the data point can be a mail server, a system of record, among others. Each of these data points can also include a timestamp. The timestamp of a data point can identify when the data point was either generated (in the case of an electronic activity such as an email) or the record object that serves as a source of the data point was last updated (in the case when the data point is extracted from a system of record). Each data point can further be associated with a trust score of the source of the data point. The trust score of the source can be used to indicate how trustworthy or reliable the data point is. The data point can also be associated with a contribution score that can indicate how much the data point contributes towards a confidence score of the value associated with the data point. The contribution score can be based on the trust score of the source (which is based in part on a health score of the source) and a time at which the data point was generated or last updated.

A confidence score of the value can indicate a level of certainty that the value of the field is a current value of the field. The higher the confidence score, the more certain the value of the field is the current value. The confidence score can be based on the contribution scores of individual data points associated with the value. The confidence score of the value can also depend on the corresponding confidence scores of other values of the field, or the contribution scores of data points associated with other values of the field.

The table below illustrates various values for various fields and includes an array of data points that contribute to the respective value. As shown in the table, the same electronic activity can serve as different data points for different values. Further, the table illustrates a simplified form for the same of convenience and understanding.

Different values can be supported by different number of data points. The three electronic activities shown in FIG. 6B (652a-c) are included in the table below. Using the table and the representations 662a-c of the node profile, one can understand how the system 200 is capable of determining values of fields of node profiles and changes to node profiles as more electronic activities and data points are processed by the system 200.

The signature 660b is different from the signature 660a in that the title of the person John Smith has changed from Director to CEO. The data points supporting or contributing the value Director include the first electronic activity 652a but not the second electronic activity 652b. Also, the data points include information received from systems of records including data points that correspond to time periods after the value is no longer accurate. For instance, the data point DP ID225 is a data point supporting the value "Director" for the node profile even though person has been promoted to CEO. The system 200 is configured to process and accept all data points but can assign different contribution scores based on the source of the data point and allow the system 200 to accurately maintain a state of the node profile even if some of the data that is received may be inaccurate or stale.

As will be described further below, it can be challenging to match electronic activities to node profiles. The system 200 can match the third electronic activity 652c to the node profile corresponding to the node profile representation 662 even though the electronic activity identified a different email address, a different company name, and a different office number. In some embodiments, the system 200 can determine, by parsing the electronic activity, information about the sender that can be used to identify the correct node profile. In this particular case, the system 200 can rely on the first name, last name, and cell phone number (which is generally unique) to map the electronic activity to the correct node profile 662 as opposed to other node profiles including the name John Smith.

TABLE 1

| | Data Point # | DP ID | TimeStamp | Activity ID | Source | Trust Score | Contribution Score |
|---|---|---|---|---|---|---|---|
| Field: First Name | | | Value: John [Confidence score] = 0.8 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID343 | Mar. 1, 2018 1 pm ET | EA-017 | Email | 100 | 0.7 |
| | Data Point 4: | DP ID458 | Jul. 1, 2018 3 pm ET | EA-098 | Email | 100 | 0.8 |
| | Data Point 5: | DP ID576 | Sep. 12, 2015 3 pm ET | SOR-145 | Talend | 20 | 0.2 |
| Field: First Name | | | Value: Johnathan [Confidence score] = 0.78 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID343 | Mar. 1, 2018 1 pm ET | EA-017 | Email | 100 | 0.7 |
| | Data Point 4: | DP ID458 | Jul. 1, 2018 3 pm ET | EA-098 | Email | 100 | 0.8 |
| | Data Point 5: | DP ID576 | Sep. 12, 2015 3 pm ET | SOR-145 | Talend | 20 | 0.2 |
| Field: Title | | | Value: Director [Confidence score] = 0.5 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID243 | Mar. 1, 2017 1 pm ET | EA-117 | Email | 100 | 0.65 |
| | Data Point 4: | DP ID243 | Mar. 1, 2018 1 pm ET | SOR-087 | CRM | 5 | 0.05 |
| Field: Title | | | Value: CEO [Confidence score] = 0.9 | | | | |
| | Data Point 1: | DP ID343 | Mar. 1, 2018 1 pm ET | EA-017 | Email | 100 | 0.7 |
| | Data Point 2: | DP ID458 | Jul. 1, 2018 3 pm ET | EA-098 | Email | 100 | 0.8 |
| | Data Point 3: | DP ID225 | Mar. 18, 2018 2 pm ET | SOR-015 | CRM | 65 | 0.54 |
| Field: Company | | | Value: Acme [Confidence score] = 0.6 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID343 | Mar. 1, 2018 1 pm ET | EA-017 | Email | 100 | 0.7 |
| Field: Company | | | Value: NewCo [Confidence score] = 0.9 | | | | |
| | Data Point 1: | DP ID458 | Jul. 1, 2018 3 pm ET | EA-098 | Email | 100 | 0.8 |
| | Data Point 2: | DP ID654 | Jul. 18, 2018 2 pm ET | EA-127 | Email | 100 | 0.85 |
| | Data Point 3: | DP ID876 | Aug. 1, 2018 1 pm ET | SOR-158 | Email | 100 | 0.9 |
| Field: Cell Phone | | | Value: 617-555-2000 [Confidence score] = 0.95 | | | | |
| | Data Point 1: | DP ID101 | Feb. 1, 2016 4 pm ET | EA-008 | Email | 100 | 0.6 |
| | Data Point 2: | DP ID225 | Feb. 18, 2017 2 pm ET | SOR-012 | CRM | 70 | 0.4 |
| | Data Point 3: | DP ID343 | Mar. 1, 2018 1 pm ET | EA-017 | Email | 100 | 0.7 |
| | Data Point 4: | DP ID458 | Jul. 1, 2018 3 pm ET | EA-098 | Email | 100 | 0.8 |
| | Data Point 5: | DP ID576 | Sep. 12, 2015 3 pm ET | SOR-145 | Talend | 20 | 0.2 |
| | Data Point 6: | DP ID654 | Jul. 18, 2018 2 pm ET | EA-127 | Email | 100 | 0.85 |
| | Data Point 7: | DP ID876 | Aug. 1, 2018 1 pm ET | EA-158 | Email | 100 | 0.8 |

As a result of populating values of fields of node profiles using electronic activities, the node profile manager 220 can generate a node profile that is unobtrusively generated from electronic activities that traverse networks. In some embodiments, the node profile manager 220 can generate a node profile that is unobtrusively generated from electronic activities and systems of record.

As described herein, the present disclosure relates to methods and systems for assigning contribution scores to each data point (for example, electronic activity) that contributes to a value of a field such that the same electronic activity can assign different contribution scores to different values of a single node profile and of multiple node profiles. The contribution score can be based on a number of different electronic activities contributing to a given value of a field of a node profile, a recency of the electronic activity, among others. In some embodiments, a system of record of an enterprise accessible to the node graph generation system can include data that can also contribute to a value of a field of a node profile. The contribution score can be based on a trust score or health score of the system of record, a number of different electronic activities or systems of record contributing to the value of the field of the node profile, a number of different electronic activities or systems of record contributing to other values of the field of the node profile, a recency of the value being confirmed by the system of record, among others.

In some embodiments, a method of updating confidence scores of values of fields based on electronic activity includes associating the electronic activity to a first value of a first field, assigning a first contribution score to the first value, associating the electronic activity to a second value of a second field, assigning a second contribution score to the second value, and updating a confidence score of the first value and the second value based on the first contribution score and the second contribution score.

Furthermore, the present disclosure relates to methods and systems for maintaining trust scores for sources and adjusting a contribution score of a data point for one or more values of fields of node profiles based on the trust score of a source.

E. Matching Electronic Activity to Node Profiles

The node profile manager 220 can be configured to manage node profiles by matching electronic activities to one or more node profiles. Responsive to the electronic activity parser 210 parsing the electronic activity to identify values corresponding to one or more fields or attributes of node profiles, the node profile manager 220 can apply an electronic activity matching policy to match electronic activities to node profiles. In some embodiments, the node profile manager 220 can identify each of the identified values corresponding to a sender of the electronic activity to match the electronic activity to a node profile corresponding to the sender.

Using an email message as an example of an electronic activity, the node profile manager 220 may first determine if the parsed values of one or more fields corresponding to the sender of the email message match corresponding values of fields. In some embodiments, the node profile manager 220 may assign different weights to different fields based on a uniqueness of values of the field. For instance, email addresses may be assigned greater weights than first names or last names or phone numbers if the phone number corresponds to a company.

In some embodiments, the node profile manager 220 can use data from the electronic activity and one or more values of fields of candidate node profiles to determine whether or not to match the electronic activity to one or more of the candidate node profiles. The node profile manager 220 can attempt to match electronic activities to one or more node profiles maintained by the node profile manager 220 based on the one or more values of the node profiles. The node profile manager 220 can identify data, such as strings or values from a given electronic activity and match the strings or values to corresponding values of the node profiles. In some embodiments, the node profile manager 220 can compute a match score between the electronic activity and a candidate node profile by comparing the strings or values of the electronic activity match corresponding values of the candidate node profile. The match score can be based on a number of fields of the node profile including a value that matches a value or string in the electronic activity. The match score can also be based on different weights applied to different fields. The weights may be based on the uniqueness of values of the field, as mentioned above. The node profile manager 220 can be configured to match the electronic activity to the node with the greatest match score. In some embodiments, the node profile manager can match the electronic activity to each candidate node that has a match score that exceeds a predetermined threshold. Further, the node profile manager 220 can maintain a match score for each electronic activity to that particular node profile, or to each value of the node profile to which the electronic activity matched. By doing so, the node profile manager 220 can use the match score to determine how much weight to assign to that particular electronic activity. Stated in another way, the better the match between the electronic activity and a node profile, the greater the influence the electronic activity can have on the values (for instance, the contribution scores of the data point on the value and as a result, in the confidence scores of the values) of the node profile. In some embodiments, the node profile manager 220 can assign a first weight to electronic activities that have a first match score and assign a second weight to electronic activities that have a second match score. The first weight may be greater than the second weight if the first match score is greater than the second match score. In some embodiments, if no nodes are found to match the electronic activity or the match score between the email message and any of the candidate node profiles is below a threshold, the node profile manager 220 can be configured to generate a new node profile to which the node profile manager assigns a unique node identifier 602. The node profile manager 220 can then populate various fields of the new node profile from the information extracted from the electronic activity parser 210 after the parser 210 parses the electronic activity.

In addition to matching the electronic activity to a sender node, the node profile manager is configured to identify each of the nodes to which the electronic activity can be matched. For instance, the electronic activity can be matched to one or more recipient nodes using a similar technique except that the node profile manager 220 is configured to look at values extracted from the TO field or any other field that can include information regarding the recipient of the node. In some embodiments, the electronic activity parser can be configured to parse a name in the salutation portion of the body of the email to identify a value of a name corresponding to a recipient node. In some embodiments, the node profile manager 220 can also match the electronic activity to both member nodes as well as the group nodes to which the member nodes are identified as members.

In some embodiments, the electronic activity parser 210 can parse the body of the electronic activity to identify additional information that can be used to populate values of one or more node profiles. The body can include one or more phone numbers, addresses, or other information that may be used to update values of fields, such as a phone number field or an address field. Further, if the contents of the electronic activity include a name of a person different from the sender or recipient, the electronic activity parser 210 can further identify one or more node profiles matching the name to predict a relationship between the sender and/or recipient of the electronic activity and a node profile matching the name included in the body of the electronic activity.

The node profile manager 220 can be configured to maintain a node profile data structure that maintains separate values for the same field. For instance, the electronic message can be destined to john.smith@example.com <Johnathan Smith> and the body of the email states "Dear Johnathan". The parser can be configured to identify a first name, a last name and an email address for the recipient applying logic to specific portions of the electronic activity. In certain embodiments, the node profile manager 220 can be configured to run statistical analysis of all nodes and determine that John is a very common name and thus identify that this node not only has Johnathan as first name but also John is the other First Name value. Moreover, the node profile manager 220 can be configured to determine if a value of a field is unique enough to match the electronic activity to the node based on the value of the field. If the value of the field does not meet a predetermined threshold, other values of fields may be used to match the electronic activity to a given node. In addition, values of fields may be prioritized for matching the electronic activity to the node. For instance, the name John is relatively common and as such, attempting to match an electronic activity to a node using the value "John" for the field "First Name" may be less dispositive than matching a more unique value, such as an email address. In some embodiments, the node profile manager 220 can weigh fields that have values that are relatively more unique higher than fields that have values that are relatively less unique when matching an electronic activity to a node. In some embodiments, the node profile manager 220 can be configured to restrict matching electronic activities to nodes using values of fields that are determined to not be sufficiently unique.

The node profile manager 220 can be configured to identify a node that has fields having values that match the values included in the node profile of the node. To do so, the node profile manager may determine that john.smith@example.com belongs to only one node. The node profile manager can then select that node to be the recipient of the email message. The node profile manager would then populate each of the fields of the node profile with an entry for each value of each respective field that was identified by the electronic activity parser 210. In particular, the node profile manager can generate, for each value of a field that is identified by the electronic activity parser 210, an entry in that value data structure that identifies the electronic activity, a source of the electronic activity, a time associated with the electronic activity and a number of occurrences within the electronic activity that include the value. In the email message described above, the node profile manager can update the value data structure of the Name field of the recipient node with an entry that identifies the source of the email, the time associated with the email and a total number of occurrences of the value in the email. In this case, the total number of occurrences was 2 because the first name of the recipient was listed as Johnathan and the salutation identified the name Johnathan.

Figure 7:
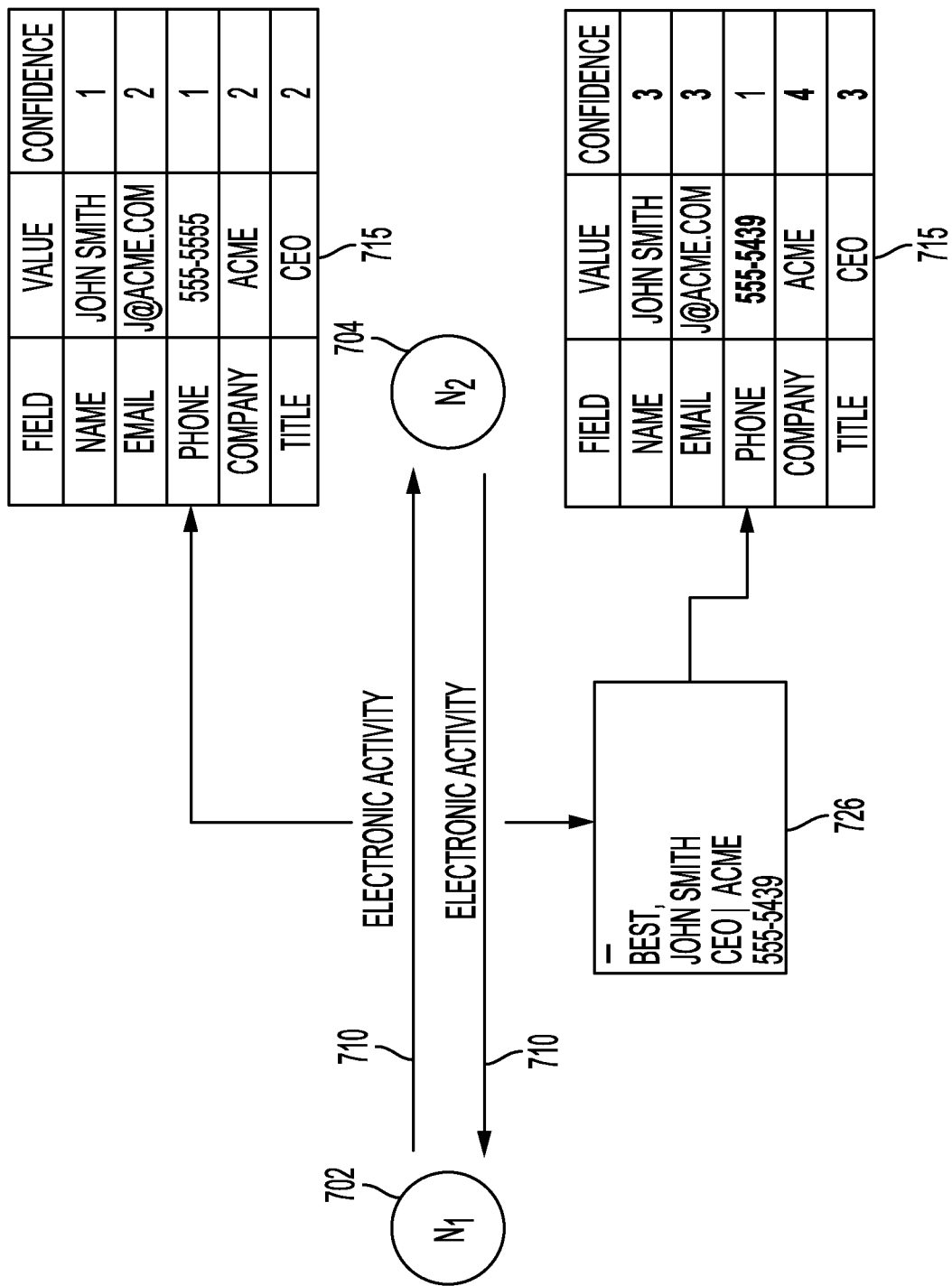
FIG. 7 illustrates a series of electronic activities between two nodes according to embodiments of the present disclosure.

Referring briefly to FIG. 7, FIG. 7 illustrates a series of electronic activities between two nodes, N1 702 and N2 704. N1 702 may correspond to a node associated with an entity whose electronic activities are ingested by the node graph generation system 200, while node N2 704 may correspond to a node external to the entity associated with the node N1. A node profile 715 for node N2 is maintained by the node profile manager 220. Before the electronic activity 710 was ingested by the node graph generation system 200, the node profile included the five fields, name, email, phone, company and job title. This information was previously included in the node profile and may have been determined by ingesting information from a system of record. At that time, the confidence score of each of the fields is 1. When the first electronic activity is ingested by the system 200, the node profile manager can update the node profile 715 and increase the confidence score of values of fields that can be verified by the electronic activity. By virtue of the electronic activity being successfully transmitted from N1 to N2, the node profile manager 220 can update the confidence score of the email value j@acme.com and the company name Acme by parsing the email address and determining that the domain name of the email matches a domain name of the company node, to which N2 belongs. In some embodiments, the node profile manager 220 may determine that the electronic activity is successfully transmitted by determining that the N1 did not receive a bounce back electronic activity that indicates that the electronic activity was not successfully transmitted. Examples of bounce back electronic activity can include emails indicating that the destination email address is invalid or incorrect, the person is no longer with company, among others.

In some embodiments, the node graph generation system 200 can, via the electronic activity parser or through some other module, parse bounce back electronic activities to determine a reason for why the electronic activity bounced back. In some embodiments, the node graph generation system 200 can use natural language processing to determine a cause for the bounce back activity. In this way, the node graph generation system 200 can determine if an email address associated with a person or node is still valid or if it is incorrect or if the person is no longer associated with the company identified by the domain of the email address.

Node N2 can then send back a response email to node N1 that includes a signature 726 in the body of the electronic activity. The node profile manager can update, from the successful transmission of the email response and the parsing of the signature, the node profile of N2 by increasing the confidence score of the name of John Smith, the title from the signature, the company name 2 times (one of which was derived by matching the domain name of the email to the domain name of the group node in the node graph) as it is included in the email address and in the signature, and further add a new value for the phone number, which is extracted from the signature. The extracted phone number can represent his direct office number, while the phone number previously maintained in the node profile can be a general company number. In some embodiments, the system can be configured to classify phone numbers as a general company number or a direct office number based on the frequency of the number appearing in different node profiles. In some embodiments, the node graph generation system 200 can be configured to classify phone numbers as a general company number or a direct office number by performing regex patterns to determine if an "ext." or an "x" followed by some numbers is included in the value. The regex can also be configured to identify phone number prefixes, such as "800." The system can identify the phone numbers as the publicly known phone number of the company. In some embodiments, the node graph generation system 200 can be configured to restrict or otherwise prevent a phone number determined to be a general company number from being inserted as a value of a personal number. In some embodiments, the node graph generation system 200 can be configured to determine the value of phone numbers of other nodes corresponding to the same company and if the system determines that the number to be added to a node matches the number of multiple other nodes belonging to the same entity or company, the system can probabilistically determine, for instance, that the number is a work number and update the number as a value in the work number field (instead of a personal number field). Similar techniques can be applied for determining or inferring other information by comparing the data of a node profile to patterns observed from a plurality of related node profiles. In some embodiments, the system can determine whether the first predetermined digits (for instance, the first 6 digits) are identical to the first predetermined digits of phone numbers of other nodes belonging to the same company. If the first predetermined digits of the number match the first predetermined digits of phone numbers of other nodes belonging to the same company, the system can determine that the number is a work number. Similarly, an address extracted from a signature can be determined to be a work address if the address matches the address of other nodes belonging to the same entity or company. In this way, any value of a field of a node extracted can be determined to be specific to a company if other nodes corresponding to people belonging to the company also include the same value for the field or inter-related values in other fields. Additional details regarding increasing or adjusting the confidence score of various values of fields of node profiles based on occurrences of electronic activities are provided herein.

Generally, the node profile manager 220 can attempt to match electronic activities, such as emails, to node profiles based on an email address. However, in some instances, a user may send or receive an email address from a second email address, such as a personal email address instead of a work email address. The node profile manager 220 can analyze the electronic activity and look at other signals from the electronic activity to see if the electronic activity should be matched to a previously established node profile that corresponds to the user that does not include the second email address instead of a creating a new node profile based on the second email address.

For instance, the node profile manager 220 can be configured to identify an email that includes an email address john.smith@gmail.com. The node profile manager 220 can determine that either no node profile includes the john.smith@gmail.com as a value of an email address field or even if the email appears as a value in the email address field of a node profile, the confidence score of the value of the email address is below a certain threshold sufficient for the node profile manager 220. In some embodiments, the node profile manager 220 can apply one or more policies or rules for generating new nodes. For instance, the node profile manager 220 can implement an email address based node profile generation policy in which the system is configured to not create new node profiles if the email address corresponds to an email address of one or more predefined email systems. For instance, the email address based node profile generation policy can include one or more rules for generating new node profiles or restricting the generation of new node profiles. In some embodiments, the node profile generation policy can restrict the creation or generation of new node profiles if the email address corresponds to an email address of one or more predefined email systems. For instance, the predefined email systems can include email systems that provide "free" email addresses like "gmail.com" or "yahoo.com". In such cases, the node profile manager 220 can be configured to use other signals from the electronic activity to attempt to match the electronic activity to a node profile for which the email address did not provide a match to a node profile. The node profile manager 220 can use fuzzy matching techniques including a first name, last name, email address prefix, a phone number or any other information that can be extracted from the email address to match the electronic activity to an existing node profile. In some embodiments, the node profile manager 220 can also identify other node profiles to which the electronic activity can be matched and identify likely node profiles based on connection strengths between the node profiles to which the electronic activity can be matched and the one or more likely node profiles.

As discussed above, in the case that John Smith inadvertently sent an email from his Gmail address as opposed to his company email address, john.smith@example.com, the node profile manager 220 can use one or more of the first name, last name, phone number or other information included in the signature of the email to match the electronic activity to a node profile that includes the email address, john.smith@example.com. In this way, if other signals are pointing or expecting a work email address, the electronic activity will be matched to the node profile with the work email address. The system can determine additional signals from the electronic activity. For instance, the system can parse the electronic activity to determine if the electronic activity includes text or strings that match one or more predetermined strings or keywords that are mapped to the person's work. For instance, the predetermined keywords can include product names of his company, his company's name, among others. In addition, the system can identify one or more participants of the electronic activity and determine if any of the participants correspond to node profiles with which the person (John) has had exchanged electronic activities in the past.

F. Node Profile Value Prediction and Augmentation

The node profile manager 220 can be configured to augment node profiles with additional information that can be extracted from electronic activities or systems of record or that can be inferred based on other similar electronic activities or systems of record. In some embodiments, the node profile manager 220 can determine a pattern for various fields across a group of member nodes (such as employees of the same company). For instance, the node profile manager 220 can determine, based on multiple node profiles of member nodes belonging to a group node, that employees of a given company are assigned email addresses following a given regex pattern. For instance, [first name].[last name]@[company domain].com. As such, the node profile manager 220 can be configured to predict or augment a value of a field of a node profile of an employee of a given company when only certain information of the employee is known by the node profile manager 220.

| First Name | Last Name | Company Name | Email address |
|---|---|---|---|
| John | Smith | Example | john.smith@example.com |
| George | Baker | Example | george.baker@example.com |
| Adam | Jones | Example | (unknown) adam.jones@exampl.com (predicted) |
| (unknown) Linda (predicted) | (unknown) Chan (predicted) | Example | linda.chan@example.com |

As shown in the table above, the node profile manager 220 can be configured to determine that the email address for Adam Jones is adam.jones@example.com by observing a regex pattern the company Example uses when assigning email addresses to its employees. In some embodiments, the node profile manager 220 can update the email address field of Adam Jones accordingly. In some embodiments, the node profile manager 220 can be configured to transmit an email to adam.jones@example.com to check whether the email address is valid or if a bounce back email is received. If no bounce back email is received indicating that the email address is not valid or cannot be found, the confidence score of adam.jones@example.com can increase even though the email address was unknown to the node graph generation system 200 based on the electronic activities ingested by the system 200.

Similarly, the node profile manager 220 can infer the first and last names of people having email addresses corresponding to a company by parsing information using the known regex patterns. As shown above, the node profile manager 220 can predict that the name of the person associated with the email address linda.chan@example.com is Linda Chan based on the regex pattern observed from other known node profiles maintained by the node profile manager 220. In some embodiments, the node profile manager 220 can infer the first and last names of people having email addresses corresponding to a company by also using other data points in the electronic activity, such as parsing email header metadata, email signature, or a greeting at the top of the email body to correlate with and confirm the name, predicted from the regex pattern above. As previously described with respect to the description associated with Table 1, the system can rely on multiple data points to match an electronic activity to a particular node profile (for instance, relying in part on the cell phone number included in the signature as discussed with respect to Table 1). In this way, further confirmation of the inference of the first name and/or last name can be obtained, thereby improving the accuracy of the node profile and the overall node graph. It should further be appreciated that if multiple people have the same name or initials, the company may assign alternate email address naming conventions for such people. For instance, a company may include a middle initial in the email address for person if the email address generated using the company's primary regex pattern for assigning email addresses is already taken. In such cases, the node profile manager 220 may again further rely on other data points in the electronic activity, such as parsing email header metadata, email signature, or a greeting at the top of the email body to infer the first and last names of the person.

In this way, by knowing the regex patterns of email addresses assigned by a company, the node profile manager 220 can be configured to predict email addresses of people at the company for which we have some information. Furthermore, if an email address is known, we can predict other information not otherwise known based on the email address. In some embodiments, even if some information is known, the confidence score of that information can be updated based on the node profile manager 220 being configured to predict certain values.

In some embodiments, the node profile manager 220 can be configured to maintain both work and personal phone numbers and work and personal geographical locations of node profiles. The node profile manager 220 can be configured to determine if a phone number extracted from an electronic activity is a work phone number or a personal phone number through one or more verification techniques. In some embodiments, the node profile manager 220 can be configured to compare the phone number of a node with phone numbers of other nodes belonging to the same company or branch/office. Corporations generally will assign phone numbers to employees that are similar to one another, for instance, all the numbers of the corporation can be 617-550-XXXX. As such, the node profile manager 220 can categorize a phone number as a work number for a node if the phone number starts with 617 550 when at least a threshold number of nodes belonging to the same email domain @example.com also have the phone number beginning with 617-550. In some embodiments, the threshold number can be 2, 3, 4, 5, or more. In some embodiments, the threshold number can be based on a percentage of another value, such as a total number of nodes belonging to the same domain and also having the phone number beginning with the same subset of digits. Conversely, the node profile manager 220 can be configured to categorize a phone number as a personal number if the phone number starts with a different set of numbers. It should be appreciated that more broadly, the node profile manager 220 can be configured to extract a regex pattern or specific template of numbers by comparing the phone numbers of multiple node profiles corresponding to the same corporation.

In some embodiments, the node profile manager 220 can be configured to compare a location of a person with an area code of a phone number associated with the person to determine if a phone number is to be classified as a work phone number or a personal phone number. If the person lives in the same area as the company's office, the person's personal phone number can have similar first few digits as the company's general phone number. In some such embodiments, the node profile manager 220 can be configured to negate the similar digits between the person's phone number and the company's assigned phone numbers to determine if the number identified in the node profile or to be included in the node profile is to be classified as a work phone number or a personal phone number. If the person lives in an area that is further away from the company based on existing information in the node profile, the node profile manager 220 can be configured to classify a number similar to the company's general phone number or having an area code corresponding to an area where the company is located as a work phone number. If the person lives in an area close to the company, the node profile manager 220 can be configured to identify the digits of the phone number that match the company's general phone number and use the remaining digits to determine if the number corresponds to a work phone number or a personal phone number of the person.

If the person lives far away from their work address, the node profile manager 220 can be configured to reduce the likelihood of assigning, as a personal phone number, a phone number that has an area code corresponding to the person's work address. More generally, the node profile manager 220 can be configured to rely on additional fields to determine if a particular number belongs to a work phone number or a personal phone number of the person.

As described herein, the node profile manager 220 can be configured to used information from node profiles to predict other values. In particular, there is significant interplay between dependent fields such as phone numbers and addresses, and titles and companies, in addition to email addresses and names, among others.

G. Electronic Activity Tagging

The tagging engine 265 can be any script, file, program, application, set of instructions, or computer-executable code that is configured to enable a computing device on which the tagging engine 265 is executed to perform one or more functions of the tagging engine 265 described herein.

The tagging engine 265 can use information identified, generated or otherwise made available by the electronic activity parser 210. The tagging engine can be configured to assign tags to electronic activities, node profiles, systems of record, among others. By having tags assigned to electronic activities, node profiles, records ingested from one or more systems of record, among others, the node graph generation system 200 can be configured to better utilize the electronic activities to more accurately identify nodes, and determine types and strengths of connections between nodes, among others. In some embodiments, the tagging engine 265 can be configured to assign a confidence score to one or more tags assigned by the tagging engine. The tagging engine 265 can periodically update a confidence score as additional electronic activities are ingested, re-ingested and analyzed. Additional details about some of the types of tags are provided herein. A tag can be one or more bits that can be used by the system to label The tagging engine 265 can assign one or more tags to electronic activities. The tagging engine 265 can determine, for each electronic activity, a type of electronic activity. Types of electronic activities can include meetings, electronic messages, and phone calls. For meetings and electronic messages such as emails, the tagging engine 265 can further determine if the meeting or electronic message is internal or external and can assign an internal tag to meetings or emails identified as internal or an external tag to meetings and emails identified as external. Internal meetings or emails may be identified as internal if each of the participants or parties included in the meeting or emails belong to the same company as the sender of the email or host of the meeting. The tagging engine 265 can determine this by parsing the email addresses of the participants and determining that the domain of the email addresses map to the domain name or an array of domain names, belonging to the same company or entity. In some embodiments, the tagging engine 265 can determine if the electronic activity is internal by parsing the email addresses of the participants and determining that the domain of the email addresses map to the same company or entity after removing common (and sometimes free) mail service domains, such as gmail.com and yahoo.com, among others. The tagging engine 265 may apply some additional logic to determine if all emails belong to the same entity and use additional rules for determining if an electronic activity is determined to be internal or external. The tagging engine 265 can also identify each of the participants and determine whether a respective node profile of each of the participants is linked to the same organization. In some embodiments, the tagging engine 265 can determine if the node profiles of the participants are linked to a common group node (such as the organization's node) to determine if the electronic activity is internal. For phone calls, the tagging engine 265 may determine the parties to which the phone numbers are either assigned and determine if the parties belong to the same entity or different entities.

In some embodiments, the node graph generation system 200 can be configured to generate, maintain and update an array of domain names that belong to the same company or entity. The node graph generation system 200 may do so by monitoring electronic activities and predicting whether certain domain names belong to the same entity. The node graph generation system 200 can monitor a large number of electronic activities of an entity and determine multiple email accounts of a first domain communicate with multiple email accounts of a second domain in a manner that appears to be internal communications. In some embodiments, the node graph generation system 200 can automatically identify all possible domain names of the company based on a frequency of communications that look like internal communications between identified members of a company name, the fact that in multiple systems of record majority of the communicating node profiles belong to the same or related company profile, or by a similarity of the ending part of domain names, for example "us.ibm.com" and "us.ibm.com". Electronic activities can appear to be internal communications based on analyzing the words used in emails, the meeting numbers used in meeting and calendar invites, as well as determining if the email addresses match certain regex rules that may indicate that the domain names belong to the same company. For instance, electronic activities include email addresses having domain names us.example.com and uk.example.com may increase a likelihood that both us.example.com and uk.example.com appear to belong to the same company, Example. In some embodiments, if there a certain number of emails from certain users of us.example.com to other users of uk.example.com and the emails appear to be internal communications, the node graph generation system 200 or the node profile manager 220 can be configured to update the node profile of the company, Example, to include both domain names, us.example.com and uk.example.com. It should be appreciated that the node graph generation system 200 can then automatically update other node profiles and tags previously assigned to electronic activities responsive to determining that two domains belong to the same company. It should further be appreciated that the node graph generation system 200 can also automatically update confidence scores of certain values of fields of other node profiles and confidence scores of tags previously assigned to electronic activities responsive to determining that two domains belong to the same company.

In some embodiments, the tagging engine 265 can assign an internal tag or external tag to an electronic activity by applying certain logic. For instance, the tagging engine can determine that the electronic activity is internal if all the domains associated with the electronic activity are internal (or belong to the same domain). In some embodiments, if the tagging engine 265 determines that only some of the domains are internal and one or more domains are personal (i.e. not business external), then the tagging engine can be configured to attempt to match the personal email addresses to nodes and see if those nodes are linked to the same company. If the tagging engine fails to match the personal email addresses to nodes and see if those nodes are linked to the same company, the tagging engine can be configured to tag the electronic activity as external and may not link the electronic activity to a group node belonging to the domain. In some embodiments, if the tagging engine 265 determines that some domains of the email addresses included in the electronic activity are internal and some are business external, the tagging engine 265 can be configured to link the electronic activity to the group node corresponding to the external company, and further determine if individual nodes matching the email address (or first and last names) exist, and if so, linking the electronic activity with the respective individual nodes. In the event that the tagging engine 265 cannot identify an individual node that matches the email address or first and last names, the system 200 can create new individual nodes based on the respective email address or first and last names that were used to unsuccessfully identify the individual node. In the event that no individual (people) or group (company) nodes match, and the domain corresponding to the electronic activity doesn't belong to the list of free/public domains like @gmail then the system 200 can be configured to automatically create a new group (company) node or generate a flag or notification for an administrator to take an action.

The tagging engine 265 can further assign a sent tag to emails that are sent by a node associated with the data source provider from which the electronic activity was received or a received tag to emails that are received by a node associated with the data source provider from which the electronic activity was received.

In addition, the tagging engine can be configured to assign an inbound tag to received electronic activities corresponding to meeting invitations and assign an outbound tag to electronic activities corresponding to meeting invitations transmitted to other people. Moreover, meetings can be tagged with additional tags, such as a "future" tag when a meeting is scheduled for a time in the future. The "future" tag is subsequently replaced with a "past" tag once the time at which the meeting is scheduled to occur is in the past. Moreover, the tagging engine 265 can further assign tags indicating if the meeting took place or not based on other signals, such as electronic activities exchanged within a predetermined time frame of the scheduled meeting time as described herein or containing written confirmations that the meeting took place or not, such as follow-up notes between participants or cancellation notice emails. For electronic activities identified as meetings, the tagging engine 265 can further assign a tag identifying if the meeting is in person or if the meeting is a conference call. In some embodiments, the tagging engine 265 can employ a meeting type policy to determine the type of meeting. In some embodiments, the policy can include rules for parsing the location portion or body of a meeting to determine the location. If the location identifies a physical address or a room or if one of the participants included in the email is a non-human participant associated with a meeting room or other type of rooms, the tagging engine 265 can determine that the electronic activity is an in-person meeting and can assign an in-person meeting tag indicating that the meeting is an in-person meeting. In some embodiments, an in-person tag can be assigned to the electronic activity and a confidence score can be determined for the in-person tag that is assigned.

The confidence score associated with the in-person tag can be indicative of a likelihood that the meeting is actually an in-person meeting. The tagging engine 265 can further be configured to assign an occurrence tag that can be used to indicate a likelihood that the meeting occurred. The tagging engine 265 can further be configured to assign a respective participant attendance tag for each participant that attended the meeting.

To determine the confidence score associated with the in-person tag, the node graph generation system 200 can scan or analyze electronic activities associated with the participants of the meeting (and in some embodiments, the electronic activities of all users of the system 200) to identify receipts or other electronic activity, communications, among others indicative of the user physically going to the meeting. In some embodiments, the system 200 can scan electronic activities to find flight information, transportation receipts, and ride-sharing receipts, which may include information that would indicate the user physically going to the location associated with the meeting. For instance, if the meeting is at 100 Main St, San Francisco, Calif. on a certain date, electronic activities from an airline identifying a local airport may be used to increase the confidence score of the in-person tag. Similarly, even a flight cancellation receipt may increase the confidence score of the in-person tag. This is because even though the person may not have attended the meeting, the proof that a flight was reserved indicates that the meeting was intended to be an in-person meeting. The occurrence tag, which indicates whether the meeting actually occurred, can have its own confidence score. The greater the confidence score of the occurrence tag, the more likely the meeting occurred. As such, a flight confirmation email may increase the confidence score of the occurrence tag, while a flight cancellation email may conversely, decrease the confidence score of the occurrence tag. If multiple participants receive flight cancellation emails, the system may decrease the confidence score of the occurrence tag as it may be indicative of the meeting being canceled. However, if multiple participants received flight reservation emails and only a subset of the participants received flight cancellation emails, the system may not decrease the confidence score of the occurrence tag by the same amount as the system may assume that the meeting is still occurring but only the subset of participants are not attending. In such cases, the system may decrease the confidence score of the participant attendance tag for those participants that received flight cancellation emails. Moreover, the system can detect and parse an electronic receipt from a ride sharing service identifying one of the addresses as or near the meeting location (for example, 100 Main St, San Francisco, Calif.) and use the electronic activity to further increase the confidence score of the in-person meeting tag as well as the occurrence tag and the participant attendance tag.

On the other hand, the tagging engine 265 can determine that the meeting is a conference call by applying the meeting type policy and determining if a phone number or dial-in instructions are provided in the electronic activity. Furthermore, the tagging engine 265 may receive information from other engines or modules of the system to determine if participants are in close proximity to one another, based on time zone and location estimation algorithms used to predict a location of a node as well as determine or predict the locations of the participants based on electronic activities that occur within a predetermined time window of the meeting time that involve the participants. Some of the rules rely on determining a predicted work schedule of the node, a predicted location of the node, and inferred behavior before and after the meeting that can be determined from other electronic activities.

In some embodiments, the tagging engine 265 or the system 200 can be configured to cause the system 200 to initiate a call to a phone number included in a meeting invite and responsive to joining the meeting, identify one or more participants of the meeting for instance, based on identifying the phone number from which each of the participants is calling in and comparing those phone numbers to the data in the node graph or node profiles used to generate the node graph, converting speech to text, voice recognition, voice footprinting, among others. In some embodiments, the tagging engine can determine the participants who attended the meeting based on the attendees that accessed a link to a web session and in some such embodiments, used their email address to log into the web session. In some embodiments, the tagging engine 265 can determine what time a participant joined, a level of contribution of the participant during the meeting, how long the participant attended the meeting for, and generate one or more additional tags based on one or more of the participants' involvement.

As described above with respect to in-person meetings, the tagging engine 265 can also provide occurrence tags for conference call or virtual meetings as well as attendance tags for participants of such meetings. The occurrence tags can have respective confidence scores indicating the likelihood that the meeting actually occurred. Similarly, the participant attendance tags can be assigned to participants and can have respective confidence scores indicating the likelihood that the participant actually attended the meeting. The confidence scores of the occurrence tags and the attendance tags can be determined based on electronic activities that reference the meeting. In some embodiments, an electronic activity representing a phone log of a users phone dialing into to a meeting number can be used to increase the confidence score of the occurrence tag of the meeting as well as the confidence score of the attendance tag.

The tagging engine 265 can further be configured to assign tags to people identified or included in one or more electronic activities. These tags can identify a role of the person included in the electronic activity. The tags can include a sender tag indicating a participant as a sender of the electronic activity or an organizer tag indicating a participant as an organizer of a meeting. Other similar types of tags can be assigned to participants based on whether they are included in the To line, the CC line or the BCC line. The tagging engine 265 can further be configured to tag participants based on the context of the electronic activity. For instance, if the electronic activity is determined to be associated with an opportunity, the tagging engine can assign tags to various participants, including tags indicating who the buyer is, who the seller is, who the decision maker is, who the champion is, among others. This information can be determined based on node profiles of the participants, their level of involvement in the electronic activity or the opportunity in general, among others. The tags can be assigned with certain confidence scores. As additional electronic activities are processed, the confidence scores of these tags can increase or decrease.

In some embodiments, natural language processing can be used to parse electronic activities exchanged between the participants to determine the type of meeting. For instance, an electronic activity exchanged after the meeting may indicate a phrase such as "Thanks for the lunch" which may indicate that the meeting was an in-person meeting, among others. In some embodiments, the tagging engine 265 can further tag electronic activities, such as meetings, with tags indicating if the meeting actually took place. As described above, the tagging engine 265 can tag a meeting as having taken place responsive to identifying a subsequent electronic message that included a phrase such as "Thanks for the lunch." In some embodiments, the tagging engine can determine that the meeting is an in-person meeting by detecting an address or physical location in the body or location fields of the electronic activity. The tagging engine can further attribute a confidence score to the tag based on various data points the tagging engine relies on to determine that the electronic activity corresponds to an in-person meeting. The confidence score of the tag can increase or decrease based on additional electronic activity parsed by the system. For instance, electronic activity exchanged between the participants that may include various phrases that are detected via natural language processing, for instance, "great seeing you," or "thanks for lunch" can increase the confidence score of the in-person tag indicating that the meeting is an in-person meeting. In addition, the electronic activity exchanged between the participants can increase the confidence score of the participant attendance tags of the sender and recipient of the email. Similarly, electronic activities including receipts of transportation (for instance, UBER/LYFT/flight receipts) to or from the physical location associated with the meeting may be used to increase the confidence score of the in-person tag assigned to the meeting, the occurrence tag assigned to the meeting and the participant attendance tag assigned to respective participants of the meeting. Additional details regarding tagging electronic activity are provided herein.

The tagging engine 265 can further assign tags indicating if an email is a blast email. In some embodiments, the tagging engine 265 can determine if an email is a blast email by parsing the message header of the email, identifying a message identifier field of the email and extracting the value of the message identifier field. The tagging engine can then compare the value of the message identifier field and compare the value to values of other electronic activities to determine if the values partially match. Furthermore, the tagging engine 265 can compare the words included in the body or subject line of the electronic activities that at least partially match and if the ratio of similar words to different words exceeds a threshold, the tagging engine 265 can determine if the email is a blast email. In some embodiments, the tagging engine 265 can determine electronic activities corresponding to a blast email by analyzing multiple electronic activities and identifying a subset of the multiple electronic activities as blast emails responsive to determining that each electronic activity of the subset has a low variability of word count relative to the other electronic activities in the subset and a low variability in a language complexity index relative to the other electronic activities in the subset.

In some embodiments, other signals may be used to determine if the email is a blast email, for instance, a time at which the emails were sent, and if a similar email was previously sent to a large number of people. In some embodiments, the tagging engine 265 can assign a blast email tag to an instant electronic activity responsive to determining that a similar electronic activity that is similar to the instant electronic activity above a predetermined similarity threshold was associated to a large number of nodes in a node storage database maintained by the system 200. In certain embodiments, the tagging engine 265 can learn from previously tagged electronic activities known to be blast emails and use the learnings from such electronic activities to assign a tag to an instant email having language that is similar above a predetermined similarity threshold to one or more electronic activities previously tagged as blast emails. By determining if an email is a blast email, effort estimation can be more accurately computed.

The tagging engine 265 can further assign tags indicating if an email is a cold email. In some embodiments, the tagging engine 265 can determine if an email is a cold email by applying natural language processing to identify patterns or signals that may indicate that the email is a cold email or by determining a tone of an email. In some embodiments, the tagging engine 265 may determine that an email is a cold email if the participants of the email have not exchanged any electronic activity in the past. In some embodiments, the tagging engine 265 may determine that an email sent from a sender to a recipient is a cold email if the recipient of the email has not previously transmitted a response to any electronic activity sent from the sender to the recipient in the past. In some embodiments, even if the recipient of the email has not previously transmitted a response to any electronic activity sent from the sender to the recipient in the past the tagging engine 265 may determine that an email sent from a sender to a recipient is not a cold email if the recipient and the sender have communicated via other forms of communication or via other email addresses associated with a respective node of the sender or recipient in the past. In this way, if the recipient starts a new job and gets a new email address, electronic activities sent to the new email address by a sender who has previously communicated with the recipient at the old job would not be classified or tagged as a cold emails because the node graph would indicate that the sender has communicated with the recipient in the past albeit via a different email address of the recipient that is determined based on the values of email addresses stored in a node profile of the recipient. In some embodiments, the tagging engine 265 can determine if an email is a cold email based on a number of cold emails the sender has sent in the past to one or more recipients as well as by looking at the node graph to determine a number of nodes with which the sender and recipient are commonly connected.

The tagging engine 265 can further assign tags indicating a classification of the electronic activity based on the participants included in the electronic activity. For instance, if one of the participants is a lawyer, the tagging engine 265 can assign a tag indicating that the electronic activity relates to legal. Moreover, the tagging engine 265 can further assign tags indicating a classification of the electronic activity based on the subject matter included in the electronic activity. The tagging engine 265 can determine a subject matter based on natural language processing, keywords, regex patterns or other rules that may be used to determine the subject matter. In some embodiments, filtering policies that may be provided or configured by users, companies, accounts, among others, may be used by the tagging engine 265 to assign one or more tags. Such tags can be used for filtering, matching electronic activities to record objects of systems of record, determining if emails are personal or business related, among others.

In some embodiments, the tagging engine 265 can be configured to determine if an electronic activity is a personal electronic activity or if it is a business related electronic activity. In some embodiments, the tagging engine 265 can determine that an electronic activity is personal based on parsing the contents of the electronic activity. In some embodiments, the tagging engine 265 can determine that the electronic activity is personal if the electronic activity is sent during non-work hours and the context of the electronic activity is unrelated to work. In some embodiments, the tagging engine 265 can determine that the electronic activity is personal if the participants of the electronic activity have titles or job functions that typically do not overlap or correspond to companies that do not generally engage in work related activities. In some embodiments, the tagging engine 265 can also evaluate various features, characteristics or values of fields of node profiles of the participants of the electronic activity to determine whether the electronic activity is personal. For instance, the tagging engine 265 may determine that the electronic activity is likely to be personal if the participants of the electronic activity have the same last name, as derived from the header of the electronic activity, the body or contents of the electronic activity, a signature included in the electronic activity or from the node profiles of the participants of the electronic activity. It should be appreciated that the tagging engine 265 may not need to rely on information stored in a node profile of a participant of the electronic activity to determine if the electronic activity is personal. For example, the tagging engine 265 can determine if the participants share the same last name by parsing the header of the electronic activity, the body or contents of the electronic activity, a signature included in the electronic activity. Further, if the participants have previously communicated with one another using their personal email addresses or if the contents of the electronic activity suggest that they have a prior relationship outside of work, the tagging engine 265 can determine that the participants may be related outside of work and may be configured to determine that the electronic activities exchanged between them are personal electronic activities. The tagging engine 265 can be configured to tag such electronic activities with a personal tag indicating that the electronic activity is determined to be personal. As described herein, the tagging engine 265 or the system, in general, can assign a confidence score to the tag based on how confident the system believes the electronic activity is personal (or on-work related) in nature, based on a number of methods, described above.

In some embodiments, the system 200 or the node profile manager 220 can be configured to determine that two node profiles have a personal (non-professional) relationship either based on the electronic activities exchanged between them that may be tagged with a personal tag. The system can then tag the two node profiles as having a personal relationship. The system can further determine a confidence score for the tag classifying the two node profiles based on how confident the system is in its prediction that the two node profiles have a personal relationship. In some embodiments, the system 200 or the node profile manager 220 can further determine if two nodes have a personal relationship based on commonalities in values in their node profiles, for instance, their home addresses (if they are neighbors), college or school affiliations (alumni/classmates), same last names, other non-professional affiliations, or other signals that may indicate the two node profiles may have a personal relationship.

The system 200 or the tagging engine 265 can be configured to use the personal tag between the node profiles to classify subsequent electronic activities exchanged between the node profiles. In some embodiments, as described below, the system can be configured to restrict matching electronic activities with a personal tag to record objects. The system can further be configured to either unmatch or unlink previously matched electronic activities from record objects of systems of record or remove such activities from existing data structures.

It should be appreciated that the system can conversely or similarly determine that certain electronic activities are professional in nature and tag such electronic activities with a professional tag. The system 200 can also be configured to determine that relationships between node profiles may also be professional based on their respective node profiles as well as past electronic activities exchanged between them.

It also should be appreciated that the system 200 or the tagging engine 265 can conversely or similarly determine that certain electronic activities can be more professional in nature. In some embodiments, the tagging engine 265 can determine that an electronic activity is professional if the content of the electronic activity relates to sales, recruiting, scheduling an appointment or other business related activities. The tagging engine 265 can then assign a professional tag to such an electronic activity indicating that the electronic activity is professional in nature. The tagging engine 265 can further assign a tag indicating that the electronic activity is relating to sales, recruiting or scheduling an appointment based on the context of the electronic activity. Such tags can be used to determine whether or not to match the electronic activity to a record object of a system of record. For instance, if the electronic activity relates to sales, the system 200 can tag the electronic activity with a sales tag, which the system 200 can use to determine to match the electronic activity to a record object of one or more systems of record as a sales related electronic activity can be a useful data point for a company in evaluating various aspects of their business processes. In another example, electronic activities relating to scheduling can be provided a scheduling tag, which can be used by the system 200 to filter out or restrict such electronic activities from being matched to record objects. Restricting certain electronic activities from being matched to record objects reduces the computing resources required for matching electronic activities to record objects by reducing the total volume of electronic activities to match. Restricting certain electronic activities from being matched to record objects also reduces the amount of noise in systems of record as scheduling related electronic activities add noise to the system of record.

It should be appreciated that certain tags, such as scheduling tags can be used to filter out electronic activities from a queue of electronic activities that the system 200 may attempt to match to record objects. Other such types of tags may include personal tags indicating that the electronic activity is personal, internal tags indicating that the electronic activity as internal to a company, among others.

The tagging engine 265 can further identify certain types of electronic activities that may enhance the generation of the node graph or further define roles of nodes. For instance, in an out of office email response, a person may identify a second person to contact in their absence. The tagging engine 265 can tag the electronic activity as an out of office response but further allow the node profile manager 220 to update the node profile of the nodes to indicate the potential relationship between the person who is out of office and the second person to contact in their absence or create a new node profile for that person if such a node profile doesn't yet exist.

The tagging engine 265 can assign additional tags, such as vacation tags that can be used by the node profile manager 220 to update the node profile of the node accordingly. The tagging engine 265 can assign a vacation tag to an electronic activity responsive to determining that the electronic activity corresponds to the person being on vacation. The node profile manager 220 can parse the timing of the vacation from the electronic activity and update the node profile of the person on vacation. This information can then be passed to one or more systems of record and cause the systems of record to update their settings for the given person.

In addition, the tagging engine 265 can be configured to assign a 'no longer with company' tag to an electronic activity responsive to parsing the electronic activity. This information can then be passed to one or more systems of record and cause the systems of record to update their settings for the given person. In addition, the 'no longer with company' tag can cause the system 200 to stop future emails to be sent to the person, and also trigger the system 200 to determine which company that person joined.

In some embodiments, the tagging engine 265 can be configured to assign a 'parental leave' tag to an electronic activity responsive to parsing the electronic activity. The parental leave tag can be helpful to predict when a person may be returning to work. In addition, the system 200 can assign a parental leave tag to a node profile and further associate the node profile to one or more other nodes or persons that have been identified as taking over the responsibilities of the person on parental leave.

In some embodiments, the tagging engine 265 can tag an electronic activity with a deceased tag responsive to parsing the electronic activity. In some embodiments, the system 200 can then update the associated node profile indicating that the person is deceased.

In some embodiments, the tagging engine 265 can identify a unique electronic activity identifier for the electronic activity and generate a plurality of tags to assign to the electronic activity. The tagging engine 265 can generate tags to indicate if the electronic activity is external or internal, the participants associated with the electronic activity, an amount of time to generate or perform the electronic activity, job titles or seniority levels of the participants based on their job titles, departments in the organization, to which participants may belong based on their job titles, any values, opportunities or record objects with which the electronic activity may be linked or otherwise associated, one or more stages of the sales opportunity or any other system of record process, among others.

The tagging engine 265 can be configured to assign custom tags based on one or more tagging policies of one or more users or subscribers of the system 200. For instance, a subscriber of the node graph generation system 200 may desire to generate custom tags that allows the subscriber to tag all electronic activity including ride sharing receipts that identify the company's address. The subscriber may choose to then use these tags to identify all electronic activity that include ride sharing receipts that identify the company's address to gather information about the employees' use of ride sharing to and from work. The subscriber can use the information to improve business processes, such as considering providing a shuttle service to employees or negotiating with a ride sharing company for discounted pricing. The tagging engine 265 can provide a subscriber an interface through which subscribers can define policies for assigning such custom tags.

It should be appreciated that custom tags can be defined using one or more pieces of information from electronic activities. For instance, custom tags can be defined for certain email addresses, certain names, certain combination of senders and recipients, as well as based on words, phrases or other content included in the subject line or body of an electronic activity. For instance, emails that include "legal@example.com" can be tagged as Legal. Emails that mention "cell" or "mobile" and a regex pattern that matches a cell phone number in the body of an email but not part of the signature block of the email can be tagged as Cell. Emails that include a regex pattern that matches a social security number in the body of an email can be tagged as social security number, while emails that include a regex pattern that matches a credit card number in the body of an email can be tagged as credit card number. The tagging engine 265, the filtering engine 270 or the node graph generation system 200 can then use these tags to process the electronic activities tagged with these tags in accordance to one or more processing policies, such as filtering policies described herein. The filtering policies can also be customized for a given user, company or subscriber of the system 200 such that a company can deploy rules to handle such emails in accordance with the company's specific rules.

The tagging engine 265 may iteratively tag and re-tag the same electronic activities as more information is received. The tagging engine can be configured to recalculate, re-ingest and re-featurize, and re-tag all data associated with electronic activities to further refine the tags.

The tagging engine 265 can tag electronic activities based on context derived from features of such electronic activities. As described above, the tagging engine 265 can assign tags indicating a type of meeting: in-person vs. conference call; internal vs. external, a location of the participants to determine if the meeting is an in-person meeting, a time zone of the meeting, countries associated with participants of the meetings, among others.

In some embodiments, the tagging engine 265 can identify if the meeting is a conference call or a web-based meeting. In some embodiments, the type of activity can determine the types of tags to assign to the activity. For instance, for meetings, the tagging engine 265 can assign the following tags: External, internal, in-person, conference call, and custom tags, based on NLP, regex and other rules, customized by the user. For emails, the tagging engine 265 can assign the following tags: External, internal, sent, received, blast, cold. In some embodiments, blast detection techniques can be used to determine if the email is a blast email. These techniques include natural language processing analysis, blast email header analysis, volume of electronic activity for a given node, as well as MIME message data. Generally, blast emails do not include a Blast Message ID that is common across all of the blast emails. As such, detecting an email as a blast email is quite complex. In fact, blast emails are generally generated to appear as non-blast emails and as such, the present disclosure provides techniques that are based on the low variability of language complexity and word count. In some embodiments, the blast email tag assigned can include metadata identifying, for instance, the number of emails in a blast, the tool used to send the blast. The blast email tag can be used to group all emails of the blast and can include metadata about the group of emails. The tagging engine can deploy artificial intelligence to stitch the blast message ID together across multiple emails to identify if a portion of a message ID is common across multiple emails. For calls, the tagging engine 265 can assign tags to the call indicating if the call was electronically logged or manually entered. The call can be tagged based on the caller and the receiver, duration, disposition, etc.

In some embodiments, the tagging engine 265 can employ custom policies for tagging electronic activities. For instance, the tagging engine can tag every first meeting with a company as a new business meeting. The tagging engine can tag every meeting with a CXO title, such as CEO, CMO, COO, CLO, CFO, CSO, as CXO. The tagging engine can tag every meeting with CFO as finance. A reporting engine can then use these tags to generate custom reports for instance, a report identifying all new business meetings, or all activities involving finance, among others.

Tags can also be assigned for certain words, such as product names, taglines, competitor mentions, among others. By parsing emails of employees to identify the use of certain words or phrases specifically defined for a particular entity, the tagging engine can tag such electronic activities to particular products and use such electronic activities to determine if training is needed, if the correct messaging is being used or if the employees are implementing the latest messaging outlined by the company. For instance, a company can train reps to say X, but then train reps to say Y, and then use tags (from NLP) to determine which reps actually say Y. For example, if a company has 18,000 sales reps, how does the company ensure their employees are using the new training or actively selling a new product. In addition, the tagging engine 265 can apply policies to tag electronic activities based on a sentiment analysis. For instance, the tagging engine 265 can apply employee activities tags based on, negative or positive sentiment with the mention of the company's competitor or the company's feature.

In some embodiments, the tagging engine 265 can assign tags based on predicting likelihood of deal or business process completion and time to completion from electronic activities. Additional details regarding how this is determined is described herein and based in part on stage classification and the roles of the participants in the electronic activities.

In some embodiments, tags can be defined by rules. Some rules can be global rules, company rules defined by company, team level rules and user level rules.

H. Filtering Engine

The filtering engine 270 can be any script, file, program, application, set of instructions, or computer-executable code that is configured to enable a computing device on which the filtering engine 270 is executed to perform one or more functions of the filtering engine 270 described herein.

The filtering engine 270 can use information identified, generated or otherwise made available by the tagging engine 265. The filtering engine 270 can be configured to block, remove, redact, delete, or authorize electronic activities tagged or otherwise parsed or processed by the tagging engine 265. For example, the tagging engine 265 can be configured to assign tags to electronic activities, node profiles, systems of record 9360, among others. The filtering engine 270 can be configured with a policy or rule that prevents ingestion of an electronic activity having a specific tag or any combination of tags, such as a credit card tag or social security tag. By applying filtering rules or policies to tags assigned to electronic activities, node profiles, or records from the one or more systems of record, among others, the node graph generation system 200 can be configured to block, delete, redact or authorize electronic activities at the ingestion step or redact out parts or whole values of any of the fields in the ingested electronic activities. Additional details about some of the types of filtering based on tags are provided herein.

I. Source Health Scores Including Field-Specific Health Scores, Overall Health Scores and Determining Trust Scores Based on Health Scores The source health scorer 215 can be any script, file, program, application, set of instructions, or computer-executable code that is configured to enable a computing device on which the source health scorer 215 is executed to perform one or more functions of the source health scorer 215 described herein. The source health scorer 215 is configured to access a system of record and retrieve all data stored in the system of record. The source health scorer 215 can then identify each record object stored in the system of record and determine, for each record object, a number of missing values of fields. The source health scorer can then generate a field-specific score for each field indicating a health or quality of each field of the system of record. The source health scorer 215 can further determine an overall health score for the source based on the field-specific scores of each field. In some such embodiments, the overall health score is based on missing field values.

The source health scorer 215 can further be configured to determine if the values of fields of record objects are accurate by comparing the values to node profiles maintained by the node profile manager 220 or to record objects maintained by the record objects manager. Based on the number of values that are inconsistent with the values maintained by the node graph generation system 200, the source health scorer can generate a health score for the system of record.

The source health scorer 215 can similarly generate a health score for each system of record. The source health scorer 215 can then compare the health score of a given system of record to the aggregate health scores of a plurality of systems of record to determine a relative trust score of the system of record. In some embodiments, the source health scorer 215 can assign different weights or scores to different types of systems of record. The source health scorer 215 may assign lower health scores to data included in a system of record that is generated using manual entry relative to node profiles that are automatically populated or generated by the node graph generation system 200 based on electronic activities.

Further, different types of sources can include emails, or email signatures within an email, one or more systems of record, among many other source types. The trust score of a source can be determined based on the health score of the source, at least in the case of a system of record. In some embodiments, the trust score assigned to electronic activity such as an email can be greater than a trust score assigned to a data point derived from a system of record as the system of record can be manually updated and changed. Additional details regarding the health score of a system of record are described below.

In some embodiments, the health score of a system of record maintained by a data source provider can be determined by comparing the record objects of the system of record with data that the system has identified as being true. For instance, the system 200 can identify, based on confidence scores of values (as described below) of fields, that certain values of fields are true. For instance, the system may determine that a value is true or correct if multiple data points provide support for the same value. In some embodiments, the multiple data points may for example, be at least 5 data points, at least 10 data points, or more. The system 200 can then, for a value of a field of a record object of the system of record, compare the value of the system of record to the value known to the system to be true. The system can repeat this for each field of a record object to determine if any values of a record object are different from the values the system knows to be true. In some embodiments, when determining the health score, the system may only compare those values of fields of record objects of the system of record that the system has a corresponding value that the system knows is true. For instance, the system may know that a phone number of a person "Roger Nadal" is 617-555-3131 and may identify such a number as true based on multiple data points. However, the system may not know an address of the person Roger Nadal. In such an instance, the system may only compare the phone number of the record object corresponding to Roger Nadal to determine the health score of the system of record but not compare the address of the person Roger Nadal as the system does not know the address of Roger Nadal. Furthermore, even if the node profile of Roger Nadal had an address but the confidence score of the address was below a predetermined threshold, the system would not compare the address from the system of record to the address of the node profile since the system does not have enough confidence or certainty that the address is true. As such, the system can be configured to determine the health score of a system of record by comparing certain values of record objects of the system of record to values the system knows as true or above a predetermined confidence score. In this way, in some embodiments, the health score of the system of record is based on an accuracy of the data included in the system of record rather than how complete the system of record is not.

As described above, the health score of a system of record can be an overall health score that can be based on aggregating individual field-specific health scores of the system of record. It should be appreciated that the system 200 can assign different weights to each of the field-specific health scores based on a volume of data corresponding to the respective field, a number of values that does not match values the system 200 knows to be true, among others.

In certain situations, the system 200 can compute trust scores for data points based on the health score of a system of record. In some embodiments, the system 200 can compute the trust score based on the overall health score of the system of record that is the source of the data point. However, in some embodiments, it may be desirable to configure the system 200 to provide more granularity when assigning a trust score to a system of record that is the source of the data point. For instance, a company may meticulously maintain phone numbers of record objects but may not be so meticulous in maintaining job titles of record objects such that the field-specific health score for the phone number field of the system of record is much better than the field-specific health score for the job title field and also better than the overall health score of the system of record determined based on the aggregate of the respective field-specific health scores of fields of the system of record. In some embodiments, as will be described herein, if a data point supporting a phone number of a node profile is provided by the system of record, the system 200 may be configured to determine a trust score for the data point based on the field-specific health score of the field "phone number" for the system of record rather than the overall health score of the system of record, which is lower because the field-specific health score of the field "job title" of the system of record is much lower than the field-specific health score of the field "phone number." By determining trust scores based on the field-specific health scores of systems of record, the system 200 may be able to more accurately rely on the data point and provide a more accurate contribution score of the data point as will be described herein. Additional concepts relating to health scores and trust scores are provided herein with respect to section 5 relating to monitoring health scores of systems of record.

J. Node Field Value Confidence Scoring

The attribute value confidence scorer 235 can be any script, file, program, application, set of instructions, or computer-executable code, that is configured to enable a computing device on which the attribute value confidence scorer 235 is executed to perform one or more functions of the attribute value confidence scorer 235 described herein. The attribute value confidence scorer 235 can be configured to determine a confidence of each value of an attribute of a node profile. The confidence of a value is determined based in part on a number of electronic activities or sources that contribute to the value, time since each electronic activity provided support or evidence of the value, time since the field value in the source system of record was last modified or confirmed by a human operator, as well as the source of the electronic activity. Electronic activity that is received from mail servers or another source that does not involve manual entry may be assigned a greater weight (or trust/health score) than a source that involves manual entry, such as a customer relationship management tool.

The attribute value confidence scorer 235 can be configured to determine a confidence of each value of an attribute of a node profile. An attribute or field can have multiple candidate values and the value with the highest confidence score can be used by the node graph generation system for confirming or validating the value of the field. The attribute value confidence scorer 235 can apply one or more scoring algorithms to determine the likelihood that each value is a correct value of the attribute. It should be appreciated that a value does not need to be current to be correct. In some embodiments, as new entities are onboarded into the system, electronic activities and systems of record corresponding to systems of record of the new entities can be processed by the system 200. In processing these electronic activities and systems of record, some electronic activities can be associated with dates many years in the past. Such electronic activities are not discarded. Rather, the system processes such electronic activities and information extracted from these electronic activities are used to populate values of fields of node profiles. Since each data point is associated with a timestamp, the data point may provide evidence for a certain value even if that value is not a current value. One example of such a value can be a job title of a person. The person many years ago may simply have been an associate at a law firm. However, that person is now a partner at the firm. If emails sent from this person's email account are processed by the system 200, more recently sent emails will have a signature of the person indicating he's a partner, while older emails will have a signature of the person indicating he's an associate. Both values, partner and associate are correct values except only partner is the current value for the job title field. A confidence score of the current value may be higher in some embodiments as data points that are more recent may be assigned a higher contribution score than data points that are older. Additional details about contribution scores and confidence scores are provided below.

In some embodiments, a node profile can correspond to or represent a person. As will be described later, such node profiles can be referred to as member node profiles. The node profile can be associated with a node profile identifier that uniquely identifies the node profile. Each node profile can include a plurality of attributes or fields, such as First name, Last name, Email, job title, Phone, LinkedIn URL, Twitter handle, among others. In some embodiments, a node profile can correspond to a company. As will be described later, such node profiles can be referred to as group node profiles. The group node profile can be similar to the member node profile of a person except that certain fields may be different, for example, a member node profile of a person may include a personal cell phone number while a group node of a company may not have a personal cell phone number but may instead have a field corresponding to parent company or child company or fields corresponding to CEO, CTO, CFO, among others. As described herein, member node profiles of people and group node profiles of companies for the most part function the same and as such, descriptions related to node profiles herein relate to both member node profiles and group node profiles. Each field or attribute can itself be a 3-dimensional array. For instance, the First name attribute can have two values: first name_1|first name_2, one Last name value and three email address values email_A|email_B|email_C. Each value can have an Occurrence (counter) value, and for each occurrence that contributes to the Occurrence value, there is an associated Source (for example, email or System of record) value and an associated timestamp (for example, today, 3:04 pm PST) value. In this way, in some embodiments, each value of a field or attribute can include a plurality of arrays, each array identifying a data point or an electronic activity, a source of the data point or electronic activity, a time associated with the data point or electronic activity, a contribution score of the data point or electronic activity and, in some embodiments, a link to a record of the data point or electronic activity. It should be appreciated that the data point can be derived from a system of record. Since systems of records can have varying levels of trust scores, the contribution score of the data point can be based on the trust score of the system of record from which the data point was derived. Stated in another way, in addition to each attribute being a 3-dimensional array, in some embodiments, each value of an attribute can be represented as a plurality of arrays. Each array can identify an electronic activity that contributed to the value of the attribute, a time associated with the electronic activity and a source associated with the electronic activity. In certain embodiments, the sub-array of occurrences, sources and times can be a fully featured sub-array of data with linkage to where the data came from.

K. Node Profile Inferences

Certain information about a node can be inferred by the node graph generation system 200 based on information included in electronic activities ingested by the system 200. For instance, the node profile manager 220 or the electronic activity tagging engine 265 can infer if a person has left a job or switched jobs if the occurrence counter for a first value stops increasing or the frequency at which the occurrences of the first value appear has been reduced and the occurrence counter for a second value is increasing or the occurrences are more recent or are received from a source that has a higher trust score indicating that the person has changed email addresses, which can indicate that the person has switched jobs. In certain embodiments, the system 200 can determine if the second value corresponds to an email address corresponding to another employer or another company. In some embodiments, the system 200 can determine if the domain name of the email address corresponds to a list of known domain names corresponding to personal, non-work email addresses (for instance, gmail.com, outlook.com), among others. In some embodiments, the system 200 can determine if the domain name is associated with a predetermined minimum number of accounts with the same domain name. The node profile manager 220 can look at relevancy of Source, recency of time and Occurrences to determine whether to update the email field from the first email (Email_A) to the second email (Email_B).

In some embodiments, the attribute value confidence scorer 235 described herein can provide mechanisms to confirm validity of data using multiple data sources. For instance, each electronic activity can be a source of data. As more electronic activities are ingested and increase the occurrence of a value of a data field, the system can confirm the validity of the value of the field based on the number of occurrences. As such, the system described herein can compute a validity score of a value of a field of a node profile based on multiple data sources. For instance, the system can determine how many data sources indicate that the job title of the person is VP sales and can use the health score of those sources to compute a validity score or confidence score of that particular value. In addition, the timestamp associated with each electronic activity can be used to determine the validity score or confidence score of that particular value. More recent electronic activities may be given greater weight and therefore may influence the validity score of the particular value more than electronic activity that is much older.

It should be appreciated that electronic activity that is generated and ingested in real-time or near real-time can be assigned a greater weight as the electronic activity has no bias, whereas data input manually into a system of record may have some human bias. In certain embodiments in which data is imported from systems of records, the weight the data has on a confidence score of the value is based on a trust score of the system of record from which the data is imported.

In some embodiments, the attribute value confidence scorer 235 can determine a confidence score of a data point based on the data sources at any given time. A data point can be a value of a field. For example, "VP, product" can be a value for a job title of a node profile. The attribute value confidence scorer 235 can utilize the electronic activities ingested in the system to determine how many electronic activities have confirmed that the value for the job title is VP, product for that node in the email signatures present in those electronic activities. In some embodiments, the attribute value confidence scorer 235 can take into account a recency of the activity data and the source type or a health score of the source type to determine the confidence score of the value of the field. In some embodiments, the node profile manager can determine a current value of a field based on the value of the field having the highest confidence score.

L. Stitching Time Series Together

The system can be configured to maintain a time series array for each field of a node profile that can be used to determine a timeline of events associated with the node. The system can maintain the time series array based on time-stamps of all data sources of all values for each field of the node. For instance, the timeline can be used to determine a career timeline with work history information, a series of job title changes indicating promotions, among other things. In addition, the timeline of events can track a person's movement across companies or geographic locations over time as well as a list of other nodes or persons the company has been affiliated or associated with at different points in time. For instance, the job title of a node profile can include the following values over a period of time: director|vp sales|president|CEO. In certain embodiments, each of the values of the title can have an increase in a confidence score at different times and as a confidence score of a given value of the title field increases, the confidence score of the preceding value of the title field decreases.

M. Node Connections

The node pairing engine 240 can be any script, file, program, application, set of instructions, or computer-executable code that is configured to enable a computing device on which the node pairing engine 240 is executed to perform one or more functions of the node pairing engine 240 described herein. The node pairing engine 240 can compute a connection strength between nodes based on electronic activity associated with both of the nodes. More of the recent electronic activity between the two nodes will indicate a greater connection strength. Moreover, with different tags assigned to those electronic activities, the node pairing engine 240 can further determine the relationship between the two nodes and the context in which the two nodes are connected. For instance, two nodes may be connected through their work on one or more opportunities or one node may report to the second node, among others. The context behind the relationships can be derived from the electronic activity associated with the two nodes as well as other electronic activity associated with each node independent of the other node. In certain embodiments, the node pairing engine 240 can use metadata from the electronic activities to infer connection strength or relationships. For instance, the node pairing engine can compute an average time a node takes to respond to another node and use the average time to respond to determine a connection strength. In some embodiments, the average time to respond is inversely proportional to the strength of the connection. Furthermore, the node pairing engine 240 can look at other information relating to the electronic activities to infer connection strengths. If a node responds to another node outside of business hours can be an indicator of connection strength or connection relationships.

The node pairing engine 240 can determine a connection strength between nodes at a given point in time across a timeline. As the nodes exchange further electronic activity, the connection strength can increase. The system is configured to determine the connection strength at a particular time period by filtering the electronic activities based on their respective times. In certain embodiments, the node pairing engine 240 can recalculate a connection strength between nodes responsive to a trigger. In some embodiments, the trigger can be based on a confidence score falling below a predetermined threshold indicating that the confidence in a particular value is unstable or unusable. For instance, the trigger can be satisfied or actuated when the node pairing engine 240 determines that the confidence score of a particular value of a field, such as a current employer of a person is below a predetermined confidence score (indicating that the person may no longer be at a particular company). In certain embodiments, certain changes to values in fields can trigger recalculating a connection strength irrespective of activity volume, for instance, when a new value under the employer field is added in the node.

In some embodiments, the node pairing engine 240 can determine a connection strength between two nodes by identifying each of the electronic activities that associate the nodes to one another. In contrast to other systems that may rely on whether a node has previously connected with another node, the node pairing engine 240 can determine a connection strength at various time periods based on electronic activities that occur before that time period. In particular, the node pairing engine 240 can determine staleness between nodes and take the staleness to determine a current connection strength between nodes. As such, the node pairing engine 240 can determine a temporally changing connection strength. For instance, the node pairing engine 240 can determine how many interactions recently between the two nodes. The node pairing engine 240 can determine whether the connection between the two nodes is cold or warm based on a length of time since the two nodes were involved in an electronic activity or an amount of electronic activity between the two nodes. For instance, the node pairing engine 240 can determine that the connection strength between two nodes is cold if the two nodes have not interacted for a predetermined amount of time, for instance a year. In some embodiments, the predetermined amount of time can vary based on previous electronic activity or past relationships by determining additional information from their respective node profiles. For instance, former colleagues at a company may not have a cold connection strength even if they do not communicate for more than a year.

Figure 8:
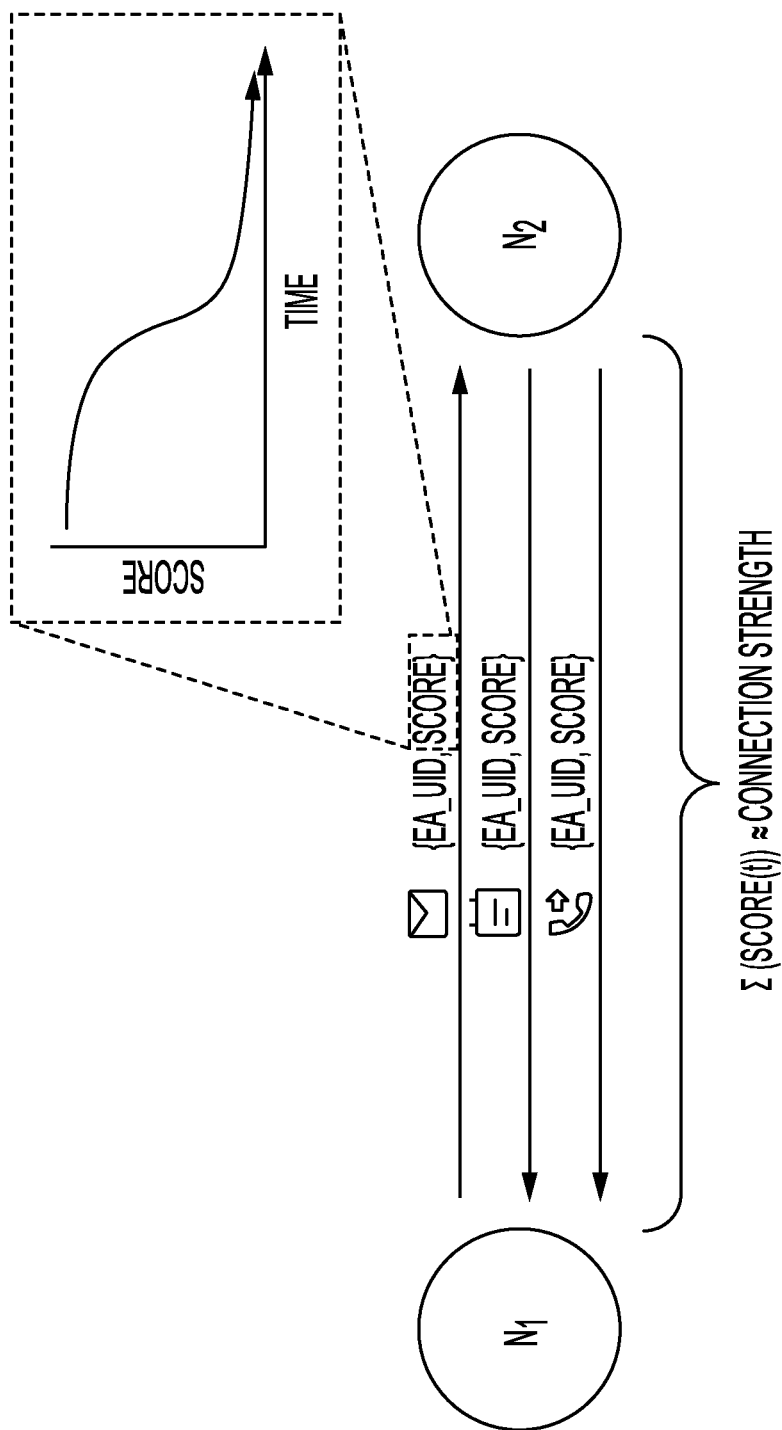
FIG. 8 illustrates electronic activities involving two nodes and the impact a time decaying score has on the connection strength between the two nodes according to embodiments of the present disclosure.

Referring briefly to FIG. 8, FIG. 8 illustrates electronic activities involving two nodes and the impact a time decaying relevancy score has on the connection strength between the two nodes. As shown in FIGS. 8, N1 and N2 may exchange a series of electronic activities. The node pairing engine 240 or the system 200 can maintain a log of each of the electronic activities involving both nodes. Each electronic activity can have a unique electronic activity identifier and can identify a type of activity and maintain a time decaying relevancy score that can decrease in strength over time as time goes by. The node pairing engine 240 can compute the connection strength in part by taking the sum of the respective time decaying relevancy score of each of the electronic activities between the two nodes. In some embodiments, the node pairing engine 240 can take into account other factors for computing the connection strength, for instance, by comparing one or more fields of the node profiles. For instance, nodes that belong to the same organization, report to each other via a clear reporting logic (and lack of reporting up alternative nodes) or have previously worked together can contribute to the connection strength between the nodes.

In certain embodiments, the node pairing engine 240 can determine that a first node reports to a second node based on monitoring electronic activity exchanged between the two nodes as well as electronic activity that includes both nodes. In some embodiments, the node pairing engine 240 can apply one or more rules to predict a relationship between two nodes based on the metadata information associated with the electronic activities including both nodes.

In some embodiments, the connection strength between two nodes can be greater if the node pairing engine 240 can determine, from the electronic activities involving the two nodes, a type of relationship between the two nodes. For instance, if the node pairing engine 240 can determine that one of the nodes is the only known superior node and the other of the nodes is the likely subordinate (instead of simply knowing that the two nodes are colleagues or on the same team), the node pairing engine 240 can increase the connection strength between the two nodes.

In some embodiments, the node pairing engine 240 can be configured to determine the connection strength between two nodes by monitoring the type of electronic activities exchanged between them, the time of day, the day of the week, the mode of communication (email versus telephone versus text message versus office phone versus cell phone), and the duration of such communications. The system 200 can determine that if two nodes are communicating over a weekend, the connection is stronger than other connections that may only have communications limited to weekdays during office hours. The system 200 can also determine that the connection strength between two nodes may be strong if the two nodes are responding to each over the weekend, if they follow up with phone calls after receiving emails, or other patterns that may indicated a strong connection strength.

The node pairing engine 240 can be configured to identify a plurality of node pairs that have a strong connection strength. The node pairing engine 240 can then apply machine learning techniques to analyze electronic activities between the nodes of the node pair as well as analyze the node profiles of each node and the nodes to which each of the nodes are connected. The node pairing engine 240 can then generate a connection strength determination model that can be configured to determine the connection strength between two nodes using the model that is trained on node pairs known to have a strong connection strength. In some embodiments, the node pairing engine can further train the model with node pairs that have a weak connection strength in a similar fashion.

The node parsing engine 240 or the tagging engine 265 can further tag the connection between the nodes as professional, personal, colleagues, ex-colleagues, alumni, classmates, among others. These tags can be updated as more and more electronic activities are processed over time and the confidence score of these tags can be adjusted accordingly. The connection strength between nodes can be used by companies to determine which employee to assign to leads, accounts, or opportunities based on the node's connections strengths with the lead, employees at the account, and employees of the account that may likely be working on the opportunity. Additional details about assigning employees to record such record objects are described below with respect to Section 12.

N. Node Resolution

The node resolution engine 245 can be any script, file, program, application, set of instructions, or computer-executable code that is configured to enable a computing device on which the node resolution engine 245 is executed to perform one or more functions of the node resolution engine 245 described herein.

The node resolution engine 245 is configured to resolve nodes to which electronic activities are to be linked or otherwise associated. The node resolution engine 245 can use the parsed information from the electronic activity to identify values included in node profiles to determine a match score between the electronic activity and a given node profile. The node resolution engine 245 can match the electronic activity to one or more node profiles based on a match score between the electronic activity and each of the node profiles exceeding a certain threshold. Different fields are assigned different weights based on the uniqueness of each value. In some embodiments, the uniqueness of each value can be determining how many node profiles include the same value for the given field relative to the total number of node profiles.

In some embodiments, the node resolution engine 245 may match the electronic activity to the nodes between which the electronic activity occurred. The node resolution engine 245 or the node pairing engine can establish an edge between the two nodes corresponding to the electronic activity.

In some embodiments, the node resolution engine 245 may not be able to determine if the electronic activity matches any of the existing node profiles maintained by the node profile manager. In some such embodiments, the node resolution engine 245 can cause a new node profile to be generated and populated with values extracted from the electronic activity. Before the node resolution engine 245 or other module of the system 200 determines to generate a new node, the node resolution engine 245 can be configured to execute a node creation process. In some embodiments, the node resolution engine 245 can determine if the metadata of the electronic activity has attributes that are high confidence that match, such as phone number, LinkedIn ID, or email address. At the initial stage, the node resolution engine 245 can create a temporary node because not enough information is known to match the electronic activity to an existing node. As a response to the electronic activity is received, additional information can be parsed from the response to the electronic activity, which can then be used to further populate the temporary node. The temporary node can then be matched to existing node profiles to determine if an existing node matches the temporary node. If so, the temporary node can be merged with the existing node profile. In some embodiments, the process of merging involves appending the temporary node with another node because there might be mutually exclusive information that should be added.

In some embodiments, the node resolution engine 245 can perform identity resolution or deduplication based on one or more unique identifiers associated with a node profile. For instance, if one system of record provides a first email address, uniquename@example1.com and another system of record provides a second email address, uniquename@example2.com, while there is not a direct match, the node resolution engine 245 can resolve the two identifiers if there is a statistically significant number of matching or near matching fields, tags, or other statistical resemblances.

In particular, the node resolution engine 245 can parse the string before the @ in the email to determine one or more of a first name and last name of the person. The node resolution engine 245 can apply several techniques to do so. First, the node resolution engine 245 can check to see if there are any rules in place for the domain name of the email that indicate a particular pattern for assigning email addresses by the domain. For instance, does the company associated with the domain assign email addresses using any of the following conventions: firstname.lastname@domainname.com, FirstInitialLastname@domainname.com, firstname@domainname.com, among others. This can be determined by looking at node profiles (and email addresses) of other people belonging to the same company. Second, the node resolution engine 245 can parse the string before the @ to attempt to recognize names from the strings. The node profile manager 220 maintains node profiles that include first names and last names and as such, the node resolution engine 245 can attempt to match a sequence of characters in the string to the list of first names and last names to see if certain names are included in the string. Upon identifying names from the string, the node resolution engine 245 can determine if the name is typically a first name or a last name based on a frequency of such names being first names or last names. Upon identifying the names with some level of statistical confidence, the node resolution engine 245 can identify a first name and a last name of a person associated with the email address and may use the first name, the last name and the company name to try and match the email address to an existing node profile of the person.

In some embodiments, the node resolution engine 245 or the node profile manager 220 can build a frequency distribution of first and last names from information included in the node profiles maintained by the node profile manager 220. The node resolution engine 245 can determine from a full name, a first name and a last name based on certain names being more common as last names and other names being more common as first names. The node resolution engine 245 can then determine a domain of the email. The node resolution engine can then calculate the probability that the string before the @ in the email corresponds to a person.

In some embodiments, the node resolution engine 245 can further determine if additional fields that could be matching—such as a social handle or a phone number to then have more surface to compare one node to other nodes to identify if any of the nodes can be merged.

In some embodiments, the node resolution engine can utilize time zone detection to resolve if two nodes belong to the same person. The system 200 can compute a time zone of each node by monitoring their electronic activities and deducing that the time zone they are in is based on the times at which the electronic activities are ingested by the system 200. For instance, the node resolution engine 245 can determine that two nodes are different if the time zones deduced from their electronic activity match different time zones.

In some embodiments, the node resolution engine 245 can be configured to periodically perform deduplication by comparing each node to every other node to determine if two nodes can be merged.

O. Systems of Record Data Extraction

The record data extractor 230 can be any script, file, program, application, set of instructions, or computer-executable code, that is configured to enable a computing device on which the record data extractor 230 is executed to perform one or more functions of the record data extractor 230 described herein.

The record data extractor 230 can be configured to extract data from one or more records of one or more systems of record. The record data extractors 230 can identify record objects included in a system of record and extract data from each of the record objects, including values of particular fields. In some embodiments, the record data extractor 230 can be configured to extract values of fields included in the record object that are also included in the node profile maintained by the node graph generation system 200.

P. Linking Electronic Activity to Systems of Record Data

The electronic activity linking engine 250 can be any script, file, program, application, set of instructions, or computer-executable code, that is configured to enable a computing device on which the electronic activity linking engine 250 is executed to perform one or more functions of the electronic activity linking engine 250 described herein. Additional details regarding the electronic activity linking engine is provided below.

Q. Systems of Record Record Object Management

The record object manager 255 can be any script, file, program, application, set of instructions, or computer-executable code that is configured to enable a computing device on which the record object manager 255 is executed to perform one or more functions of the record object manager 255 described herein. The record object manager 255 can be configured to maintain data regarding record objects of multiple systems of record and can be configured to augment information for a record object by extracting information from multiple record objects across a plurality of systems of record. The record object manager 255 can function as a systems of record object aggregator that is configured to aggregate data points from many systems of record, calculate the contribution score of each data point, and a timeline of the contribution score of each of those data points. The record object manager 255 or the system 200 in general can then enrich the node graph generated and maintained by the node graph generation system 200 by updating node profiles using the data points and their corresponding contribution scores. In certain embodiments, the record object manager 255 can be further configured to utilize the data from the node graph to update or fill in missing data in a target system of record provided the data in the node graph satisfies a predetermined confidence value. Additional details regarding the record object manager 255 is provided below.

R. Organizational Node Graph

The data source provider network generator 260 can be any script, file, program, application, set of instructions, or computer-executable code, that is configured to enable a computing device on which the data source provider network generator 260 is executed to perform one or more functions of the data source provider network generator 260 described herein. Additional details relating to the functionality of data source provider network generator 260 are provided below with respect to the generation of a company cloud described in Section 9.

2. Systems and Methods for Linking Electronic Activity to Systems of Record

At least one aspect of the disclosure relates to systems and methods of linking electronic activities to record objects of systems of record. The linking can be performed by the electronic activity linking engine 250 (and other components) of the node graph generation system 200 illustrated in FIG. 4.

Enterprises and other companies spend significant amount of resources to maintain and update one or more systems of records. Examples of systems of records can include customer relationship management (CRM) systems, enterprise resource planning (ERP) systems, document management systems, applicant tracking systems, among others. Typically, these systems of records are manually updated, which can result in multiple issues. First, the information that is updated into the systems of records can be incorrect either due to human error or in some cases, malicious intent. Second, the information may not be updated in a timely manner. Third, employees may not be motivated enough to even update the systems of records, resulting in systems of records that include outdated, incorrect, or incomplete information. To the extent that enterprises rely on the data included in their systems of records to make projections or predictions, such projections and predictions may also be inaccurate as the data relied upon is also inaccurate. The present disclosure aims to address these challenges that enterprises face with their existing systems of records. In particular, the present disclosure describes systems and methods for linking electronic activities to record objects included in one or more systems of record. Electronic activities, such as electronic mail, phone calls, calendar events, among others, can be used to populate, update, and maintain states of record objects of systems of record. As electronic activities are exchanged between users, these electronic activities can be parsed to not only update a node graph as described above, but further update shadow record objects for one or more systems of records of enterprises that have provided access to such systems of record to the data processing system 9300 shown in FIG. 3 or the node graph generation system 200. As described herein, the shadow record objects can be synced with the record objects of the one or more systems of records of the enterprises. In some embodiments, the electronic activities can be used to directly update the one or more systems of records of the enterprises without first updating a shadow record object. As described herein, and also referring to FIG. 3, the updating of record objects with electronic activity can refer to updating record objects within systems of record 9360 and/or shadow record objects within the shadow systems of record. By way of the present disclosure, the node graph generation system 200 can use the electronic activities to populate, maintain, and update states of record objects of systems of record.

As described herein, the node graph generation system 200 can include the electronic activity linking engine 250 that is configured to link electronic activities to record objects of one or more systems of record. By linking the electronic activities to such record objects, the electronic activity linking engine 250 can be configured to update states of one or more record objects based on the electronic activities.

Linking electronic activities to record objects can also be referred to as matching or mapping the electronic activities to record objects. Linking the electronic activities to the record objects can provide context to the electronic activities. The linked electronic activities can be stored in association with one or more record objects to which the electronic activity is linked in a system of record. Linking an electronic activity to a record object can provide context to the electronic activity by indicating what happened in the electronic activity or record object, who was involved in the electronic activity or record object, and to what contact, node, person or business process, the electronic activity or record object should be assigned. Linking the electronic activity to the record object can indirectly provide context as to why the electronic activity occurred. For example, the linking of electronic activity, such as an email, to a lead record object (in the context or a customer relationship management system) can provide context to the email that the email was sent to establish or further a lead with the intent of converting the lead into an opportunity (and the lead record object into an opportunity record object). Although the description provided herein may refer to record objects and business processes corresponding to customer relationship management systems, it should be appreciated that the present disclosure is not intended to be limited to such systems of records but can apply to many types of systems of record including but not limited to enterprise resource planning systems, document management systems, applicant tracking systems, among others. For the sake of clarity, it should be appreciated that electronic activities can be matched to record objects directly without having to link the electronic activities to node profiles. In some embodiments, the electronic activities can be matched to node profiles and those links can be used to match some of the electronic activities to record objects.

Figure 9:
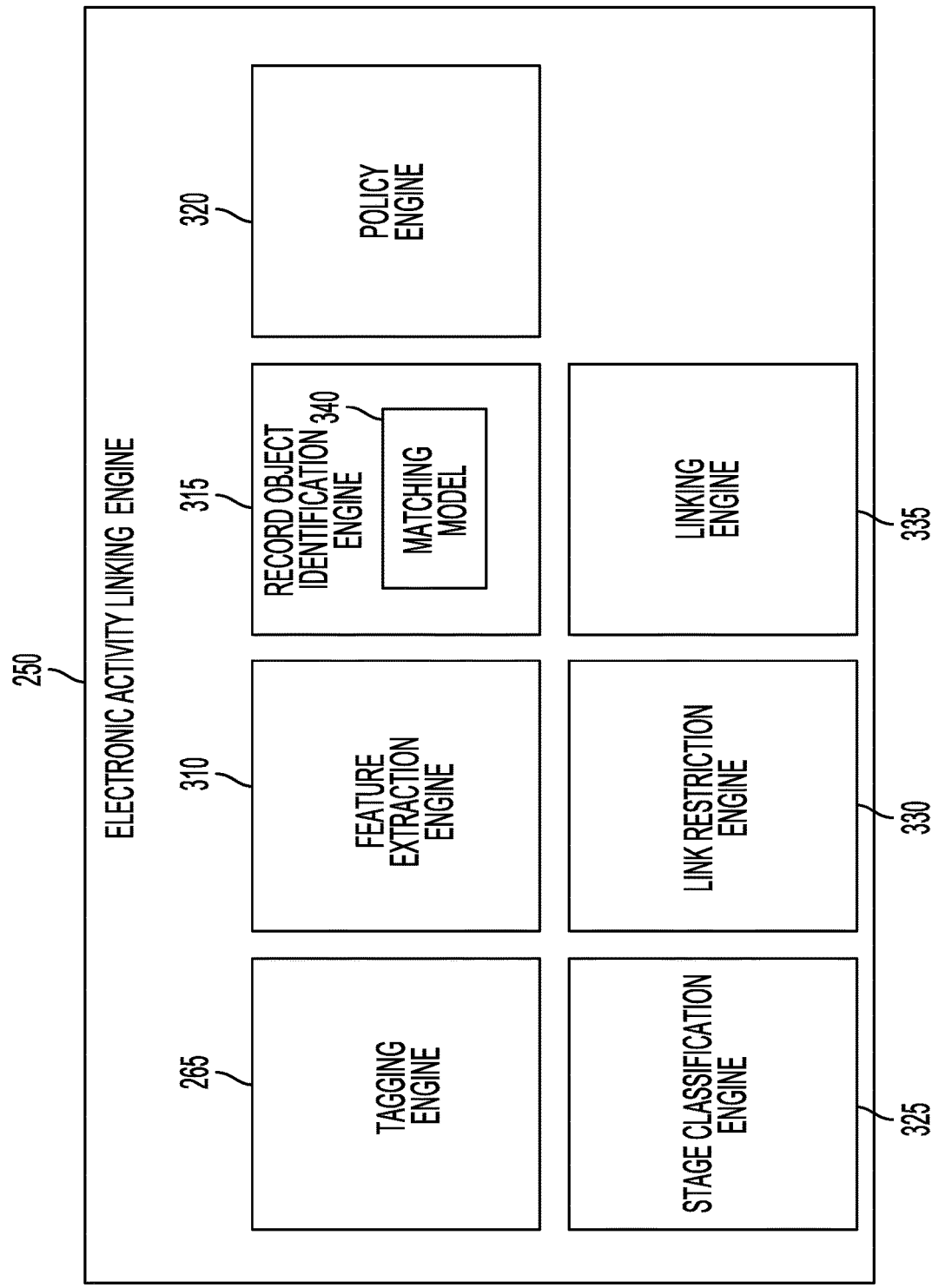
FIG. 9 illustrates a block diagram of an example electronic activity linking engine according to embodiments of the present disclosure.

Referring now to FIG. 9, FIG. 9 illustrates a block diagram of an example electronic activity linking engine 250. The electronic activity linking engine 250 can use metadata to identify a data source provider associated with an ingested electronic activity and identify a corresponding system of record. The electronic activity linking engine 250 can match the electronic activity to a record object of the corresponding system of record. The electronic activity linking engine 250 can include, or otherwise use, a tagging engine, such as the tagging engine 265 described above to determine and apply tags to the ingested electronic activities. The electronic activity linking engine 250 can include a feature extraction engine 310 to extract features from the electronic activities that can be used to link electronic activities with one or more record objects of systems of records. In some embodiments, some of the features can include values corresponding to values stored in one or more node profiles maintained by the node graph generation system 200. The features, however, can include other information that may be used to in conjunction with information also included in node profiles to link the electronic activity to one or more record objects included in one or more systems of record.

The electronic activity linking engine 250 can include a record object identification module 315 to identify which record object or objects within a system of record to match a given electronic activity. The electronic activity linking engine 250 can include a policy engine 320. The policy engine 320 can maintain policies that include strategies for matching the electronic activities to the record objects. The electronic activity linking engine 250 can include a stage classification engine 325 to determine a shadow stage for a given opportunity record object. The electronic activity linking engine 250 can include a link restriction engine 330 that can apply one or more policies from the policy engine 320 when linking electronic activities to record objects. The linking engine 250 can link the electronic activity to the record object identified by the record object identification module 315. Additional details regarding each of the components 310-335 are further provided herein.

The features extraction engine 310 of the electronic activity linking engine 250 can be any script, file, program, application, set of instructions, or computer-executable code, that is configured to enable a computing device on which the features extraction engine 310 is executed to extract or identify features from one or more electronic activities and/or corresponding node profiles maintained by the node graph generation system 200 and use the extracted or identified features to generate corresponding feature vectors for the one or more electronic activities.

The features extraction engine 310 can be a component of the electronic activity parser 210 or otherwise interface with the electronic activity parser 210 to parse electronic activities and extract features from electronic activities. For example, the electronic activity parser 210 can parse ingested electronic activities, such as, emails, calendar meetings, and phone calls. The features extraction engine 310 can, for each electronic activity, extract various features from the electronic activity and in some embodiments, from one or more node profiles corresponding to the electronic activity, that the electronic activity linking engine 250 can use to link the electronic activity to one or more record objects of the one or more systems of record. In some embodiments, before an electronic activity can be linked to a record object of a system of record, the electronic activity can be matched to one or more node profiles in the node graph. In this way, the features extraction engine 310 can generate, based on the parsed data from the electronic activity parser 210, a feature vector for the electronic activity that can be used to link the electronic activity to a record object based on features extracted from the electronic activity as well as one or more node profiles of the node graph.

The feature vector can be an array of feature values that is associated with the electronic activity. The feature vector can include each of the features that were extracted or identified in the electronic activity by the feature extraction engine 310. For example, the feature vector for an email can include the sending email address, the receiving email address, and data parsed from the email signature. Each feature value in the array can correspond to a feature or include a feature-value pair. For example, the contact feature "John Smith" can be stored in the feature vector as "John Smith" or "name: John Smith" or "first name: John" "last name: Smith." As described herein, the matching model 340 can use the feature vector to match or link the electronic activity to a record object. The feature vector can include information extracted from an electronic activity and also include information inferred from one or more node profiles of the node graph generation system 200. The feature vector can be used to link an electronic activity to at least particular record object of a system of record by matching the feature values of the feature vector to a record object. For instance, if the feature vector includes the values "John" for first name and "Smith" for last name, the electronic activity linking engine 250 can link the electronic activity to a record object, such as a lead record object that includes the name "John Smith" assuming other matching conditions are also met.

The features for an electronic activity can be explicit from the electronic activity. The explicit features can be determined from the metadata or content of the electronic activity. For example, the "sender's email address" of an email can be parsed from the email's header value, as described in relation to FIG. 5A. In some embodiments, some features for an electronic activity can be derived from the electronic activity. The derived features can be determined or implied based on explicit features of the electronic activity or determined from node profiles of the node graph described above. For example, an example electronic activity may not include a name of the company to which the sender belongs. In such a case, the feature extraction engine 310 can extract the name of the company to which the sender belongs from a node profile of the sender, which can include the name of the company. The name of the company can be retrieved from the node profile of the sender and saved as a value in the feature vector once retrieved from the node profile associated with the sender.

The features included in the feature vector for an electronic activity can include features associated with the generator (or sender) of the electronic activity and features associated with the recipient (or receiver) of the electronic activity. For example, sender's email address and the recipient's email address can both be used as features of the electronic activity. The features for an electronic activity can include, but are not limited to, a contact role, contact name, sender email address, recipient email address, domain, list of recipient email addresses, estimated effort, and time, features extracted from email contents using natural language processing, features extracted from email signature, time of the email sent/delivery, among others. The feature vectors can be used to match electronic activities to record objects of one or more systems of record.

The feature extractor engine 310 can further identify one or more tags assigned to an electronic activity or one or more node profiles associated with the electronic activity by the tagging engine 265 and include those tags or information relating to those tags in the feature vector. In some embodiments, these tags can be used to provide context to certain electronic activities, which can be used by the electronic activity linking engine 250 to link electronic activities to record objects of one or more systems of records.

The record object identification module 315 can be any script, file, program, application, set of instructions, or computer-executable code, that is configured to enable a computing device on which the record object identification module 315 is executed to determine or select one or more record objects to which an electronic activity should be linked or matched.

Figure 10:
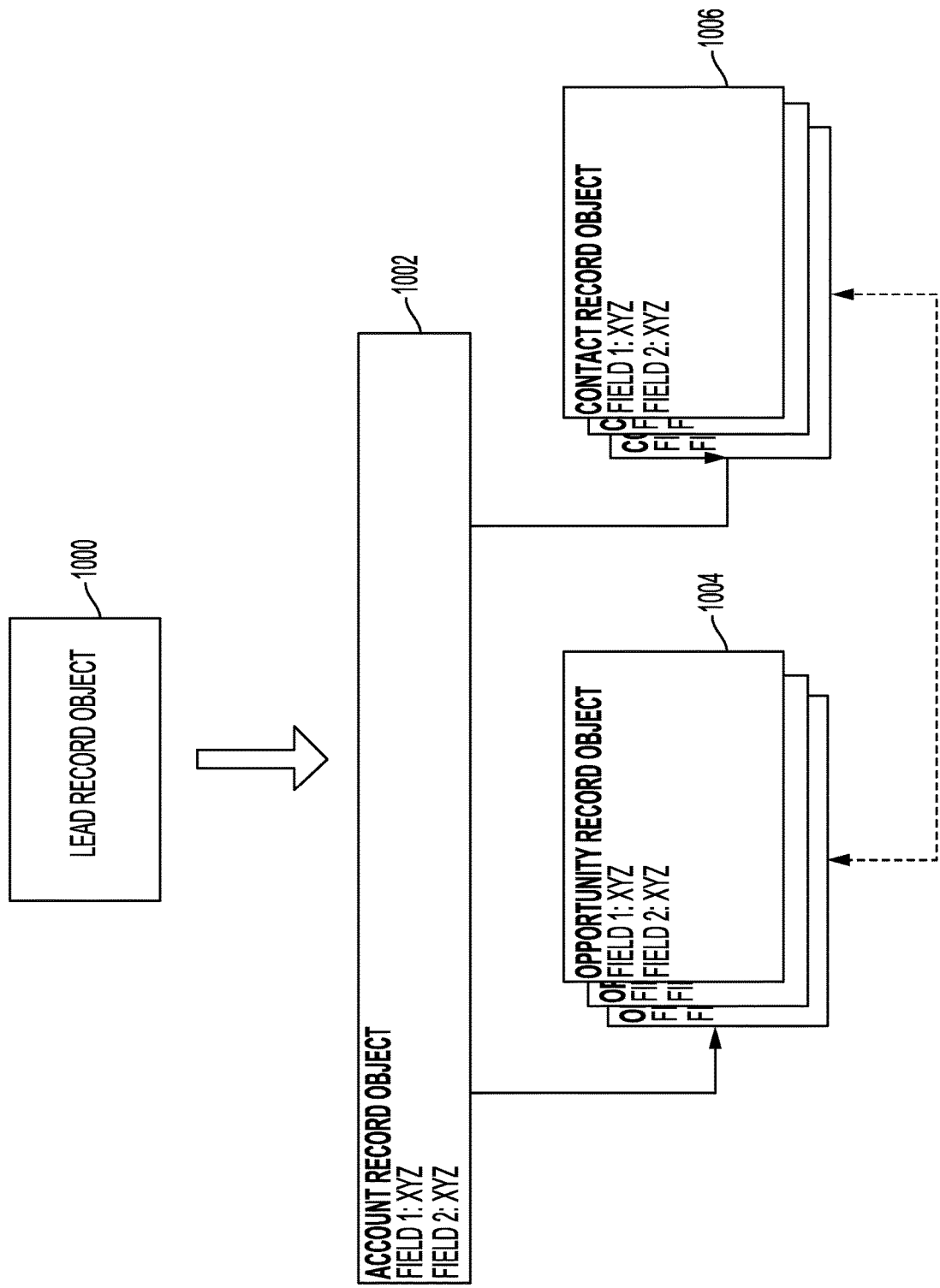
FIG. 10 illustrates a plurality of example record objects, and their interconnections, according to embodiments of the present disclosure.

Briefly referring to FIG. 10, among others, FIG. 10 illustrates a plurality of example record objects, and their interconnections. The record objects shown in FIG. 10 can be record objects or data records of a system of record, such as a customer relationship management (CRM) system. It should be appreciated that other types of systems of records and record objects may exist and can be integrated with the node graph generation system 200. For instance, other systems of records can include Applicant Tracking Systems (ATS), such as Lever, located in San Francisco, Calif. or Talend by Talend Inc., located in Redwood City, Calif., enterprise resource planning (ERP) systems, customer success systems, such as Gainsight located in Redwood City, Calif., Document Management Systems, among others.

The systems of record can be one or more of shadow systems of record of the data processing system 9300 or the systems of record of the data source providers. Additional details relating to the shadow systems of record of the data processing system 9300 are provided below. As illustrated in FIG. 10, the record objects can include a lead record object 1000, an account record object 1002, an opportunity record object 1004, or a contact record object 1006. Each of the different types of record objects can generally be referred to as record objects.

Each record object can be a data structure or data file into which data is stored or associated. The lead record object 1000 can be a low quality object that includes unqualified contact information typically received through a web inquiry. A lead record object can correspond to one or more stages. Upon reaching a final "Converted" stage, a lead record object can be converted in a one-to-many relationship into a Contact record object (person), an Account record object (company, if new, or added to existing account) and an Opportunity record object (if there is an opportunity for a deal here or added as contact role into existing opportunity).

For example, the lead record object 1000 can include the contact information for a lead or prospective buyer. The lead record object 1000 can include fields, such as, Address, City, Company, CompanyDunsNumber, Description, Email, Industry, NumberOfEmployees, Phone, job title, and Website, among others.

The account record object 1002 can be a data structure that includes fields associated with an account that is held with the data source provider. The fields can include AccountNumber, BillingAddress, Description, Industry, Fax, DunsNumber, LastActivityDate, MasterRecordId, Name, NumberOfEmployees, Ownership, Website, YearStarted, and IsPersonAccount, among others. A system of record can include an account record object 1002 for each of the data provider's customers. The system of record can include multiple account record objects 1002 for a given customer. For example, the system of record can include an account record object 1002 for each division of a given customer. The account record object 1002 can be stored with one or more opportunity record objects 1004.

In some embodiments, the CRM can include partner record objects, which can also be referred to as partner account record objects. A partner account record object can be similar to an account record object. The partner account record object can include an additional field to designate the record object as a partner account record object rather than a standard account record object. The partner account record object can be an account record object that is associated with a partner to the data source provider. For example, the partner account record object can be an account record object for a distributor of the data source provider that distributes goods to the company of the account record object.

The opportunity record objects 1004 can be data structures that include a plurality of fields for a given opportunity. The opportunity can indicate a possible or planned deal with a customer for which an account record object is already stored in the system of record. The opportunity record objects 1004 can include fields such as AccountId, Amount, CampaignId, CloseDate, Description, ExpectedRevenue, Fiscal, HasOpenActivity, IsClosed, IsWon, LastActivityDate, Name, OwnerId, StageName, Territory2Id, and Type, among others. One or more contact record objects 1006 can be associated with the account record object 1002. The contact record objects 1006 can be data structures that include fields associated with a contact. The contact record object 1006 can include fields such as AccountId, AssistantName, Birthdate, Department, Description, DoNotCall, Email, Fax, FirstName, HasOptedOutOfEmail, HomePhone, LastName, MailingAddress, and MobilePhone, among others.

One or more contact record objects 1006 can be associated with an opportunity record object 1004 via an Opportunity Contact Role object (OCR). For example, a lead to sell a service to a potential customer can convert into an opportunity record object 1004 when the customer begins the negotiation process to purchase the service. A contact record object 1006 can be generated for each of the customer's employees involved in the purchase. Each of the contact record objects 1006 can be associated with the opportunity record object 1004 for the sale via Opportunity Contact Roles, which contain their own metadata about involvement of specific individuals in the opportunity, such as their Role in this particular opportunity or whether they are the Primary Contact of the Account in this Opportunity.

In some embodiments, a lead record object 1000 can be converted into a contact record object 1006, an account record object 1002, and an opportunity record object 1004. For example, a lead record object 1000 can be converted into a new contact record object 1006, account record object 1002, and opportunity record object 1004 once the lead record object 1000 after a predetermined number and nature of electronic activities are associated with the lead record object 1000. Continuing this example, the lead record object 1000 can be generated based on a web inquiry from an interested party (lead) or via a cold email being sent to a potential new customer. If the customer responds and passes qualification criteria, the lead record object 1000 can be converted into a new contact record object 1006, account record object 1002, and opportunity record object 1004. In some embodiments, the lead record object 1000 can be converted into a, for example, contact record object 1006 that can get attached to or linked with an existing account record object 1002 and an existing opportunity record via an Opportunity Contact Role record.

The fields of each of the different record object types can include hierarchical data or the fields can be linked together in a hierarchical fashion. The hierarchical linking of the fields can be based on the explicit or implicit linking of record objects. For example, a contact record object 1006 can include a "Reports To" field into which an identifier of the contact can be stored. The "Reports To" field can indicate an explicit link in a hierarchy between two contact record objects 1006 (e.g., the first contact record object 1006 to the contact record object 1006 of the person identified by the "Reports To" field). In another example, the linking of the record objects can be implicit and learned by the electronic activity linking engine 250. For example, the electronic activity linking engine 250 can learn if multiple customers have the same value for a "Parent Account" field across multiple system of record sources with high trust score and derive a statistically significant probability that a specific account belongs to (e.g., is beneath the record object in the given hierarchy) another account record object.

Referring to FIG. 9, among others, the record object identification module 315 can determine, for a given electronic activity to which record object the electronic activity should be linked. Linking the electronic activity to one or more record objects can enable the status, metrics, and stage of the deal or opportunity to be tracked and analyzed, or the context in which the electronic activity was performed to be understood programmatically. Linking electronic activities to the record objects can also enable employee performance to be measured as described herein. The record object identification module 315 can identify a record object of one of the data processing system's shadow systems of record using the feature vectors and node graph. In this way, the record object identification module 315 can assist, aid or allow the electronic activity linking engine 250 to match the electronic activity with a record object using one or more matching models 340.

The record object identification engine 315 can include one or more matching models 340. A matching model 340 can be trained or programmed to aid in matching electronic activities to record objects to allow the electronic activity linking engine 250 to link the electronic activities to the matched record objects. For example, the record object identification engine 315 can include or use one or more matching models 340 to assist, aid or allow the electronic activity linking engine 250 to match electronic activities to record objects. In some embodiments, each of the one or more matching models 340 can be specific to a particular data source provider, electronic activity type, or record object type. In some embodiments, the record object identification engine 315 can include a single matching model that the record object identification engine 315 can use to match electronic activities ingested by the data processing system 9300 to any number of a plurality of record objects of a plurality of systems of records. In some embodiments, the matching models 340 can be data structures that include rules or heuristics for linking electronic activities with record objects. The matching models 340 can include matching rules (which can be referred to as matching strategies) and can include restricting rules (which can be referred to as restricting strategies or pruning strategies). As described further in relation to FIGS. 11 and 12, the record object identification engine 315 can use the matching strategies to select candidate record objects to which the electronic activity could be linked and use the restricting strategies to refine, discard, or select from the candidate record objects. In some embodiments, the matching models 340 can include a data structure that includes the coefficients for a machine learning model for use in linking electronic activities with record objects.

In some embodiments, the matching model 340 used to link electronic activities to one or more record objects can be trained using machine learning or include a plurality of heuristics. For example, as described above the features extraction engine 310 can generate a feature vector for each electronic activity. The matching model 340 can use neural networks, nearest neighbor classification, or other modeling approaches to classify the electronic activity based on the feature vector. In some embodiments, the record object identification engine 315 can use only a subset of an electronic activity's features to match the electronic activity to a record object.

In some embodiments, the record object identification engine 315 can use matching models 340 trained with machine learning to match, for example, the electronic activity to a record object based on a similarity of the text in and the sender of the electronic activity with the text in and sender of an electronic activity previously matched to a given electronic activity. In some embodiments, the matching model 340 can be updated as electronic activities are matched to record objects. For example, a matching model 340 can include one or more rules to use when matching an electronic activity to a record object. If a user matches an electronic activity to a record object other than the record object to which the electronic activity linking engine 250 matched the electronic activity, record object identification engine 315 can update the matching model 340 to alter or remove the rule that led to the incorrect matching.

In some embodiments, once an electronic activity is matched with a record object, a user can accept or reject the linking. Additionally, the user can change or remap the linking between the electronic activity and the record object. An indication of the acceptance, rejection, or remapping can be used to update the machine learning model or reorder the matching strategies as discussed in relation to FIGS. 11 and 12. The updated model can be used in the future linking of electronic activity to nodes and the nodes to record objects by the record object identification engine 315. To train the machine learning models, the system can scan one or more systems of record that include manually matched electronic activity and record objects. The previous manually matched data can be used as a training set for the machine learning models.

In some embodiments, the matching model 340 can include a plurality of heuristics with which the record object identification engine 315 can use to link an electronic activity to one or more record objects. The heuristics can include a plurality of matching algorithms that are encapsulated into matching strategies. The record object identification engine 315 can apply one or more matching strategies from the matching models 340 to the electronic activity to select which record object (or record objects) to link with the electronic activity. In some embodiments, the record object identification engine 315 can use the matching strategies to select candidate record objects to which the electronic activity can be linked. The record object identification engine 315 can use a second set of strategies (e.g., restricting strategies) to prune the candidate record objects and select to which of the candidate record objects the electronic activity should be linked.

The application of each strategy to an electronic activity can result in the selection of one or more record objects (e.g., candidate record objects). The selection of which matching strategies to apply to an electronic activity can be performed by the policy engine 320. The policy engine 320 is described further below, but briefly, the policy engine 320 can generate, manage or provide a matching policy for each of the data source providers 9350. The policy engine 320 can generate the matching policy automatically. The policy engine 320 can generate the matching policy with input or feedback from the data source provider 9350 to which the matching policy is associated. For example, the data source provider (for example, an administrator at the data source provider) can provide feedback when an electronic activity is incorrectly linked and the matching policy can be updated based on the feedback.

A given matching policy can include a plurality of matching strategies and the order in which the matching strategies should be applied to identify one or more record objects to which to link the electronic activity. The record object identification module 315 can apply one or more of the plurality of matching strategies from the matching models 340, in a predetermined order specified or determined via the matching policy, to identify one or more candidate record objects. The record object identification module 315 can also determine, for each matching strategy used to identify a candidate record object, a respective weight that the record object identification module 315 should use to determine whether or not the candidate record object is a good match to the electronic activity. The record object identification module 315 can be configured to compute a matching score for each candidate record object based on the plurality of respective weights corresponding to the matching strategies that were used to identify the candidate record object. The matching score can indicate how closely a record object matches the electronic activity based on the one or more matching strategies used by the record object identification module 315.

One or more of the matching strategies can be used to identify one or more candidate record objects to which the electronic activity linking engine can match a given electronic activity based on one or more features (e.g., an email address) extracted from the electronic activity or tags assigned to the electronic activity. In some embodiments, the features can be tags assigned by the tagging engine 265. In some embodiments, the electronic activity can be matched to a node profile that is already matched to a record object, thereby allowing the record object identification module 315 to match the electronic activity to a record object previously matched or linked to a node profile with which the electronic activity may be linked. In addition, the matching strategies can be designed or created to identify candidate record objects using other types of data included in the node graph generation system, or one or more systems of record, among others. In some embodiments, the matching strategies can be generated by analyzing how one or more electronic activities are matched to one or more record objects, including using machine learning techniques to generate matching strategies in a supervised or unsupervised learning environments.

Figure 11:
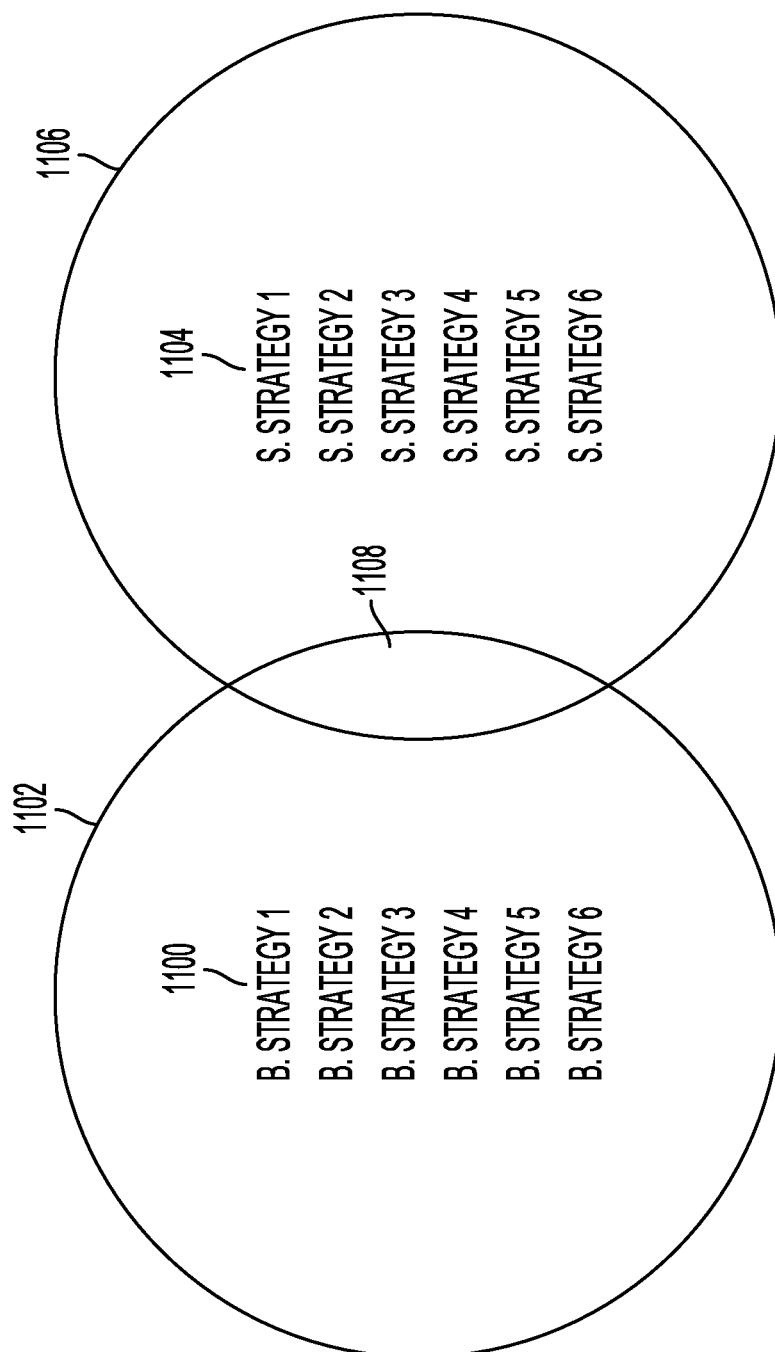
FIG. 11 illustrates the restriction of a first grouping of record objects with a second grouping of record objects according to embodiments of the present disclosure.

Subsequent strategies can be applied to prune or restrict the record objects that are selected as potential matches (e.g., candidate record objects). For example, and also referring to FIG. 11, FIG. 11 illustrates the restriction of a first grouping 1102 of record objects with a second grouping 1106 of record objects. A first plurality of strategies 1100 can be applied to select a first grouping 1102 of record objects. A second plurality of strategies 1104 can be applied to identify a second grouping 1106 of record objects that can be used to restrict or prune the first grouping 1102 of record objects. For example, the record object identification module 315 can select the record object to which the electronic activity is linked from the overlap 1108 of the groupings 1102 and 1106.

Figure 12:
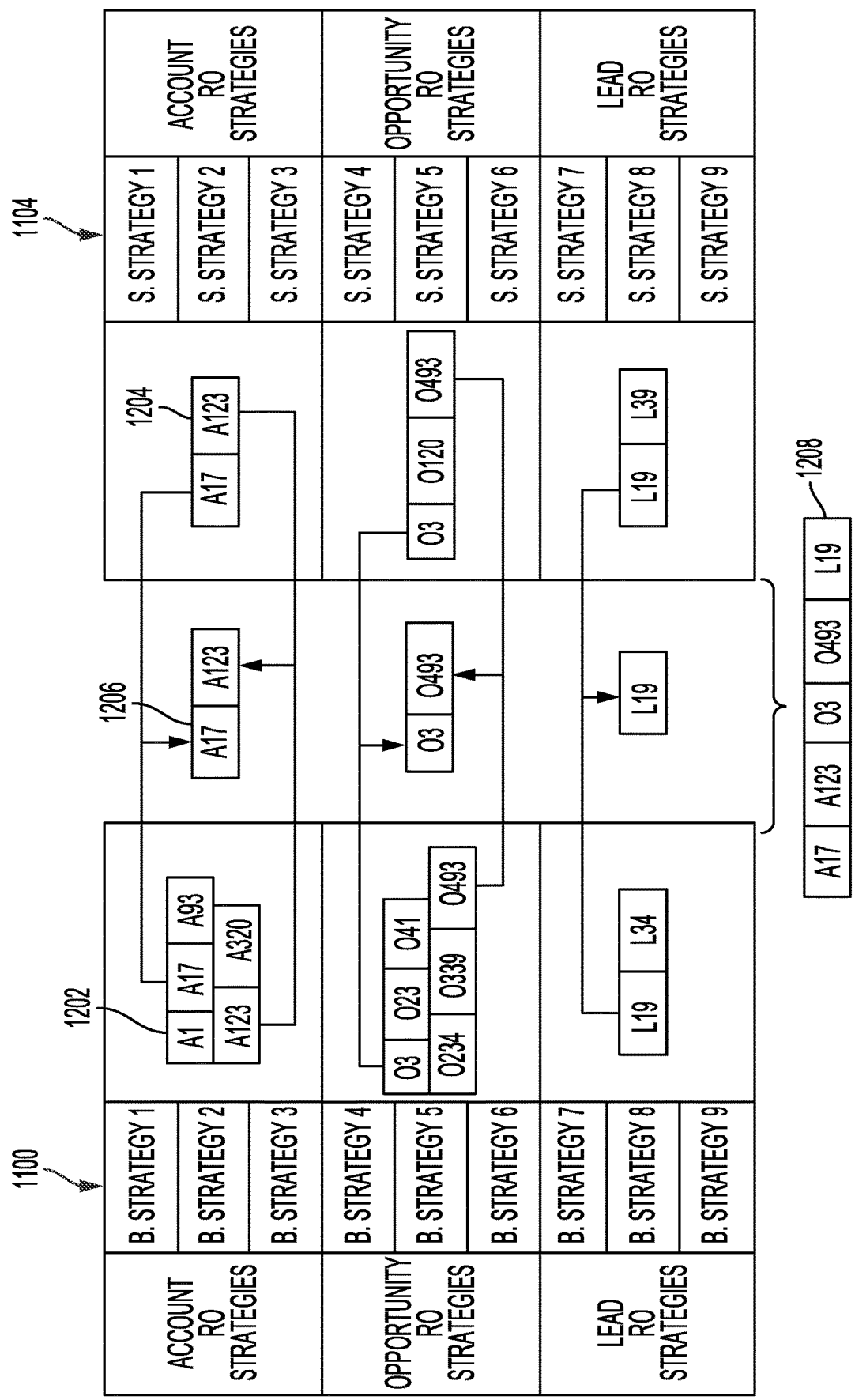
FIG. 12 illustrates the application of a plurality of matching strategies and then pruning of the matched record objects with a second plurality of matching strategies according to embodiments of the present disclosure.
Figure 15:
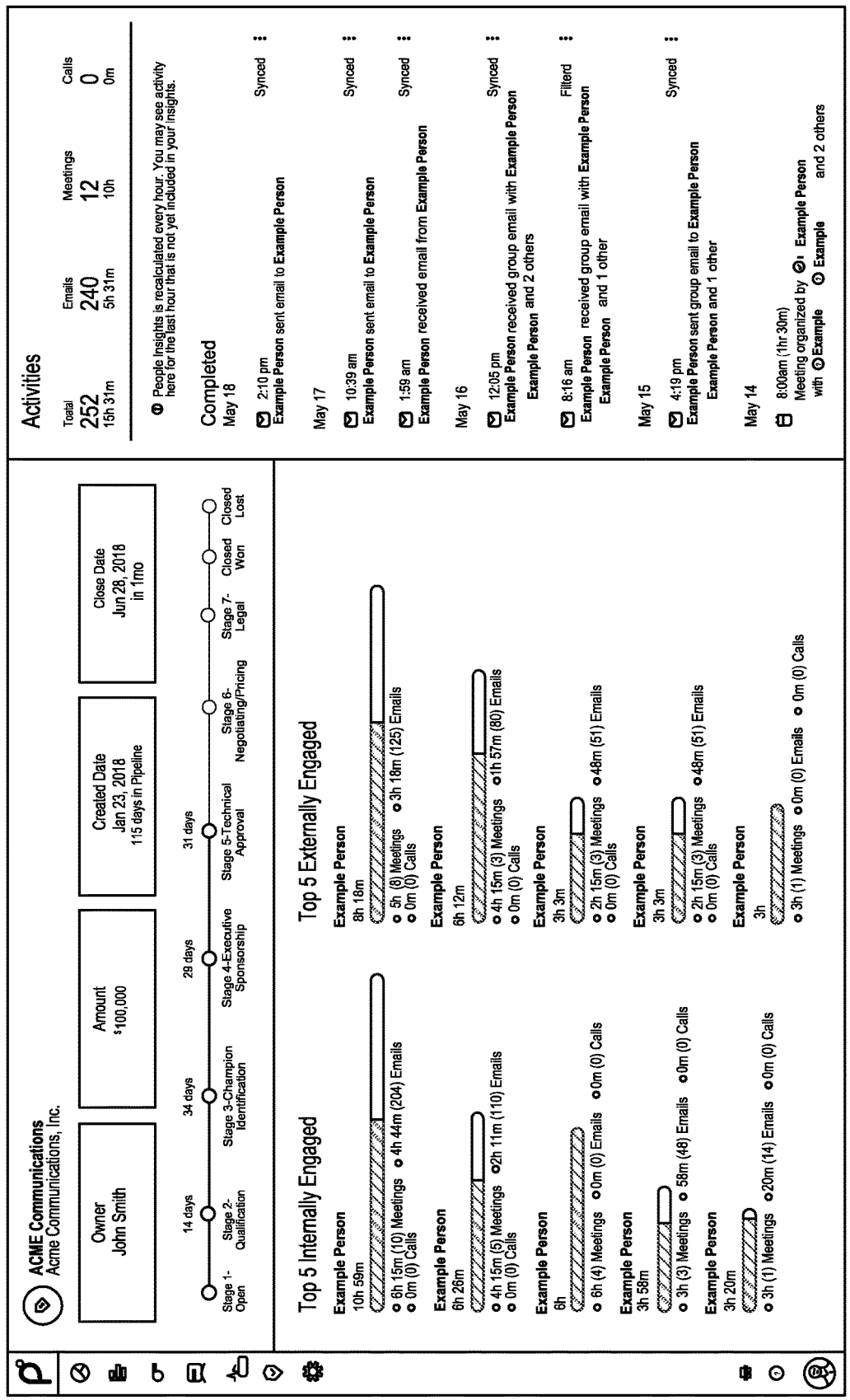
FIG. 15 illustrates an example user interface identifying a record object corresponding to an opportunity according to embodiments of the present disclosure.

For example, and also referring to FIG. 12, among others, FIG. 12 illustrates the application of a first plurality of matching strategies and a second plurality of matching strategies to generate one or more grouping of record objects and then selecting record objects that satisfy both the first plurality of matching strategies and the second plurality of matching strategies. In some embodiments, the first plurality of matching strategies can be configured to generate the first grouping 1102 of record objects shown in FIG. 11, while the second plurality of matching strategies 1104 can be configured to generate the second grouping 1104 of record objects. In some embodiments, the first plurality of matching strategies 1100 can be associated with one or more recipients of the electronic activity to be matched and the second plurality of matching strategies 1104 can be associated with a sender of the electronic activity to be matched. The candidate record objects selected by the first plurality of matching strategies 1100 and the second plurality of matching strategies 1104 can be filtered, pruned or otherwise discarded from being matched with the electronic activity using restricting strategies (described further below). In some embodiments, the first plurality of strategies can be referred to as buyer-side or recipient-side strategies and the second plurality of strategies can be referred to as seller-side or sender-side strategies. The policy engine 320 can select one or more matching strategies of the first plurality of matching strategies 1100, second plurality of matching strategies 1104 and restricting strategies for the record object identification engine 315 to apply in a predetermined order. The matching strategies of the first plurality of matching strategies 1100 and the second plurality of matching strategies 1104 can each be configured to select one of the types of record objects. For example, the matching strategies 1100 and 1104 can each be configured to select one of a lead record object 1000, an account record object 1002, an opportunity record object 1004, a partner record object, among others. For example, a matching strategy can be used to match an electronic activity to an account record object 1002 in the shadow systems of record based on an email address extracted from the electronic activity via a number of sequentially used matching strategies. The restriction strategies can be used to remove one or more record objects that are selected by any of the first plurality of matching strategies 1100 or any of the second plurality of matching strategies 1104.

In an example where the electronic activity includes the email "john.smith@example.com," the record object identification module 315 can use a first matching strategy, such as a matching strategy for selecting the account record object based on email addresses to identify one or more candidate record objects that may match the email address field of the electronic activity. First, the record object identification module 315 can return all contact record objects with "john.smith@example.com" in the email field. The record object identification engine 315 can then identify the account record objects that are linked with each of the contact record objects with "john.smith@example.com" in the email field.

In some embodiments, if the system was not able to find a contact record object with the field (or other fields) containing "john.smith@example.com", the system can use a secondary matching strategy 1100 and find an account record object with the domain name that matches the domain name of the email "@example.com". If after applying the restricting strategies and eliminating possible options, only one account with such domain name is left, the system would have identified the account to which potential contact with email address "john.smith@example.com" should belong and the original electronic activity should be linked to. In this case, the system could automatically create a contact record with email "john.smith@example.com", linked to the account record with domain name "example.com" and then associate electronic activity from which this process started to the newly created contact record object and right account record object. It is worth noting that the order in which matching strategies 1100 and 1104 and the restriction strategies are applied can impact and modify outcomes of matching model 340.

Still referring to FIG. 12, the record object identification engine 315 can use one or more of the matching strategies 1100 associated with account record objects to generate a matched candidate record object array 1202 that identifies one or more candidate record objects that were identified based on the matching strategies 1100 associated with account record objects. The record object identification engine 315 can generate three matched record object arrays 1202. Each of the matched record object arrays can be associated with a different one of the record object types. For example, the record object identification engine 315 can generate an account record object array, an opportunity object array, a contact object array, a lead object array, and a partner object array (not shown). The results (e.g., the returned record objects) for a given matching strategy 1100 can be appended to the record object array 1202 for the associated record object type. For example, matching strategy 1100(1) can be used to return the account record objects with UIDs A1 and A17, the matching strategy 1100(2) can be used to return the account record object with the UID A93, and the matching strategy 1100(3) can be used to return the account record object with the UIDs A123 and A320.

The recipient-side matching strategies 1100 can include a plurality of matching strategies. The matching strategies can be arranged in a predetermined and configurable order. The matching strategies of the recipient-side strategies 1100 can include one or more of matching to opportunity record objects based on contact role, matching to account record objects based on contact record objects, matching to account record objects based on domains, matching to opportunity record objects based on contacts, matching to partner account record objects based on contacts, matching to partner account record objects using domains, among others. The record object identification engine 315 can use the recipient-side strategies 1100 to select a plurality of candidate record objects to form record object arrays 1202.

Each value in the matched record object arrays 1202 can include an indication of one of the record objects that was matched using the matching strategies (e.g., the recipient-side strategies 1100). For example, the matched record object arrays 1202 can include an array of UIDs associated with each of the record objects that were matched by the record object identification engine 315 using the matching strategies. In some embodiments, each value in the array can be a data pair that includes the matched record object UID and a score indicating how confident the system is on the match between the electronic activity and the record object. The score can be based on the matching strategy which returned the given record object. In some embodiments, the score may be adjusted based on previous matches and how a user accepted or modified the previous matches. In some embodiments, a record object can be selected multiple times; for example, a first and a second matching strategy can each select a given record object. A score can be associated with each matching strategy and the score for the record object selected by multiple matching strategies can be an aggregate (for example, a weighted aggregate) of the scores associated with each of the matching strategies that selected the record object. The scores can indicate how well the selected record object satisfied the one or more matching strategies.

The record object identification engine 315 can select record objects based on matching strategies for each of the participants associated with the electronic activity. For example, the electronic activity can be an email with a sender and a plurality of recipients. The sender and the plurality of recipients can be the participants that are associated with the electronic activity. The record object identification engine 315 can apply each of the matching strategies for each of the participants. Multiple matching strategies for a given participant can return the same record object multiple times. A matching strategy applied to multiple participants can return the same record object multiple times. The score that the record object identification engine 315 assigns to each selected record object can be based on the number of times the given record object was returned after the matching strategies were applied for each of the electronic activity's participants. For example, a first record object can be returned or selected four times and a second record object can be returned or selected once. The record object identification engine 315 can assign the first record object a higher relative score than the second record object that was only selected once.

In some embodiments, the record object identification engine 315 can select record objects using matching strategies that select record objects based on tags. The electronic activity can be parsed with a natural language processor and the tags can be based on terms identified in the electronic activity. Parsing the electronic activity with the natural language processor can enable the electronic activity to be matched to record objects by mention. For example, the electronic activity can be parsed and the term "renewal" can be identified in the electronic activity. A "renewal" tag can be applied to the electronic activity. A matching strategy to select record objects based on tags can select a renewal record object opportunity with the electronic activity and include the renewal record object opportunity in the record object array 1202. In another example, the system 200 can identify identification numbers contained in the electronic activity for which tags can be assigned to the electronic activity. The identification numbers can include serial numbers, account numbers, product numbers, etc. In this example, and assuming a tag identifying an account number is assigned to the electronic activity, a matching strategy to select record object based on tags can select an account record object that includes a field with the account number identified in the electronic activity's tag.

The record object identification engine 315 can apply one or more of a plurality of sender-side strategies 1104 that can be used to select one or more candidate record objects included in one or more second set of record object arrays 1204. In some embodiments, the record object identification engine 315 can apply one or more of a plurality of sender-side strategies 1104 to restrict or prune the record objects selected using the matching strategies 1100. By applying the set of sender-side strategies 1104, the record object identification engine 315 can generate the second set of record object arrays 1204 that can be used to prune or restrict the first set of record object arrays 1202. For example, the record object identification engine 315, applying a sender-side strategy 1104 that selects accounts record objects based on an account owner, can select the account record object with UID A17 and A123. The record object identification engine 315 can use sender-side strategies such as selecting record objects for matching based on account teams associated with one or more participants of the electronic activity. For example, the record object identification engine 315 can select a record object that identifies the sender of the electronic activity. As a member of the account team associated with the record object.

The record object identification engine 315 can prune the identified candidate record object by determining the intersection of the first set of record object arrays 1202 (produced with matching strategies 1100) and the second set of record object arrays 1204 (produced with matching strategies 1104). For example, the account record object array 1202 generated with the set of matching strategies 1100 is, in the example illustrated in FIG. 12, {A1, A17, A93, A123, A320}. The account object array 1204 generated with the set of sender-side strategies 1104 is {A17, A123}. The record object identification engine 315 can determine that the intersection array 1206 of the account record object array 1202 and account record object array 1204 is {A17, A123}. In this way, the sender-side strategy restricted the record objects A1, A93 and A320 from being selected as a match to the incoming electronic activity. The record object identification engine 315 can combine the intersection arrays 1206 generated by the intersection of the sender-side strategies 1104 and the recipient-side strategies 1100 to generate an output array 1208. The output array 1208 can include indications of record objects and the weights or scores associated with each of the record objects.

The record object identification engine 315 can also use restriction strategies to further prune or restrict out record objects selected using the matching strategies 1100 and 1104. The record object identification engine 315 can use the restriction strategies to select one or more record objects to which the electronic activity should not be matched. For example, although this example is not reflected in FIG. 12, the record object identification engine 315 can use a restriction strategy to select record objects A1 and A17 to generate a restriction record object array including {A1, A17}. If, using the recipient-side matching strategies, the record object identification engine 315 selects record objects A1, A3, A10, and A17 to generate {A1, A3, A10, A17}, the record object identification engine 315 can remove A1 and A17 from the record object array because they were identified in the restriction record object array as record object to which the electronic activity should not be matched.

In some embodiments, the record object identification engine 315 can apply the restriction strategies once the record object identification engine 315 selects one or more record objects with the sender-side strategies 1104 or the recipient-side strategies 1100. The record object identification engine 315 can apply the restriction strategies before the record object identification engine 315 selects one or more record objects with the sender-side and recipient-side strategies. For example, the restriction strategies can be one of the below-described matching filters.

In some embodiments, the output array 1208 can include one or more record objects that can be possible matches for the electronic activity. The selection from the output array 1208 can be performed by the below described record object identification engine 315. If the output array 1208 only includes one record object, the electronic activity can be matched with the record object of the output array 1208. In some embodiments, the electronic activity is only matched with the record object if the confidence score of the record object is above a predetermined threshold. The confidence score of the record object indicates a level of confidence that the record object is the correct record object to which to link the electronic activity. If the output array 1208 includes multiple record objects, the electronic activity can be matched with the record object having the highest confidence score (given that the highest confidence score is above the predetermined threshold). If the output array 1208 does not include any record objects, the confidence score of the record objects are not above the predetermined threshold, or multiple record objects have the same confidence score above the predetermined threshold, the system can request input from the user as to which record object to match the electronic activity. In these cases, the matching strategies can be updated based on the input from the user.

In some embodiments, the record object identification engine 315 can group or link contact record objects on one or both sides of a business process into groups. The record object identification engine 315 can use the groups in the matching strategies. For example, the record object identification engine 315 can group users on a seller side into account teams and opportunity teams. Account teams can indicate a collection of users on the seller side that collaborate to close an initial or additional deals from a given account. Opportunity teams can be a collection of users on the seller side that collaborate to close a given deal. The record object identification engine 315 can add a user to an account or opportunity team by linking the contact record object of the user to the given account team record object or opportunity team record object. The record object identification engine 315 can use account team-based matching strategies or opportunity team-based matching strategies to select record objects with which the electronic activity can be matched.

In some embodiments, at periodic intervals, the record object identification engine 315 can process the electronic activities linked with account record objects and opportunity record objects to generate account teams and opportunity teams, respectively. For a given account record object, the record object identification engine 315 can count the number of times that a seller side user interacts with the account record object (for example, is included in an electronic activity that is linked or matched to the account record object). For example, the record object identification engine 315 can count the number of times the user was included on an email or sent an email that was linked with the account record object. If the count of the interactions is above a predetermined threshold, the record object identification engine 315 can add the user to an account team for the account record object. In some embodiments, the count can be made over a predetermined time frame, such as within the last week, month, or quarter. The record object identification engine 315 can perform a similar process for generating opportunity teams. In some embodiments, the account teams and opportunity teams can be included in the matching and restriction strategies used to match an electronic activity with a record object. Conversely, if the count of the interactions of a particular user is below a predetermined threshold within a predetermined time frame (for example, a week, a month, three months, among others), the record object identification engine 315 can remove the user from the account team or the opportunity team.

In some embodiments, the record object identification engine 315 can select record objects with which to match a first electronic activity based on a second electronic activity. The second electronic activity can be an electronic activity that is already linked to a record object. The second electronic activity can be associated with the first electronic activity. For example, the system 200 can determine that the first and second electronic activities are both emails in a threaded email chain. The system can determine the emails are in the same thread using a thread detection policy. The thread detection policy can include one or more rules for detecting a thread by comparing subject lines and participants of a first email and a second email or in some embodiments, by parsing the contents of the body of the second email to determine if the body of the second email includes content that matches the first email and email header information of the first email is included in the body of the second email. If the second electronic activity is an earlier electronic activity that is already matched to a given record object, the record object identification engine 315 can match the first electronic activity to the same record object.

The policy engine 320 can be any script, file, program, application, set of instructions, or computer-executable code that is configured to enable a computing device on which the policy engine 320 is executed to manage, store, and select matching strategies. The policy engine 320 can generate, manage, and store one or more matching strategy policies for each of the data source providers. For example, the policy engine 320 can generate matching strategy and restriction strategy policies for each division or group of users within a data source provider.

In some embodiments, a matching policy can include a data structure that indicates which matching strategies to apply to an electronic activity for a given data source provider. For example, the matching policy can include a list of matching strategies that are used to select record objects. The list of matching strategies can be manually created by a user or automatically generated or suggested by the system. In some embodiments, the policy engine can learn one or more matching strategies based on observing how one or more users previously matched electronic activities to record objects. These matching strategies can be specific to a particular user, group, account, company, or across multiple companies. In some embodiments, the policy engine can detect a change in linkages between one or more electronic activities and record objects in the system of record (for example, responsive to a user linking an electronic activity to another object inside a system of record manually). The policy engine can, in response to detecting the change, learn from the detected change and update the matching strategy or create a new matching strategy within the matching policy. The policy engine can be configured to then propagate the learning from that detected change across multiple matching strategies corresponding to one or more users, groups, accounts, and companies. The system can also be configured to find all past matching decisions that would have changed had the system detected the user-driven matching change before, and update those matching decisions retroactively using the new learning.

In some embodiments, the matching policy can also identify which restriction strategies to apply to an electronic activity for a given data source provider. For example, the restriction policy can include a list of restriction strategies that are used to restrict record objects. The list of restriction strategies can be manually created by a user or automatically generated or suggested by the system. In some embodiments, the policy engine can learn one or more restriction strategies based on observing how one or more users previously matched or unmatched electronic activities to record objects. These restriction strategies can be specific to a particular user, group, account, company, or across multiple companies. In some embodiments, the policy engine can detect a change in linkages between one or more electronic activities and record objects in the system of record (for example, responsive to a user linking or unlinking an electronic activity to another object inside a system of record manually). The policy engine can, in response to detecting the change, learn from the detected change and update the restriction strategy or create a new restriction strategy within the restriction policy. The policy engine can be configured to then propagate the learning from that detected change across multiple restriction strategies corresponding to one or more users, groups, accounts, and companies. The system can also be configured to find all past matching decisions that would have changed had the system detected the user-driven restriction change before, and update those matching decisions retroactively using the new learning.

The policy engine 320 can update the matching policy with input or feedback from the data source provider to which the matching policy is associated. For example, the data source provider can provide feedback when an electronic activity is incorrectly linked and the matching policy can be updated based on the feedback. Updating a matching policy can include reordering the matching strategies, adding matching or restriction strategies, adjusting individual matching strategy behavior, removing matching strategies, or adding restriction strategies. The link restriction engine 330 can be any script, file, program, application, set of instructions, or computer-executable code, that is configured to enable a computing device on which the link restriction engine 330 is executed to limit to which record objects an electronic activity can be linked.

In some embodiments, data source providers can generate restriction policies or restriction strategies that include rules that indicate conditions under which electronic activities should not be linked to record objects. For example, restriction policies can include rules that prevent internal emails from being linked to a record object. Other restriction policies can limit bot emails (e.g., emails sent to a plurality of people or an email sent as an automatic reply), non-person electronic activity (e.g., electronic activity, such as calendar activity, associated with an asset, such as a conference room), activities, related to persons, who are working in sensitive or unrelated positions (e.g. HR employees), activities, related to persons who do not "own" specific records in the system of record or who do not belong to specific groups of users, or to private or personal electronic activities (e.g., non-work-related emails). These restriction policies or restriction strategies can include one or more matching filters described herein.

The restriction policies can be generated automatically by the system or can be provided by the data source provider. Different restriction policies can be linked together to form a hierarchy of restriction policies, preserving the order in which they should be applied. For example, restriction policies can be set and applied at a group node level (e.g., company level), member node level (e.g., user level), account level, opportunity level, or team level (e.g., groups of users such as account teams or opportunity teams). For example, a restriction policy applied at the company level can apply to the electronic activity sent or received by each employee of the company while a restriction policy applied at the user level is only applied to the electronic activity sent or received by the user.

The link restriction engine 330 can use the restriction policies to remove or discard record objects from the output array 1208. For example, if a restriction policy indicates that electronic activity from a given employee should not be linked to record object A17 and record object A17 is included in the output array 1208, the link restriction engine 330 can remove record object A17 from the output array 1208.

In some embodiments, the link restriction engine 330 can apply the restriction policies to electronic activities prior to the matching performed by the record object identification module 315. For example, if a restriction policy includes rules that calendar-based electronic activity for a conference room should not be linked to any record object, the link restriction engine 330 can discard or otherwise prevent the record object identification module 315 from linking the electronic activity to a record object.

The tagging engine 265 can be any script, file, program, application, set of instructions, or computer-executable code that is configured to enable a computing device on which the tagging engine 265 is executed to generate tags for the electronic activity. The tagging engine 265 can generate or add tags to electronic activity based on information generated or otherwise made available by the record object identification module 315 and the matching model 340. The tagging engine 265 can generate a tag array that includes each of the plurality of tags assigned or associated with a given electronic activity. By having tags assigned to electronic activities the node graph generation system 200 can be configured to better utilize the electronic activities to more accurately identify nodes and record objects to which the electronic activity should be linked.

In addition to the above described tags, the tagging engine 265 can assign tags to an electronic activity based on the output of the record object identification module 315 and matching model 340, among other components of the system described herein. For example, the tagging engine 265 can add one or more tags indicating to which record objects the record object identification module 315 returned as candidate record objects for the electronic activity. For example, and also referring to FIG. 12, the tagging engine 265 can add tags to indicate each record object contained within the output array 1208. In some embodiments, the tagging engine 265 can add a tag for each record object contained within the output array 1208. In some embodiments, the tagging engine 265 can add a tag for each record object contained within the output array 1208. In some embodiments, the tagging engine 265 can include a tag only for the record object in the output array 1208 that most closely matches the electronic activity.

The linking generator 335 can be any script, file, program, application, set of instructions, or computer-executable code that is configured to enable a computing device on which the linking generator 335 is executed to link electronic activities to record objects. As described above, the system can generate and maintain a shadow system of record for each of a data source provider's system of record. The data source provider's system of record can be referred to as a master system of record or tenant-specific system of record. The linking generator 335 can select a record object from the record object array 1208 and link the electronic activity to the selected record object in the shadow system of record. For example, the record object identification engine 315 can use the confidence scores of the record objects in the record object array to select a record object with which to match the electronic activity.

Also referring to FIG. 12, the linking generator 335 can link the electronic activity to one or more of the record objects included in the output array 1208. In some embodiments, the linking generator 335 can link the electronic activity to one or more record objects in the output array 1208. For example, the linking generator 335 may only link the electronic activity to the record object in the output array 1208 that most closely matches the electronic activity. In some embodiments, the linking generator 335 links the electronic activity with only one of the record objects in the output array 1208 (e.g., the record object having the highest score).

Linking the electronic activity with a record object can include saving the electronic activity (or an identifier thereof) into the shadow system of record in association with the record object. For example, each record object can include a unique identifier. The electronic activity can be saved into the system of record and the record object's unique identifier can be added to a record object field of the electronic activity to indicate to which record object the electronic activity is linked. In some embodiments, each electronic activity can be assigned a unique identifier. The electronic activity's unique identifier can be added to a field in the shadow record object to indicate that the electronic activity is associated with the shadow record object. In some embodiments, the shadow record object can be matched or synced with a record object in a client's system. When the shadow record object and the record object are synced, data, such as the electronic activity's unique identifier in the above example, can be copied to the corresponding field in the matched record object of the client's system. For example, if the linking generator 335 matches an email to a given record object in the shadow system of record, when synced the email can be matched to the given record object in the client's system of record.

By linking the electronic activities to record objects, the system can generate metrics regarding the electronic activities. The metrics can include engagement scores for users, employees, specific deals or opportunities, managers, companies, or other parties associated with a system of record. Additional details regarding metrics and the calculation thereof are described below in Section 11, among others. The engagement scores can indicate amongst other things how likely an opportunity (or deal) is to close successfully (or unsuccessfully) or whether the number of contacts in the account are sufficiently engaged with the sales representative to prevent the account from disengaging with the company. The engagement scores can provide an indication of an employee's productivity and can indicate whether the user should receive additional training or can indicate whether the user is on track to achieve predefined goals. The metrics can be calculated dynamically as the electronic activities are matched to nodes and record objects or the metrics can be calculated in batches, at predetermined intervals. Metrics can also be based on the content or other components of the electronic activity in addition to or in place of the linking of the electronic activity to a node and record object.

For example, FIG. 13 illustrates an example calculation for calculating the engagement score of an opportunity record object. The example calculation can include an electronic activity weight 1300, a volume vector 1302 indicating a count of each electronic activity type, a seniority weight 1304, and a department weight 1306. As illustrated in FIG. 13, the electronic activity linking engine 250 can determine the engagement score by collecting each of the electronic activities associated with a given opportunity record object. The electronic activity linking engine 250 can count the volume (e.g., number) of each type of electronic activity linked with the opportunity record object. For example, the electronic activity linking engine 250 can tag each ingested electronic activity as being an in-person meeting electronic activity, a conference call electronic activity, a received email electronic activity, a sent email electronic activity, a cold email electronic activity, a blast email electronic activity, or a call, among others. The electronic activity linking engine 250 can also tag the electronic activity using NLP. For example, electronic activity linking engine 250 can tag an email based on mentions of a competitor, product, specific people, specific places, or other phrases contained within the electronic activity. The electronic activity linking engine 250 can also generate tags based on the combination of other tags, linking information, and fields within linked objects.

The count of each of the different types of electronic activities can be stored in the volume vector 1302. The volume vector 1302 can be multiplied by the weight or points assigned to each of the different electronic activities. The weight or points associated with each of the electronic activity types in the electronic activity weight can indicate the significance of the electronic activity to the successful completion of the deal. In some embodiments, the weights can be set by the electronic activity linking engine 250. The weights can be set based on the sales motion of the given tenant or data source provider. Each weight can be a normalized value that can represent the significance a given feature, or collection of electronic activities. For example, an email including the VP of Sales can be given a higher weight when compared to an email that only includes managers. In some embodiments, the electronic activity linking engine 250 can reference an organizational hierarchy derived from the node graph and assign relatively higher weights to electronic activities that involve people relatively higher in the organizational hierarchy. For example, having repeated, in-person meetings with a CxO at a prospective client or company can be more beneficial to the successful closing of the deal than cold calling a random contact at the company. Accordingly, the in-person meeting is assigned a higher weight (50 points) that the call, which is assigned a relatively lower weight of 1.

The engagement score can also be based on a seniority weighting factor. The seniority weighting factor can then be applied to the volume weighted scores of the electronic activities. The seniority weighting factor can apply a weighting based on those included on or involved with the electronic activity. In some embodiments, the feature extraction engine 310 can determine which contacts or people are associated with electronic activity. For example, the feature extraction engine 310 can parse the TO: and CC: fields of an email (an example electronic activity) and then, using the node graph, determine seniority, department, job title, or role of each contact listed on the email at their current and past roles. In some embodiments, the seniority weighting factor can be based on the contact record objects to which the matching model 340 (or other component of the system) matched the electronic activity.

The engagement score can also be based on a department weighting factor. The department weighting factor can be normalized across all the departments (such as within a company or account). In some embodiments, once the system determines which contacts are associated with the electronic activity, as described above, the system can determine the department of each of the contacts using the node graph.

The stage classification engine 325 can be any script, file, program, application, set of instructions, or computer-executable code, that is configured to enable a computing device on which the stage classification engine 325 is executed to determine or predict a stage of a deal or opportunity.

In some embodiments, record objects can be associated with a plurality of stages. In some embodiments, the record object can be an opportunity record object or any other record object that describes a business process, such as a sales process, a hiring process, or a support ticket. The stages can be defined by the system or by the data source provider.

Using the example of an opportunity record object in a sales process, the stages can indicate the steps taken in an opportunity or deal from the beginning of the deal to the final disposition of the deal (e.g., close and won or closed and lost). The stages can include, but are not limited to: prospecting, developing, negotiation, review, closed/won, or closed/lost.

Each of the stages can be linked to different tasks or milestones. For example, a sales representative can develop a proposal during the "developing" stage. Each of the stages can be linked to different actions taken by the sales representative or prospect contacts, associated contacts or other people. For example, initially during the prospecting and developing stages a sales representative may be involved in the opportunity or deal. At a later stage, such as negotiations, a sales manager may become involved in the deal.

The stages can be based on the contacts present or involved on both sides of the deal. For example, as the deal advances to higher stages, more senior people may be included in the electronic activities. The stage of the deal can be based on the identification or introduction of an opportunity contact role (OCR) champion. In some embodiments, an administrator or user of the system of record can link the opportunity record object with a contact record object and designate the contact of the contact record object as an opportunity contact role. The champion can be a person on the buyer side of the deal that will support and provide guidance about the deal or opportunity to the seller side. In some embodiments, the OCR champion can be selected based on one or more rules. For example, the one or more rules can include setting the person identified as the VP of sales (or other specific role) as the OCR champion. In some embodiments, the OCR champion can be selected based on historical data. For example, the historical data can indicate that in 90% of the past deals a specific person or role was the OCR champion. Based on the historical data, when the person is added as a recipient of an electronic activity, the person can be identified as the OCR champion. The OCR champion can also be identified probabilistically based on tags associated with the electronic activities linked to the opportunity record object or content within the electronic activities.

In some embodiments, OCRs can be configurable by the company on an account by account basis. Depending on the type, size or nature of the opportunity, the customer or account involved in the opportunity may have different types and numbers of OCRs involved in the opportunity relative to other opportunities the same customer is involved in. Examples of OCRs can include "Champion," "Legal," "Decision Maker," "Executive sponsor" among others.

The system 200 can be configured to assign respective opportunity contact roles to one or more contacts involved in an opportunity. The system 200 can be configured to determine the opportunity contact role of a contact involved in the opportunity based on the contact's involvement. In some embodiments, system 200 can determine the contact's role based on a function the contact is serving. The function can be determined based on the contact's title, the context of electronic activities the contact is involved in, and other signals that can be derived from the electronic activities and node graph. In addition, the system 200 can assign the contact a specific opportunity contact role based on analyzing past deals or opportunities in which the contact has been involved and determining which opportunity contact role the contact has been assigned in the past. Based on historical role assignments, the system 200 can predict which role the contact should be assigned for the present opportunity. In this way, the system 200 can make recommendations to the owner of the opportunity record object to add contacts to the opportunity or assign the contact an opportunity contact role.

In some embodiments, the system 200 can determine that a contact should be assigned an opportunity contact role of "Executive Sponsor." The system may determine this by parsing electronic activities sent to and from the contact and identify, using NLP, words or a context that corresponds to the role of an Executive sponsor. In addition, the system can determine if the contact has previously been assigned an opportunity contact role of executive sponsor in previous deals or opportunities. The system can further determine the contact's title to determine if his title is senior enough to serve as the Executive sponsor.

In some embodiments, the electronic activity linking engine 250 can use a sequential occurrence of electronic activities to determine contact record objects that should be linked or associated with an opportunity record object. The electronic activity linking engine 250 can also determine the roles of people associated with the contact record objects linked to an opportunity. The identification of people associated with opportunity and account record objects (and their associated roles) can be used to determine stage classification, group of contacts on the buyer side that are responsible for the purchase, and for many other use cases. In some embodiments, the sequential occurrence of electronic activities can be used to determine the role or seniority of users involved in a business process. For example, initial emails linked with an opportunity record object can involve relatively lower-level employees. Later emails linked to the opportunity record object can include relatively higher-level employees, such as managers or Vice Presidents. The electronic activity linking engine 250 can also identify the introduction of contacts in a chain of electronic activities, such as a series of email replies or meeting invites, to determine a contact's participation and role in a business process. For example, the electronic activity linking engine 250 can use NLP and other methods to identify the introduction of a manager as a new OCR based on an email chain.

It should be appreciated that in some embodiments, the node graph generation system 200 can include node profiles corresponding to each of the contact record objects included in one or more shadow systems of record or master systems of records. As sequential electronic activities traverse the system 200, the node graph generation system 200 can parse the electronic activities and determine that additional email addresses are being included or some existing email addresses are being removed in subsequent electronic activities. The node graph generation system can identify node profiles corresponding to the email addresses being added and establish links or relationships between the node profiles included in the electronic activity. As the electronic activity linking engine 250 links electronic activities to record objects, such as opportunity record objects, node profiles included in the electronic activity are also linked to the opportunity record object. The stage classification engine can use this information to classify a stage of the opportunity based in part on node profiles linked to the record object and based on the involvement of the node profiles in the electronic activities that can be determined using effort estimation techniques, volumes of emails exchanged, as well as based on NLP of the content to identify the role of each of the node profiles, as well as historical patterns of linkage of similar node profiles to similar record objects, as discussed below.

In some embodiments, the electronic activity linking engine 250 can also determine a contact's role based on the tags of the electronic activity in which the contact was included. For example, relatively higher-level employees, such as managers, can be more likely to be included electronic activities such as in person meeting invites and conference calls. The electronic activity linking engine 250 can also use NLP on the content of electronic activities to determine the role of contacts. For example, the electronic activity linking engine 250 can process the content of the electronic activities to identify terms that may indicate a role of a contact. For example, an email can include the phrase "my assistant Jeff will schedule the meeting." The electronic activity linking engine 250 can identify the phrase "my assistant Jeff" and include in the contact record object associated with Jeff the role of "assistant." The electronic activity linking engine 250 can also determine that the sender of the email is more likely to be a manager because the sender of the email has an assistant.

Similar to how the record object manager 255 maintains the shadow systems of record and corresponding record objects, the stage classification engine 325 can maintain a shadow stage indicating a stage the stage classification engine 325 determines is the current stage for the deal or opportunity. The stage classification engine 325 can determine or estimate the stage of the opportunity using a top-down algorithm or a bottom-up algorithm. With the top-down algorithm, the data source provider can provide a policy that includes a plurality of rules. The rules can indicate requirements for entering or exiting a stage. For example, the data source provider's policy may include a rule indicating that an opportunity cannot progress to a negotiation stage until a procurement manager is involved in the deal on the buyers side. In this example, the stage classification engine 325 can monitor the ingested electronic activities. When the stage classification engine 325 detects that the system has linked an electronic activity (such as an email) to the opportunity record object and the electronic activity includes a contact that is a procurement manager (as determined, for example, via the node graph), the stage classification engine 325 can set the shadow stage to negotiation stage. In some embodiments, the shadow stage can be synced to the data source provider's stage for the given record object. In some embodiments, the stage classification engine 325 can update a stage of a record object of the master system of record to match the shadow stage of the corresponding record object determined by the stage classification engine 325. In some such embodiments, the client may provide or select a configuration setting that allows the stage classification engine 325 to update the stage classification of a record object of the master system of record of the client. In some embodiments, the stage classification engine 325 can use a bottom-up approach to predict or determine the stage. The stage classification engine 325 can use machine learning to predict or determine the stage of a deal or opportunity. For example, the stage classification engine 325 can combine the features from each of the electronic activities linked to an opportunity record object into a feature vector. The stage classification engine 325 can use a neural network, or other machine learning technique, to classify the deal into one of the stages based on the feature vector. The machine learning algorithm can be trained using the progression of previous deals through the stages. In some embodiments, the stage classification engine 325 can map the feature vector and plurality of electronic activities to a specific stage as defined by the data source provider. In some embodiments, the stage classification engine 325 can map the feature vector and plurality of electronic activities to a normalized stage as defined by the system. The normalized stages can be used with different data source providers to provide a translatable staging system or nomenclature across the different data source providers. The stage classification engine 325 can maintain mappings between the normalized stages and the stages of the different data source providers. For example, the stage classification engine 325 can define five, normalized stages. A first data source provider can define a deal or opportunity as including 7 stages. A second data source provider can define a deal or opportunity as including 3 stages. The stage classification engine 325, for the first data source provider, may map stages 1 and 2 to normalized stage 1, stage 3 to normalized stage 2, stage 4 to normalized stage 3, stage 5 to normalized stage 4, and stages 6 and 7 to normalized stage 5. Accordingly, the data source provider's stages can be mapped to the normalized stages based on the tasks, requirements, or content of the stages rather than by the naming or numbering of the stages.

The stage classification engine 325 can map the electronic activities or feature vector to one of the five normalized stages. The indication of which normalized stage the electronic activities or feature vector was mapped to can be saved as a shadow stage. When syncing the shadow stage to the master stage of the data source provider, the stage classification engine 325 can map each of the normalized stages to the stages as defined by the data source provider. For example, the first normalized stage may be mapped to the first stage as defined by the data source provider and the second normalized stage may be mapped to the second and third stages as defined by the data source providers.

3. Systems and Methods for Linking Electronic Activities to Record Objects Maintained on Systems of Record As described above, the system can maintain one or more shadow systems of record and shadow stages for each of the data source providers. The shadow systems of record can mirror the data source provider's systems of record at different instances in time. In some embodiments, as described above, electronic activities ingested by the system from a given data source provider are linked to the data source provider's shadow systems of record to enable the system to perform analysis and generate metrics regarding the data source provider's systems of record. In some embodiments, the system can synchronize the linked electronic activities between the shadow systems of record and the data source provider's master systems of record.

The record object manager 255 can maintain data regarding the record objects in the shadow systems of record and the master systems of record. The record object manager 255 can synchronize shadow systems of record and master systems of record for each of the data source providers. In some embodiments, to synchronize the shadow systems of record and the master systems of record the record object manager 255 can detect changes in the master systems of record. The changes can include added, deleted, or modified account record objects, opportunity record objects, or lead record objects or any other record objects. For example, the record object manager 255 can determine that a new account record object was generated at the master system of record and generate a corresponding copy of the new account record object at the shadow system of record. The corresponding copy of the new account record object at the shadow system of record can be a copy of the new account record object at the master system of record. Responsive to adding the new record object, the system can reprocess previously processed electronic activities to determine if the electronic activities should be matched with the new record object.

Detecting if modifications occurred to the record objects of the master system of record can include determining if one or more fields of the record object changed or if the linking of electronic activities with the record object changed. For example, during a previous synchronization cycle the record object manager 255 could link an electronic activity with a first record object at the master system of record. After the synchronization, a user at the master system of record may modify linkage to link the electronic activity with a second record object. In another example, the system can detect that an additional field value was added. For example, location data can be added to location field of a record object. The record object manager 255 can resynchronize the updated record object to identify potential new matches based on the added location data. The system can also reevaluate previous matches and determine if the location data makes the match with the previous matches more or less likely. The record object manager 255 can determine that the electronic activity was linked by the user to a different record object. The record object manager 255 can provide an indication of the change to the record object identification module 315 as feedback so that matching model 340 can update its machine learning models or matching strategies. In some embodiments, a user can add additional information or change information in a record object. Responsive to the change to the record object, the system can perform the rematching of the electronic activity with nodes and record objects.

The record object manager 255 can synchronize changes to the shadow systems of record to the master systems of record. For example, new linkings of electronic activities to record objects can be synchronized to the master system of record. Synchronizing the shadow system of record to the master system of record can include adding any linked electronic activities since the last synchronization cycle to the master system of record. The electronic activities can be linked to the same record object in the master system of record to which they are linked in the shadow system of record. In some embodiments, the record object manager 255 can add a flag or tag to the electronic activity when the electronic activity is synchronized from the shadow system of record to the master system of record. The flag can include an indication that the electronic activity was synchronized from the shadow system of record. In some embodiments, setting of the flag can cause the master system of record to prompt a user of the master system of record to confirm that the electronic activity was linked to the correct record object. In some embodiments, setting of the flag can cause the master system of record to provide a visual indication to a user of the master system of record that the flagged electronic activity was linked and synchronized from a shadow system of record. In some embodiments, the user can confirm or decline the addition of the linked electronic activity from the shadow system of record. Based on the approval or disapproval of the linked electronic activity, the system can update the matching strategies.

4. Systems and Methods for Generating a Multi-Tenant Master Instance of Systems of Record Using Single-Tenant Instances In some embodiments, the system 200 or the system 9300 shown in FIG. 3 as described herein can generate a multi-tenant master instance of the systems of record. The multi-tenant master instance of the systems of record can include data from a plurality of master systems of record from a plurality of different data source providers, which can be referred to as tenants, or from the plurality of shadow systems of record, which can themselves be mirrors or copies of master systems of record from the different tenants. In some embodiments, the multi-tenant master instance of the systems of record can be a combination of the record objects from the separate shadow systems of record.

As described herein, the system 200 or the system 9300 shown in FIG. 3 can include shadow systems of record that correspond to respective master systems of record belonging to respective data source providers. In some embodiments, each of the shadow systems of record (and corresponding master systems of record) can include a plurality of record objects. The record object manager 255 can synchronize the record objects (or data therein) from each of the shadow systems of record or master systems of record from different tenants into a multi-tenant master instance of the systems of record. As such, the multi-tenant master instance of the systems of record can include all of the data included in each record object of the one or more shadow systems of record and the corresponding master systems of record. The multi-tenant master instance of the systems of record can be used to further enrich the node profiles maintained by the node profile manager 220.

The multi-tenant master instance of the systems of record maintained by the system 200 or the system 9300 shown in FIG. 3 can be used to synchronize data between the master systems of record from the different tenants as well as improve the multi-tenant master system of record and individual master systems of record of the data source providers using parsed and normalized activity data received from electronic communications servers of the data source providers. Moreover, the system can update one or more node profiles maintained by the node profile manager 220 using the data from the record objects of the one or more master systems of record. The record object manager 255 can sync fields or data between node profiles and record objects such as, but not limited to, names, phone numbers, email address, domains, other contact information, address, D-U-Ns numbers, job titles, department IDs and other standard company or person information. In some embodiments, some types of systems of record can include record object (and data) types that are not included in other types of systems of record such that one or more of the systems of record may not support all record object types or data types maintained in the multi-tenant master system or record.

The record object manager 255 can populate data from the record objects from the individual master systems of record into the multi-tenant master instance of the systems of record. The record object manager 255 can also be configured to synchronize the record objects (or data contained therein) from the multi-tenant master instance of the systems of record back to the individual shadow systems of record enabling data to be shared between the different tenants. In some embodiments, each shadow system of record can include data that is obtained from a corresponding master system of record of a specific data source provider. This data can be shared with or accessed by the record object manager 255, which can use the data from each of the shadow systems of record to update the multi-tenant master instance of the systems of record. Moreover, the record object manager 255 can further update the record objects included in the multi-tenant master instance of the systems of record from the node profiles of the nodes maintained by the node profile manager 220. The record object manager 255 can then use the data included in the multi-tenant master instance of the systems of record, which has been updated from multiple systems of records and the node profiles, to update one or more of the shadow systems of records, which can then be used to update the corresponding master systems of records of the data source providers.

Data source providers or tenants that provide access to their systems of record can establish, via the system 9300, one or more controls or settings to manage how the data in their respective systems of record are treated. In some embodiments, a tenant can select a setting that restricts the system 9300 from using the information included in the tenant's system of record to update the master instance of the systems of record maintained by the system 9300. In some embodiments, a tenant can select a setting that restricts the system 9300 from using the information included in the tenant's system of record to update systems of record of other tenants maintained by the system 9300. Furthermore, in some embodiments, a tenant can select a setting that restricts the system 9300 from using only certain information, such as sensitive or competitive information included in the tenant's system of record to update the master instance of the systems of record maintained by the system 9300. The system 9300 can provide individual tenants control as to how the data included in a tenant's system of record can be updated, used and shared. For instance, a tenant can select a configuration setting that restricts the system 9300 from updating the tenant's system of record.

Each record object can include a plurality of fields that are populated with data regarding a given record object. As one example, a contact record object can include fields for first name, last name, email, mobile phone number, office phone number, among others. A user can populate the fields of the contact record object at the master system of record of one of the tenants (e.g., one of the data source providers). The record object manager 255 can synchronize the populated fields into the corresponding fields of the record object in the shadow system of record. The node profile manager 220, described herein, can generate a first node (e.g., a member node). The node profile manager 220 can populate the fields of the first node with the data from the contact record object. In this example, a second user can populate the fields of a second contact record object in a second master system of record of a different tenant. Once synchronized to the system, the node profile manager 220 can generate a second node based on the second record object. In some embodiments, the node resolution engine 245 can determine that the first node and the second node are associated with the same contact. For example, the node resolution engine 245 can determine that the email fields of the first and second nodes are populated with the same email address. Determining that the first and second nodes are associated with the same contact, the node resolution engine 245 can merge the first and second nodes such that the merged node includes data from both the first and the second nodes. The record object manager 255 can sync the merged fields back to the respective record objects and master systems of record.

For example, and continuing the above example, the first user may have entered a phone number into a contact field but not a department identifier into a department field of the first user's respective contact record object. The second user may have entered the department identifier into the department field but not the phone number into the second user's respective contact record object. The record object manager 255 can determine the two contact record objects are associated with the same person and merge the data into the multi-tenant master instance of the systems of record maintained by the system 200. In some embodiments, the node profile manager 220 can generate a node for the person in the node graph. To sync or otherwise update the merged data back to the respective contact record objects in the corresponding shadow system of record or the corresponding master system of record, the record object manager 255 can update the first user's contact record object with the department identifier and the second user's contact record object with the phone number. In some embodiments, the record object manager 255 can set a flag indicating the multi-tenant master instance of the systems of record as the source of the updated data in the record objects.

When syncing data between the different tenant systems of record and the multi-tenant master instance of the systems of record, the record object manager 255 can resolve conflicts between record objects and field values in the different systems of record that include different data. The record object manager 255 can resolve the conflicts using the above-described node graph. For example, the record object manager 255 can select between conflicting data by selecting the data that has highest likelihood of being accurate. The system 200 can, via the node profile manager 220, maintain confidence scores of different values of fields to determine a likelihood of the value being accurate. In some embodiments, two values of the same field may both be accurate except one may be more current than the other. In such embodiments, the record object manager 255 can select the value that is accurate and more current. As described herein, a confidence score of a value can be based on contribution scores of one or more data points serving as evidence for the value. The contribution scores of the data points can be based in part on a recency of the data point and a trust score of the source indicating how trustworthy the source is. The trustworthiness of a source, such as a system of record, can be based on a health score of the source, which can be determined based on how many values of record objects of the system of record match values the system 200 knows to be true or accurate and how many values of the record objects do not match values the system 200 knows to be true or accurate.

The record object manager 255 can also resolve conflicts based on the time series of the data for the respective fields. For example, an email field that was recently updated by a user may indicate that the contact recently changed their email address and that the newer email address is an updated email address and not an inaccurate email address. Furthermore, such data may be re-confirmed by extracting the newer email address from an email signature in an electronic activity received from an electronic communications server associated with one of the data source providers. In some embodiments, the record object manager 255 can periodically execute batch jobs to synchronize the shadow and master systems of record. For example, each evening the record object manager 255 can synchronize the shadow and master systems of record. When synchronizing the record objects, the record object manager 255 can reprocess previously synced record objects (and the fields therein) to determine if the record objects should be updated. For example, based on the electronic activities processed during the day, the confidence score associated with a value of a field of a record object in the shadow system of record may have decreased below a predetermined threshold and the record object manager 255 can remove the value from the field of the record object of the shadow system of record during the daily sync.

In some embodiments, the synchronization between from the shadow system or record to the master system of record can be governed by privacy policies. For example, electronic activities, record objects, or data contained therein can be flagged to be labeled as private by the system or a user and may not be synced to the master system of record or to other tenant systems of record. In some embodiments, for little known or possibly sensitive data, the system may not sync fields back to systems of record until the data in the field is identified in a predetermined number of systems of record. For example, if a contact record object for John Smith from a first tenant lists the cell phone of John Smith, the cell phone number may not be synced to other tenants' master systems of record until the system 200 identifies the cell phone number in the contact record object of a predetermined number (e.g., 3) of tenant master systems of record, meaning that at least 2 other companies, connected to the system 200 also possess the phone number for John Smith.

5. Systems and Methods for Monitoring Health of Systems of Record

In some embodiments, the system described herein can be used to monitor the health of a system of record. The source health scorer 215 can monitor the health of the system of record and can calculate a health score for the system of record. The health score for the system of record can be used to determine or otherwise calculate a trust score for the system of record.

The health (or health score) of a system of record can provide an indication of the accuracy or completeness of a system of record's data. In some embodiments, the health score can be calculated with respect to the given system of record. For example, the health score can indicate that 20% of the records within the system of record are inaccurate. In some embodiments, the health score can be calculated with respect to the other data processing systems. For example, the health score can indicate that the completeness of the systems of record' database is in the 97th percentile when compared to the completeness of other systems of record.

The health score can be based on the completeness of data in the system of record and/or the accuracy of the data in the system of record. For example, each record object in a system of record can include a plurality of fields. In some embodiments, the completeness of the system of record can be based on the ratio of the total number of populated standard fields to the total number of unpopulated standard fields. In some other embodiments, the completeness of the system of record can be based on the ratio of the total number of populated standard and supplemental fields to the total number of unpopulated standard and supplemental fields. In some embodiments, fields of record objects in systems of record can be classified as standard fields if they are common among different systems or record. Examples of standard fields can include company name, company phone number, company address as record objects across different systems of records for the same company may each include this information. Similarly, for record objects directed towards individuals, the standard fields can include first name, last name, work phone number, title as record objects across different systems of records for the same individual may each include this information. Other fields that are not standard fields can include custom fields or fields that include supplemental information that is not common across different systems of record can be classified as supplemental fields. Examples of supplemental fields can include fields such as opportunity contact role, years of experience, industry, as these fields may not be common across multiple systems of record.

In some embodiments, the health score can be based on the total count of the fields that are populated or just the total count of the standard fields that are populated. In some embodiments, the health score can also be based on the accuracy of the data populated into the standard fields. The system can determine the accuracy of the data in the standard fields by comparing the data to other instances of the data in other systems of record or in the multi-tenant master instance. For example, the system can determine that the first tenant system of record indicates a phone number for a given contact is 555-5555. A second and third tenant system of record can indicate that the phone number for the given contact is 555-4433. The system can determine that the phone number in the first tenant system of record is incorrect or not current because more tenants (with health scores satisfying a certain threshold) include the 555-4433 phone number. The accuracy of the data can also be based on the health score associated with data source from which the data was received. For example, the phone number may not be changed when contradicted by a source with a low health score. The accuracy of data can also be based on electronic activities and the confidence score of values of fields maintained in node profiles of the system 200. The accuracy of data included in a system of record can be determined by comparing data included in the record objects of the system of record to information included in corresponding node profiles maintained by the system 200. As described above, the node profiles can be updated with information extracted from electronic activities, which are unbiased and not self-reported or manually entered. Based on the comparison of the data included in the record objects of the system of record and the corresponding node profiles, the source health scorer can determine a health of the system of record. The health score can also be time dependent. For example, the health score can decay with time because the data in the system of record can become stale if the data is not updated or not checked. In some embodiments, newer data can have a greater probability of being accurate. For example, a newly entered job title for a contact may be accurate and indicate a promotion.

In some embodiments, the health score can be based on the links between record objects. For example, the system of record may require that each opportunity record object be linked with a least one contact record object. In these examples, the data fields within the record objects may be complete but the source health scorer 215 can reduce the system of record's health score or assign a lower health score to a system of record responsive to determining that the system of record does not include proper links between one or more opportunity record objects and corresponding contact record objects or any other record objects with which the one or more opportunity record objects should be linked. In some embodiments, the source health scorer 215 can base the health score on the accuracy of the links between the record objects of the system of record. For example, the system can process the electronic activities already linked to the system of record to perform historical matching based on using the techniques described herein to generate predictions for linking between the system or record's record objects. If the linkages between the record objects do not match the predicted matches, the source health scorer 215 can assign the system of record a lower health score.

The source health scorer 215 can also calculate or otherwise determine a trust score for each data point included in an array of a value of a node profile maintained by the system 200 or that contributes towards a value in a record object maintained by the system 200. The trust score can be based on the source of the data point. In some embodiments, the trust score can be based on a health score of the source of the data point. For instance, some systems of record can be better maintained than others. The source health scorer 215 can perform a health check on a system of record to compute a health score for the system of record. The health score of the system of record can be used to assign a trust score. In contrast to data points whose source is a system of record, a data point whose source is an electronic activity ingested by the system 200 can have a higher trust score since electronic activities do not have health related issues as they are not manually input or updated. Systems of record are generally manually input and updated and therefore can include inaccuracies or may be stale resulting in lower health scores, and thereby, lower trust scores. In some embodiments, the source health scorer 215 can assign a trust score of 100% or a maximum rating to data points derived from electronic activities.

6. Systems and Methods for Generating Recommendations to Improve Health Based on a Node Graph Generated from Electronic Activity In some embodiments, the system described herein can make recommendations based on the health and trust scores associated with a system of record or data source provider. The source health scorer 215 or other components of the system can generate the recommendations based on metrics of the systems of record, record objects therein, and the trust and health scores associated with the systems of record.

The source health scorer 215 can determine, for each field type, of number of standard fields not populated with data. For example, the source health scorer 215 can determine, for a given system of record, that 75% of the contact record objects include domain fields that are not populated with a website field value. In this case, the recommendation can be that the data source provider should update the domain fields of the contact record objects. In some occurrences, the system can automatically fill in a predetermined percentage of the missing field values in a given system of record to automatically improve the health score of the given system of record. Given a significant number of systems of record, connected to the multi-tenant system of record instance and the source health scorer 215, such a system can systematically and continuously improve the health scores of all connected systems of record. Stated in another way, by generating or maintaining a multi-tenant system of record that can be used to update one or more master systems of record maintained by customers or enterprises, a network of systems of record are created with automated data entry, thereby allowing each of the master systems of records to get updated. This will result in an improvement in the health and corresponding health score of each of the master systems of record through the network effect until all of the master systems of record are identical and, in some embodiments, pristine or perfect.

In some embodiments, the recommendations can indicate to a data source provider that the data within the system of record is stale or out of date. For example, if a first company is sold to a second company, the system can alert the data source provider to update the company or other information in its systems of record based on the sale of the first company. The recommendations can also include updates to field values, organizational charts, job titles, employment changes, and changes to an organization, such as mergers and acquisitions.

7. Systems and Methods for Filtering and Database Pruning

At least one aspect of the present disclosure is directed to systems and methods for filtering and database pruning. For example, the tagging engine 265 can assign tags based on the contents of the electronic activity, associations of the electronic activity with specific nodes, people, or companies, confidence and trust scores, information in record objects, or other information associated with the electronic activity. The rules used by the tagging engine 265 to generate tags can be used by one or more systems or components described herein. In some cases, the rules used by the tagging engine 265 to generate tags can generate filter tags, which can be configured to cause the system to block, delete, remove, drop or redact the electronic activity associated with the filter tag.

A system, such as the data processing system 9300 depicted in FIG. 3, the node graph generation system 200 depicted in FIG. 4, the tagging engine 265 depicted in FIG. 4, the electronic activity linking engine 250 depicted in FIG. 9, or one or more components thereof, may perform significant computationally extensive processing on various types of electronic activities or records as depicted in FIG. 3. Since a large volume of electronic activities associated with sending or receiving electronic activities are received by the systems or components depicted in FIG. 3, 4, or 9 in accordance with the process flow 9302 depicted in FIG. 9, it can be challenging to efficiently process such data without causing excessive delay or latency issues. Further, databases associated with the systems and components depicted in FIGS. 3, 4 and 9, as well as third-party databases with which the systems depicted in FIGS. 3, 4 and 9 can interface or communicate, may store or maintain records that may be stale, sensitive, corrupt, erroneous, or otherwise not needed or not wanted. As such, systems and methods of the present technical solution can provide filtering at an ingestion step 9307 as depicted in the functional flow diagram of FIG. 9302, as well as scrubbing of records maintained in one or more databases, using parsing techniques, rules or machine learning.

The node graph generation system 200 can, via ingestor 205, receive electronic activities. The electronic activities can include, for example, electronic messages or electronic calendar events and associated metadata. The ingestor 205 can receive the electronic activities from one or more data source providers 9350, which can include an electronic messaging or mail server. The ingestor 205, upon receiving the electronic activities, can format the metadata or otherwise manage or manipulate the data to facilitate further processing. The ingestor 205 can receive the electronic activities in real-time, asynchronously, on a periodic basis, based on a time interval, in a batch process or batch download, or responsive to a trigger of event.

The tagging engine 265 can, using one or more rules, policies, or techniques, tag the electronic activities such that the filtering engine 270 can apply a content filter to the tagged electronic activities to determine whether to filter out the electronic activity or authorize or approve the electronic activity for further processing, or redact a portion of the electronic activity. The filtering engine 270 can filter out the electronic activity, which can refer to or include redacting out sensitive or private parts of the electronic communications or preventing the entire electronic activity (or metadata thereof) from being forwarded to another component or memory of the system so that the electronic activity is prevented or blocked from further processing or storage. Preventing the electronic activity from being further processed or stored can reduce unnecessary computing resource utilization or memory utilization as well as prevent sensitive or private information from being carried from systems of record or activity data sources to other systems of record.

The electronic activity parser 210 can provide an alert, tag, notification, label or other indication of the reason the electronic activity was filtered out, blocked or deleted or redacted. The indication can indicate the type of filter or rule that triggered or caused the removal or redaction.

In some embodiments, the tagging engine 265 can tag the electronic activities with a filter tag based on one or more rules or policies. The filtering engine 270 can then filter out the electronic activities based on the assigned filter tag or cause another system or component to filter out the electronic activity responsive to the filter tag. For example, the tagging engine 265, using technologies such as regular expressions, pattern recognition or NLP, can tag the electronic activity to cause the filtering engine 270 to block ingestion of the electronic activities or perform other filtering in downstream systems.

The system 200 can be configured to provide, via the filtering engine 270, various types of filtering techniques that may be applied to electronic activities during ingestion, during processing of the electronic activities, or when attempting to match electronic activities to record objects of shadow systems of record or master systems of record.

As described herein, the filtering engine 270 can be configured to apply different types of filtering techniques. As will be described herein, the filtering engine 270 can apply filters based on the content included in electronic activities. Such filters may be referred to as content filters. The filtering engine 270 can also apply logic based filters based on one or more logic based rules for filtering electronic activities. Such filters may be referred to as logic based filters. In addition, the filtering engine 270 may apply filters to restrict matching of electronic activities to node profiles or restrict matching of electronic activities to one or more record objects of systems of records. Additional details regarding the different types of filters are provided herein.

As described herein, the filtering engine 270 can apply various filtering techniques at a user specific level, a company level, a system level, among others. These filtering techniques can be controlled by users, administrators of a company, administrators of the system 200, among others.

A. Content Based Filtering

The filtering engine 270 can be configured to perform content filtering. Content filtering involves performing one or more actions on an electronic activity based on the content of the electronic activity. In some embodiments, the actions can include restricting ingestion of the electronic activity into the system 200. In some embodiments, the action can include redacting a portion or all of the content included in the electronic activity. In some embodiments, the action can include restricting matching the electronic activity to a node profile or restricting matching the electronic activity to one or more record objects.

As described herein, the tagging engine 265 or electronic activity parser 210 can identify terms, text, content or other information in the body or metadata of the electronic activity. The tagging engine 265 can then apply a rule, policy, logic, machine learning algorithm, or natural language processing techniques to assign one or more tags to the electronic activity based on the identified terms, text, content or other information in the body or metadata of the electronic activity. The tag can include a content filter tag or other type of tag that the filtering engine 270 can use to perform content filtering. In some embodiments, the tagging engine 265 can be configured to apply a tagging policy that uses keywords and NLP to identify portions of electronic activities that satisfy one or more filtering rules. The tagging engine 265 can then tag such electronic activities with appropriate content filter tags that the filtering engine 270 can use to either redact portions of the tagged electronic activity, block the entire tagged electronic activity from being ingested, stored, or otherwise processed. In some embodiments, the filtering engine 270 can be configured to parse electronic activities to determine if the respective electronic activity includes any of one or more predetermined keywords, phrases, regex patterns or content in the electronic activity. Responsive to determining that the electronic activity includes any of one or more predetermined keywords, phrases, regex patterns or content in the electronic activity, the filtering engine 270 can restrict ingestion of the electronic activity into the system 200.

In some embodiments, the tagging engine can tag the electronic activity with a tag indicating that the electronic activity includes sensitive information. In some embodiments, the tagging engine 265 can be configured to assign specific content filter tags based on the type of content detected in the electronic activity. For instance, the tagging engine 265 can assign a social security tag responsive to detecting a social security number (or any other number that matches a regex pattern corresponding to a social security number). In some embodiments, the tagging engine 265 can run one or more algorithms to identify various types of information for which a content filtering rule applies. Accordingly, the tagging engine 265 may determine if the electronic activity includes content that satisfies a content filtering rule, the tagging engine 265 may assign one or more content filter tags to the electronic activity indicating that the electronic activity includes content that may be subject to a content filtering rule. In some such embodiments, the content filter tag can include additional information that the system 200 or the filtering engine 270 can use to determine a basis for why the electronic activity satisfies the content filtering rule.

Based on the type of content filter tag assigned to the electronic activity, the filtering engine 270 can take one or more actions on the electronic activity. In some embodiments, the tagging engine 265 can tag the electronic activity with a content filter tag that the filtering engine 270 can use to determine what action to take on the electronic activity. For instance, in the example of the tagging engine 265 assigning a social security tag responsive to detecting a social security number (or any other number that matches a regex pattern corresponding to a social security number) in the electronic activity, the filtering engine can be configured to parse the electronic activity to identify the content that matches the regex pattern of the social security number and can apply a redaction policy to the electronic activity, causing the filtering engine 270 to redact the number from the electronic activity. It should be appreciated that the filtering engine 270 can redact the content by either obscuring the text with a visual marker, replacing the numbers with text indicating that the content is redacted, or other techniques for redacting text. The system can be configured to determine other types of sensitive information including credit card numbers, bank account numbers, date of births, or other sensitive or confidential information for which the filtering engine 270 may include one more filtering rules.

In some embodiments, the tag can indicate a type of data or field present in the electronic activity, such as a social security number or credit card number, in which case the filtering engine 270 can be configured with a policy to redact out sensitive information from electronic activities or filter out electronic activities tagged as containing credit card numbers or social security numbers or other sensitive or private information or perform any other action.

B. Tag Based Filtering

As described above, the filtering engine 270 can use one or more content filters or content filtering policies to filter the electronic activity. In some embodiments, the filtering engine 270 can be configured to filter electronic activities based on one or more tags assigned by the tagging engine 265. Some of the tags assigned by the tagging engine 265 can be used to filter electronic activities, either from ingestion by the system 200 or from matching or linking the electronic activity to record objects of one or more systems of record. The tags assigned by the tagging engine 265 can be used for purposes other than filtering, for instance, for updating node profiles, determining connection strengths between nodes, understanding context of electronic activities, among others.

The tagging engine 265 can first tag all electronic activities based on numerous tagging methods as described herein. Thereafter, the filtering engine 270 can determine or choose to filter content out based on one or more tags, and otherwise determine or choose to allow further processing or storage of electronic activity based on other tags. The tagging engine 265 can determine to generate, apply or assign a tag, such as a filter tag, based on a regular expression. A regular expression (or regex or regexp) can include a sequence of characters that define a pattern. Example regular expressions can be configured to detect credit card numbers, social security numbers, license numbers, date of birth or any other combination of words or numbers. The tagging engine 265 can be configured with a regex for a credit card number. For example, a regex for a credit card number can be defined as a sequence of 13 to 16 digits, with specific digits at the start that identify the card issuer. The tagging engine 265 can be configured with predetermined digits of card issuers. The tagging engine 265 can apply the credit card number detection technique to the electronic activity (or metadata thereof) to detect or determine whether the electronic activity contains a credit card number. If the tagging engine 265 determines that the electronic activity contains a credit card number responsive to applying or searching for the credit card regex, the tagging engine 265 can apply a filter tag to cause the filtering engine to filter out the electronic activity or redact out the credit card number.

The tagging engine 265 can determine to apply a filter tag based on predetermined keywords. The keywords can indicate topics, concept or terms. Keywords can include, for example, "Credit Card No." or "License No." or "SSN" or "SSID", etc. Keywords for topics to be filtered out can include, for example, "medical record", "health record", "doctor visit", etc. The system 200 can use a master list of keywords that can be used to form a Global Keyword Based Content Filter that can be applied across all (new and existing) customers or users of the system 200. It should be appreciated that the system 200 can be configured to generate, maintain, use or otherwise access keyword ontology or one or more machine learning models trained on keywords, clusters of text or other documents to build the master list of keywords. The content filter can be global or the content filter can be specific to a customer, user or other category or level. The system 200 can continue to update this global list of keyword based content filter. The system 200 can use filters based on a natural language processing technique to determine or identify synonyms, translations into other languages, or related keywords.

As described herein, a filter or filter tag can be applied or generated for a type of electronic activity. For example, a type of electronic activity can be adding a non-human participant (e.g., a room, device, projector, printer, display, etc.) to an electronic meeting event. The system 200 can use a filter to prevent or block further processing on an electronic activity associated with adding a non-human participant or prevent a non-human participant from being matched or from being created as a new record in the multi-tenant, shadow, or other systems of record.

C. Logic-Based Filtering

The filtering engine 270 can be configured to perform logic-based filtering in which the filtering engine 270 applies one or more logic-based rules to filter electronic activities. The logic filter can include a set of logic-based rules that can be used to filter electronic activities. The filtering engine 270 can be configured to execute one or more logic filtering policies by identifying structured metadata around an electronic activity or record object, and then blocking the electronic activity or record object from being ingested by the system 200 based on identifying the structured metadata. In some embodiments, the logic-based filtering can apply one or more rules or heuristics to restrict matching an electronic activity to a node profile or to one or more record objects of systems of record. In some embodiments, the logic-based filtering can restrict an electronic activity from being matched to a particular record object if the electronic activity was sent by a bot or is sent to a personal email address (such as a gmail address or a hotmail address, among others).

In one example, the system 200, an administrator of the data source provider or a user of the system 200 can establish a logic-based filter to restrict ingesting electronic activities that satisfy one or more logic-based rules. In this example, the administrator of the data source provider can establish a logic-based filter to restrict ingestion of electronic activities that relate to one or more predetermined federal, state, or local government agencies, for instance, the CIA, NSA or FBI. The administrator can create one or more logic based rules that restrict the system 200 from ingesting the electronic activity into the system 200 if the electronic activity can be matched to an account type field having a value of government, or if the electronic activity is sent from or received by a domain name that matches a contains a domain name that matches any of the predetermined federal, state, or local government agencies, or if the contents of the email include certain predetermined character strings (for instance, CIA, NSA or FBI) or if the system 200 otherwise determines that the electronic activity is in any possible way related to the CIA, NSA or FBI.

D. Matching Filter

As described above, matching filters can be a type of restriction strategy or restriction policy that can be used to restrict electronic activities from being matched to record objects. These matching filters can be a part of, include or use one or more restriction strategies to prevent electronic activities from being linked to particular record objects or a particular system of record in general. In some embodiments, the matching filter can restrict matching electronic activities to record objects if the matching score between the electronic activity and the record object is less than or equal to a predetermined threshold (e.g., 70%, 60%, 50%, etc.). The matching score can indicate how closely the electronic activity matches the record object.

In some embodiments, users of a system of record can be configured to establish one or more restriction strategies or matching filters to restrict matching electronic activities to certain record objects. The user can be a user associated with the record object. In some embodiments, the user can be an administrator of the system of record and can establish one or more matching filters that can be used to restrict matching. For instance, an administrator can establish a matching filter that restricts matching electronic activities including a credit card number to certain record objects. In some embodiments, the matching filters can include multiple rules, which when satisfied, restrict the electronic activity from being matched to a certain record object. In some embodiments, the matching filters can be used to restrict electronic activities from being matched to record objects even if the record object was selected by one or more matching strategies 1100 and 1104 as described above.

E. Nlp Based Tags and Filtering

The tagging engine 265 can determine to apply a filter tag, or the filtering engine 270 can determine to perform filtering, based on natural language processing. Natural language processing can refer to parsing metadata associated with the electronic activity to identify a meaning, concept, topic or other higher level concept associated with the metadata. Natural language processing techniques or algorithms can determine whether the electronic activity contains or is regarding a concept that is to be filtered out.

Natural language processing can be used to determine whether an electronic activity is a personal electronic activity or a business electronic activity. The filtering engine 270 can perform or execute the filter to redact out sensitive content, block or prevent further processing of personal electronic activities, and authorize or approve further processing of business related electronic activities. The tagging engine 265 when determining to apply a filter tag, or the filtering engine 270 when determining whether to perform filtering, can determine whether the electronic activity is personal based on a tag from the tagging engine or an email identifier used by the sender or recipient (e.g., a domain of the email address indicating personal use (or typically used for personal use) versus a domain indicating a business use or corresponding to an employer of the sender or recipient). The system 200 (e.g., via electronic activity parser 210, tagging engine 265, or filtering engine 270) can further determine personal or business electronic activities based on keywords, terms, topics, or concepts of the electronic activity (e.g., vacation-related versus order or purchase related). In some cases, the system 200 can determine that an electronic activity was sent using a personal electronic mail address, but the content of the electronic activity was to further a business objective. Thus, the system 200 can initially determine to block the electronic activity, but then determine to authorize or approve the electronic activity, thereby overriding an initial filter layer.

The system 200 can use a natural language processing engine that can be configured to parse text or keywords in different languages and determine synonyms or equivalent concepts across multiple languages. For example, the system 200, using the natural language processing engine, can determine the equivalent of a keyword in English but in Japanese, and, therefore, be configured to perform tagging and filtering in multiple languages. The NLP engine can further expand a keyword into a number of synonyms or related keywords. Thus, even if the list of keywords used for filtering are not comprehensive, the system can still perform robust tagging and filtering.

F. Machine Learning Based Filtering

The system 200 can use machine learning to determine whether to filter an electronic activity. Machine learning can refer to a training set of data that includes metadata for electronic activities that are to be approved or authorized for further processing, as well as metadata for electronic activities that are to be filtered out based on both structured data and also on vectorized content of the communications. For example, if words in the electronic activities are converted into vectors with word2vec or similar technology, a machine learning model can be trained based on the content of the electronic activities alongside (not mutually exclusive) with natural language processing systems. The machine learning based filter can automatically establish, based on the training set, features, weights or other criteria that indicate whether or how an electronic activity should be tagged. In some embodiments, the system 200 can then determine if the electronic activity should be approved or filtered out based on the one or more tags. Thus, by using a machine learning technique, the system 200 can automatically determine features, weights or criteria to detect in metadata of the electronic activity to determine whether to tag and then filter out or authorize the electronic activity for further processing.

G. Filtering Based on Bot Detection

The machine learning filtering technique can include bot detection. The system 200 (e.g., electronic activity parser 210, tagging engine 265 or filtering engine 270) can use or be configured with a bot detection machine learning algorithm to detect whether the electronic activity was sent by a bot—such as an automatic electronic activity generator. If the electronic activity was transmitted by a bot, the tagging engine 265 or the filtering engine 270 can tag the electronic activity with a tag indicating that the electronic activity was generated by a bot. In some embodiments, the filtering engine 270 can remove or prevent further processing or storage of the electronic activity (e.g., responsive to the tagging engine 265 tagging the electronic activity with a filter tag or a tag indicating that the electronic activity was transmitted by a bot). The system 200 can leverage or use the node graph to automate populating a blacklist of email addresses or other unique identifiers associated with bots through bot detection for syncing. For example, if an electronic activity is from a bot, that information may not be matched, linked or synced to a system of record. In some embodiments, the system 200 can detect bots based on the node graph since the node graph can indicate that a node of the sender bot is associated with edges of interactions between other nodes that indicate heavy one-way interactions across a large number of nodes. Thus, by measuring or detecting edge connection strength between the sender bot node and other nodes, or in some embodiments, comparing the number of inbound interactions (received electronic activities) and outbound interactions (transmitted electronic activities) between the sender bot node and other nodes, the system can classify non-human participants. For instance, non-human participants, such as no-reply@example.com generally transmit emails to a large number of other nodes but only receive a much smaller number of emails from other nodes, thereby allowing the system 200 to classify the email no-reply@example.com as a bot. The system 200 can use or apply similar techniques to detect and classify other types of non-human communication patterns and activity participants. For example, conference room email addresses only get added to meetings but never send or receive regular (non-meeting invite) emails and thus can be classified as Conference Room bots. Furthermore, the system 200 can identify a bot by parsing the email address or name associated with the email address. For instance, the bot detection algorithm can detect that an email address including "no-reply" is associated with a bot. In some embodiments, the bot detection algorithm can parse an electronic activity and determine, using NLP, that the email address associated with the sender is a bot based on language indicating not to send a reply to the electronic activity.

H. Using Feedback to Improve Filtering Techniques

The system 200 can tune or improve the machine learning techniques based on feedback. For example, upon applying the machine learning techniques to electronic activities, the system 200 can provide the filter decision to an administrator or other user of system 200. The user can input whether the filter decision was correct or incorrect. If the filter decision was correct, the machine learning filter can maintain the weights or rules used to make the filter decision, or increase weights used to make the filter decision. If the filter decision was incorrect, the system 200 can modify the features, weights or criteria in an attempt to correct the filter decision. Similarly, the system 200 can use user input to modify features, weights, or criteria for other types of tagging or filtering, including, for example, natural language processing, rules, linking, or other logic flows that can be improved, enhanced or otherwise benefit from user input. In some embodiments, the machine can be configured to update the weights based on feedback without any intervention of a user or administrator.

I. Global Pattern Based Process Filter

Since end users can send/receive sensitive information from various systems (e.g., Human Resource systems, payroll systems, benefits systems, applicant tracking systems, recruiting systems, medical bill payment systems, phone bill payment systems, utility bill payment systems, banking or financial institutions, ride sharing systems, etc.) that could include highly sensitive information like payroll, benefits, hiring/termination letters, feedback on hiring a candidate or a cell phone bill which includes call details, the filtering engine 270 can block or prevent such electronic activities from being further processed or ingested by one or more components of the node graph generation system 200 or electronic activity linking engine 250 by maintaining a Global Pattern Based Process Filter which is applicable for all nodes. This can include a pattern based process filter that can identify rules to detect automated emails based on a 'from' and other fields; trigger a job to generate an automated systems blacklist; obtain a global blacklist from a storage or database; and apply a global pattern based process to filter out automated system electronic activity. Patterns can also be based on or applied to different fields or aspects of electronic activities, such as other data in an electronic message, meeting or calendar entry, telephone transcript, etc.

To generate such filters, the tagging engine 265 or filtering engine 270 can use bot detection techniques to identify bots automatically and blacklist the identified bots. Further, and in some embodiments, the tagging engine 265 can use natural language processing or machine learning techniques to automatically assess sensitivity of data from a new sender. For example, if a new source starts sending emails to multiple users, and greater than a threshold percentage (e.g., 70%, 80%, 90% or some other percentage) of the emails contain sensitive or confidential information (e.g., social security numbers), then the system 200 can automatically generate and apply a global filter to automatically blacklist this source.

J. Hierarchy of Filtering Rules

The system 200 (e.g., via electronic activity parser 210, tagging engine 265 or filtering engine 270) can apply one or more layers of filters. The system 200 can apply the one or more layers of filters in parallel or serially. The system 200 can select one or more layers of filters to apply to an electronic activity based on a policy, rule or other logic. Layers of filters can refer to or include different types of filters or different configurations for filters. Layers of filters can refer to or include different type of filter controls or thresholds. Layers of filters can correspond to a hierarchy. For example, a first filter layer can include filtering policies, rules or logic established, based on or customized for a node in the node graph (e.g., a member node, an employee node, a user node, or an individual node). A second filter layer can include filtering policies, rules or logic established, based on or customized for an account. The account can refer to buyer account established by a seller for the buyer. A third filter layer can include filtering policies, rules or logic established, based on or customized for an organization. The organization can refer to or include a buyer organization, such as a company. A fourth filter layer can include filtering policies, rules or logic established by governmental agencies. A fifth filter layer (or master filter layer) can include filtering policies, rules or logic established, based on or customized for an administrator or provider of the node graph generation system 200 or electronic activity linking engine 250. Different entities can establish various types of filters with various thresholds, controls, rules or policies.

As described below, the system 200 can be configured to apply different types of filtering policies. Each of the filtering policies outlined below can correspond to one of the filter layers described above.

K. Entity-Defined Filtering Policies

The system 200 can select one or more filters to apply to an electronic activity or all electronic activity ingested. The system 200 can select the one or more filters based on the metadata associated with the electronic activity. The system 200 can select the one or more filters to apply based on filtering rules defined for an account, a user, a group of users within an enterprise, an enterprise, or the system 200.

i. Account-Specific Filtering Policies

The filtering engine 270 can maintain account-specific filtering policies that include one or more rules defined for one or more accounts. For instance, the filtering engine 270 can be configured to apply filters to emails either transmitted by or received by a specific account, such as an email account. In some embodiments, the account-specific filtering policy can include one or more rules to apply one or more content filters, logic-based filters or matching filters on electronic activities corresponding to the specific account. For instance, the filtering engine 270 can apply an account-specific filtering policy to an account, such as an email address corresponding to a bot. In one example, the account-specific filtering policy can include a rule to restrict matching any emails transmitted by the account to a record object of a system of record. The account-specific filtering policy can be defined by a user, an administrator of the enterprise, or an administrator of the system 200.

ii. User-Specific Filtering Policies

The filtering engine 270 can maintain user-specific filtering policies that include one or more rules defined for specific users. For instance, the filtering engine 270 can be configured to apply filters to emails either transmitted by or received by a specific user. In some embodiments, the user-specific filtering policy can include one or more rules to apply one or more content filters, logic-based filters or matching filters on electronic activities corresponding to the specific user. For instance, the filtering engine 270 can apply a user-specific filtering policy that includes restricting certain electronic activities sent by the user from being linked to one or more systems of record or to the node profile of the user. For instance, the user may define a rule to restrict any emails between the user and their lawyer from being linked to one or more systems of record or to the node profile of the user. In another example, the user may define a rule to restrict emails sent to the user's spouse at a given company to be linked to record objects of the company. The user-specific filtering policy of a user can be defined by a user, an administrator of the enterprise, or an administrator of the system 200.

iii. Group-Specific Filtering Policies

The filtering engine 270 can maintain group-specific filtering policies that include one or more rules defined for specific groups of users. For instance, the filtering engine 270 can be configured to apply filters to emails either transmitted by or received by users defined within a specific group of users. In some embodiments, the group-specific filtering policy can include one or more rules to apply one or more content filters, logic-based filters or matching filters on electronic activities corresponding to the specific group of users. For instance, the filtering engine 270 can apply a group-specific filtering policy that includes restricting certain electronic activities sent by a user of the group from being linked to one or more systems of record or to the node profile of the user. For instance, a user of the group or an administrator of the enterprise associated with the group or the system 200 may define a rule to redact text included in any emails between one or more users of the group before storing the electronic activity in the system 200 or any record object with which the electronic activity is matched. The group-specific filtering policy of a user can be defined by a user, an administrator of the enterprise, or an administrator of the system 200.

iv. Enterprise-Specific Filtering Policies

The system 200 can select the one or more filters to apply based on enterprise-specific filtering policies. For example, an administrator of a first enterprise or customer of the system 200 can indicate to remove electronic activity accessed via a mail server of the first customer having metadata that matches a regex for a credit card number, whereas an administrator of a second enterprise or customer of the system 200 can indicate to remove electronic activity accessed via a mail server of the second customer having metadata that matches a keyword or regex pattern for a credit card number. In this example, the system 200 applies enterprise-level filtering rules that may be defined by specific enterprises on how to process electronic activities received from their electronic communications servers. The enterprise-specific filtering policy of a user can be defined by an administrator of the enterprise or the system 200.

v. System Defined Filtering Policies

The filtering engine 270 can maintain system-specific filtering policies that include one or more rules defined for the system 200. For instance, the filtering engine 270 can be configured to apply filters to all electronic activities processed by the system 200. For instance, the system-specific filtering policy can include one or more rules to apply one or more content filters, logic-based filters or matching filters on electronic activities accessible by or ingested by the system 200. For instance, the filtering engine 270 can apply a system-specific filtering policy that includes tagging all electronic activities that include numbers matching a credit card regex pattern with a credit card tag indicating that the electronic activity includes a credit card. The system 200 can then be configured to determine if the filtering engine 270 is to take any additional actions on the electronic activity with the credit card tag, for example, redacting the credit card information, restricting matching the electronic activity to record objects, among others. The system-specific filtering policy can be defined by an administrator of the system 200.

L. Sensitive Information Filter

The system 200 can determine to filter out an electronic activity responsive to detecting sensitive information or data in or associated with the electronic activity. For example, upon detecting or identifying a social security number or a financial account number in the electronic activity, or a tag indicating sensitive information, the system 200 can filter out the electronic activity. This is an example of one type of content filtering.

M. Source Based Filtering

The system 200 can select the filter to apply based on who is a sender or recipient of the electronic activity or a source of the electronic activity (for example, whose mail server the electronic activity came from). In some cases, the system 200 can select one or more filters to apply or apply all filters that are configured or compatible with the electronic activity. This is similar to the user-specific filtering policy described above. In one example, the data source provider of a system of record can establish a rule that causes the system 200 to restrict any emails coming from a craigslist.org domain from being matched to any record object of the system of record.

N. Previous Communication Activity Filter

The system 200 can filter out the electronic activity if there have been no previous electronic activities between the sender and recipient of the electronic activity. However, the system 200 can authorize or approve the electronic activity if electronic activities have occurred between a node in close proximity in the node graph to the sender node or recipient node. In some embodiments, two nodes may be in close proximity in the node graph if they have a connection strength above a predetermined threshold. In some embodiments, two nodes may be in close proximity in the node graph if they have either exchanged electronic activity with each other or with a predetermined number of connection nodes in common. Thus, the system 200 can determine to approve or filter out electronic activities based on the extent to which prior electronic activities between the sender and recipient have occurred (e.g., a metric associated with one or more prior activities satisfying a threshold).

O. Geographic Location Based Filters

The system 200 can select filters based on a geographic location inferred for a node associated with the electronic activity. In some embodiments, a geographic location can be inferred for a node based on detecting a time zone based on timestamps of electronic activities transmitted by the sender node. In some embodiments, the filtering engine 270 can be configured to apply one or more filtering rules based on a geographic location of the sender or recipient of the electronic activity. In some embodiments, geographic location based filtering may be applied in conjunction with the previous communication activity filter or other types of filters. For instance, the system 200 can be configured to restrict matching electronic activities sent to a first user from a second user if the number of communications between the two users is less than a certain threshold and the first user is in a particular geographic region, for instance, Massachusetts.

In some embodiments, the system 200 can authorize or approve further processing or storage of electronic activities if a user has consented to the further processing or storage of such electronic activities. The system 200 can authorize or approve further processing or storage of electronic activities if, based on the overall volume or nature of communications, as well as keywords or context, the metadata associated with the electronic activity indicates an opportunity, contract, or other relationship. The system 200 can determine, using the overall volume, context and nature of electronic activities, (which can be determined using keywords, machine learning or natural language processing), whether the electronic activity is indicative of a legitimate business interaction (e.g., amount of time spent on electronic activities, number of electronic activities, roles, or type of electronic activity such as in-person, video conference, web conference, telephone call). Responsive to this determination, the system 200 can authorize or approve the electronic activity for further processing, or conversely delete, remove or block further processing or storage of the electronic activity if the electronic activity is not indicative of a legitimate business interaction.

Using the filters, the system 200 can determine which electronic activities are to be processed by the system or added, stored or linked to nodes in a node graph or a system of record or one or more systems of record. As described herein, the filtering techniques can be used to prevent sensitive or private electronic activities from being linked or stored in a system of record. The filter can work by (1) completely filtering out the electronic activity, or (2) filtering out/blocking ingestions of the content of the electronic activity, while the electronic activity itself, without the content body, is synced and a graph edge between the sender and recipient of the electronic activity is created, or (3) by redacting out sensitive parts of the electronic activity.

In some cases, the filtering engine 270 can be configured to apply one or more filtering policies to one or more systems of record to scrub or remove data from the systems of record that satisfy the one or more filtering policies. For example, a system of record of an enterprise can be pruned using one or more enterprise-specific filters to remove electronic activities or other values or data from the system of record of the enterprise that satisfy the one or more enterprise-specific filters. For instance, an administrator of an enterprise can establish a new filtering policy to redact social security numbers from any electronic activities that include social security numbers and that are also matched to the systems of records of the enterprise. The filtering engine 270 can be configured to evaluate, responsive to the new filtering policy, each electronic activity previously matched to the systems of record of the enterprise to identify if the electronic activity includes a social security number and if so, redact the social security number from the electronic activity.

It should be appreciated that the filtering engine 270 can be configured to apply one or more filtering policies defined by a user of the system, an administrator of the enterprise or an administrator of the system 200 to prune one or more systems of record, a shadow system of record, or a master system of record.

In some embodiments, the system 200 can identify electronic activities or record objects having personal email domains. The system 200 can maintain a static list of all personal email domains to determine which domains are personal and which domains are not personal. However, to prevent personal electronic activity from being matched or synced to the system of record, the filtering engine 270 can allow linking and syncing based on the domain name.

8. Systems and Methods for Threshold-Based Data Management

At least one aspect of the present disclosure is directed to systems and methods for threshold-based data management. The system 200, such as the tagging engine 265, filtering engine 270, electronic activity parser 210 or other component or module, can analyze a data source provider's system of record to identify with which contacts or nodes, employees or users associated with the data source provider have sufficient activity above a predetermined level or threshold. Responsive to the system 200 determining that the level of activity between a user associated with the data source provider and a contact or node is equal to or greater than (i.e. satisfies) a predetermined threshold, the system 200 can authorize, allow, or approve for storage an electronic activity between the user associated with the data source provider and the contact or node. For example, if the user associated with the data source provider has communicated with the contact or node before or had a certain number of communications or certain number of communications of a certain type or certain context, then the system 200 can determine that level of interaction satisfies a threshold and proceed to store the electronic activity or metadata or other information associated with the electronic activity or the node or contact. In this way, cold emails, unsolicited emails or other types of electronic activities that do not warrant being linked to the system of record of the data source provider can be restricted from being linked to the system of record of the data source provider.

The system 200 can detect, using keywords, machine learning or natural language processing, whether the electronic activity is indicative of a legitimate business interaction based on the volume, nature, content or context of the electronic activity or based on the number of electronic activities transmitted between the user associated with the data source provider and the contact. For example, the system 200 can detect a legitimate business interaction based on the amount of time the contact or user associated with the data source provider spent on electronic activities. In some embodiments, the system 200 can detect a legitimate business interaction based on a number of electronic activities, roles, direction of the electronic activity such as inbound or outbound, or type of electronic activity such as in-person, video conference, web conference, or telephone call. Responsive to determining whether the electronic activity is indicative of a legitimate business interest, the system 200 can authorize or approve the electronic activity for further processing, or otherwise delete, remove or block further processing or storage of the electronic activity.

In some embodiments, the system 200 can leverage a node graph to determine the level of activity between an employee associated with the system of record and a contact. The system 200 can determine the level of activity based on the number of electronic activities transmitted by the employee to the contact, the number of electronic activities transmitted by the contact to the employee, or the type of electronic activities being transmitted, information associated with the electronic activities (e.g., calendar invite for a teleconference or in-person meeting, blast email, etc.). In some embodiments, the system 200 can authorize or approve the electronic activity if electronic activities have occurred between a node in close proximity in the node graph to the sender node or recipient node. In some embodiments, two nodes may be in close proximity in the node graph if they have a connection strength above a predetermined threshold. In some embodiments, two nodes may be in close proximity in the node graph if they have either exchanged electronic activities with each other or with a predetermined number of common nodes. Thus, the system 200 can determine to approve or filter out electronic activities based on whether prior electronic activities between the sender and recipient have occurred, or the extent to which prior electronic activities between the sender and recipient have occurred (e.g., a metric associated with one or more prior activities satisfying a threshold).

In some embodiments, the system 200 can scan or crawl the content of electronic activities received from a contact or node to detect proof of consent or other indication of interest (e.g., detecting a type of intent) using natural language processing. If the system 200 determines, based on the content of the electronic activities, that the contact gives permission to store data associated with the contact, then the system 200 can proceed to store the data associated with the contact.

As described above, the system 200 can be configured to determine if electronic activities are personal or business, and through such electronic activities between two nodes, classifying the relationship between the two nodes as either personal or business (and then tagging such relationship as personal/business and then other parts of system 200 can use such tags to perform one or more functions or actions, including filtering, matching, among others).

In some embodiments, certain companies may establish one or more rules to limit the initiation of communications from an employee of the company to other nodes or people outside of the company. The system 200 can be configured to assist such companies by identifying contacts of the employees that the employee may be allowed to contact based on the employee's previous electronic activities with other nodes or people or based on certain types of introductions.

To do so, the system can be configured to detect business or professional introductions from electronic activities. In some embodiments, the system can be configured to determine if an electronic activity, using NLP or other techniques, whether an electronic activity can be tagged with an "introductory" tag. The tagging engine 265 can determine if an electronic activity or a sequence of electronic activities should be tagged with an introductory tag responsive to determining that the context of the electronic activity is one that relates to an introduction. The system 200 can then determine the participants of the electronic activity and create a tag or an indication in their respective node profiles or elsewhere in the system 200 that the participants have been introduced and qualify as contacts. Upon qualifying the participant as a contact of the other participant, if the other participant is an employee of a company that employs rules limiting the types of people the employee can contact, the system 200 can identify the participant as a person the employee can contact. In some embodiments in which the system 200 can update one or more systems of the company, the system can provide an indication to the system that the employee is authorized to contact that person now that the person is a contact of the employee.

9. Systems and Methods for Maintaining an Electronic Activity Derived Member Node Network At least one aspect of the present disclosure is directed to systems and methods for maintaining an electronic activity derived member node network. For example, a member node profile for a member node in a node graph can include information such as first name, last name, company name, phone number, email address, and job title, among others. However, it may be challenging to accurately and efficiently populate fields in a member node profile due to large number of member nodes who may change companies, get promotions, change names (for instance via marriage, or change locations, among others. Furthermore, permitting self-reporting on information in member node profiles by member nodes can result in erroneous data values, improper data values, or otherwise undesired data values. Having erroneous data values in a member node profile that are unsubstantiated by data points serving as evidence to a value of a node profile can cause downstream components or functions that perform processing using the member node profiles to malfunction or generate faulty outputs.

Thus, systems and methods of the present disclosure can generate an electronic activity derived member node network that includes member node profiles for member nodes that are generated or updated based on electronic activity processed by the system. By generating the member node profiles for the member nodes using electronic activities or systems of records and a statistical analysis, the system 200 can update member node profiles using electronic activities, record objects of systems of record and other data points as described above. The system 200 can generate or update member node profiles using data included in systems of record of data source providers, and validate values included in the member node profile using electronic activities and record objects and a statistical analysis.

Furthermore, the node graph generation system 200 can further establish links, connections or relationships between member node profiles based on electronic activities exchanged between them or other electronic activities processed by the node graph generation system 200. These established links, connections or relationships and the corresponding node profiles form the node graph generated by the node graph generation system 200.

By generating the member node profiles and the corresponding node graph by processing electronic activities traversing through or being processed by the node graph generation system 200 and accessing information included in one or more systems of record, the node graph generation system 200 can generate the member node profiles using a statistics-driven analytics process based on the electronic activities, thereby improving upon existing node graphs that are generated based on self-reported information by users. Such existing node graphs are not dynamically updated automatically based on electronic activities and may include information that is inaccurate or not vetted as the information is self-reported with no or little verification.

Furthermore, as the node graph generated by the system 200 is generated in part using electronic activities that are continually being generated and transmitted, the node graph can remain current and up to date without requiring any self-reporting on the part of the nodes associated with the node profiles. Furthermore, given that the node graph is updated as more electronic activities are generated, the system can, using certain parameters, such as dates, be able to determine a status of the node graph at any particular point in time. This is because the node graph is generated, in part, based on electronic activities that are time-stamped and as such, electronic activities that occur before the particular point in time can be used to determine the status of the node graph while electronic activities occurring after the particular point in time can be discarded from the analysis relating to determining the status of the node graph (and individual node profiles) at the particular point in time.

To generate the member node profiles, the node graph generation system 200, or components thereof such as the node profile manager 220, can receive electronic activities including any information related to the electronic activities. The node graph generation system 200 can maintain an array of a time series data set of data points or sources for every value of every field, parameter, or attribute of every node. As also described above with respect to the node profile manager 220, the node graph generation system 200 can associate node profiles of the node graph to electronic activities, or update node profiles that form the node graph based on updates detected by the system 200 responsive to parsing the electronic activities. The node graph generation system 200 can automatically detect potential changes to fields of node profiles of the node graph based on patterns in the electronic activities, and then determine to trigger an update to the node graph. The node graph generation system 200 can sync with one or more systems of records to determine additional information that can be used to update one or more member node profiles. As described herein, updating a node profile does not necessarily mean changing a value of a node profile. In some embodiments, updating the node profile can include adding additional data points to a value data structure to increase or adjust a confidence score of a value corresponding to the value data structure. In some embodiments, the data points can be electronic activities. In some embodiments, the data points can be values determined from record objects of one or more master systems of record. In some embodiments, the system 200 can receive information from record objects of one or more systems of record and use the information to create new node profiles or update existing node profiles by adding data points to support values of fields of such node profiles.

Each node profile can include values that are based on one or more data points. The system is configured to determine, for a particular time, a state of any node profile. The state of the node profile at any given time can be a representation of the node profile using electronic activities and systems of record data that occurred prior to the given time. For instance, the system is configured to output a job title of a given node at a particular date, for example, Dec. 2, 2017. The system can do so by discarding any electronic activity generated after Dec. 2, 2017 and any data from a system of record that was modified after Dec. 2, 2017.

Similarly, the system can be configured to detect changes to a node profile and generate a timeline of changes to values of fields of the node profile. For instance, the system can be configured to detect that a node has changed jobs or gets a new title, among others, based on monitoring electronic activities accessible to the system. For instance, the system can determine that a node has changed jobs if the system detects bounce back activity from the email address of the node and also detects that a person with the same name, phone number in the email signature (or other values) as the node is sending emails from a new email address, perhaps, around the same time that the system detects bounce back email activity from the email address of the node. Similarly, the system can detect a change in the job title based on a change in a signature of the node. The system can then identify a date that the signature was first changed to reflect the new title and mark that date as a date of the title change. In this way, the system can detect when users or nodes get promotions, demotions, join new divisions, leave jobs, start new jobs, among others.

In some embodiments, the system 200 can be configured to provide companies access to data collected, generated and managed by the system 200. The data managed by the system 200 can be used to provide insights to the companies, improve the accuracy of data maintained in one or more systems of record of the companies, among others. In some embodiments, the companies that receive access to the data managed by the system 200 can provide access to data maintained by one or more systems of record of the company as well as electronic communications servers (for example, email servers, messaging servers, among others) of the company, phone servers of the company, as well as other data sources maintained or under the control of the company.

Upon a company providing access to the servers storing data of the company to the system 200, the system 200 can be configured to establish one or more communication interfaces with the one or more servers storing the company's data. The servers storing the company's data can include the email servers, messaging servers, the systems of record servers, among others. Upon establishing communication interfaces with these servers, the system 200 can be configured to receive data from each of the servers storing the company's data. The system 200 can ingest the data and process it as described with respect to FIG. 3 and others.

In some embodiments, the system 200 can receive a large number of electronic activities from the electronic communication servers storing electronic activities of the company. These electronic activities can include all electronic activities accessible by the electronic communication servers. Some of the electronic activities received can be emails that were sent many years ago. However, such electronic activities can still be processed by the system 200 even though electronic activities from other electronic communication servers that were generated more recently have previously been processed by the system 200.

Similarly, the system 200 can receive data from one or more systems of record of the company. The systems of record can include record objects that include values of fields. The system 200 can be configured to ingest the data from these record objects of the systems of record and process the data included in the record objects.

The system 200 can be configured to process these electronic activities and record objects by updating one or more node profiles maintained by the system 200 or generating new node profiles responsive to determining that certain electronic activity or record objects do not match any existing node profile with a certain minimum level of confidence. The system can be configured to determine, for each electronic activity ingested by the system 200, whether the electronic activity can be used as evidence to support any value of a field of any existing node profile maintained by the system 200. The system can do so by attempting to match the electronic activity to node profiles of the system 200. Responsive to identifying a node profile with which to match the electronic activity, the system can add the electronic activity as a data point to a value of the field of the node profile that was used to match the node profile with the electronic activity. Similarly, the system can match record objects to node profiles by matching values of node profiles to values of existing node profiles. Once a node profile is matched with an electronic activity or record object, the system can determine if there are any values included in the electronic activity or record object that does not previously exist in the node profile. If so, the system can add a value to a corresponding field of the node profile and add the electronic activity or record object as a data point supporting the added value.

It should be appreciated that the system 200 can be configured to ingest and process each and every electronic activity maintained by the electronic communication servers under the control or direction of the company as well as each and every record object maintained in one or more systems of record of the company. As such, a large amount of electronic activity and record objects are processed and can be used to update existing node profiles maintained by the system 200 or generate new node profiles for the system 200. As additional companies share access to their data with the system 200 and the system 200 processes the data, the node profiles maintained by the system 200 will be further enriched and the data included in the node profiles will be more accurate. Moreover, data that is less accurate will have lower confidence scores while data that is more accurate will have higher confidence scores as there will be more data points that will be contributing towards the confidence score of the correct values. In this way, the node profiles will become more accurate. As a result, as more companies are on boarded and share access to their data with the system 200, the node graph generated from the node profiles will also become more accurate further increasing the accuracy of the system and each of the node profiles and corresponding node graph. For example, the node graph generation system 200 can detect a change in an electronic mail address status responsive to an electronic message bouncing back due to the message being undeliverable or otherwise not deliverable to the sent address, or having an automated "no longer with company" auto-responder. The node graph generation system 200 can further detect information from the electronic activities or the one or more systems of record with which the node graph generation system 200 (or electronic activity linking engine 250) interacts in order to obtain, infer or determine additional information that can be added to the member node profile. By parsing data from a bounce back electronic activity or auto-responder generated electronic activity, the system 200 can determine various pieces of information. For example, by applying natural language processing to auto-responder generated electronic activities, the system can detect different events corresponding to a node profile associated with the email address for which the auto-responder generated electronic activity was generated. In one example, the autoresponder generated electronic activity can indicate that the person is on a vacation. Such autoresponder generated electronic activities can either mention the word "vacation" or some other synonym or words that may suggest a vacation. The electronic activity can also identify a return date indicating a date when the person will return to the office. The electronic activity can also identify another person (along with an email address, title and phone number, if present) to contact while the person is on vacation. The system can be configured to update the node profile of the person to indicate that the person is out of the office until the return date and further update the node profiles of the person and the other person to indicate a connection or relationship between them. The system can learn from the autoresponder generated electronic activity to determine who else to talk to at the company on a specific matter while the person is on vacation. Moreover, the system can monitor different autoresponder generated electronic activities generated responsive to the same email address to determine other connections of the person if different autoresponder generated electronic activities include different people. Furthermore, the system can use the information from the autoresponder generated electronic activity, for example, the other persons, to determine an organizational structure within the company. For instance, if multiple autoresponder generated electronic activities generated responsive to multiple email addresses of different people identify the same person to contact in their absence, the system may determine that each of the different people report to the same person or are assisted by the same person.

In another example, the electronic activity can be a bounce back electronic activity indicating that the email address is no longer active or the person is no longer with company. Such an electronic activity can be referred to as a soft bounce. In such an example, the system can be configured to determine that the person associated with the email address is no longer at the company by parsing the contents of the electronic activity. In another related example, the electronic activity can be a bounce back electronic activity indicating that the email was not deliverable. In such examples, the system can be determined to apply heuristics to determine a cause for the bounce back by identifying the email that triggered the bounce back activity. If there is no other reason, such as the email size being too big, or if multiple recipients, connected to the system 200 have received similar non-deliverable reports over a period of time, the system can make an assumption that the person has left the company. The system may wait for multiple bounce back electronic activities generated responsive to the email address to confirm that the person has left the company. Upon the system confirming that the person has left the company via natural language processing of a soft-bounce electronic activity or multiple bounce back electronic activities responsive to the same email address, the system can update the node profile to indicate that the user is no longer at the company.

The system can further be configured to identify if any electronic activities generated after the date that the bounce back electronic activity was generated that mention the person's name, city and state (for example, in a signature of the email) or other values of the node profile can be matched to the node profile. The system can eventually determine an electronic activity that matches various values of the node profile and can parse the electronic activity to identify a new email address of the node profile. The system can use the bounce back activity as well as the subsequent electronic activity that matched the node profile to identify various events associated with the person. For example, the system can determine that the person left his previous job before the time of the bounce back activity and started a new job on or before the date of the subsequent electronic activity. In some embodiments, multiple electronic activities need to be processed to confirm if a person has left a company or started at a new company. Furthermore, the system can be configured to update the node profile of the person by adding additional electronic activities including the new email of the person once the system determines that the new email address belongs to the node profile of the person. This information can be used to generate or maintain a job timeline (e.g., start date and end date) of the person and can be used to detect when a user changes jobs for instance, or other information associated with the member node.

In some embodiments, auto-responder electronic activities generated responsive to receiving an email can include additional information that can be parsed to better understand the role of the person to whom the electronic activity was sent including identifying people to contact in the person's absence, when the person will become available if at all, and whether the person is still at the company or not.

For instance, an auto-responder generated electronic activity indicating that a user is on maternity or paternity leave may not include an expected date of return or may identify one or more other people to contact during the person's leave. The system may be configured to detect a maternity or paternity leave related autoresponder generated electronic activity. The system can detect the first time the auto-responder generated electronic activity was generated by analyzing multiple electronic activities matched to the node profile of the person. The system can then determine, based on typical maternity or paternity leaves for the company (by monitoring other people's email activity in similar cases) a likely return date for the person and can update the node profile of the person to reflect that they are on maternity or paternity leave. In other embodiments, the system 200 can determine the return date by parsing the contents of the auto-responder generated electronic activity.

The system 200 as described herein can be configured to parse bounce back and auto-responder generated electronic activities to update node profiles or determine additional information about node profiles. In some embodiments, the system 200 can be configured to establish connections with one or more third-party data sources, for instance, marketing automation or mass mailing systems, to receive additional data from such data sources. In some embodiments, the system 200 can access the data for companies that also provided access to their electronic communication servers and systems of record. The system can then harvest the data related to bounce back activity based on electronic activities sent via or generated by the third-party data sources, such as marketing automation systems, and use the data related to bounce back activity to increase the number of bounce back electronic activities the system 200 ingests or can access, thereby further increasing volume of data and further enriching member and group node profiles and the node graph.

In addition to the examples provided herein, the system can be configured to provide job timeline verification, based on electronic activities. The node graph generation system 200 (e.g., via 200 electronic activity parser 210) can identify a sender and recipient of an electronic activity. As described above, the system 200 is configured to attempt to match the electronic activity to a node profile corresponding to the sender and one or more node profiles corresponding to the respective recipients. In some embodiments, the system is unable to match the electronic activity to a node profile of a sender or a recipient if the system has not previously generated a node profile for the sender or recipient. When the node graph generation system 200 detects a new recipient or sender of the electronic activity, based on an identifier such as an email address, the node graph generation system 200 can create a new member node profile for the new recipient or sender. The node graph generation system 200 can, in some cases, determine, using a deduplication and identity resolution process, that the new member node profile matches or is the same as a previously generated node profile. The node graph generation system 200 can identify, using one or more parsing or processing techniques, a first name and a last name associated with electronic activity. For example, the node graph generation system 200 can parse an electronic signature in the body of the electronic activity or email to identify a first name, last name, job title, phone number, or other contact or identifying information. The node graph generation system 200 can identify fields that have values that do not change when a person moves from one job to another, such as their first name, last name, personal phone number, or other usernames or identifiers not tied to the job. By identifying information that does not change with the job and information that likely changes with the job (e.g., company email address, work phone number or job title), the node graph generation system 200 can map, match, or link the newly created member node profile with a previously generated or created node profile. The previously generated node profile may have included a different email address, such as an email address with a different domain that may correspond to a previous employer, while for example, the mobile phone number stayed the same. The system can determine, thereafter, that the new electronic activity associated with the new email address corresponds to the same member node, but that the member node has switched or changed jobs. Accordingly, the system can set or establish an approximate start date in the job timeline responsive to detecting the new email address.

Further, the node graph generation system 200 can establish, set or update the previous job timeline with an end date. The node graph generation system 200 can establish, set or update the previous job timeline with the end date responsive to detecting bounce-back emails to the previous email address or the last communication with the member node profile that went through using their old email address. The node graph generation system 200 can further corroborate the end date based on detecting the start date for the new job based on the new email address having the new domain different from the previous domain.

The node graph generation system 200 can update additional information about the member node profile, such as a new company name, a new company address, a new company phone number, a new email address, a new job title, among others. The node graph generation system 200 (e.g., via node profile manager 220) can detect various pieces of information with which to update the node profile by parsing an electronic signature embedded or included in an electronic activity such as an email sent from the new email address. The node graph generation system 200 can use a statistics-driven analysis technique to determine the new company name, the new company address, the new company phone number, the new job title, among others. For example, if the sender of the electronic activity sends 10 electronic messages to 10 different recipients within a predetermined time interval and using the same electronic signature containing the same company name, company address, company phone number, and job title, then the node graph generation system 200 can be configured to update the node profile of the member node to reflect new values for company name, company address, company phone number, and job title.

Furthermore, the confidence score of each of these values can be determined and increased as additional emails are sent and received via the new company email address. In some cases, the confidence score in the job title can be further determined based on the recipients of the electronic activities. The system can be configured to maintain, for a given job title of a person, a mapping of volume or distribution of emails to people having certain titles. For instance, a CEO is more likely to send emails to other CEOs or C level executives than a person having a title of associate. Similarly, a person with a sales related title is likely to send more outbound emails than a person with a title related to Human Resources. As such, the system can be configured to determine a confidence score of the job title based on the contribution scores of data points supporting the value but also based on whether the person's emailing activity matches that of other people with similar titles. Stated in another way, in this example, the node graph generation system 200 can perform job title verification based on evaluating node profiles linked to electronic activities that identify the person's new email address.

The node graph generation system 200 can use the member node profile to maintain an accurate organization chart for a given company. For example, a field in a member node profile can include a "Reports to" field. The node graph generation system 200 can maintain, for each value of the "Reports to" field of a node profile, an array of data points identifying sources that include record objects having the "Reports to" field for the node profile to determine the confidence score of the value. In some embodiments, based on the values of the reports to field of multiple node profiles belonging to the same group node or company, the node graph generation system can maintain an organization chart for the company. In some embodiments, job titles of various node profiles can further be used to determine the organization chart. Furthermore, the organization chart can further be determined based on parsing electronic activities, including but not limited to out of office and other autogenerated electronic activities that may include information identifying links between certain node profiles. Moreover, using effort estimation and analyzing the content of electronic activities exchanged between two nodes, the system can further determine a relationship between the two nodes including predicting a boss-subordinate relationship between nodes.

In some embodiments, the node graph generation system 200 can detect job title changes and use the detected change to reevaluate or update an organization chart. The node graph generation system 200 can utilize master data model to match member nodes in a member node graph to a group node in a group node graph (e.g., a company graph). The node graph generation system 200 can use the member node graph to build, generate or update a group node graph that can include a hierarchy or organizational structure comprised of member nodes from the member node graph. As the node graph generation system 200 detects changes or updates to the member node profile of a member node based on parsing electronic activities and email signatures therein, and determines that a confidence score of a value of a field in the member node profile associated with the detected change warrants updating the member node profile, the node graph generation system 200 can update the value in the corresponding field in the member node profile, as well as update a hierarchical organization or structure in the corresponding group node graph or network.

The node graph generation system 200 can present one or more member node profiles for display. The node graph generation system 200 can present the member node profiles for display via a webpage, website, browser, application, or via other presentation medium. For example, the node graph generation system 200 can present a member node profile for display via a mobile application executing on a client computing device having a display device. In some cases, the node graph generation system 200 can present the member node profile via audio output, such as via a voice interface.

The node graph generation system 200 can be configured to hide or otherwise prevent or block from display one or more fields in the member node profile. The member node, such as the owner of the member node profile, can establish the configuration as to which fields, or values thereof, to hide from display. The node graph generation system 200 can provide access control options via a computing device to a member node or user thereof. The node graph generation system 200 can generate a graphical user interface or other type of user interface to present the access control options, as well as receive selections or modifications to such access control options. Using the access control interface generated and provided by the node graph generation system 200, the user can control which fields are presented for display via the web page, for example. In some cases, the user can control which accounts can access the member node profile of the user, or, on a more granular level, control which account can access which fields or values in the member node profile.

In some cases, the node graph generation system 200 can allow a third-party device to request access or request presentation of a value of a particular field in a member node profile. The node graph generation system 200 can receive the request and forward the request to the member node via an electronic activity. The member node can accept or reject the request. In the event the member node accepts the request for access to the value in the field, the node graph generation system 200 can, automatically and responsive to accepting the request, update the access configuration profile for the member node profile. Thus, the node graph generation system can hide or unhide one or more fields (or values) from one or more third-parties or computing devices based on the preferences of the owner of the member node profile.

10. Systems and Methods for Monitoring Performance of Node Profiles

As described herein, the node graph generation system 200 can be configured to ingest and process large amounts of electronic activity that are provided by one or more electronic communications servers storing electronic activities belonging to or associated with one or more enterprises or companies.

The system 200 can only ingest and process those electronic activities to which the enterprises or companies provide access. The system 200 can also be configured to ingest and process data from systems of record maintained by one or more servers. Similar to electronic activities, the system 200 can only ingest and process those systems of record to which the enterprises or companies provide access. As described herein, the system 200 can process electronic activities and record objects of systems of record to update node profiles of nodes, link or match electronic activities to record objects of the one or more systems of record accessible to the system 200, determine or predict a stage of a business process, among others.

The node graph generation system 200 can further be configured to process electronic activities and record objects of one or more systems of record of a company to determine insights for the company. For instance, the node graph generation system 200 can provide insights to Company A by processing electronic activities and record objects that Company A has made accessible to the node graph generation system 200. The insights can include metrics at a company level, a department level, a group level, a user level, among others. The insights can identify patterns, behaviors, trends, metrics including performance related metrics at a company level, a department level, a group level, a user level, among others. Additional details relating to the insights are described herein.

The node graph generation system 200 can include a performance module 280 that can be configured to generate performance profiles for a company. In some embodiments, the performance profile can be a performance profile of an employee of the company. In some embodiments, the performance profile can be a performance profile of a department of the company, a group within a department, or individual employees of the company. The performance module 280 can generate the performance profiles using data accessible by the node graph generation system 200. In some embodiments, the performance module 280 can generate the performance profiles using all data including electronic activities and systems of record accessible by the node graph generation system 200 from multiple companies. In some other embodiments, the performance module 280 can generate the performance profiles for a company only using data provided by the company to the node graph generation system 200. In some embodiments, the performance module 280 can be configured to generate certain types of performance profiles for employees, groups, departments of a company that has provided access to the system 200 while generating other types of reports or insights for other node profiles of the system 200 that are not employees of the company.

The performance module 280 can be configured to predict employee success at a company or in a job role. The performance module 280 can, based on an analysis of electronic activities as well as information stored in one or more systems of record, predict the success of the member node. For example, the performance module 280 can generate a performance profile for the member node. The performance profile can be a statistics driven performance profile. The performance profile can be based on electronic activities and information stored in one or more systems of record. For example, the performance profile can be based on a number or amount of electronic activities associated with the member node during a time interval, a type of the electronic activities, the amount of time the member node spends generating or preparing the electronic activities (e.g., amount of time spent writing an email), the recipients of the email, natural language processing of the email, etc.

For example, the node graph generation system 200 (via performance module 280), using job history and performance history reconstructed from an internal member node graph, can generate a performance score, purchasing preference, decision making power, interests or other information for the member node. By syncing information associated with the systems of record and electronic activities with the member node graph, the node graph generation system 200 can generate or extrapolate types of opportunities or features on the public profile.

For example, the node graph generation system 200 can determine that a member node performs medical device sales, the member node's territory is the northeast region, the member node prefers or is more successful when doing in-person sales, the member node prefers or more successful when doing CEO level sales, or an average deal size or amount. To do so, the node graph generation system 200 can parse or featurize information corresponding to tasks or activities (e.g., deals) associated with the member node (e.g., a salesperson or other knowledge worker) that is derived from one or more record objects stored in the one or more systems of record. By parsing or generating features from the record objects, the node graph generation system 200 can update a member node profile to reflect various performance information derived from record objects in one or more systems of record as well from electronic activities. The node graph generation system 200 can generate various outputs derived from record objects in one or more systems of record and electronic activities. Outputs can include a performance score or performance grade indicating how well a member node has performed or may perform in general, at a type of task, in a specific job or under certain circumstances of a job or job environment, as determined by the communications metadata, extracted from the node graph.

For example, the node graph generation system 200 can generate an output corresponding to a performance score or performance grade of a user based on an average seniority of attendees to a meeting initiated, established, conducted or led by the user. The node graph generation system 200 can determine the average seniority of attendees to the meeting established by the user by parsing electronic activities associated with the meeting (e.g., calendar invite or emails) to identify the attendees, and further determining the seniority of the attendees based on a member node profile for the attendees or metadata associated with the electronic activities. The node graph generation system 200 can generate an absolute performance score based on the determined seniority of the attendees. In some cases, the node graph generation system 200 can compare the average seniority of attendees to a meeting established by a first user with the average seniority of attendees to meetings established by other users. The system 200 can be configured to determine or measure the number of communications a user is involved in, the types of communications the user is having (by using NLP and other semantic analysis techniques to determine context of communications), and the roles of the people the user communicates with. These metrics or other metrics can be representative of future success. For instance, the system has been configured to determine that employees who drive meetings with a higher average seniority of attendees are more likely to be successful than employees who drive meetings with a lower average seniority of attendees. As such, the use of the tagging engine 265 and the node profiles to assign tags to meetings indicating roles of attendees, seniority of attendees (such as CxO) can be used by the system to predict or measure employee performance and success.

In some embodiments, the system can be configured to track employee activity behavior. The system can utilize supervised or unsupervised machine learning to determine behaviors that result in future success for the employee. For instance, the system 200 can determine that the number of communications a user is involved in, the types of communications the user is having (by using NLP and other semantic analysis techniques to determine context of communications), and the roles of the people the user communicates with are all behaviors, traits, features, metrics or other signals that can be used to predict future success based on training the system 200 on past or other current employees identified as being successful and other employees identified as unsuccessful.

In some embodiments, the system 200 can generate or maintain, for one or more roles of a company, a standardized performance profile generated based on aggregating performance profiles of a plurality of performance profiles of users in the role previously identified as being successful in the role. The system 200 can compare the users performance profile generated based on the users activity behavior to the standardized performance profile to predict a likelihood of success of the user and can further be configured to provide feedback to the user on how to improve their performance based on the comparison.

The system 200 can be configured to generate a performance profile of a user based on the users role as different roles may perform vastly different functions. Two employees in different roles may both be very successful in their roles but their electronic activity footprints may appear very different. For instance, a successful customer success manager's electronic activity footprint or behavior may have a regular cadence of meetings (in-person or telephonic) with each of their customers. Different customers may require different cadence of meetings but a successful customer success manager may maintain the cadence for each of their customers. For the system to determine how well an employee is performing, the system can be configured to monitor, for each customer, whether the employee is having regular, recurring meetings with the customer that matches the cadence of meetings the employee is supposed to have with the customer. The system can determine this based on analyzing the employee's electronic activities to see if meeting requests are sent within particular time periods and meetings actually occur. As described herein with respect to tagging, the system 200 can confirm whether a meeting happened and this information can be used to determine if the employee is having regular meetings. As such, the node graph generation system 200 can determine a performance of a user based on a cadence of meetings with each of the user's customers. The regularity of the cadence can be based on the number of meetings with customers within a time interval, such as a week, two weeks, month, two months, etc.

Furthermore, the system 200 can be trained or configured to use the cadence of meetings for the user's customers to determine a user's level of engagement with the customers. The user's level of engagement can be used as a signal to quantify a user's performance as an employee as a low level of engagement can predict that the customer may disengage with the company or may look elsewhere to service their needs. The system 200 can maintain a user engagement model for each customer or customer type that is based on one or more parameters or metrics. The user engagement model can be used as a benchmark. The system 200 can then compare the user's level of engagement with the user engagement model to determine if the user's level of engagement is below, the same or above the benchmark. If the user's level of engagement is below the benchmark, the system can notify the user or the company and provide tips to increase the level of engagement to improve customer satisfaction and/or reduce the likelihood that the customer may leave.

In some embodiments, a users performance can be measured on his electronic activity behavior. For instance, for employees in certain roles, the employee's performance can be based on how quickly the employee responds to emails, how much time the employee spends preparing responses to the emails, as well as various other metrics, parameters or attributes that can be determined from the emails the employee sends. In some embodiments, an employee's response time to emails from a customer can be used as a metric to determine the employee's level of engagement with the customer. The employee's response time to emails from the customer can be compared to the employee's response time to other customers to determine the employee's level of engagement with that customer. Furthermore, the quality of the employee's responses may also provide an indication of the employee's level of engagement. For instance, the system 200 can be configured to determine an amount of time the employee spent drafting the email based on a time estimation model that analyzes the number of words, the choice of words, the time difference between when the email to which the employee is responding to was received and the time the response was sent, among others. In some embodiments, the time estimation model can take into account the titles of the participants of the email.

In another example, the node graph generation system 200 can determine the performance score for a user based on the amount of time it takes to receive a response to a ping or electronic activity transmitted by the user. For example, if the user is a recruiter, the recruiter's performance can be based on how quickly he gets job candidates to respond to their email as well as how many job candidates respond to their email, and how many emails (or follow up emails) on average it takes a job candidate to respond to the recruiter. The system 200 can be configured to determine that recruiters that have lower response times (time it takes the candidate to reply to the recruiter) have a higher performance score than recruiters with higher response times. Furthermore, the system 200 can be configured to determine that recruiters with higher response rates (number of candidates who actually respond) and lower average number of emails it takes to receive an initial response to the email perform better than recruiters with lower response rates and higher average number of emails to receive initial responses. It should be appreciated that the system 200 can be configured to generate such statistics for every user type or node having a certain title and comparing the statistics of such users or nodes to generate a benchmark for various parameters that may be factors that contribute to a performance of a user or node.

In yet another illustrative example, the node graph generation system 200 can determine, from the member node graph profile and one or more record objects in one or more systems of record, that a member node performs deals in the northeast region and that the deals are more likely to close when there a certain number of in-person meetings associated with that deal. The node graph generation system 200, utilizing this performance information, can generate an extrapolation curve to determine how well the member node might perform in the future, or forecast performance of the member node. The node graph generation system 200 can generate the performance forecast based on historical electronic activities, one or more record objects, and a member node profile. Similarly, the node graph generation system 200 can determine based on a low performance score that the employee is likely to fail or leave the company.

In some cases, the node graph generation system 200 can match a member node with a candidate deal or potential deal or ongoing deal. For example, the node graph generation system 200 can match a representative to the right potential or ongoing deal. The node graph generation system 200 can match the representative to the deal based on a social proximity territory assignment, which can be based on a strength of overall relationships of the representative with a certain type of person or member node (e.g., buyers, such as someone who as the authority to close a deal, at target accounts). The node graph generation system 200 can determine that the more people the representative has a relationship with at a target account, the more likely the representative is to succeed with the target account. As such, the node graph generation system 200 can match the representative with target accounts with which the representative has the most relationships as well as the most of strong relationships with people at the target account that are associated with closing a deal or other successful outcome.

The node graph generation system 200 can match representatives to a target account or deal based on a selling style of the representative. For example, the node graph generation system 200 can determine that a target account or buyer prefers a certain type of selling style, such as primarily face-to-face vs over the phone, or meeting certain people at the target account such as the CEO. The node graph generation system 200 can then identify representatives that sell using these styles or are known to perform well using these styles, and then assign the representative to the corresponding target account. For example, if a representative is determined to perform well when meeting a CEO based on analyzing historical deals, electronic activities or profile information, then the node graph generation system 200 can match the representative with a target account that is associated with successful outcomes when the CEO of the target account meets with the representative.

11. Systems and Methods for Providing a Company Cloud

At least one aspect of the present disclosure is directed to systems and methods for providing a company cloud. The company cloud can identify a plurality of companies or enterprises. Each company included in the company cloud can be represented as a company or group node and each group node can include or be linked to one or member node profiles corresponding to people belonging to or affiliated with the company. The company cloud can refer to or include a group node graph or network of group nodes. A group node can be a representation of a company and include fields. Fields can include, for example, a company name, a company phone number, a company address, a unique identifier for the company, a company size, a company location, or other information associated with the company. The group node can further be linked to one or more member node profiles corresponding to people who are either employed by the company or in some embodiments, have some affiliation with the company.

In some embodiments, one or more values of the fields of the group node can be populated based on values of one or more member node profiles belonging to nodes that are employed or affiliated with the company. For example, values of various fields such as company name, phone number, address, among others may be derived from node profiles of its employees. In some embodiments, the values of the fields may be associated with value data structures including entries identifying data points that support the value. Such data points can be data points that support values of fields of member node profiles belonging to employees of the company associated with the group node.

Similar to how member node profiles are generated and updated as described above, the node graph generation system 200 can generate company or group nodes using the same sources of data, namely, electronic activities and data from systems of record.

In some embodiments, the node graph generation system 200 can analyze systems of record of different data source providers (for example, enterprises) to identify multiple account record objects representing the same company. The multiple account record objects representing the same company can be maintained in different systems of record belonging to different enterprises. For instance, multiple companies can maintain an account record object for the company, Acme. A first enterprise can maintain a first account record object for the company Acme. The first account record can include a first value for the field Company Phone Number. A second enterprise can maintain a second account record object for the same company Acme. The second account record object can include a second value for the field Company Address. The node graph generation system 200 or the data source provider network generator 260 can create a group node profile for the company Acme by extracting values from both the first account record object and the second account record object such that the group node profile is richer in information than each of the respective first and second account record objects. In some embodiments, the node graph generation system can further be configured to maintain a master account record object for the company that includes values from each of the account record objects across multiple systems of record such that the master account record object of the system 200 is richer in information than each of the respective account record objects across the multiple systems of record. In the example above, the group node profile and the master account record object can include the first value for the field Company Phone Number and the second value for the field Company Address.

The node graph generation system 200 can add or update values of one or more fields of the group node profile for the first group node. In some embodiments, the first time the node graph generation system 200 detects or identifies an account record object or electronic activity to be associated with a particular group node profile of a company, the node graph generation system 200 can create or establish a group node profile for the company. Thereafter, the node graph generation system 200 can continually amend or update that group node profile with additional information or updated information. Further, as the node graph generation system 200 receives conflicting information for the group node profile from different record objects of different systems of record maintained by different data source providers, the node graph generation system 200 can resolve the conflicts using rules, policies, or a confidence score of a value of an attribute or field of a group node profile, for example.

In some cases, the node graph generation system 200 can determine that different systems of record may have different values for the same field for the same group node profile corresponding to a particular account or company. The node graph generation system 200 can use one or more techniques to determine the correct value for the field for the group node profile, or the most accurate or likely to be correct value for the group node profile. The node graph generation system 200 can use techniques for generating or determining the confidence score of a value of an attribute or field in a group node profile. For example, the node graph generation system 200 via the attribute value confidence scorer 235 can determine a confidence score for each value for each attribute or field in the group node profile based on an array of data points maintained for each value.

By analyzing, parsing or otherwise processing multiple systems of record and electronic activities, the node graph generation system 200 can generate a master group node profile for a company or account that contains one or multiple values for one or more of the fields. Similar to member node profiles, the system 200 can be configured to generate a confidence score for each value of the one or more fields that is based on contribution scores of each of the data points supporting the value as evidence.

As described above with respect to member node profiles, the group node profiles can also be updated as more information is ingested by the system 200. In some embodiments, the system 200 can ingest new electronic activities and data from systems of record and periodically update the member node profiles based on the new data. In some embodiments, the system is configured to ingest and process new data once a day, once a week, among others. In some embodiments, the system can ingest and process new data as new systems of record are made accessible to the system. In some embodiments, the system can be configured to ingest and process new data responsive to a request from a user or an administrator of the system 200. In some embodiments, the system 200 can be configured to update the node graph, which can include both group nodes and member nodes, responsive to ingesting or processing the data. The system 200 can be configured to update tags or associated confidence scores assigned to previously processed electronic activities. Furthermore, the system 200 can be configured to update value data structures of node profiles by removing electronic activities previously assigned to a value but determined responsive to new data that the electronic activities were previously assigned to a particular value or node profile based on insufficient data. In some embodiments, such changes to node profiles can be made responsive to determining that the tag or electronic activity is improperly assigned or classified. It should be appreciated that as more data is ingested by the system 200, certain classifications and tags can be misclassified or assigned but can be corrected by the system based on the new data. As such, the node graph generation system 200 can update the group node profiles on a periodic basis, based on a time interval, responsive to a request, or based on new or updated insights or information that is derived from electronic activity data flowing through the system 200 as a time series dataset.

In an illustrative example, a field in an account level for a First Company can be "Parent Account" field. The parent account field can have a value, linking to the record of "Second Company" because Second Company can be the parent company of the First Company. The node graph generation system 200 can determine that this is a field in an account and then extrapolate that this field denominates a parent company in a complex corporate structure when a Second Company owns a First Company, thereby resulting in the Second Company being named in the "Parent Account" field. The node graph generation system 200 can analyze, for example, 50 different systems of record to identify 50 different account record objects that contain an account for the First Company. The node graph generation system 200 can then determine, for each of the 50 different account record objects, the value of the parent account field. If all 50 of account record objects have the same value in the account field (e.g., Second Company), then the node graph generation system can establish a group node profile for a group node in the master group node graph for the account for the First Company to include the value "Second Company" in the parent account field. The node graph generation system 200 (e.g., via attribute value confidence scorer 235) can use one or more policies, rules, weighting systems, scores or other logic to select a value to use for the account field in the group node profile for the group node profile in the master group node graph. For example, the node graph generation system 200, via attribute value confidence scorer 235, can leverage a time-series calculation of values of this field across multiple systems of record, while taking into account a confidence score and recency of each value of each field, where the more recent values are assigned a higher weight.

The node graph generation system 200 can analyze the systems of record on a period basis or based on some other time interval and detect a change in values in fields. The node graph generation system 200 can, responsive to detecting a change in some or all of the systems of record, update the group node profile. For example, the node graph generation system 200 can update the group node profile responsive to detecting the change in 5 of the 50 account record objects of the 50 systems of record. The node graph generation system 200 (e.g., via attribute value confidence scorer 235) can determine that while only 10% of the account record objects reflect a change in the value, that these 10% of account record objects are reflecting an accurate change (e.g., based on high trust scores of the systems or sources that produced the change, and a recency of the field change) and, therefore, the master group node graph is to be updated. The node graph generation system 200 can determine, for example, that this 10% of systems of record are associated with a relatively high trust score which may cause the attribute value confidence scorer to generate a higher confidence score for values of fields received from such systems of record or other score relative to some or all of the remaining 90% of systems of record. Thus, the node graph generation system 200 can detect a change in company ownership or subsidiary status based on a subset of systems of record and before other systems of record are updated to reflect such ownership or organizational change, thereby reducing latency in updating organizational structure across all systems of record, connected to the system.

12. Systems and Methods for Improving Member Node Performance Based on Electronic Activity At least one aspect is directed to systems and methods for improving member node performance based on electronic activity. The node graph generation system 200, or one or more component thereof, can analyze electronic activities associated with member nodes to generate a member node profile for a member node in a member node graph. The node graph generation system 200 can identify metrics for each member node profile based on the electronic activities. The node graph generation system can correlate the metrics with desired performance outcomes or results, including but not limited to closed sales, recruited candidates, or renewed contracts to identify which metrics are correlated with desired performance outcomes. Based on identifying the desired metrics that result in desired outcomes, the node graph generation system 200 can set one or more goals for member nodes, as well as help track those goals to increase the likelihood that the member node achieves the desired performance outcome, thereby improving the likelihood that the member node achieves the desired performance outcome.

In some embodiments, the node graph system 200 can include a recommendation engine 275. The node graph system 200 (via recommendation engine 275) can provide a recommendation or set a target goal for a member node. The node graph generation system 200 can, for example, provide these recommendations or target goals to one or more member nodes or one or more group nodes based on historical matching electronic activities to desired performance outcomes. The node graph generation system 200 (or one or more component thereof) can match electronic activities to desired performance outcomes stored or indicated in one or more systems of record.

The node graph generation system 200 can include a performance module designed and constructed to determine a performance metric or performance level of a member node based on electronic activities. To generate a recommendation, the node graph generation system 200 (via a performance module 280 and recommendation engine 275) can identify member node performance as compared to a member node's past performance or as compared to the performance of other member nodes that have a similar role or otherwise share similar characteristics. The node graph generation system 200 (e.g., via a member node performance module) can determine a performance of a member node. For example, the node graph generation system 200 can identify electronic activities associated with multiple member nodes that are linked to a group node in a group node graph. The node graph generation system 200 can then identify a system of record associated with the group node. The system of record can include account record objects, lead record objects, opportunity record objects, deal record objects or other types of record objects. The system of record can include stages for any business process, such as opportunities with stages, recruiting of candidate with interview stages, renewing contract with renewal stages, etc. In an illustrative example, an opportunity record object can include multiple sequential stages for the opportunity, such as a first stage, second stage, third stage, and a fourth stage, where the first stage indicates an initial stage and the fourth stage indicates a final or completion stage for the opportunity. The node graph generation system 200 can correlate electronic activities with the opportunity record objects as well as the stages of the opportunity record objects. The node graph generation system 200 can determine metrics based on electronic activities that are associated with an opportunity advancing stages or not advancing stages. For example, the node graph generation system 200 can correlate that, on average: 5 emails and 1 in-person meeting occurred in a time interval for an opportunity before it moved from a first stage to a second stage; 10 emails and 2 in-person meetings occurred during a time interval for an opportunity to move from a second stage to a third stage; 15 emails and 3 in-person meetings occurred during a time interval for an opportunity to move from a third stage to a fourth stage; and 20 emails and 4 in-person meetings occurred during a time interval for an opportunity to move from a third stage to a fourth or final stage. By determining metrics that are correlated with advancing an opportunity from one stage to another based on electronic activities correlated with stages in opportunity record objects stored in a system of record, the node graph generation system 200 (or component or module thereof) can predict or forecast metrics that, when met, are likely to result in the desired performance outcome. The node graph generation system 200 can determine which metrics of electronic activities have the highest correlation to successful outcomes in order to generate goals.

For example, when a member node enters a first stage of a process described in a system of record (e.g., a first stage of an opportunity, recruiting process, contract renewal, etc.), the node graph generation system 200 can identify, for a similar opportunity and a similar member node, the metrics that, on average, likely resulted in a desired performance outcome of advancing from the first stage to a second stage. The node graph generation system 200 can further provide an indication of these metrics to the member node as a goal or target metrics to improve the likelihood that the member node advances from the first stage to the second stage. The node graph generation system 200 can further provide metrics estimated to advance from each stage to the final stage. The node graph generation system 200 can generate the estimate by benchmarking across member nodes in similar roles working on similar processes in order to identify the desired performance outcomes and metrics associated with such desired performance outcome. For example, the benchmarking process can include identifying member nodes that conduct interviews in a recruiting process to identify metrics associated with candidates that accepted an offer to join a company in order to provide an estimate of a metric that might result in a desired outcome. An example metric for this example can include a response time or response quality associated with emails between the interviewer and the candidate before or after the interview. Other example metrics can include the duration of the interview, whether the interview was face-to-face or telephonic, or whether the interviewer or candidate was late to the scheduled interview based on natural language processing of the correspondence between the candidate and the interviewer.

In another example, the node graph generation system 200 can identify member nodes linked to a group node that perform well or have desired performance outcomes. The node graph generation system 200 (e.g., via recommendation engine 275) can identify a temporal aspect to the metrics associated with the member node. The node graph generation system 200 can determine when member node first joined the group node or was first linked to the group node (e.g., a job start date or beginning date), and how the member node's performance and behavior metrics evolved over time. This initial time interval can be referred to as a ramp-up period (e.g., when an employee first joins a company and then gets up to speed or ramps up). The node graph generation system 200 can identify metrics associated with a successful ramp-up period based on identifying member nodes that are associated with desired performance outcomes based on reaching desired stages in an opportunity record object (i.e. by analyzing how successful employees had ramped in the past). Thus, by analyzing electronic activities and a corresponding system of record to determine data driven metrics associated with desired performance outcomes determined by linking activities with record objects describing process stages (e.g., an opportunity record) in the system of record, the node graph generation system 200 can generate or identify goals to set for member nodes that are in a ramp-up period or other time interval, such as during a performance improvement plan (a plan, set up by employee's manager to bring the employee to optimal performance after a period of poor performance). The node graph generation system 200 can further reevaluate the member node's metrics to update the goals or set new goals by comparing current metrics (e.g., actual actions or performance) associated with the member node's current electronic activities with the desired metrics (e.g., planned actions or performance) for electronic activities correlated with the desired performance outcome or result.

In some embodiments, the system 200 can be configured to compare performances of employees of a company by monitoring the employee's contribution to opportunity record objects and the progression of the stages the opportunity record object goes through. For instance, a high performing employee may be involved in electronic activities that are linked to opportunity record objects that advance from one of the stages to another stage much quicker than another employee with the same role. Similarly, a high performing employee may be involved in electronic activities that are linked to a greater number of opportunity record objects that advance from one of the stages to another stage than another employee with the same role. As such, by tracking the opportunity record objects with which an employee is linked, a performance of the employee can be determined and the employee's metrics can be used to set certain benchmarks that can then be used to determine a performance of another employee with a similar role or generate a ramp up schedule based on the employee's metrics. For example, the node graph generation system 200 can determine that when a member node completes 25 calls in a week, reaches out to 10 companies in a week, has 5 in-person meetings in a week, and then writes 100 emails in the same week, then the member node should be able to complete a number of deals or advance a desired number of stages in one or more deals or otherwise achieve an expected performance outcome after a certain time (e.g., a time delay between input activities and outcome results). The metric can refer to or include an attribute of an activity, such as an amount of the activity. The metric can be a binary value that indicates a yes or no, such as "did you have a meeting with 10 people", with a value of 1 or 0 indicated yes or no, respectively. In some cases, the metric can be a count, a ratio, a time value, or a percentage value, based on any combination/formula, calculated from any number of data points in the member node graph or systems of record. The metrics can vary in granularity based on the data the node graph generation system 200 can analyze via electronic activities or one or more systems of record. Based on previous or historical activity, the node graph generation system 200 can predict, forecast or estimate what activity should occur to achieve a desired outcome, and propose or set goals for a member node or group node accordingly. The node graph generation system 200 (e.g., via the electronic activity linking engine) can correlate the electronic activities with the stages or desired outcomes as stored or determined in the system of record or an opportunity record object thereof. The electronic activity linking engine can match, correlate, link or otherwise associate electronic activities with outcomes (e.g., advancing stages, won, lost, etc.) stored in the system of record.

The node graph generation system 200 can generate an automated employee ramp-up schedule based on the previously identified high performing member nodes based on internal user data. The node graph generation system 200 identifies high performing member nodes based on electronic activities associated with the member nodes matching desired outcomes as indicated in opportunity record objects stored in a system of record (e.g., system of record 9360) or stored in a shadow or temporary system of record associated with the node graph generation system 200, or otherwise stored in a master system of record. With this automatically generated ramp-up schedule containing metrics for electronic activities that is correlated with high performing member nodes, the node graph generation system 200 can provide goals or recommendations to new member nodes that are beginning a new job or new role at a company. Such recommendations can be especially relevant for employees in sales, customer success, recruiting, or other functions.

To generate the ramp-up schedule for a new member node (e.g., a new hire), the node graph generation system 200 can identify a high performing member node that has a node profile that is similar to the member node profile of the new member node. The node graph generation system 200 can compare member node profiles based on values of fields of the member node profiles, such as geographic area, type of industry, experience, or any other field of the member node profile. The node graph generation system 200 can then identify metrics associated with the similar member node profile of the high performing member node and generate a ramp-up schedule using the metrics.

To identify the metrics, the node graph generation system 200 can normalize the metrics for a time interval. The node graph generation system 200 can identify metrics for the high performing member node that occurred during a time interval that is similar or relevant to the new member node profile. For example, the node graph generation system 200 can identify the first two weeks of employment by determining when the first email was actually sent by the employee, and then identifying the metrics for electronic activities that correspond to the first two weeks of the high performing member node's employing at the company. These first two weeks may not indicate a high performance. For example, the high performing member node may not have been high performing with reference to desired outcomes in matching opportunity record objects in a system of record for another 6 months; however, the metrics associated with electronic activities that occurred in the first two weeks or other time interval prior to the desired performance outcomes may nonetheless be indicative or relevant to the high performance level of the high performing member node. Thus, the node graph generation system 200 can select the metrics of electronic activities that occurred in the first two weeks and provide those metrics as goals or target goals or target metrics for the new member node without setting a goal or expectation that the member node achieve a desired opportunity stage in the initial time interval, but, instead, with the goal that the new member node may achieve the desired performance with references to opportunity stages during a later or subsequent time interval. The node graph generation system 200 can correlate metrics to outcomes (e.g., all metrics of electronic activities that correlate with positive outcome), and then compare new employee to a previously successful employee.

The node graph generation system 200 can normalize the time interval or otherwise account for environmental factors or external factors associated with the time interval that can affect the metrics associated with electronic activities or performance outcomes. For example, the node graph generation system can take into account a seasonal component by detecting a reduction in electronic activities during a vacation time interval. The node graph generation system 200 can determine or detect the vacation based on identifying an automatic out of office reply in outbound electronic activities corresponding to the member node. The node graph generation system 200 can determine or detect the vacation based on identifying a vacation calendar entry electronic activity corresponding to the member node. The node graph generation system 200 can identify the vacation responsive to determining that a volume of electronic activity or responsiveness to electronic activities during a predetermined time interval is below a threshold for the email account of the node profile, or the hours during which emails are sent vary from a traditional time range or time zone for the member node (e.g., whether electronic activities or communications are clustered around business hours). By determining that the new member node may be on vacation—or that a high performing member node's metrics were associated with a vacation—the node graph generation system 200 can remove or filter out metrics or data during the vacation period so as not to set improper or erroneous goals that might be faulty due to a vacation time interval, or so as not to determine that the new member node is underperforming or not meeting goals due to the new member node being on vacation.

The node graph generation system 200 (e.g., via recommendation engine 275) can provide the target goal or recommendation to the member node, or a manager member node that may then propagate the target goal to employee member nodes. A manager member node can refer or correspond to a person whose role is a manager of employees or a team of people. The member node profile can include a field that denominates a role of the member, such as manager or employee. The member node profile can further include a field that denominates who the manager is, such as a "managed by" field. In some embodiments, the recommendation engine 275 can include or interface with a machine learning engine that obtains feedback from a manager member node and adjusts the recommendations or target goals accordingly. For example, the node graph generation system 200 can identify manager member nodes that are linked to employee member nodes that are performing with a desired outcome based on a system of record. The node graph generation system 200 can further identify that when new employee member nodes are linked or join the network of the manager member node, the new employee member node ramps up in a desired time interval and to a desired performance level. The node graph generation system 200 can receive human input from a manager corresponding to a manager member node. Based on the human input, the node graph generation system 200 can determine that the manager member node sets goals that are effective or successful in improving the performance of the employee member nodes. The node graph generation system 200 can receive, via the manager member node or one or more employee member nodes, the target goals and input these target goals into a machine learning engine or otherwise compare the input target goals with automatically generated target goals to tune or update the generation of target goals. Thus, the node graph generation system 200 (or recommendation engine 275) can receive human input from high performing managers in order to update the recommendation engine 275 and improve the generation of recommendations or goals for member nodes.

The node graph generation system 200 can include a performance module 280 designed and configured to determine a performance of a member node. The performance module 280 can identify when metrics of a member node do not meet or exceed the target goal metrics set for the member node. The node graph generation system 200 can recommend to the manager to establish, responsive to detecting that the metrics for electronic activities for a member node do not satisfy the target goals, a performance improvement plan for the member node. The performance improvement plan can be based on a difference between the member nodes' current metrics and the target metrics. The performance improvement plan can be further based on identifying a similar member node to the underperforming member node that also previously underwent a performance improvement plan but is high performing now. The performance improvement plan can be based on human input received from a manager member node. Thus, the node graph generation system 200 (e.g., via recommendation engine 275) can generate a customized or tailored performance improvement plan that is based on a similar member node whose activity levels and goal attainment indicates that the similar member node successfully completed a performance improvement plan and is now a high performing member node. The node graph generation system 200 can generate this customized or tailored performance improvement plan using human input from a manager that is deemed, by the recommendation engine 275, to be a high performing manager.

The node graph generation system 200 can set performance benchmarks for a member node, a plurality of member nodes (for example, a team of member nodes), group nodes, industry nodes representing a plurality of group nodes belonging to the same industry, nodes within a geographic territory, or any other collection or group of nodes. The node graph generation system 200 can establish benchmarks for performance based on analyzing the performance of one or more groups of nodes having similar characteristics. The node graph generation system 200 can identify similar groups of nodes based on a group size (e.g., number of member nodes in the group node), revenue of the group node, industry associated with the group node, geographic region of the group node, or other characteristic. These characteristics can be set or stored or inferred from a group node profile associated with the group node of a group node graph.

The node graph generation system 200 can generate income estimates for member nodes based on performance outcomes derived from electronic activities associated with the member node. For example, the node graph generation system 200 can determine how performance outcomes map to income, for example in sales, and then estimate income based on metrics of electronic activities that match the performance outcome stored in an opportunity record object in a system of record. The node graph generation system 200 can perform a deal-by-deal benchmarking to determine an income estimate. The system 200 can identify successful historical deals that are similar to a target deal. The system 200 can determine whether the types or quantities of electronic activities (or other metrics associated with electronic activities) associated with the successful historical deals are similar to the electronic activities metrics that are occurring in the target deal. If the system 200 determines that the target deal is on track to be a successful deal based on the electronic activities metrics for historical similar deals that were successful, then the system 200 can determine that the target deal will be successful, or more likely to close, so the representative member node for the deal is likely to keep a commission. The node graph generation system 200 can provide an indication to the member node on a periodic or other time interval with current metrics of electronic activities and target metrics for electronic activities in order to achieve the desired income. Based on deal-by-deal benchmarking, the system 200 can determine how many deals of what type the member node needs to close in a year to make the desired income. Based on the number and type of deals, the system 200 can set the goal electronic activities metrics for the member node that are likely to result in closing the deals. For example, a member node may want to make $50,000 per year, then the node graph generation system 200 can notify the member node that they need to have 10 in-person external meetings per week, write 100 emails to external contacts, and make 25 phone calls to external contacts (e.g., metrics for electronic activities that are were associated with similar deals that were successful).

The node graph generation system 200 can detect, based on analyzing electronic activities, whether the member node is satisfying the target goals. If the member node is not satisfying the target goals to achieve the desired income, the node graph generation system 200 can predict the reduction in income relative to the desired income and notify the member node of the reduction in income that may result from missing the target goals. The system 200 can tie current performance level to future projected wins (e.g., successful deals), and hence to future projected income.

In some embodiments, an employee's compensation may be based on the performance of the team that the employee is managing. For such an employee, such as a team manager, the node graph generation system 200 can help establish a compensation structure for the team manager member node that is based on the performance of his team, which is based on the individual performance outcomes of the employee member nodes the team manager manages. In some embodiments, the system 200 can analyze electronic activities (and corresponding record objects to which the electronic activities are matched) relating to the team managed by the team manager to determine or predict the performance of the team. The system 200 can then generate specific actions that the team manager or his team can or should take to improve the performance of the team or to achieve previously established goals. More generally, the node graph generation system 200 can establish goal outcomes and recommend actions based on analyzing electronic activities or accessing or analyzing systems of record. The node graph generation system 200 (e.g., via performance module 280) can compare electronic activity metrics or aggregated activity metadata for similar processes (e.g., sales deals, recruitment process, etc.) to determine a performance outcome for the member node participating in the process. The node graph generation system 200 can generate such goal outcomes or recommend actions (e.g., electronic activities) with varying granularity, for instance, hourly, daily, weekly, bi-weekly or monthly, among others. The node graph generation system 200 can establish a sales compensation system based on analyzing electronic activities or accessing or analyzing systems of record. Thus, the node graph generation system 200 can automate the process of goal setting for team management, or setting team management on autopilot, based analyzing electronic activities or accessing or analyzing systems of record.

The node graph generation system 200 can set a manager member node goal of having every employee member node perform a certain number and type of electronic activities in a certain time interval. In some cases, the manager member node goal can include aggregate activity metadata associated with electronic activities, such as response rates from C-level executives, meeting attendance rates, or meeting reschedule rates. The node graph generation system 200 can detect that the goal was not met by a first employee member node, and then perform an early warning prediction that the first employee member node may not be ramping up on time. The node graph generation system 200 can tie this missed goal detection with an indication that the first employee member node may not be ramping up on time. For example, out of 50 member nodes that succeeded at a company, their metrics trended in accordance with curve X, whereas the first employee member node's metrics trend in accordance with curve Y, which may not intersect with curve X, therefore the first employee member node may not be ramping up in a satisfactory manner. Metrics can indicate a cadence, response time to emails, number of calls, etc.

The node graph generation system 200 can identify different patterns for different industries or different types of processes (e.g., sales, recruiting, etc.). The node graph generation system 200 can establish goals for each type of deal or opportunity or industry based on the patterns. The node graph generation system 200 can, for example, establish patterns to advance stage with a specific OCR or champion. For example, the node graph generation system 200 can establish metrics for electronic activities that are tailored or customized for the specific OCR with which the seller is interacting. For example, the node graph generation system 200 can estimate for a specific deal to advance to a next stage, there should be a certain number of electronic activities with the OCR during a time interval; so, the node graph generation system 200 can set that as the goal for the time interval. The number of electronic activities can be based on or include a number of people in a meeting, average seniority of people in a meeting, or other granular indicators.

The node graph generation system 200 can generate an effort estimation model for each member node based on electronic activities or metrics thereof. The metrics can indicate low responsiveness, empty times on calendar during key business hours, or other predictors that someone is not putting in a threshold level effort. The node graph generation system 200 can detect a drop off in metrics as a drop off in effort. The node graph generation system 200 can detect a drop off or lack of participation in certain types of activities as an indication of low effort and thus predict a person being disengaged and preparing to leave the company.

13. Systems and Methods for Assigning Employees to Business Processes Including Leads, Accounts, and Opportunities Companies typically assign employees to certain leads or accounts in a round robin fashion. As new leads or accounts are identified, a company may assign a different sales rep to the lead or account without attempting to match the sales rep to the lead or account. However, none of the assignments of sales reps to leads or accounts or opportunities with such accounts is data driven, automated or objective in nature.

As described herein, companies can maintain various systems of record, including a customer relationship management system, which the company can use as a holding system for descriptions of business processes. The system of record can include lead record objects identifying leads that the company may pursue, account record objects identifying accounts to which the company sells one or more products or services, opportunity record objects identifying deals or opportunities between the company and the account, among others.

The present disclosure describes systems and methods for automatically assigning employees of a company to certain business processes of the company using a data driven approach. Before describing specific examples of different business processes to which employees of a company can be assigned, it should be appreciated that the system 200 can automatically assign employees to certain business processes by taking advantage or utilizing other aspects of the system 200.

As described herein, the system 200 can be configured to receive and parse electronic activities, link such electronic activities to node profiles of a node graph, update the node profiles based on the contents of the electronic activities, match the electronic activities to record objects of one or more systems of record of companies, generate activity patterns of node profiles including but not limited to communication styles, response rates, response times, communication mode preferences, among others. These insights and others can be determined by the system 200 based on the electronic activities the system 200 parses.

The system 200 can be configured to automatically assign at least one employee of a company to one or more record objects or provide recommendations to the company (for instance, the data source provider) to assign the at least one employee to the one or more record objects. The system 200 can be configured to automatically assign or generate a recommendation to assign a business process or associated record object to an employee of a company associated with the business process. Perhaps, more generally, the system 200 can automatically match or generate a recommendation to match or pair an employee of a company and a record object of a system of record of the company.

In some embodiments, to do so, the system 200 can be configured to maintain, for each employee of the company, an availability of the employee based on a status of one or more record objects to which the employee is assigned. In some embodiments, the employee can be assigned to a first number of lead record objects, a second number of account record objects and a third number of opportunity record objects. The system 200 can further determine, for each of the opportunity record objects, a stage of the opportunity record object. Moreover, the system can determine an amount of time the employee needs to spend on the opportunity based on the stage of the opportunity record object, a size of the deal associated with the opportunity, an expected or predicted time frame for closing the opportunity, and other parameters associated with the opportunity record object. The system can determine, based on each record object to which the employee is assigned, an availability schedule of the employee that identifies the employee's availability during various time periods, including for example, the next week, the next two weeks, the next month, the next quarter, the next year, among others.

The system 200 can be configured to automatically match or generate a recommendation to match or pair an employee of a company and a record object of a system of record of the company by using one or more rules that may be specific for different types of record objects. In some embodiments, the rules can be learned by analyzing previous matches between employees and record objects and the success or failures of such matches. The rules can be learned using machine learning or other techniques.

The following sections describe how the system can automatically match or generate a recommendation to match or pair an employee of a company and different types of record objects of a system of record of the company.

A. Matching Employees and Lead Record Objects

This section relates to matching employees and lead record objects, assigning employees to lead record objects or assigning lead record objects to employees. A lead record object can identify a person who can be an early interest for the company. Determining how successful an assignment of a lead to an employee is likely to be is based on several factors. Some of these factors include i) a quality of the lead; ii) behaviors or business practices of the employee; iii) behaviors or business practices of the lead; and iv) availability of the employee to service the lead, among others. Out of these factors, the availability of the employee to service the lead can be a more important factor. This makes sense because a salesperson currently working on 5 late stage deals likely will not have the availability to service the lead, which will result in the company losing the lead because the salesperson was unable to commit enough time to building a relationship with the lead. Examples of behaviors or business practices of the employee can be their preferences to want phone calls over emails or in person meetings, a desired time of day factoring in their time zone during which the employee likes to communicate with leads, or an employee's comfort level with dealing with leads having certain titles, for example, CIO, CEO or other executive level leads. Similarly, the behaviors, preferences and business practices of the lead can also be relevant.

In one embodiment, the system 200 can be configured to first determine, for a given lead, a plurality of employees of the company that may be potentially be assigned to the lead. These employees may be salespersons. The system 200 can then determine the availability of each of the salespersons and based on their respective availabilities, the system 200 can select a subset of the salespersons as candidate salespersons. The system can then determine, for each candidate salesperson, the behaviors, preferences and business practices of the candidate salesperson that the system 200 can derive from parsing electronic activities linked to a node profile of the candidate salesperson. The system 200 can then compare the determined behaviors, preferences and business practices of the candidate salesperson to behaviors, preferences and business practices of the lead (which can also be determined by the system 200 by parsing electronic activities linked to a node profile of the lead). In some embodiments, the system 200 can be configured to determine the behaviors, preferences and business practices of the candidate salesperson as it relates to the lead by only analyzing electronic activities exchanged between the salesperson and other leads in the past. Similarly, the system 200 can be configured to determine the behaviors, preferences and business practices of the lead as it relates to the plurality of candidate salespersons by only analyzing electronic activities exchanged between the lead and other salespersons in the past. The system 200 can then determine a match score between the candidate salesperson and the lead based on the comparison and either automatically assign the candidate salesperson to the lead or vice versa or provide a recommendation to assign the candidate salesperson to the lead or vice versa to the administrator or user of the system of record in charge for assigning leads to employees.

In some embodiments, the system 200 can use other signals or factors for matching leads to employees. For instance, if the system 200 can determine if the lead has any prior connection with any of the candidate salespersons and also determine a connection strength and type of connection between the lead and the candidate salesperson. As described herein, the system 200 can maintain a connection strength between node profiles of the system 200 and as such, the system can use the connection strength between the lead and the candidate salespersons as a factor to determine which candidate salesperson to match to the lead.

The system 200 can be configured to assign different weights to different factors used for matching leads and employees. In some embodiments, the system can enable each company to establish its own rules or policies for recommending matches between leads and employees. In some embodiments, the system 200 can be configured to train a machine learning model to match leads and salespersons based on analyzing a salesperson's matches with leads in the past as well as analyzing the lead's matches with other salespersons in the past.

By way of this solution, the system 200 can reduce the number of candidate salespersons the company needs to consider for each new lead thereby allowing the person responsible for assigning leads to employees to spend less time pairing leads to employees while improving the likelihood of success of converting the lead by selecting candidate employees that are most likely going to succeed with this lead based on objectively analyzing historical electronic activities. Moreover, at present, companies are focusing on lead generation without optimizing the conversion of existing leads. The solution described herein aims to determine which employee is most likely to convert the lead to optimize the company's ability to convert each and every lead of the company.

B. Matching Employees and Account Record Objects

In contrast to the concept of matching employees and leads described above, this section relates to matching employees to accounts. An account or an account record object corresponds to a customer of the company. Each account can be linked to one or more lead record objects and opportunity record objects. In contrast to lead assignments described in the previous section, account assignment is similar except that a lead is one person while an account includes a group of people.

The system 200 can be configured to identify an account of a company to which to assign one or more employees of the company to service the account. The system 200 can be configured to identify each of the contacts at the account. The contacts may be identified by analyzing the contact record objects of the system of record to identify which contacts are linked to the account. In some embodiments, the system can utilize the node graph of the system to analyze ode profiles that currently work at the account. The system can then run an analysis for each employee of the plurality of employees of the company that may be a candidate to service the account based on the employee's function or job description. Upon selecting a set of candidate employees from the plurality of employees of the company, the system 200 can determine, for each employee, a connection strength between the employee and each of the contacts at the account. The system can then aggregate, for the employee, the connection strengths between the employee and each of the contacts by applying different weights based on the role, title or function of the contact within the account, which can all be determined by the system through the system of record or the node profiles maintained by the system 200. The system can then determine, from the aggregated connection strengths of each of the plurality of employees, at least one employee to assign or recommend assigning to the account. As mentioned above, the contacts at the account with which the employee has relationships can be weighted based on their role, title or function.

In some embodiments, the system 200 can take into account other factors other than connection strengths prior to assigning the employee to the account. In particular, the system 200 can also consider the geographical proximity between the employee and the account or the contacts within the account. The system 200 can also consider the employee's selling style or other behavioral patterns and compare them to the buying style of the contacts within the account to determine whether or not to assign the employee to the account. In addition, the system 200 can take into account past experiences of the employee with the contacts or the account itself. For instance, the system 200 can determine if the employee has previously worked for or with the account at a previous job. The system 200 can also determine if the employee has previously worked with any of the contacts included in the account. The system 200 can also determine if the employee has previously worked with similar types of accounts, for instance, if the account is Verizon, the system can determine if the employee has worked with AT&T given that AT&T is in the same sector as Verizon and so the employee may be a better fit for an account such as Verizon. In some embodiments, the system 200 an also determine an availability of the employee to determine if the employee has the capacity to service the account.

In some embodiments, the system can determine a target persona for the account. For instance, if the account is a marketing department of a customer, the system can be configured to generate a target persona that corresponds to the marketing department as opposed to an accounts department. The system can then attempt to identify employees within the company that most closely match the target persona corresponding to the marketing department as this employee will be most likely to best serve the account.

The system 200 can also be configured to take into account other employees to assign to the account as part of a sales team. As such, the system 200 may be configured to determine whether or not to assign an employee to the account based on which other employees are already assigned to the account or are candidates to be assigned to the account. The system 200 can be configured to assign an employee to the account based on the employee's relationship with other employees who are already assigned to the account, for instance, the employee is part of 3 other sales teams that include the other employees.

In addition, the system 200 can be configured to recommend additional employees to assign to the account based on selecting an employee to assign to the account. For instance, the system 200 can identify a first employee as a sales representative to the account. The sales representative generally works with a sales engineer and an account executive when selling to a company. As such, the system 200 can be configured to select a sales engineer from a plurality of candidate sales engineers and select an account executive from a plurality of candidate account executives to assign to the account based on determining that the sales engineer and the account executive have been included in sales teams with the sales representative for other accounts.

In some embodiments, the system 200 can be configured to recommend overlay resources like sales engineers to the account. The sales engineer that is recommended may be selected for recommendation responsive to the system determining that the sales engineer also has connections to the account. In addition, the system 200 can further recommend executives on the company side to which to recommend or assign to the account. By generating these additional recommendations of employees to the account, the system can be configured to automatically recommend or generate account team recommendations that the company can use to build account teams. As described herein, these account teams can be based on their relationships with contacts at the account, their past experiences with the account their past experiences working with each other on other accounts, as well as their availability to service the account, among others.

In some embodiments, the system can identify one or more people at the account who may be considered to form the buying group. The buying group can be determined by the system 200 using the node graph of the system 200 or from other systems of record accessible to the system 200. The system 200 can be configured to identify employees to assign to the account based on the target persona of the account as well as the buying group of the account. In some such embodiments, the system can adopt the same techniques and methodology described herein but adjust weights of certain factors based on the target persona of the account as well as the buying group of the account.

As described herein, the system 200 can be configured to detect account teams from electronic activities that are matched to record objects corresponding to account record objects or opportunity record objects. Detecting that an employee belongs to an account team based on electronic activities can be useful to the system 200 for matching the electronic activities identifying the employee to the appropriate record object of a system of record, among others. In some embodiments, an account team can be determined from the system of record based on linking contact record objects to an account record object, for instance. However, it should be appreciated that the system 200, as described with respect to Section 12, is configured to provide recommendations of employees to add to existing account teams or create new account teams for new accounts.

As described above with respect to matching electronic activities to record objects, the system 200 can be configured to identify candidate record objects to match electronic activities based on account teams. By being able to expand the account teams or verify if an employee should be added to an account team, the system 200 can be configured to improve its ability to match electronic activities to record objects by better identifying record objects using matching strategies involving account teams.

C. Matching Employees and Opportunity Record Objects

The system can be configured to also be configured to automatically assign or recommend assigning an employee to an opportunity record object. The system can identify employees to match to opportunity record objects in a manner similar to lead record objects and account record objects. As opportunities are business processes that need active involvement in the short term, selecting an employee to assign to the opportunity, the system can give more importance to the employee's availability in the short term relative to when the system selects an employee to match to an account. The system can be configured to determine, for each employee, their current load or available capacity based on the number of opportunities the employee is working on, what stage each of the opportunities is in, among others. As such, a described here, the system's ability to predict stage classification of opportunity record objects can be used to determine the employee's availability and based on the employee's availability, a recommendation to assign the employee to one or more opportunities that the employee is not currently assigned to.

The system can be configured to identify, for a given opportunity, one or more opportunity contact roles associated with the opportunity as well as other contacts at the account level that are involved with the activity. The system can then determine to identify candidate employees that would be a good fit for the opportunity based on a comparison of the candidate employee and the contacts involved or likely to be involved with the opportunity. Based on the determination, the system can provide a recommendation to add a candidate employee to the account team servicing the opportunity record object. As described above with respect to matching employees and lead record objects and account record objects, the system can determine similar factors to determine how good a fit the candidate employee will be for the opportunity.

D. Matching Employees and Named Account Lists

The system 200 can be configured to match employees to one or more account lists. In a scenario where a new employee joins a company, a supervisor may be assigned to assign the employee to multiple accounts or leads, among others. At present, the supervisor may simply assign the employees to accounts based on a geographical location of the employee and corresponding locations of the accounts. However, assigning employees to accounts simply based on location matching fails to optimize the employee's ability to generate new leads and opportunities.

In some embodiments, the system 200 can be configured to generate a list of accounts to which to assign an employee of the company. In some embodiments, the system 200 can receive a request from a user of the system 200 to assign or identify accounts of the company to the employee. The system 200 can first identify all of the accounts of the company to which the system 200 can possibly match the employee. The system 200 can then determine, for each account, one or more contacts at the account with which the employee has a connection. The system 200 can use the node profiles and node graph to determine these contacts. The system 200 can then determine, for each contact with which the employee has a connection, a connection strength between the contact and the employee. The system 200 can then weight each of these connections based on the account and the role of the contact within the contact. The system 200 can then determine an aggregated score between the account and the employee based on the weights and connection strengths of the employee with the contacts of the account. The system can compute the aggregated score also by factoring in a location of the employee relative to the account, a time zone of the employee relative to the account, a selling style or communication style of the employee relative to the buying style or communication system of the contacts within the account. The system can then generate a list of accounts to which to match the employee based on the aggregated scores between the employee and the respective account. It should be appreciated that other factors, such as the employee's availability, timing of potential opportunities of the account, other employees that may likely form the account team, can also be factors in computing the aggregated score between the employee and the respective account.

E. Matching Employees and Territories

Some companies may maintain one or more systems of record in which employees are assigned to territories, such as geographical regions. In some such cases, the system 200 can be configured to assign employees to territories, which may be assigned to certain accounts. Similar to how the system 200 can determine an aggregate score for each account described above, the system 200 can be configured to assign employees to territories based on determining an aggregate score between the territory and the employee by determining individual scores between accounts within the territory and the employee.

It should be appreciated that matching employees to various record objects or business processes described above can be based on objective data that is parsed from electronic activities involving the employee or electronic activities involving leads or contacts at the accounts. As such, the system 200 can be configured to rely on certain electronic activities when determining which record objects or business processes to match or assign or which employee to assign or match to the record objects or business processes of the company. In this way, a data-driven approach to selecting employees to assign to accounts can be achieved, which can result in better outcomes for the employee, the account, and the company.

It should further be appreciated that similar methodology can be used by the system 200 for identifying potential candidates to suggest to a company to hire as employees. The system 200 can analyze a candidate's connections and communication style from electronic activities linked to the node profile of the candidate and use that information to compare to accounts of the company to determine if the employee will be a good fit. Similarly, for a person looking to join new company the system 200 can identify potential candidate companies to the person based on the person's connections and communication style determined by the system 200 from electronic activities linked to the node profile of the person and information about the candidate companies and their respective accounts also maintained by the system 200.

14. Systems and Methods for Generating Data Recommendations Based on an Immutable Member Node Network At least one aspect of the present disclosure is directed to systems and methods for generating data recommendations based on an immutable member node network. The immutable member node network can refer to or include a member node network containing member nodes connected to one or more other member nodes. The member nodes can contain a member node profile that is generated by the node graph generation system 200 (or node profile manager 220) using electronic activity information or information from a master system of record. By using electronic activity information or a master system of record generated and maintained by the node graph generation system 200, the node graph generation system 200 can generate data recommendation using the immutable member node network.

The member node network may be immutable in that the member node network may be accurate and not contain erroneous data, or lack data with a confidence score that falls below a threshold. The node graph generation system 200, using the member node network (e.g., member node graph) can match member nodes to a potential group node, job, account, or opportunity based on the member node profile matching profiles, metrics or parameters associated with the group node, job, account or opportunity.

For example, the node graph generation system 200 can determine that a particular member node is represented by a member node profile that includes fields and values for the fields. The node graph generation system 200 can further determine, via a member node performance module 280, a performance score as well as performance metrics for the member node. The performance information can be correlated with metrics associated with electronic activities. The performance metrics can be granular and correspond to profile values. For example, the member node profile performance information can indicate that a member node has a high performance level when the member node performs electronic activities that include at least a first number of in-person meetings with C-level executives. For example, if the member node has five in-person meetings with C-level executives in a week, then the performance module 280 can determine that the member node is performing well based on historical performance information for the member node or similar deals. The node graph generation system 200 (or member node performance module 280) can determine the high performance level (e.g., relative to an average performance level across member nodes or a subset of member nodes). The node graph generation system 200 can then identify group nodes or group profiles associated with group nodes or companies that match the profile values correlated to the high performance level of the member node.

As described above also with respect to Section 12, the system 200 can be configured to utilize information included in the node graph to match candidate employee and companies based on the candidate employee's connections with one or more accounts of the companies to which the system 200 determines a match. In some embodiments, the system 200 can determine a match based on a candidate employee's selling style and a buying style of a buyers group of an opportunity linked to one of the accounts of a company. It should be appreciated that the system 200 can look at other signals too when making such matches and not rely simply on matching according to a selling style or for a single opportunity. In some embodiments, the system 200 can identify an employee within a company that should be put on an account team of an opportunity record object based on the selling style of the employee (or other factors such as availability, connections to the buyer group, among others).

Thus, the node graph generation system 200 can match member nodes to a group node based on performance characteristics or other metrics of the member node and the group node that are derived, inferred, or otherwise determined using electronic activities from data source providers 9350 and record objects from one or more systems of record. The node graph generation system 200 can use the electronic activities and the data in the systems of record to generation a performance profile for a member node, which can be stored in a master member node network or immutable member node network. The member node network can be immutable because it is not self-written or self-reported by individuals; instead, the node graph generation system 200 generates the performance profile and member node profile using electronic activities and systems of record, which is an independent, factual, and objective source of activity information. The node graph generation system 200 can generate the group node network containing group profiles for group nodes. The node graph generations system 200 can identify granular values that are correlated with desired performance or outcomes based on stages of opportunities or stages of other business processes, stored in record objects of a system of record or one or more systems of record.

As described herein and supplemental to the description of various terms provided above, electronic activities can include emails, electronic calendar events, electronic meetings, phone call logs, instant messages, other any other electronic communications generated by a node, received by a node, exchanged between nodes or otherwise stored on an electronic server configured to provide electronic activities to the data processing system 9300.

An individual or member node can be an electronic representation of a user, person, account of a person or user, an employee, a bot, or any other entity that may have an account or an identifier that the data processing system can generate a node profile for.

A group node can be an electronic representation of an enterprise, a company, an organization, an employer, a team of employees or people, or a plurality of member nodes that can be treated as a single entity.

A node profile can be an electronic representation of a profile of a member node or a group node. The node profile can include fields. Each field can include one or more values. An example field can be an email address. An example value can be john.smith@example.com.

A value of a field can include an array of data points identifying occurrences of the value. Each value can have a confidence score.

A data point can identify an electronic activity or other piece of information that contributes the value to the field. The data point can include or identify a source of the electronic activity, a trust score of the source of the data point, a time or recency of the electronic activity and a contribution score.

The source of the electronic activity can be a mail server, a system of record, or any other repository of electronic activities.

A trust score of the source of the data point can indicate a trustworthiness of the source of the data point. The trust score of the source can be based on a completeness of system of record maintained by the source. The trust score can also serve as an indication of how reliable the source may be.

A contribution score of the data point can indicate how much the data point contributes towards a confidence score of the value associated with the data point. The contribution score can be based on the trust score of the source, a health score of the source, and a time at which the data point was generated or last updated.

A confidence score of the value can indicate a level of certainty that the value of the field is a current value of the field. The higher the confidence score, the more certain the value of the field is the current value. The confidence score can be based on the contribution scores of individual data points associated with the value. The confidence score of the value can also depend on the corresponding confidence scores of other values of the field, or the contribution scores of data points associated with other values of the field.

A confidence score generally relates to a level of confidence that a certain piece of information is accurate. As used herein, a confidence score of a piece of information, such as an assigned tag, a value of a field of a node profile, a stage classification prediction, a record object match, can indicate a level of confidence that the piece of information is accurate. The confidence score of the piece of information can change based on a temporal basis. A node profile can include a first email address corresponding to a first job and a second email corresponding to a subsequent job. Each of the two email addresses are at respective points in time, accurate and valid. As the person switches jobs, the first email address is no longer valid but the confidence score associated with the email address can in some embodiments, remain high indicating that the first email address belongs to the node profile. Similarly, the second email address also belongs to the node profile and therefore also has a high confidence score. After the system determines that the second email address is active and functioning, the system can assign a higher confidence score to the second email address relative to the first email address since the contribution scores provided by recent data points (for example, recent electronic activities identifying the second email address) can contribute towards the higher confidence score. Similarly, any tags that are assigned to electronic activities identifying bounce back activity related to the first email address (indicating that the first email address is no longer active) can reduce the confidence score of the first electronic activity.

The health score of the source can indicate a level of health of the source. The health of the source can include a completeness of the source (for example, a system of record), an accuracy of the data included in the source, a frequency at which the data in the source is updated, among others.

A connection strength between two nodes can be based on the electronic activities associated with both the nodes. In some embodiments, each electronic activity can be used by the system to determine a connection strength between the two nodes. The contribution of each electronic activity towards the connection strength can diminish over time as older electronic activities may indicate a past connection but do not indicate a current status of the connection strength between the two nodes.

The time decaying relevancy score of an electronic activity can indicate how relevant the electronic activity is for determining a connection strength between two nodes exchanged between or otherwise associated with the two nodes. The connection strength between two nodes can be based on the time decaying relevancy scores of all of the electronic activities exchanged between or otherwise associated with the two nodes.

As further described herein, electronic activities can be linked to or matched to record objects. Record objects can be maintained in a shadow system of record maintained by the system 9300 or in some embodiments, linked or matched to record objects maintained in master systems of record that are maintained by customers or enterprises.

15. Matching Electronic Activities Directly to Record Objects of Systems of Record As described above, the system described herein can match electronic activities with one or more record objects. The system can match the electronic activities in a single-tenant or multi-tenant configuration of the system. For example, in a single-tenant configuration, the system can receive or access electronic activities from a single data source provider and match the electronic activities to record objects of a system of record of the data source provider from which the electronic activities were received or accessed. In a multi-tenant configuration, the system can receive or access electronic activities from multiple data source providers and match the electronic activities to record objects of a system of record of the respective data source provider from which the electronic activities were received or accessed. As described herein, the system can automatically match, link, or otherwise associate the electronic activities with one or more record objects. For an electronic activity that is eligible or qualifies to be matched with one or more record objects, the system can identify one or more set of rules or rule sets. Using the rule sets, the system can identify candidate record objects. The system can then rank the identified candidate record objects to select one or more record objects with which to associate the electronic activity. The system can then store an association between the electronic activity and the selected one or more record objects.

Figure 16:
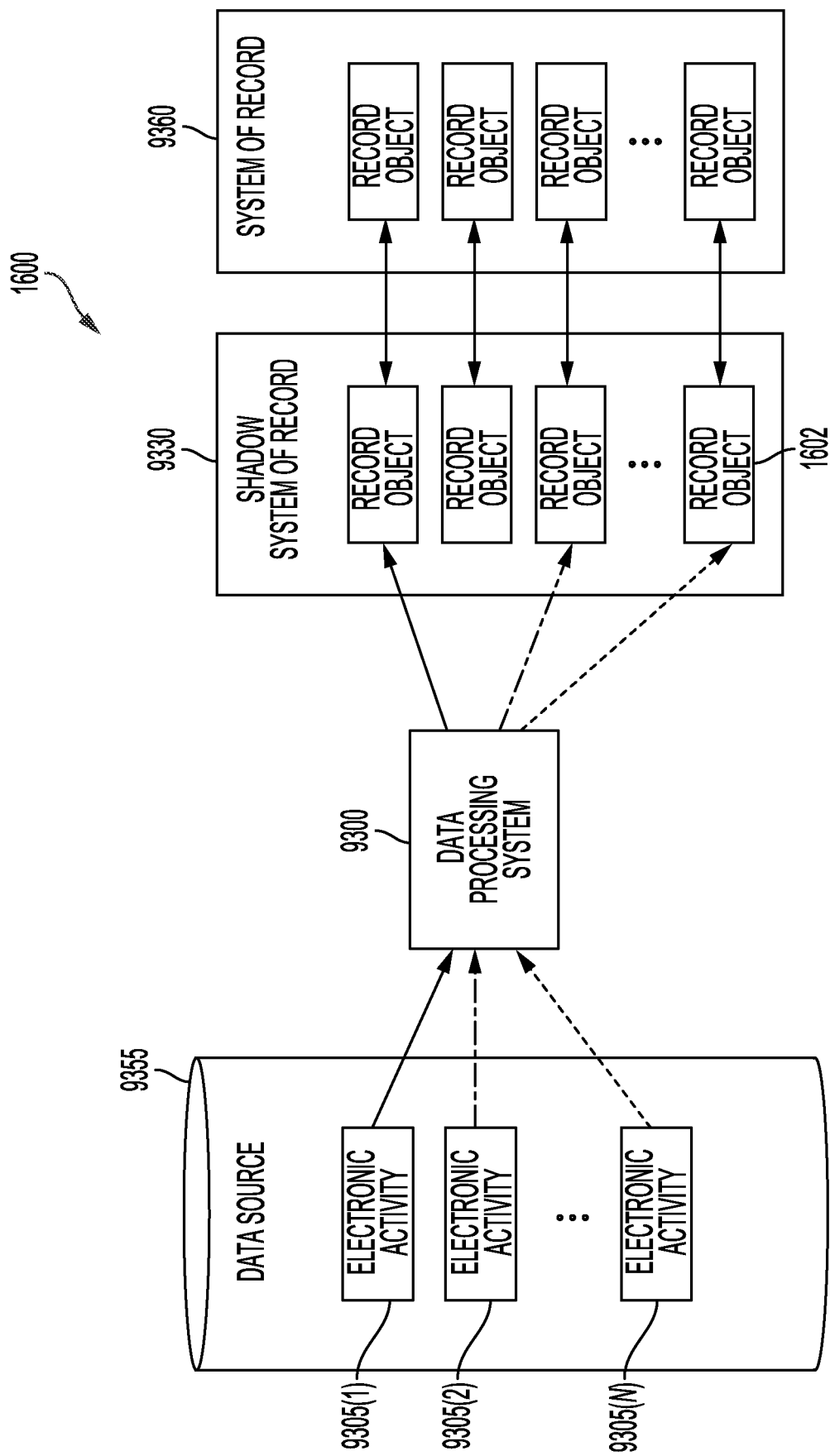
FIG. 16 illustrates a block diagram of an example process flow for processing electronic activities in a single-tenant configuration according to embodiments of the present disclosure.

FIG. 16 illustrates a block diagram of an example process flow 1600 for processing electronic activities in a single-tenant configuration. Also, with reference to FIGS. 3 and 4, among others, the data processing system 9300 can be in communication with one or more data source providers 9350. Each of the data source providers 9350 can include a data source 9355. FIG. 16 illustrates an example of a single-tenant system where the electronic activities 9305 from a single tenant (e.g., the data source provider 9350 that includes the data source 9355) is matched to the record objects 1602 of a single shadow system of record 9330. The single shadow system of record 9330 can be associated with the data source provider 9350 that provided the electronic activity. For example, the shadow system or record can include data retrieved from the record objects of the data source providers system of record. It should be appreciated that although FIG. 16 illustrates a shadow system of record including one or more shadow record objects that correspond to respective record objects of a corresponding system of record of the data source provider, the data processing system 9300 is configured to directly match the electronic activities of the data source provider to the record objects of the system of record 9360 without having to first match the electronic activity to a shadow record object of the shadow system of record 9330.

The data source provider 9350 can store electronic activity 9305(1)-electronic activity 9305(N) (generally referred to as electronic activity 9305) in the data source 9355. As described above, the electronic activities can include one or more forms of electronic activity, such as email or other forms of electronic communication. The data processing system 9300 can access or otherwise retrieve the electronic activity 9305 from the data source 9355. For example, the above-described electronic activity ingestor 205 can be configured to ingest electronic activities in a real-time or near real-time basis for accounts of one or more enterprises, organizations, companies, businesses, institutions or any other group associated with the data source providers. The electronic activity ingestor 205 can ingest electronic activities. For example, when a data source provider subscribes to a service provided by the data processing system 9300, the data source provider can provide access to electronic activities maintained by the data source provider by going through an onboarding process. That onboarding process can enable the data processing system 9300 to access electronic activities owned or maintained by the data source provider in one or more data sources 9355. For example, the data sources 9355 can be, but are not limited to, mail servers, one or more systems of record, one or more phone services or servers of the data source provider, among other sources of electronic activity. The electronic activities ingested during an onboarding process may include electronic activities that were generated in the past, perhaps many years ago, that were stored on the electronic activities' sources. The data processing system 9300 can be configured to ingest (and re-ingest) the electronic activities from one or more data sources 9355 on a periodic basis, including daily, weekly, monthly, or any reasonable frequency.

The data processing system 9300 can match the electronic activities 9305 to one or more record objects 1602 of the shadow system of record 9330. The record objects 1602 of the shadow system of record 9330 can be synced with the record object 1602 of the system of record 9360. Syncing the shadow record objects 1602 with the record objects 1602 of the system of record 9360 can include adding values from fields of the shadow record objects 1602 to the corresponding values, such as matched electronic activities 9305, of the record objects 1602 in the system of record 9360. In some embodiments, the data processing system 9300 can match the electronic activities 9305 directly to the system of record 9360. For example, the data processing system 9300 can match the electronic activities 9305 to the record objects in the system of record 9360 without matching the electronic activities 9305 to the record objects in the shadow system or record 9330.

Figure 17:
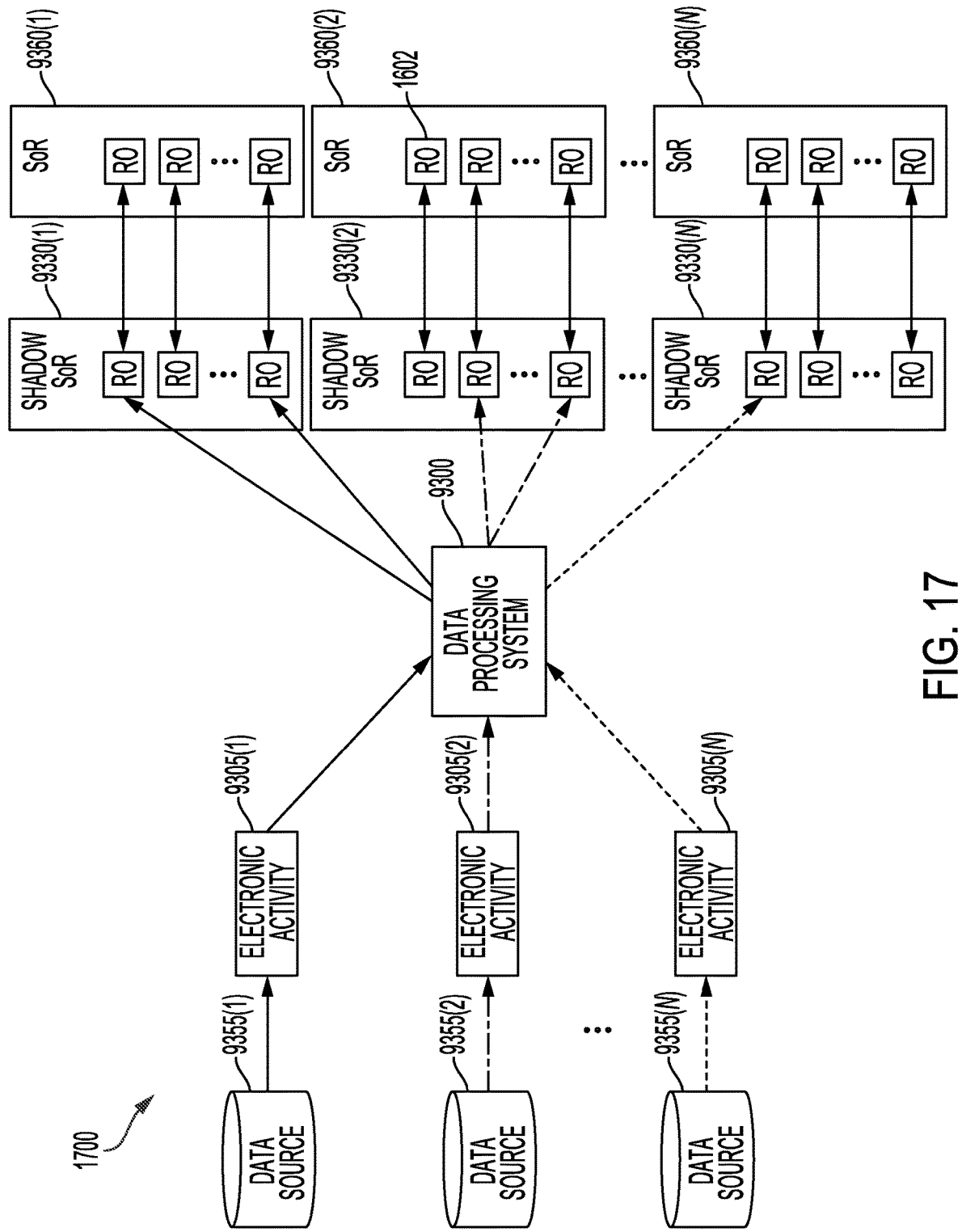
FIG. 17 illustrates a block diagram of an example process flow for processing electronic activities in a multi-tenant configuration according to embodiments of the present disclosure.

FIG. 17 illustrates a block diagram of an example process flow 1700 for processing electronic activities in a multi-tenant configuration. As illustrated by the process flow 1700, the multi-tenant configuration can include a plurality of data sources 9355(1)-9355(N), each of which can be a component of a respective data source provider 9350(1)-9350(N). The data processing system 9300 can receive or access electronic activities 9305 from each of the respective data sources 9355(1)-9355(N).

The data processing system 9300 can identify from which of the data sources 9355, each of the respective electronic activities 9305 were received and then match the electronic activities 9305 with one or more record objects 1602 associated with the data source provider 9350.

For example, and as illustrated in FIG. 17, the data source 9355(1) can be associated with the shadow system or record 9330(1), the data source 9355(2) can be associated with the shadow system or record 9330(2), and the data source 9355(N) can be associated with the shadow system or record 9330(N). The data processing system 9300 can match the electronic activity 9305(1), from the data source 9355(1), with two of the record objects 1602 in the shadow system of record 9330(1). The data processing system 9300 can match the electronic activity 9305(2), from the data source 9355(2), with two of the record objects 1602 in the shadow system of record 9330(2). The data processing system 9300 can match the electronic activity 9305(N), from the data source 9355(N), with one of the record objects 1602 in the shadow system of record 9330(N).

In some embodiments, the data processing system 9300 can match the electronic activities 9305 directly to the systems of record 9360. For example, the data processing system 9300 can match the electronic activities 9305 to the record objects in the system of record 9360 without matching the electronic activities 9305 to the record objects in the shadow systems or record 9330.

Figure 18:
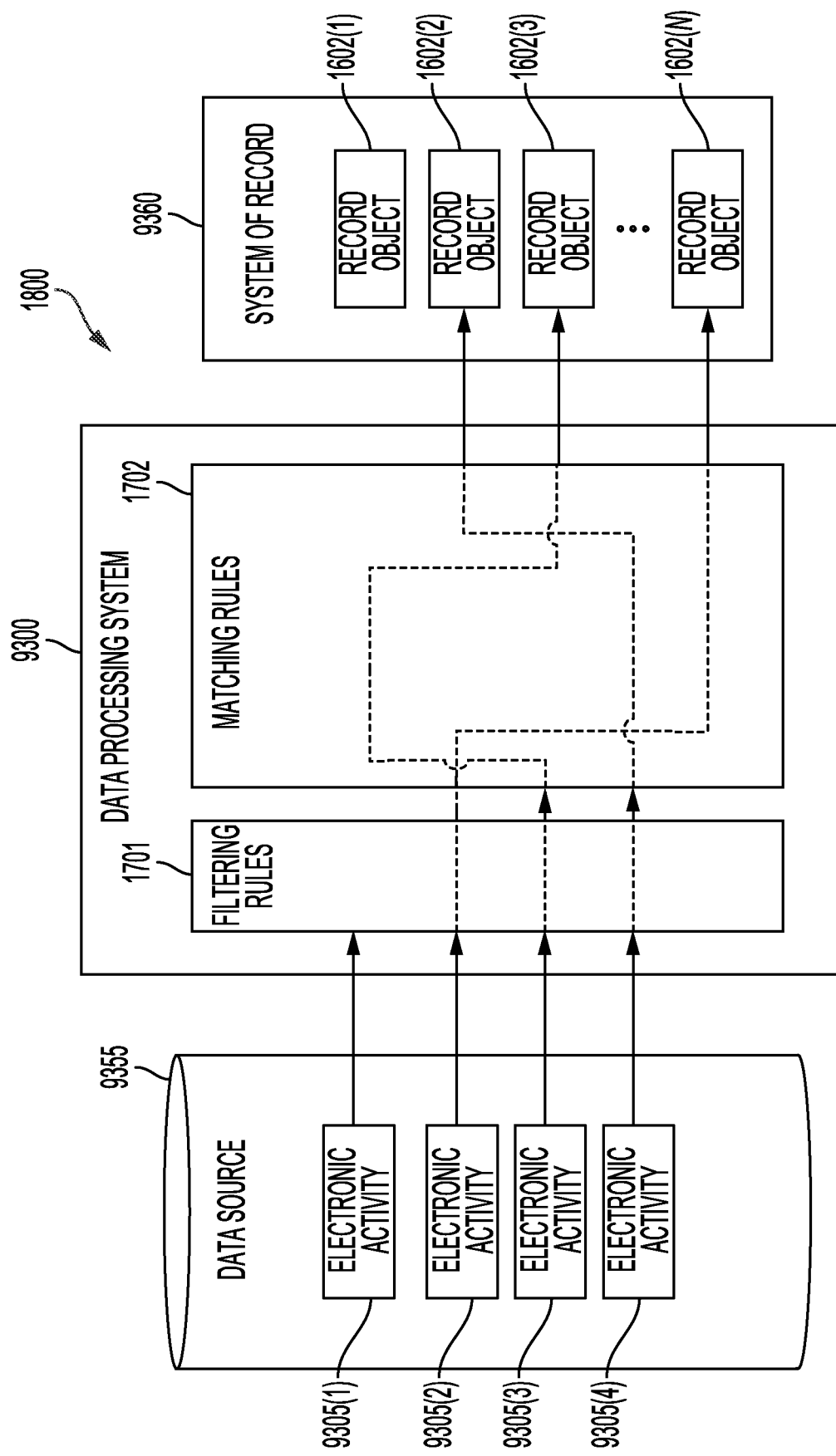
FIG. 18 illustrates a block diagram of an example process flow for matching electronic activities with record objects according to embodiments of the present disclosure.

FIG. 18 illustrates a block diagram of an example process flow 1800 for matching electronic activities 9305 with record objects 1602. The data source 9355 includes a plurality of electronic activities 9305 that are accessed by or transmitted to the data processing system 9300. The data processing system 9300 can include a filtering rule set 1701 and matching rules 1702. The data processing system 9300 can use the filtering rule set 1701 and the matching rules 1702 to map the incoming electronic activities 9305 to one or more of the record objects 1602 in the system of record 9360.

Also, with reference to FIGS. 11 and 12, among others, the data processing system 9300 can include one or more filtering rule sets 1701. The filtering rule sets 1701 can include rule sets for filtering or excluding electronic activities 9305 from the matching process. For example, when the data processing system 9300 processes an incoming electronic activity 9305, the data processing system 9300 can first process the electronic activity 9305 with the filtering rule sets 1701 before attempting to match the electronic activity 9305 with a record object 1602. As illustrated in FIG. 18, the electronic activity 9305(1) can be received by the data processing system 9300. The data processing system 9300 can process the electronic activity 9305(1) with the filtering rule set 1701 before the data processing system 9300 passes the electronic activity 9305(1) to the matching rules 1702. As illustrated in FIG. 18, the electronic activity 9305(1) is processed with the filtering rule set 1701 and is restricted from further processing and is not matched with one of the record objects 1602.

The filtering rule set 1701 can include a plurality of rules or heuristics for determining whether the electronic activity 9305 should be restricted from further processing including matching the electronic activity to a record object. The rules can be keyword-based. For example, the rules can include a list of keywords. The data processing system 9300 can process the text of the electronic activity 9305 and determine whether one or more of the keywords are present in the electronic activity 9305. The data processing system 9300 can determine the electronic activity 9305 should be restricted if the data processing system 9300 identifies one of the keywords in the electronic activity 9305. The data processing system 9300 can identify identical matches of the keyword. The data processing system 9300 can identify approximate or fuzzy matching of the keyword (e.g., the data processing system 9300 can identify misspellings or plurals of the keyword). In some embodiments, the keywords can include wildcards. For example, the keyword may be only the base or root of a word. The rules can be pattern-based. For example, the rules can include regex patterns with which the data processing system 9300 processes the text of the electronic activities 9305. For example, the regex pattern can be configured to identify social security numbers.

If the data processing system 9300 determines that the electronic activity 9305 is selected with one of the rules of the filtering rule set 1701, the data processing system 9300 can stop further processing or ingestion of the electronic activity 9305. For example, if the electronic activity 9305 is an email that includes a social security number and one of the rules of the filtering rule set 1701 is configured to identify social security number patterns, the data processing system 9300 can identify the email with the rule and stop ingestion of the email such that the email is not matched to one of the record objects 1602. The electronic activities 9305 identified by the filtering rule set 1701 can be ingested but are restricted from being matched to one or more record objects. For example, the electronic activity 9305 may be restricted from being matched to a record object, but the data processing system 9300 can use the data in the electronic activity 9305 to populate fields with values in the above-described node profile graph.

The data processing system 9300 can include one or more matching rules 1702. The rules of the matching rules 1702 can include rules for matching electronic activities 9305 with one or more record objects 1602. Also referring to FIGS. 11 and 12, among others, the rules for matching the electronic activities 9305 to record objects 1602 can be grouped into sets such as buyer-side rules or strategies that match electronic activities 9305 to record objects 1602 based on data related to the recipient of the electronic activity 9305. Another example filtering rule set 1701 can include a grouping of rules based on seller-side rules or strategies that match electronic activities 9305 to record objects 1602 based on data related to the sending of the electronic activities 9305. The data processing system 9300 can match the electronic activities 9305 to the record objects 1602 based on a plurality of matching rules 1702. For example, the electronic activity 9305(3) is matched with the record object 1602(3) based on a plurality of matching rules 1702(1). In some embodiments, the matching rules 1702 can be to select a group of record objects. The data processing system 9300 can then select a candidate record object from an intersection of the groups of record objects. For example, the candidate record object may be the record object that is selected by each of the matching rules 1702.

Figure 19:
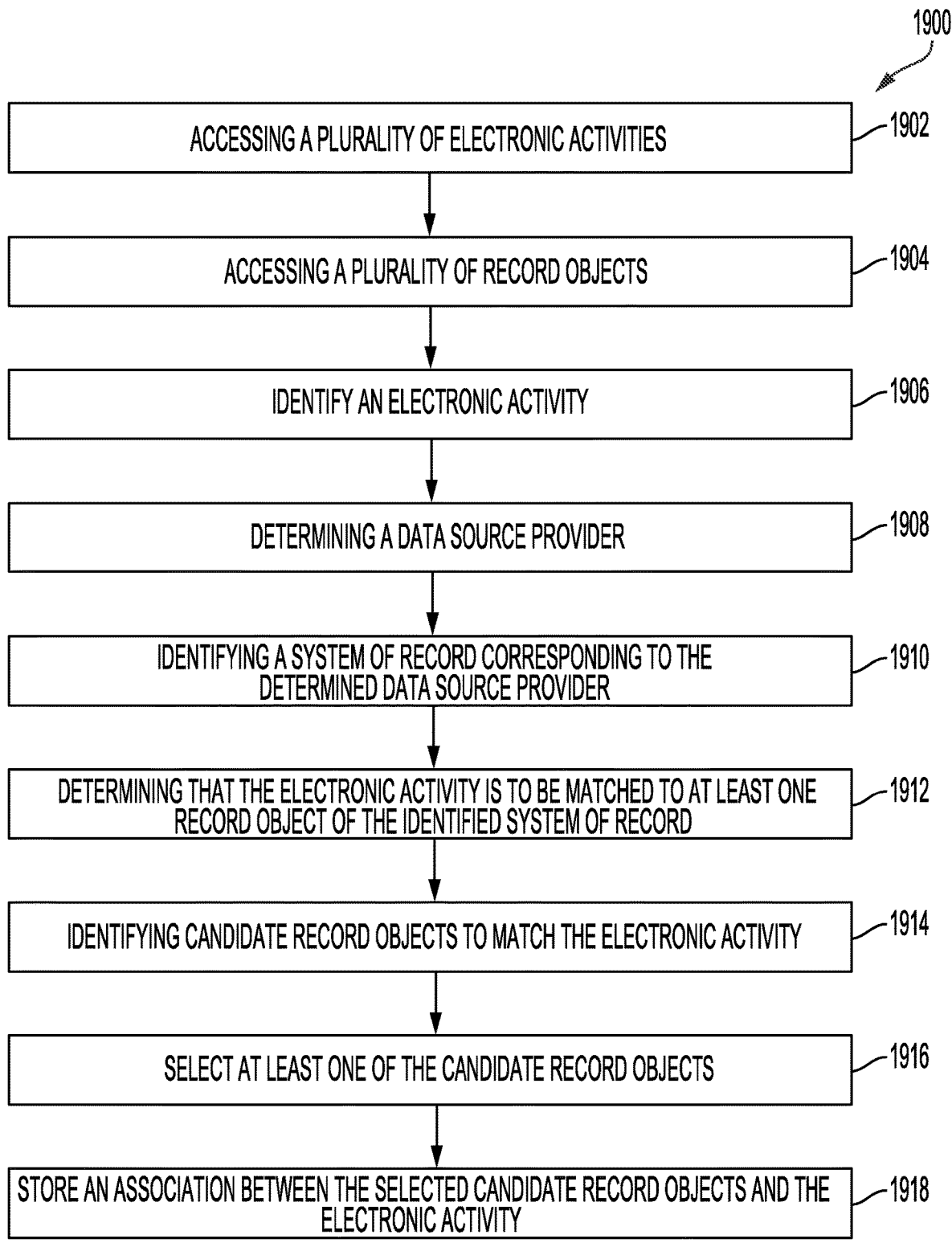
FIG. 19 illustrates a block diagram of an example method to match electronic activities directly to record objects according to embodiments of the present disclosure.

FIG. 19 illustrates a method 1900 to match electronic activities directly to record objects. The method 1900 can include accessing a plurality of electronic activities (BLOCK 1902). With reference to FIGS. 16-18, among others, the data processing system 9300 can access a plurality of electronic activities. The electronic activities can be transmitted to the data processing system 9300 from data source providers. The data processing system 9300 can retrieve the electronic activities from the data source providers. For example, the data source provider can include or be an email server. The data processing system 9300 can have the authority to access the emails stored on the email server through an API or an HTTP method (e.g., a GET method).

The method 1900 can include accessing a plurality of record objects (BLOCK 1904). The method 1900 can include accessing, by the data processing system 9300, a plurality of record objects. The data processing system 9300 can access the record objects for a plurality of different systems of record, as described above in relation to FIG. 17. For example, the data processing system 9300 can make a call to the systems of record 9360 that are associated with each of the data source providers from which the data processing system 9300 retrieved electronic activities at BLOCK 1902. The data processing system 9300 can generate a copy of the accessed record objects. The data processing system's copy of the access record objects can be referred to as shadow record objects.

As described above in relation to FIG. 10, each of the record objects can be of a record object type. For example, the record objects can be lead record objects, account record objects, opportunity record objects, or contact record objects. The record objects can be any type of record object in a system of record. The other systems of records can include Applicant Tracking Systems (ATS), such as Lever, located in San Francisco, Calif. or Talend by Talend Inc., located in Redwood City, Calif., enterprise resource planning (ERP) systems, customer success systems, such as Gainsight located in Redwood City, Calif., and Document Management Systems, among others.

The data processing system 9300 can retrieve the record objects from servers that correspond to the data source provider or data source from which the data processing system 9300 retrieved the electronic activities 9305. The data processing system 9300 can retrieve the record objects 1602 from a system of record 9360. The data processing system 9300 can retrieve the record objects 1602 through an API call. For example, the data processing system 9300 can retrieve a first plurality of record objects corresponding to a first system of record of a first data source provider and second plurality of record objects corresponding to a second system of record of a second data source provider.

As described above in relation to FIG. 17, among others, the system can be configured in a multi-tenant configuration. In a multi-tenant configuration, the data processing system 9300 can retrieve a respective plurality of record objects that correspond to each of the data source provider (e.g., tenants) associated with the data processing system 9300. For example, the data processing system 9300 can retrieve a plurality of record objects from a system of record for each of the data source providers.

Each of the record objects can include one or more object fields and corresponding object field values. For example, the record objects can be data structures and the object field values can be values of object fields of the data structure. For example, for a contact record object, the data structure can include fields such as, but not limited to, name, address, email, and phone number, which can be filled with respective field values.

The method 1900 can include identifying an electronic activity (BLOCK 1906). The method 1900 can include identifying, by the data processing system 9300, an electronic activity of the plurality of electronic activities to match to one or more record objects. The data processing system 9300 can identify an electronic activity that is a candidate for matching to one or more record objects. The data processing system 9300 can determine that an electronic activity is a candidate for matching to one or more record objects based on the filtering and exclusion rules. For example, if the electronic activity is identified by one or more filtering or exclusion rules the electronic activity can be disregarded from consideration for matching to a record object.

The data processing system 9300 can identify electronic activities as candidates based on one or more tags applied to the electronic activity. The above-described tagging engine 265 can assign one or more tags to the electronic activity when the electronic activity is ingested or processed. For example, if all the participants associated with the electronic activity are internal (e.g., each participant has an email address with the domain of the data source provider), the tagging engine 265 can tag the electronic activity as internal. The data processing system 9300 can be configured such that electronic activities tagged as internal are not matched to record objects. In another example, if the electronic activity includes a participant that is associated with an account record object, the data processing system 9300 can tag the electronic activity as a candidate for matching.

As described above in relation to FIGS. 5A-5C and 6B, the data processing system 9300 can identify and extract content from the electronic activities. For example, the data processing system 9300 can identify participants associated with the electronic activity. The participants can be the sender or the receiver of the electronic activity. The data processing system 9300 can identify the participants associated with the electronic activity by identify the sender's email address and the recipient's email address.

In some embodiments, the data processing system 9300 can assign one or more tags to the electronic activity. The data processing system 9300 can assign tags to the electronic activities based on the content included in the electronic activity or the metadata therefor. For example, the tags can be based on one or more character strings identified in the body of the electronic activity, in the metadata of the electronic activity, or in related electronic activities.

For example, the electronic activity can be an email message and the data processing system 9300 can identify keywords within the email's body. The keywords can be identified by the above-described tagging engine 265. The keywords can identify the subject matter, phrases, accounts, topics, identification numbers, or other terms in or related to the subject of the electronic activity.

The method 1900 can include determining a data source provider (BLOCK 1908). The method 1900 can include the data processing system 9300 from which of the data source providers, the data processing system 9300 received the electronic activity. For example, the data processing system 9300 can receive electronic activity from a plurality of data source providers. In some embodiments, when the data processing system 9300 receives the electronic activity, the electronic activity can label or store the electronic activity in a database in association of the data source provider that provided the electronic activity.

The method 1900 can include identifying a system of record (BLOCK 1910). The data processing system 9300 can identify a system of record that corresponds to the data source provider that the data processing system 9300 identified at BLOCK 1908. The data processing system 9300 can identify a plurality of candidate record objects that are associated with the data source provider. For example, and referring to FIGS. 3, 4, and 16-18, among others, once the data processing system 9300 identifies a system of record 9360, the data processing system 9300 can identify the record objects in the system of record 9360 as candidate record objects to which the electronic activity can be matched. The data processing system 9300 can match the electronic activity with one or more of the record objects in the system of record 9360.

In some embodiments, the data processing system 9300 can identify the shadow record objects in the shadow system of record as candidate record objects. For example, and referring to FIG. 3, the system of record from each data source provider can be copied into the data processing system 9300 as shadow system of record 9330. Each of the shadow systems of record 9330 can include a plurality of record objects that are shadow record objects of the record objects in the data source providers system of record 9360. The data processing system 9300 can match the electronic activity to one of the identified shadow record objects. The data processing system 9300 can directly match the electronic activity to one or more record objects in the shadow system of record 9330, one or more record objects in the system of record 9360, or one or more record objects in both the shadow system of record 9330 and the system of record 9360 subject to limitations of the system of record 9360. In some embodiments, the data processing system 9300 can match the electronic activity to one or more record objects in the shadow system of record 9330, which can then be synced with the record objects in the system of record 9360. In some embodiments, the data processing system 9300 can match the electronic activity to more than one record object in the shadow system of record 9330. In some such embodiments, the data processing system 9300 can determine the shadow record object with which the electronic activity most closely matches (or has the highest match score) and cause the electronic activity to match the corresponding record object in the system of record 9360.

In some embodiments, each of the electronic activities can be associated with a domain. For example, the domain can be identified by the sending email address of the electronic activity. The data processing system 9300 can identify the system of record based on a domain associated with an email address of the sender of the electronic activity.

The method 1900 can include determining whether the electronic activity can be matched to a record object (BLOCK 1912). The data processing system 9300 can determine if the electronic activity can be matched to a record object by applying a first policy. The policy can include one or more filtering rules.

For example, and also referring to FIGS. 4 and 18 among others, the filtering engine 270 can first process the electronic activity with filtering rules 1701 to determine whether the electronic activity should be blocked, removed from further processing, redacted, or deleted from the data processing system 9300.

The above described filtering engine can determine the electronic activity should not be matched to a record object based on one or more filtering rules. The filtering rules can restrict the data processing system 9300 from performing further processing or matching on the electronic activity. The filtering rules can include a keyword rule configured to restrict electronic activities including a predetermined keyword; a regex pattern rule configured to restrict electronic activities including one or more character strings that match a predetermined regex pattern; a logic-based rule configured to restrict electronic activities based on the participants of the electronic activities satisfying a predetermined group of participants; or any combination thereof.

The filtering rules can be defined by the data source provider of the electronic activity and the system of record to which to match the electronic activity. For example, the data source provider can define rules for electronic activities that should not be matched to the record objects in its system of record 9360.

In some embodiments, the filtering engine 270 can restrict electronic activities from being matched to a record object by applying one or more rules to the electronic activity to identify the electronic activities that should not be matched with a record object. The rules can include determining that the electronic activity includes one or more predetermined words included in a list of restricted words. For example, electronic activities that include terms or phrases related to a specific product identified by the data source provider or department (e.g., legal department) associated with the data source provider can be identified by the filtering engine 270 for restriction from further processing.

In some embodiments, the filtering engine 270 can restrict electronic activity from being matched with a record object if the electronic activity includes any character strings that has a regular expression pattern that matches a predefined regex pattern included in a list of restricted regex patterns. For example, the filtering engine 270 can include a list of restricted regex patterns that can include a pattern to identify social security numbers, bank account numbers, credit card numbers, dates of birth, or other sensitive information.

The filtering engine 270 can restrict electronic activity from being matched with a record object by determining that the sender of the electronic activity match a sender included in a list of restricted sender list. For example, the email address of the company's general counsel can be included on a restricted sender list and all of the emails sent by the general counsel will be restricted out by the filtering engine 270. The filtering engine 270 can restrict electronic activity from being matched with a record object by determining that a recipient of the electronic activity matches a recipient included in a restricted recipient list. For example, the filtering engine 270 may restrict out any email or electronic activity sent to a human resource manager. The filtering rules 1701 can include one or more rule sets. The rules in the filtering rules 1701 can be defined by the data processing system 9300. The rules can be global rules that the data processing system 9300 can apply to the electronic activities of each data source provider. The data processing system 9300 can include semi-global rules that are applied to the electronic activities from a subset of the data source providers. For example, the data processing system 9300 can have finance semi-global rules that are applied to the electronic activities from data source providers involved in the business of finance. The rules can be defined or otherwise configured by the data source provider and applied to only the electronic activities associated with the data source provider.

The filtering engine 270 can restrict electronic activity from being matched with a record object based on a sender-recipient pair. For example, the filtering engine 270 can include a restriction list that includes a plurality of sender-recipient pairs. When a sender of the electronic activity sends an electronic activity to one of the recipients with which the sender is paired in the restriction list, the filtering engine can restrict out the electronic activity.

If the filtering engine 270 does not restrict the electronic activity from further processing by identifying the electronic activity with the filtering rules 1701, the data processing system 9300 can determine that the electronic activity should be matched with one of the candidate record objects associated with the data source provider.

The method 1900 can include identifying candidate record objects (BLOCK 1914). The data processing system

9300 can identify one or more candidate record objects to which the electronic activity can be matched. For example, as described above in relation to FIG. 12, the electronic activity can be matched to a plurality of record objects. The data processing system 9300 can identify the candidate record objects based on applying a second policy. The second policy can include one or more rules for identifying candidate record objects based on one or more participants of the electronic activity.

Also referring to FIGS. 11, 12, and 18, among others, the data processing system 9300 can identify the plurality of record objects to which the electronic activity can be matched based on one or more rules or rule sets. The rules that identify to which of the record objects the data processing system 9300 can match the electronic activity can be included in a second policy that includes one or more rule sets. The data processing system 9300 can identify the plurality of record objects based on one or more tags assigned to the electronic activity by the tagging engine 265.

As described above, the electronic activity linking engine 250 can identify one or more candidate record objects to match the electronic activity using recipient-based rules that identify the candidate record objects based on one or more recipients of the electronic activity. The recipient-based rules can include rules for identifying the recipient based on a specific recipient (e.g., based on an email address). The recipient-based rules can include rules for identifying the recipient based on data associated with the recipient. For example, the rule can identify recipients having a predetermined domain in their email address. An indication of the recipient can be included in the identified record object as a value in an object field.

The electronic activity linking engine 250 can identify one or more candidate record objects to match the electronic activity using sender-based rules that can identify the candidate record objects based on the sender of the electronic activity. The sender-based rules can include rules for identifying the record object based on a specific sender or based on data associated with the sender. An identification of the sender can be included in the identified record object as a value in an object field.

In some embodiments, the electronic activity linking engine 250 can identify the candidate record objects based on sender-based rules or recipient-based rules or both. For example, and referring to FIG. 11, the electronic activity linking engine 250 can select a first group of candidate record object using the recipient-based rules and a second group of candidate record objects using the sender-based rules. The electronic activity linking engine 250 can match the electronic activity to one of the candidate record objects that is included in the both the first group of record objects and the second group of record objects.

In some embodiments, the matching rules can be configured to select record objects of a specific type. For example, and also referring to FIGS. 10-12, among others, the matching rules can include a first set of rules that identify account record objects, a second set of rules that identify opportunity record objects, and a third set of rules that identify lead record objects.

Each of the matching rules can have a priority level, score, or weight. The candidate record objects selected with rules with a higher priority level can be assigned a higher score. For example, if the rules select multiple record objects, the electronic activity linking engine 250 can select the candidate record object with the highest score. In some embodiments, a candidate record object can be selected multiple times. For example, a first and a second matching rule can each select a given record object. The record object selected by multiple matching strategies can be given an aggregate (for example, a weighted aggregate) of the scores associated with each of the matching rules that selected the candidate record object.

The data source provider can assign the priority level, score, rank, or weight to each of the matching rules. For example, the data source provider can assign a first priority level to a first subset of the matching rules and a second priority level to a second subset of the matching rules.

Also referring to FIGS. 5A-9, among others, the electronic activity linking engine 250 can identify candidate record objects based on matching rules that can identify record objects based on an object field value of the record object that identifies one or more nodes. One or more participants of the electronic activity can be used to select a node of a node graph.

In some embodiments, the rules can candidate record objects based on participants that are linked to a record object. For example, an account record object can include an object field that can include a plurality of values. The object field values can identify nodes of a node graph. The data processing system 9300 can, using the matching rules, select contact record objects that are associated with identified nodes of the node graph. In some embodiments, the candidate record objects can be identified based on one or more of the participants associated with the electronic activity being identified in the object field value.

The object field of the record object can identify an object owner or team, which can be user, contact, or team that is responsible for the account associated with a record object. Based on the values, the data processing system 9300 can identify a plurality of contact record objects that are associated with the object as candidate record objects.

The data processing system 9300 can identify candidate record objects based on one or more tags assigned to the electronic activity. The tagging engine 265 and the tagging of electronic activity is described above in Section G, among others. The tagging engine 265 can tag the electronic activity as specifically mentioning an account, product, contact, lead, or as including another predetermined character string. One or more of the rules can select candidate record objects based on the selecting record objects associated with the one or more tags of the electronic activity. For example, a predetermined account tag can be applied to an email if the body of the email includes an identification of the tag and the data processing system 9300 can identify the account record object associated with the account tag as a candidate record object. In another example, the electronic activity can be parsed and the term "renewal" can be identified in the electronic activity. A "renewal" tag can be applied to the electronic activity. A matching rule to select record objects based on tags can select a renewal record object opportunity with the electronic activity and identify the renewal record object opportunity as a candidate record object. As described above in relation to FIG. 12, an indication of each of the record objects identified by a matching rule can be stored in a record object array 1202.

The method 1900 can include selecting a record object (BLOCK 1916). Also referring to FIG. 12, among others, the data processing system 9300 can include identify candidate record objects to which the electronic activity can be matched. As illustrated in FIG. 12, the matching rules can identify more than one candidate record objects. The electronic activity linking engine 250 can select one or more of the candidate record objects with which to match the electronic activity.

The electronic activity linking engine 250 can select the one or more record objects from the plurality of candidate record objects based on the priority level used to select or identify each of the plurality of candidate record objects. For example, as described above in relation to FIG. 11, among others, each of the matching rules can have a priority level, score, or weight. The candidate record objects selected with rules with a higher priority level can be assigned a higher score. For example, if the rules select multiple record objects, the electronic activity linking engine 250 can select the candidate record object with the highest score. In some embodiments, a candidate record object can be selected multiple times. For example, a first and a second matching rule can each select a given record object. The record object selected by multiple matching strategies can be given an aggregate (for example, a weighted aggregate) of the scores associated with each of the matching rules that selected the candidate record object.

The data source provider can assign the priority level, score, rank, or weight to each of the matching rules. For example, the data source provider can assign a first priority level to a first subset of the matching rules and a second priority level to a second subset of the matching rules.

The method 1900 can include storing an association between the selected candidate record object and the electronic activity (BLOCK 1918). For example, the data processing system 9300 can store, in a data structure, an association between the selected candidate record objects and the electronic activity. Also referring to FIGS. 3 and 4, among others, the electronic activity can be matched to one or more candidate record objects that are record objects in a shadow system of record for the data provider that provided the electronic activity.

In some embodiments, once the electronic activity is matched with one or more record objects, the data processing system 9300 can identify subsequent electronic activities that are related to the matched electronic activities. For example, the data processing system 9300 can identify emails that are part of the same email chain. The data processing system 9300 can match each of the emails in the email chain to the one or more record objects to which the first email was matched.

In some embodiments, the electronic activity linking engine 250 can detect changes in the stored associations between electronic activities and record objects. Once the electronic activity is matched to a record object a user can accept, reject, or update the linking between the electronic activity and the matched record object. The user can manually remap the linking of the electronic activity from a first record object to a second, different record object. In another example, the data processing system 9300 may automatically rematch electronic activities at predetermined intervals or when the data processing system 9300 receives additional data.

In some embodiments, when the electronic activity linking engine 250 determines that the electronic activity is matched with a second, different record object, the electronic activity linking engine 250 can update the matching rules or policies that matched the electronic activity to the original record object. The electronic activity linking engine 250 can update the matching rules or policies such that the subsequent electronic activities are correctly matched with the correct record object.

16. Matching Electronic Activities to Record Objects of Systems of Record with Node Profiles As described above, the system described herein can match electronic activities with one or more record objects. The system can match the electronic activities in a single-tenant or multi-tenant configuration of the system. For example, in a single-tenant configuration, the system can receive or access electronic activities from a single data source provider and match the electronic activities to record objects of a system of record of the data source provider from which the electronic activities were received or accessed. In a multi-tenant configuration, the system can receive or access electronic activities from multiple data source providers and match the electronic activities to record objects of a system of record of the respective data source provider from which the electronic activities were received or accessed. As described herein, the system can automatically match, link, or otherwise associate the electronic activities with one or more record objects. In some embodiments, the system can match the electronic activity with one or more node profiles. The system can use the node profiles to identify one or more record objects with which the electronic activity can be matched. If the system determines the electronic activity is eligible or qualifies to be matched with one or more record objects, the system can match the electronic activity to one or more of the record objects identified with the node profiles using one or more set of rules or rule sets. The system can then rank the identified candidate record objects to select one or more record objects with which to associate the electronic activity. The system can then store an association between the electronic activity and the selected one or more record objects.

Figure 20:
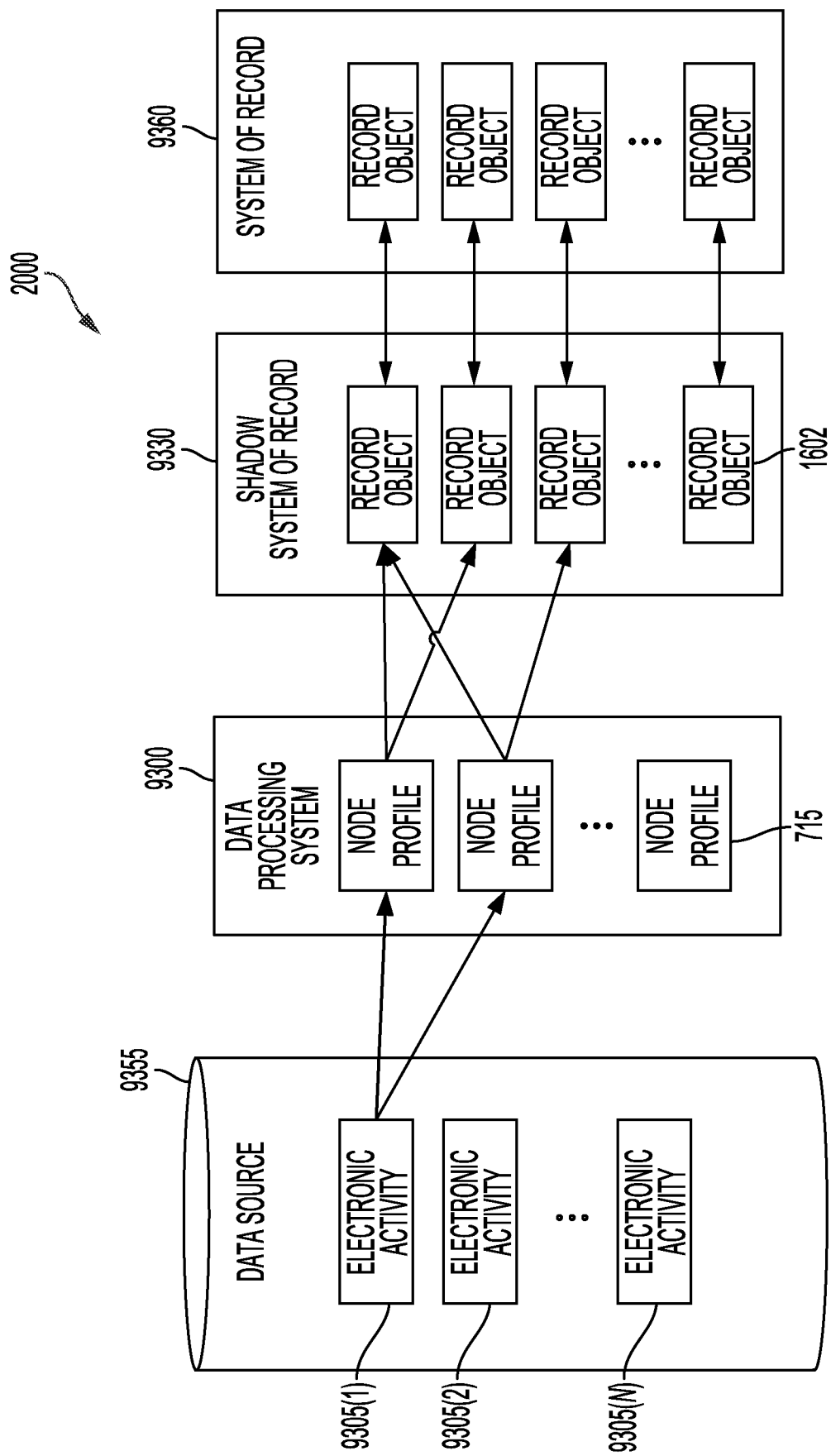
FIG. 20 illustrates a block diagram of an example process flow for matching electronic activities with record objects according to embodiments of the present disclosure.

FIG. 20 illustrates a block diagram of an example process flow 2000 for processing electronic activities. Also, with reference to FIGS. 3, 4, and 16-18, among others, the data processing system 9300 can be in communication with one or more data source providers 9350. Each of the data source providers 9350 can include a data source 9355. FIG. 20 illustrates an example of a single-tenant system where the electronic activities 9305 from a single tenant (e.g., the data source provider 9350 that includes the data source 9355) is matched to the record objects 1602 of a single shadow system of record 9330. The single shadow system of record 9330 can be associated with the data source provider 9350 that provided the electronic activity. For example, the shadow system or record can include data retrieved from the record objects of the data source providers system of record.

As illustrated in FIG. 17, among others, the system illustrated in FIG. 20 can be a multi-tenant system that can include a plurality of data sources 9355 that can each include a plurality of electronic activities 9305. The system can match the electronic activities with record objects in shadow systems of record 9330 or directly with systems of record 9360 associated with the respective data source 9355.

The data source provider 9350 can store electronic activity 9305(1)-electronic activity 9305(N) (generally referred to as electronic activity 9305) in the data source 9355. As described above, the electronic activities can include one or more forms of electronic activity, such as email or other forms of electronic communication. The data processing system 9300 can access or otherwise retrieve the electronic activity 9305 from the data source 9355. For example, the above-described electronic activity ingestor 205 can be configured to ingest electronic activities in a real-time or near real-time basis for accounts of one or more enterprises, organizations, companies, businesses, institutions or any other group associated with the data source providers. The electronic activity ingestor 205 can ingest electronic activities. For example, when a data source provider subscribes to a service provided by the data processing system 9300, the data source provider can provide access to electronic activities maintained by the data source provider by going through an onboarding process. That onboarding process can enable the data processing system 9300 to access electronic activities owned or maintained by the data source provider in one or more data sources 9355. For example, the data sources 9355 can be, but are not limited to, mail servers, one or more systems of record, one or more phone services or servers of the data source provider, among other sources of electronic activity. The electronic activities ingested during an onboarding process may include electronic activities that were generated in the past, perhaps many years ago, that were stored on the electronic activities' sources. The data processing system 9300 can be configured to ingest (and re-ingest) the electronic activities from one or more data sources 9355 on a periodic basis, including daily, weekly, monthly, or any reasonable frequency.

The data processing system 9300 can match the electronic activities 9305 with one or more node profiles 715. For example, and also referring to FIGS. 3-9, among others, the node graph generation system 200 can generate a node graph that includes a plurality of nodes. Each of the nodes can include a node profile 715, which can be a data structure that includes a plurality of fields. For example, an example node profile 715 can include fields such as, but not limited to name, email, phone, company, and job title. The system can ingest electronic activities and populate the fields with values. Also referring to FIG. 4, among others, as the system ingests additional emails the node profile manager can update the node profile 715. The node profile managed can update the node profile 715 by, for example, increasing or decreasing a confidence score of the values of fields that can be verified or contradicted by subsequent electronic activities. The node profile manager can add additional (e.g., updated) values to a field based on ingested electronic activities.

When matching an ingested electronic activity 9305 to a record object 1602, the data processing system 9300 can match the electronic activity 9305 with one or more node profiles 715. For example, the data processing system 9300 can identify or parse the sender and recipient email addresses from an email (an example electronic activity) and identify a first node profile 715 based on the senders email address and a second node profile 715 based on the recipient's email address. As illustrated in FIG. 20, the electronic activity 9305(1) can be matched with a first and a second node profile 715. For example, one of the node profiles 715 can be associated with the sender and one of the node profiles 715 can be associated with the recipient of the electronic activity 9305(1). Additional details relating to matching electronic activities to node profiles are described herein in Section 17 and the descriptions above with respect to FIGS. 2-9.

The data processing system 9300 can match the electronic activities 9305 to one or more record objects 1602 of the shadow system of record 9330 using the node profiles 715 to which the electronic activity 9305 was matched. For example, and also referring to FIG. 6A, among others, the data processing system 9300 can use one or more values 620 from one or more fields 610 to identify candidate record objects. In some embodiments, the node profiles 715 can include additional information that isn't extracted from the given electronic activity 9305 being matched to a record object. In this example, matching the electronic activity to a node profile 715 can enable the identification of additional record objects that may not be identified when using only data extracted from the electronic activity 9305. As illustrated in FIG. 20, a first node profile 715 is matched to a first and second record object 1602 and a second node profile 715 is matched to the first and a third record object 1602. Each of the node profiles 715 that are matched with a given electronic activity 9305 can match to the same record objects, different record objects, or first and second sets of record objects that at least partially intersect with one another.

The record objects 1602 of the shadow system of record 9330 can be synced with the record object 1602 of the system of record 9360. Syncing the shadow record objects 1602 with the record objects 1602 of the system of record 9360 can include adding values from fields of the shadow record objects 1602 to the corresponding values, such as matched electronic activities 9305, of the record objects 1602 in the system of record 9360. In some embodiments, the data processing system 9300 can match the electronic activities 9305 directly to the system of record 9360. For example, the data processing system 9300 can match the electronic activities 9305 to the record objects in the system of record 9360 without matching the electronic activities 9305 to the record objects in the shadow system or record 9330.

Figure 21:
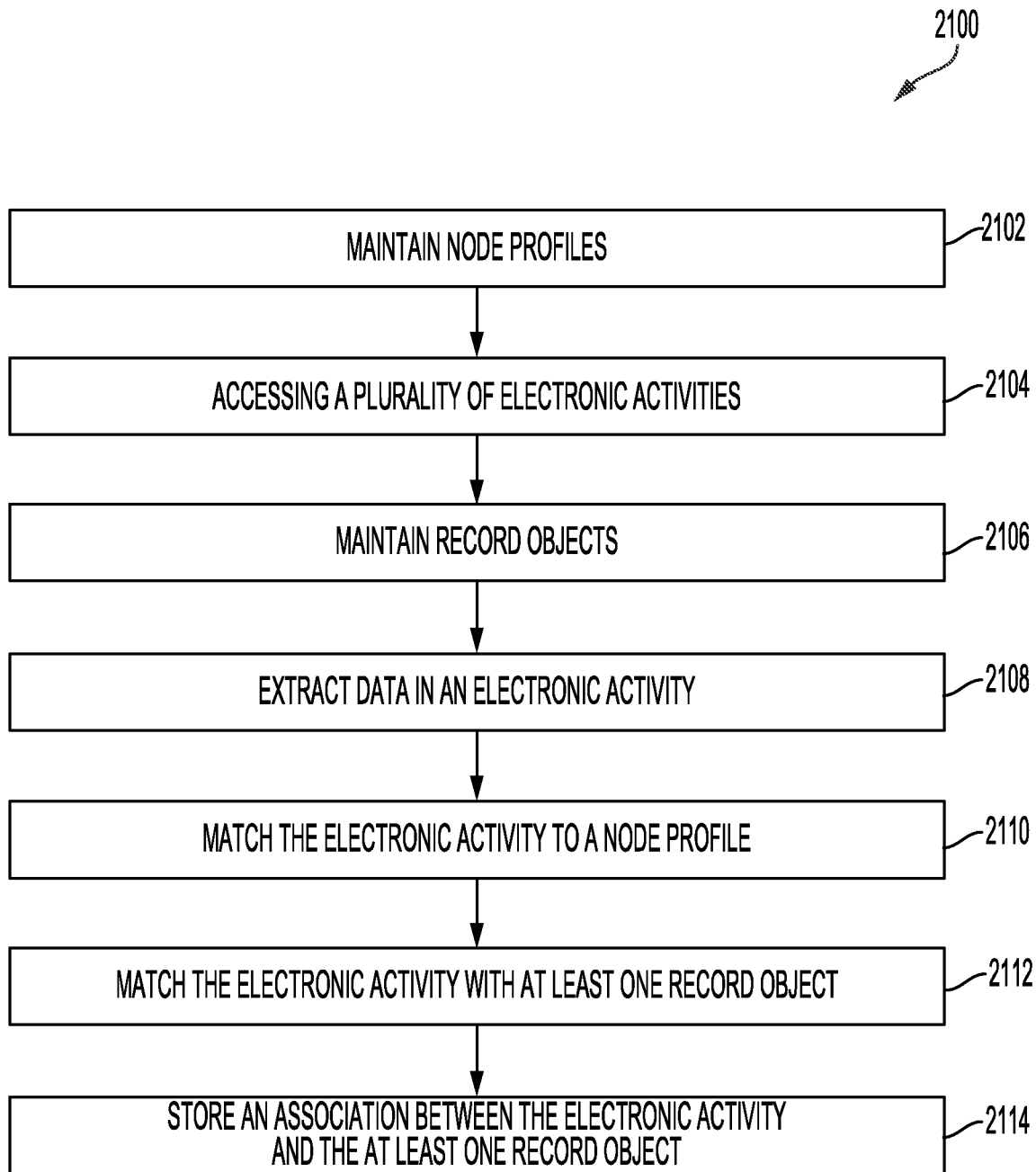
FIG. 21 illustrates a block diagram of an example method to match electronic activities with record objects according to embodiments of the present disclosure.

FIG. 21 illustrates a block diagram of an example method 2100 to match electronic activities to record objects of systems of record with node profiles. The method 2100 can include maintaining a plurality of node profiles (BLOCK 2102). The method 2100 can include maintaining, by one or more processors of the data processing system 9300, a plurality of node profiles. Also referring to FIG. 6A, among others, each of the node profiles can correspond to a different unique entity, such as a person or company. Each of the node profiles can include a plurality of fields, such as, but not limited to name, email address, company, domain, telephone number. Each of the fields can include one or more value data structures. Each of the value data structures can include node field value and one or more entries corresponding to respective data points that support the node field value of the value data structure. For example, and also referring to FIG. 6A among others, value data structure 615 can include a value 620, an occurrence metric 625, a confidence score 630 and one or more entries 635*a-n*. The entries 635 can include data (or an indication thereof) the basis for the value 620, the occurrence metric 625, and the confidence score 630.

For example, each entry 635 can identify a data source 640 from which the value was identified (for instance, a source of a system of record or a source of an electronic activity), a number of occurrences of the value that appear in the electronic activity, a time 645 associated with the electronic activity (for instance, at which time the electronic activity occurred) and an electronic activity unique identifier 502 identifying the electronic activity. In some embodiments, the occurrence metric 625 can identify a number of times that value is confirmed or identified from electronic activities or systems of record. The node profile manager 220 can be configured to update the occurrence metric each time the value is confirmed. In some embodiments, the electronic activity can increase the occurrence metric of a value more than once. For instance, for a field such as name, the electronic activity parser can parse multiple portions of an electronic activity. In some embodiments, parsing multiple portions of the electronic activity can provide multiple confirmations of, for example, the name associated with the electronic activity.

The method 2100 can include accessing a plurality of electronic activities (BLOCK 2104). The method 2100 can include accessing, by the one or more processors, a plurality of electronic activities transmitted or received via electronic accounts associated with one or more data source providers. The data processing system 9300 can update the node profiles using the electronic activities. With reference to FIGS. 16-20, among others, the data processing system 9300 can access a plurality of electronic activities. The electronic activities can be transmitted to the data processing system 9300 from data source providers. The data processing system 9300 can retrieve the electronic activities from the data source providers. For example, the data source provider can include or be an email server. The data processing system 9300 can have the authority to access the emails stored on the email server through an API or an HTTP method (e.g., a GET method).

As described herein in relation to FIGS. 4-8, among others, the data processing system 9300 can update the node profiles based on the accessed electronic activities. For example, the node profile manager 220 can maintain a node profile 715 for each unique entity, such as a person or company. As the data processing system 9300 ingests electronic activities, the node profile manager can update the node profile 715. The node profiles can be updated by changing one or more confidence scores of respective values corresponding to respective value data structures by adding additional data points to the value data structure that support the corresponding value. Furthermore, if a particular value of a field of a node profile doesn't exist, the node profile manager can add one or more additional values and corresponding value data structures to the field. The increase or decrease in the confidence score of values of fields can be based on the electronic activity. For example, when an electronic activity, such as an email is successfully transmitted to the intended destination, the node profile manager 220 can update the confidence score of the recipient email value. The data processing system 9300 can determine the email was successfully transmitted to the recipient, for example, if a bounce back email is not received in response to the email.

The method 2100 can include maintain one or more record objects (BLOCK 2106). The method 2100 can include maintaining, by the one or more processors, a plurality of record objects for one or more systems of record. Each of the record objects of the plurality of record objects can include one or more object fields having one or more object field values. As described above in relation to FIG. 20, among others, the data processing system 9300 can make a call to the systems of record 9360 that are associated with each of the data source providers from which the data processing system 9300 retrieved electronic activities. The data processing system 9300 can generate a copy of the accessed record objects. The data processing system's copy of the access record objects can be referred to as shadow record objects. The data processing system 9300 can update the shadow record objects and sync the changes back to the record objects in the tenant's system of record.

As described above in relation to FIG. 10, each of the record objects can be of a record object type. For example, the record objects can be lead record objects, account record objects, opportunity record objects, or contact record objects. The record objects can be any type of record object in a system of record. The other systems of records can include Applicant Tracking Systems (ATS), such as Lever, located in San Francisco, Calif. or Talend by Talend Inc., located in Redwood City, Calif., enterprise resource planning (ERP) systems, customer success systems, such as Gainsight located in Redwood City, Calif., and Document Management Systems, among others.

The data processing system 9300 can retrieve the record objects from servers that correspond to the data source provider or data source from which the data processing system 9300 retrieved the electronic activities 9305. The data processing system 9300 can retrieve the record objects 1602 from a system of record 9360. The data processing system 9300 can retrieve the record objects 1602 through an API call. For example, the data processing system 9300 can retrieve a first plurality of record objects corresponding to a first system of record of a first data source provider and second plurality of record objects corresponding to a second system of record of a second data source provider.

As described herein the system can be configured in a multi-tenant configuration or a single-tenant configuration. In a multi-tenant configuration, the data processing system 9300 can retrieve a respective plurality of record objects that correspond to each of the data source provider (e.g., tenants) associated with the data processing system 9300. For example, the data processing system 9300 can retrieve a plurality of record objects from a first system of record and from a second system of record.

Each of the record objects can include one or more object fields and corresponding object field values. For example, the record objects can be data structures and the object field values can be values of object fields of the data structure. For example, for a contact record object, the data structure can include fields such as, but not limited to, name, address, email, and phone number, which can be filled with respective field values.

The method 2100 can include extracting data from an electronic activity (BLOCK 2108). The method 2100 can include extracting, by the one or more processors, data included in an electronic activity of the plurality of electronic activities. For example, and referring to FIGS. 5A-5C among others, the data processing system 9300 can one or more recipients 510, one or more senders 512 of the electronic activity. The data processing system 9300 can identify a subject line 514, an email body 516, an email signature 518, and a message header 520 of the electronic activity. The message header can include additional information relating to the transmission and receipt of the email message, including a time at which the email was sent, a message identifier identifying a message, an IP address associated with the message, a location associated with the message, a time zone associated with the sender, a time at which the message was transmitted, received, and first accessed, among others. The electronic message 505 can include additional data in the electronic message 505 or in the header or metadata of the electronic message 505. In some embodiments, the electronic activity can be an email, a call entry, a calendar entry, among others.

The method 2100 can include matching the electronic activity to a node profile (BLOCK 2110). The method 2100 can include matching, by the one or more processors, the electronic activity to at least one node profile of the plurality of node profiles. The data processing system 9300 can match the electronic activity to the one or more node profiles based on determining that the extracted data of the electronic activity and the one or more values of the fields of the at least one node profile satisfy a node profile matching policy. For example, as described herein, each value in a value data structure can include a confidence score.

In some embodiments, the data processing system 9300 can identify a sender and one or more recipients of the electronic activity. For example, the data processing system 9300 can extract from the electronic activity the sender's email address and the email addresses of the one or more recipients of the electronic activity. The data processing system 9300 can match the electronic activity to a plurality of node profiles. For example, the data processing system 9300 can match the electronic activity to a first node profile based on the sender's email address. The data processing system 9300 can also match the electronic activity to one or more additional node profiles based on the extracted recipient email addresses. In some embodiments, strings or values are extracted from electronic activities and associated with candidate or potential fields to form field-value pairs. These field-value pairs extracted from an electronic activity can then be compared with corresponding field-value pairs of node profiles to identify or compute a match score between the electronic activity and respective node profiles having the field-value pairs with which the field-value pairs of the electronic activity are compared.

In some embodiments, the matching policies for the matching of the electronic activity to one or more node profiles can be based on tags associated with the electronic activity. For example, the data processing system 9300 can determine a relationship between two or more node profiles based on the one or more values of the fields of the two or more node profiles. The data processing system 9300 can assigning one or more tags to the electronic activity based on the relationship between the two or more node profiles. In one example, the data processing system 9300 can assign a personal tag to the electronic activity. For example, the node profile manager 220 can be configured to determine that two node profiles have a personal (non-professional) relationship based on the electronic activities exchanged between the users associated with the node profiles and apply a "personal" tag to the emails between the users. The system can further determine a confidence score for the tag classifying the two node profiles based on how confident the system is in the prediction that the two node profiles have a personal relationship. In some embodiments, the node profile manager 220 can further determine if two nodes have a personal relationship based on commonalities in values in their node profiles, for instance, their home addresses (if they are neighbors), college or school affiliations (alumni/classmates), same last names, other non-professional affiliations, or other signals that may indicate the two node profiles may have a personal relationship. In some embodiments, the data processing system 9300 can determine to not match an electronic activity that is associated with a personal tag to one or more record objects.

The data processing system 9300 can assign one or more tags to the electronic activity based on one or more policies. The data processing system 9300 assign the tags based on one or more node profiles associated with a sender or one or more recipients of the electronic activity. For example, the data processing system 9300 can identify, based on the body of the electronic activity, that the electronic activity is related to a sales deal and can tag the electronic activity with a sales tag. The data processing system 9300 can assign tags based on a relationship between the one or more node profiles associated with the sender and the one or more recipients of the electronic activity. For example, as described herein the data processing system 9300 can determine whether the users associated with the node profiles have a professional or personal relationship and assign a professional or personal tag to the electronic activity, accordingly. The data processing system 9300 can assign tags to the electronic activity based on one or more strings identified in the electronic activity. For example, the data processing system 9300 can parse the body of the email with regex to identify an account number and the data processing system 9300 can assign a tag based on the account number. The data processing system 9300 can assign the tags to the electronic activity based on one or more strings identified in the metadata of the electronic activity. For example, the metadata can be a header of an email and can include a domain associated with the sender of the electronic activity and the data processing system 9300 can assign a tag based on the domain identified in the header of the email.

The data processing system 9300 can match the electronic activity to one or more node profiles based on contribution scores. For example, each data point for a value in a value data structure can include a contribution score. The contribution score can indicate the contribution of the data point to the value. The data point's contribution score can be time dependent. For example, as described in relation to FIG. 7, among others, the contribution of the data point can decrease over time. In one example, a data point can have a greater contribution score if the data point was recently updated or generated when compared to a data point that was updated or generated in the past. Based on the contribution scores for each of the data points associated with the value, the data processing system 9300 can calculate a confidence score of the value of the field of the node profile. The data processing system 9300 can select the node profiles based on the confidence scores. For example, the electronic activity may match to a plurality of node profiles based on a value of a field in each of the node profiles. The data processing system 9300 can discard each of the node profiles as candidate node profiles if the value of the field in a node profile has a confidence score below a predetermined threshold.

In some embodiments, the contribution score of the data point can be based on a trust score associated with the data source provider. The data processing system 9300 can determine, for a data point, a contribution score for the data point based on the trust score associated with the data source provider. For example, a relatively low trust score can reduce the confidence score of the data point. The trust score can be based on a type of source of the data point.

The method 2100 can include matching the electronic activity to one or more record objects (BLOCK 2112). The method 2100 can include matching, by the one or more processors, the electronic activity to at least one record object of the plurality of record objects based on the extracted data of the electronic activity and object values of the at least one record object. For example, the data processing system 9300 can identify a sender of the electronic activity. The data processing system 9300 can select a first node profile of the plurality of node profiles based on the sender of the electronic activity. For example, the data processing system 9300 can identify the email address of the sender and select a node profile based on the identified email address. Based on the node profile, the data processing system 9300 can identify a first set of record objects of the plurality of record objects. For example, and also referring to FIG. 12, among others, the data processing system 9300 can identify a plurality of account, opportunity, and lead record objects based on the email address of the sender. The data processing system 9300 can also identify one or more record objects based on node field values contained in the identified node profile. For example, the node profile can include a field for teams on which the user is assigned. The field can include a value in a value data structure for each of the teams on which the user is assigned. The data processing system 9300 can select one or more record objects based on the teams identified in the node profile.

The data processing system 9300 can identify one or more record objects based on a recipient of the electronic activity.

For example, the data processing system 9300 can identify a recipient email address of the electronic activity. The data processing system 9300 can identify a second node profile of the plurality of node profiles based on the recipient of the electronic activity. The data processing system 9300 can identify a second set of record objects of the plurality of record objects based on the second node profile.

In some embodiments, the data processing system 9300 can filter or prune the first set of record objects (e.g., the record objects selected based on the sender of the electronic activity) and the second set of record objects (e.g., the record objects selected based on the recipient of the electronic activity). For example, the data processing system 9300 can identify an intersection of the first and second set of record objects (e.g., record objects that are included in both the first and second set of record objects). The data processing system 9300 can match the electronic activity to at least one of the record objects in the intersection of the first set of record objects and the second set of record objects.

In some embodiments, each of the record objects in the intersection of the first set of record objects and the second set of record objects can be referred to as candidate record objects. The candidate record objects can include one or more types of record object types. For example, the record objects can be account record objects, opportunity record objects, or lead record objects, among others. The data processing system 9300 can match the electronic activity with one or more of the record objects in candidate record objects. For example, the data processing system 9300 can match the electronic activity to record objects in the candidate record objects that have different types. For example, the data processing system 9300 can match the electronic activity to an account record object and an opportunity record object. In some embodiments, the data processing system 9300 can match the electronic activity to multiple record objects with the same type. For example, the data processing system 9300 can match the electronic activity to two candidate record objects that are both account record objects.

The method 2100 can include matching the electronic activity to one or more of the identified record objects based on one or more matching policies, rules, heuristic, or filters. The matching policies can be based on the sender and/or recipient of the electronic activity. The data processing system 9300 can identify a first set of matching policies based on the sender of the electronic activity and a second set of matching polices based on the recipients of the electronic activity. As described herein, the data processing system 9300 can identify a first set of candidate record objects based on the first set of matching policies and a second set of candidate record objects based on the second set of matching policies. The data processing system 9300 can identify an intersection between the first and second sets of candidate record objects.

For example, and also referring to FIGS. 4 and 18 among others, the filtering engine 270 can first process the electronic activity with filtering rules 1701 to determine whether the electronic activity should be blocked, removed from further processing, redacted, or deleted from the data processing system 9300. The above described filtering engine can determine the electronic activity should not be matched to a record object based on one or more filtering rules. The filtering rules can restrict the data processing system 9300 from performing further processing or matching on the electronic activity. The filtering rules can include a keyword rule configured to restrict electronic activities including a predetermined keyword; a regex pattern rule configured to restrict electronic activities including one or more character strings that match a predetermined regex pattern; a logic-based rule configured to restrict electronic activities based on the participants of the electronic activities satisfying a predetermined group of participants; or any combination thereof.

The data processing system 9300 can also use one or more policies (e.g., matching rules 1702) to select the candidate record objects. Matching policies can be defined by the data source provider of the electronic activity and the system of record to which to match the electronic activity. For example, the data source provider can define rules for electronic activities that should not be matched to the record objects in its system of record 9360. The rules can include determining that the electronic activity includes one or more predetermined words included in a list of restricted words. For example, electronic activities that include terms or phrases related to a specific product identified by the data source provider or department (e.g., legal department) associated with the data source provider can be identified by the filtering engine 270 for restriction from further processing.

In some embodiments, the data processing system 9300 can identify, using natural language processing, a string in the electronic activity. The matching policies can include matching the electronic activity to one or more record objects based on the string identified in the electronic activity. For example, the data processing system 9300 can identify a string in the body of the electronic activity. The data processing system 9300 can identify the string using regex or other pattern matching technique. The string can include an account number or other identifier. The data processing system 9300 can select the candidate record objects based on the string in the body of the electronic activity.

In some embodiments, the matching policies can match the electronic activity to one or more record objects based on tags associated with the electronic activity. The data processing system 9300 can identify a first subset of record objects based on one or more tags assigned to the electronic activity. The data processing system 9300 can then match the electronic activity to at least one record object in the first subset of the record objects based on the one or more tags assigned to the electronic activity.

The method 2100 can include storing an association between the electronic activity and one or more record objects (BLOCK 2114). The method 2100 can include storing the association in a data structure. Also referring to FIGS. 3 and 4, among others, the electronic activity can be matched to one or more candidate record objects that are record objects in a shadow system of record (or the system of record) for the data provider that provided the electronic activity.

In some embodiments, once the electronic activity is matched with one or more record objects, the data processing system 9300 can identify subsequent electronic activities that are related to the matched electronic activities. For example, the data processing system 9300 can identify emails that are part of the same email chain. The data processing system 9300 can match each of the emails in the email chain to the one or more record objects to which the first email was matched.

In some embodiments, the data processing system 9300 can detect changes in the stored associations between electronic activities and record objects. Once the electronic activity is matched to a record object a user can accept, reject, or update the linking between the electronic activity and the matched record object. The user can manually remap the linking of the electronic activity from a first record object to a second, different record object. In another example, the data processing system 9300 may automatically rematch electronic activities at predetermined intervals or when the data processing system 9300 receives additional data.

As described herein, and in relation to the stage classification engine 325, for example, once one or more electronic activities are matched to a record object (e.g., an opportunity record object), the data processing system 9300 can classify a stage of the record object. The stages can be a stage, step, or task in a business process, a sales process, a hiring process, a support ticket, or other workflow. The stages can be defined by the system or by the data source provider. For example, the data processing system 9300 can identify at least a subset of the plurality of electronic activities that are matched to a first record object. The data processing system 9300 can also identify, for each of the electronic activities matched with the record object, one or more node profiles. The data processing system 9300 can determine a stage of the first record object based on the identified one or more node profiles of each of the subset of electronic activities.

Using the example of an opportunity record object in a sales process, the stages can indicate the steps taken in an opportunity or deal from the beginning of the deal to the final disposition of the deal (e.g., close and won or closed and lost). The stages can include, but are not limited to: prospecting, developing, negotiation, review, closed/won, or closed/lost.

In some embodiments, the stages can be based on the contacts present or involved on one or more sides of the deal. For example, as the deal advances to higher stages, more senior people may be included in the electronic activities. The stage of the deal can be based on the identification or introduction of the above-described OCR. The data processing system 9300 can identify the OCR or other contacts present or involved on the deal based on the node profiles. For example, the data processing system 9300 can identify the node profiles based matched with the one or more electronic activities associated with a record object. Based on the node profiles, the data processing system 9300 can determine each of the contacts roles, positions, or titles. For example, "title" can be one of the fields in the node profile. The data processing system 9300 can use the field node value in the title field to determine the title of the person involved with the record object. The data processing system 9300 can also determine the stage of the record object based on the one or more tags assigned to the electronic activity associated with the record object.

In some embodiments, the data processing system 9300 can maintain a normalized set of stages. The normalized set of stages can be referred to as processor assigned stages. Each of the data source providers can define custom stages for the record objects of the data source provider. Each stage (of the processor assigned stages or the data source provider assigned stages) can indicate a proximity to the completion of an event, task, process, or other workflow. The data processing system 9300 can generate a mapping between the data source provider assigned stages and the processor assigned stages. For example, the stage classification engine 325 can define five, normalized stages. A first data source provider can define a deal or opportunity as including 7 stages. A second data source provider can define a deal or opportunity as including 3 stages. The stage classification engine 325, for the first data source provider, may map stages 1 and 2 to normalized stage 1, stage 3 to normalized stage 2, stage 4 to normalized stage 3, stage 5 to normalized stage 4, and stages 6 and 7 to normalized stage 5. Accordingly, the data source provider's stages can be mapped to the normalized stages based on the tasks, requirements, or content of the stages rather than by the naming or numbering of the stages.

17. Linking Electronic Activities to Node Profiles

The present solution can enable real-time or near real-time linking of electronic activities to node profiles, with increased accuracy. In some systems that maintain data regarding entities, such as individuals or enterprises, including systems of record, the data may be self-reported, such as in response to specific queries to provide data for fields such as first name, last name, title, or email. As such, this data may be inaccurate. For example, when the data was provided, the data may have been inaccurate due to the data being self-reported. At a particular instant in time after the data was provided, due to changes to the data that may have occurred subsequent to when the data was provided and before the data has been updated, the data even if it was previously correct at the time the data was provided, may also eventually become obsolete, stale or inaccurate.

The present solution described herein can match electronic activities to node profiles maintained by a node graph generation system, that can use the data included in the electronic activities to update node profiles and the values of fields of these node profiles unobtrusively and without requiring any human input. As such, the present disclosure describes solutions for maintaining node profiles that remain accurate as the node profiles do not include self-reported information submitted by a user to update the node profile and because the node profiles are automatically updated as electronic activities are ingested and processed by the system without requiring any human activity. In this way, the present solution can enable dynamic updates to node profiles and a node graph including such node profiles, rather than manual/self-reported updates.

By linking electronic activities to node profiles, the present solution can increase the accuracy and validity of the node profiles, such as by increasing a likelihood that each node profile represents the true state of the world. For example, when node profiles are used to generate a node graph indicative of a hierarchy or other relationships amongst node profiles, the present solution can more accurately represent values of fields such as hierarchical titles within enterprises that are used to generate the node graph. The present solution can more accurately rank each value of each field (each value representing a potential true state of the world) by dynamically updating the confidence score corresponding to each value responsive to extracting data from electronic activities, so that the present solution outputs an evidence-based estimation of which value is the true value with improved accuracy. As an example, a node profile can include a first email address corresponding to a first enterprise at which the user corresponding to the node profile was employed and a second email corresponding to a subsequent enterprise at which the user corresponding to the node profile was employed. Each of the two email addresses are at respective points in time, accurate and valid. As the person switches jobs, the first email address is no longer valid but the confidence score associated with the first email address can in some embodiments, remain high indicating that the first email address belongs to the node profile. Similarly, the second email address also belongs to the node profile and therefore also can have a confidence score that may start low but increase as more electronic activities including the second email address are processed by the data processing system described herein. After the system determines that the second email address is active and functioning, the system can automatically increase the confidence score of the second email address since the contribution scores provided by recent data points (for example, recent electronic activities identifying the second email address) can contribute towards the higher confidence score while automatically decreasing the confidence score of the first email address since the electronic activities supporting the first email address are getting older and no new electronic activities serve as data points for the first email address. The present solution can thus respond to changes in the true state of the world represented by the node profile using the second email, rather than relying on self-reported information which may be inaccurate and/or delayed.

Referring further to FIG. 2, among other, the node graph generation system 200 can ingest electronic activities to generate or update node profiles that are maintained by the node graph generation system 200 using data from the electronic activities. For example, as illustrated in FIGS. 5A-5C and 6B, the node graph generation system 200 can process electronic activities such as an email 505, a call entry 525, or a calendar entry 560. For example, the node graph generation system 200 can process the email 505 to identify a plurality of strings having data from the To: field 510 (to identify a recipient of the email 505), the From: field 512 (to identify a sender of the email 505), the email body 516 (to identify a recipient of the email 505), and the email signature 518 (to identify the sender of the email 505).

Using the identified plurality of strings, the node graph generation system 200 can generate activity field-value pairs. Each activity field-value pair can include a data structure that associates a particular field to a value for the field that the node graph generation system 200 extracts from the electronic activity. For example, the node graph generation system 200 can generate a FirstName-value pair associating a value of "John" to the first name field, a LastName-value pair associating a value of "Smith" to the last name field, a Title-value pair associating a value of "Director" to the title field, and a CompanyName-value pair associating a value of "ACME" to the company name field based on the email 652a illustrated in FIG. 6B. Because each electronic activity may include multiple strings having data that corresponds to a particular field, the node graph generation system can generate multiple activity-field-value pairs from each electronic activity (e.g., multiple first name-value field pairs based on information from a sender field and a signature block).

Referring further to FIG. 6A, the node graph generation system 200 can maintain a plurality of node profiles 600. Each node profile 600 includes a plurality of node field-value pairs corresponding to attributes 610 and value data structures 615. For example, the node graph generation system 200 can maintain a first node field-value pair associating a first value 620 (e.g., Va) to field 610(1), a second node field-value pair associating a second value 620 (e.g., Vb) to the field 610(1), and so on for each value. As shown for the node profile illustrated in the table above, the node graph generation system 200 can generate a first field-value pair associating a value of John to the first name field, and a second field-value pair associating a value of Johnathan to the first name field.

The node graph generation system 200 can compare the activity field-value pairs of an electronic activity to be matched to respective node field-value pairs of one or more candidate node profiles with which to match the electronic activity. The node graph generation system 200 can compare one or more activity field-value pairs of the electronic activity to corresponding node field-value pairs of a candidate node profile to determine a match score between the electronic activity and the candidate node profile. The node graph generation system 200 can identify one or more node profiles with which to match the electronic activity based on the match score. Node profiles having a match score below a predetermined threshold can be determined not to be matched.

To compute the match score, the node graph generation system 200 can iterate through each activity field-value pair, identify the field of the activity field-value pair, and identify a corresponding field of a node field-value pair of the node profile. For example, the node graph generation system 200 can identify the field of the activity field-value pair to be first name, and based on the identification, select the field of the node field-value pairs that will be used for the comparison to be the first name field of the node field-value pairs. The node graph generation system 200 can retrieve the value from the activity field-value pair, retrieve a corresponding value that is associated to the identified field of the node field-value pair, and compare the values. For example, the node graph generation system 200 can select the first name field of a first activity field-value pair, identify a corresponding first name field of a first node field-value pair, retrieve the value of the first name from the first activity field-value pair, retrieve the corresponding value of the first name from the first node field-value pair, and compare the retrieved values. With reference to the electronic activity EA-003 and node profile NPID-12 of FIG. 6B, the node graph generation system can generate an activity field-value pair of FirstName:John, identify the field to be first name, identify the corresponding first name field of each node field-value pair of the node profile NPID-12, retrieve the first name John from the activity field-value pair, and retrieve the first name John from the node field-value pair (or the first name Johnathan from the second value that is assigned to the first name field of the node profile NPID-12). The node graph generation system 200 can compare the first name John of the activity field-value pair to the first name John of the node field-value pair, and calculate a match score based on the comparison. For example, the node graph generation system 200 can assign a match score of 100 percent based on the comparison of John and John. The node graph generation system 200 may assign a match score less than 100 percent based on the comparison of John and Johnathan. The node graph generation system 200 can calculate match scores for each comparison of the electronic activity and respective candidate node profiles.

The node graph generation system 200 can compare each match score between the electronic activity and the node profile to a match score threshold to determine whether the electronic activity is to be matched to the node profile. As such, the node graph generation system 200 can use the data extracted from the electronic activity to make decisions such as whether an electronic account associated with the electronic activity was a sender or a recipient of the electronic activity. The node graph generation system 200 can calculate an average (e.g., weighted average) of each match score determined for each comparison for the electronic activity, and compare the weighted average to the match score threshold to determine whether the electronic activity matches the node profile.

The node graph generation system 200 can apply various rules to determine how to calculate the weighted average. In some embodiments, the node graph generation system 200 calculates the weighted average based on a measure of uniqueness of the field of the value used to calculate the match score. The node graph generation system 200 can apply different weights to different fields based on the rarity score of the field. The rarity score of the field can be determined by generating a count of each value of the field across all node profiles maintained by the node graph generation system. If a predetermined number or threshold of values have a frequency count that satisfies a predetermined threshold, the field can have a lower rarity score than another field in which none of the values have a frequency count that exceeds the predetermined threshold. For example, the field FirstName can have a low rarity score because there are a lot of common first names, such as John, Chris, Tom, Ben, Dave, Alex, etc. In contrast, the field Email can have a higher rarity score because email addresses are generally unique to individuals. In some embodiments, the system may determine certain emails that may not be personal to an individual but rather belong to a group and the system can discount the influence those emails that belong to a group In some embodiments, info@example.com or help@example.com may be indicative of an email address that does not belong to an individual node profile. In this way, the node graph generation system 200 can assign a first rarity score to the first name field, a second rarity score greater than the first rarity score to the last name field, and a third rarity score greater than the second value to the phone number field. Responsive to the match score satisfying the match score threshold, the node graph generation system 200 can link the electronic activity to the node profile. For example, the node graph generation system 200 can maintain an association in a data structure, the association indicating that the electronic activity is linked to the node profile.

Linking an electronic activity to a node profile includes adding an entry to each value data structure of each value of each field of the node profile that is supported by the electronic activity. As an example, let's say the electronic activity is matched to a first node profile corresponding to John Smith corresponding to a sender of the electronic activity and a second node profile Abigail Xu corresponding to a recipient of the electronic activity. The system can identify each of the values of the fields of the sender's node profile that is supported by the electronic activity, such as the first name of the sender, the last name of the sender, the company of the sender, the email address of the sender and other fields that include values that can be supported by the signature of the sender included in the email. The system can then update the value data structure of each of those values by adding an entry identifying the electronic activity as a data point. As such, the electronic activity can serve as a data point for multiple values of multiple fields of a particular node profile. Similarly, the system can identify each of the values of the recipient's node profile that is supported by the electronic activity and can add entries in respective value data structures of values of fields of the recipient's node profile that are supported by the electronic activity. In this way, the electronic activity not only can update multiple value data structures of a single node profile but can also update the value data structures of multiple node profiles thereby multiplying the impact a single electronic activity can have towards the accuracy and state of the node profiles and the node graph in aggregate.

Figure 22:
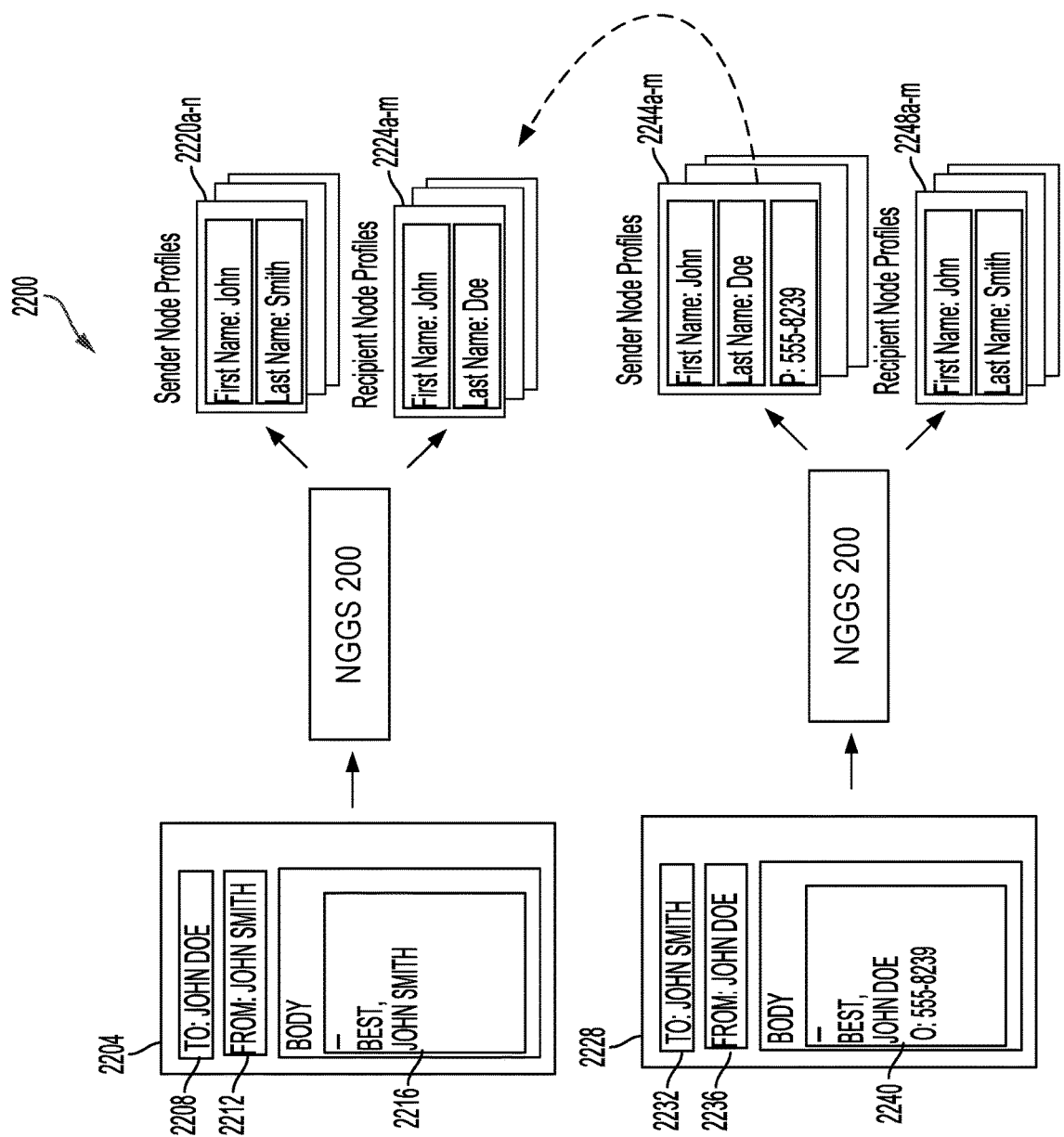
FIG. 22 illustrates a block diagram of an example process to match electronic activities with node profiles according to embodiments of the present disclosure.

Referring now to FIG. 22, FIG. 22 illustrates a process flow 2200 in which the node graph generation system (NGGS) 200 can use relationship information among multiple electronic activities to more accurately identify the subset of node profiles to which to link the electronic activities. For example, the node graph generation system 200 can identify a sender of a first electronic activity, such as an email, and a recipient of the first electronic activity, and determine that a subsequent, second electronic activity sent by the recipient to the sender is a reply to the first electronic activity. Based on this relationship and based on information extracted from the second electronic activity used to identify a second subset of node profiles that the second electronic activity is to be linked to, such as node profiles that may potentially represent the recipient, the node graph generation system 200 can effectively increase a match score of linking the first electronic activity to node profiles of the second subset (which may not necessarily have been identified as node profiles of the recipient based only on information extracted from the first electronic activity). The node graph generation system 200 can execute the process 2200 in real-time by searching for and identifying such relationships responsive to ingesting each second electronic activity, and then updating the corresponding match scores of the first electronic activity based on the links made from the second electronic activity. The node graph generation system 200 can execute the process 2200 periodically and/or in near-real time, such as in a batch processing of electronic activities.

As illustrated in FIG. 22, the node graph generation system 200 can identify a first electronic activity 2204. The node graph generation system 200 can extract a first sender 2212 of the first electronic activity 2204, and determine the first sender to be John Smith (e.g., to have first name John and last name Smith). The node graph generation system 200 can extract a first recipient 2208 of the first electronic activity 2204, and determine the first recipient to be John Doe (e.g., to have first name John and last name Doe). For example, the node graph generation system 200 can extract, from the signature block 2216 of the first electronic activity 2204, FirstName and LastName strings, and determine the FirstName and LastName string to correspond to the sender 2212 based on the FirstName and LastName strings being extracted from the signature block 2216.

The node graph generation system 200 can execute various processes described herein to identify a subset of a plurality of node profiles that match the first electronic activity 2204. For example, the node graph generation system 200 can identify a subset of the plurality of node profiles that includes a first sender subset 2220a-2220n, and a first recipient subset 2224a-2224m. The node graph generation system 200 can respectively assign sender and recipient statuses to the first electronic activity 2204 when identifying the node profiles of the subsets 2220a-2220n, 2224a-2224m. The node graph generation system 200 can identify the first sender subset 2220a-2220n by determining that match scores of comparing the electronic activity 2204 to the first sender subset 2220a-2220n satisfy the match score threshold, and determining that match scores of comparing the first electronic activity 2204 to the first recipient subset 2224a-2224m satisfy the match score threshold. There may be node profiles for which the comparison results in match scores that do not satisfy the match score threshold, such as if data extracted from the first electronic activity 2204 does not match data of such node profiles, even if such node profiles should match the first electronic activity 22b04.

The node graph generation system 200 can identify a second electronic activity 2228. The node graph generation system 200 can extract a second recipient 2232 of the second electronic activity 2228, and determine the second recipient 2232 to be John Smith. The node graph generation system 200 can extract a second sender 2236 of the second electronic activity 2228, and determine the second sender 2236 to be John Doe. The node graph generation system 200 can extract, from the signature block 2240, first name, last name, and office (or cell) phone number information. The node graph generation system 200 can process the second electronic activity 2228 to identify a subset of node profiles that match the second electronic activity 2228, including a second sender subset 2244*a-m* and a second recipient subset 2248*a-m*.

The node graph generation system 200 can determine that the second electronic activity 2228 is a reply to or a forward of the first electronic activity 2204. For example, the node graph generation system 200 can process metadata of the second electronic activity 2228 to identify a status indicator indicating that the second electronic activity 2228 is a reply to or a forward of the first electronic activity 2204. The node graph generation system 200 can parse a subject line of the second electronic activity 2228 to determine that the second electronic activity 2228 is a reply to or a forward of the first electronic activity 2204, such as if the subject line of the second electronic activity 2228 includes a string of the subject line of the first electronic activity 2204 that has been appended to the characters "RE:" or "FW" (in various type cases of those characters).

Responsive to determining that the second electronic activity 2228 is a reply to the first electronic activity 2204, the node graph generation system 200 can determine at least one of (i) the recipient of the second electronic activity 2228 is the sender of the first electronic activity 2204 or (ii) the sender of the second electronic activity 2228 is the recipient of the first electronic activity 2204. Based on these determinations, the node graph generation system 200 can update the first recipient subset 2224*a-m* to include at least one node profile of the second sender subset 2244*a-m* that did not satisfy the match score threshold when the node graph generation system 200 initially identified the first recipient subset 2224*a-m*. For example, when identifying the second sender subset 2244*a-m*, the node graph generation system 200 may have identified at least one node profile that satisfied the match score threshold because of the phone number extracted from the signature block 2240. The node graph generation system 200 can update the first sender subset 2220*a-n* to include at least one node profile of the second recipient subset 2248*a-m*. By using the send and reply relationships of electronic activities 2204 and 2228, the node graph generation system 200 can more precisely identify the subsets 2220*a-n*, 2224*a-m* to which to link the first electronic activity 2204, and more precisely identify the subsets 2244*a-m* and 2248*a-m* to which to link the second electronic activity 2228.

Figure 23:
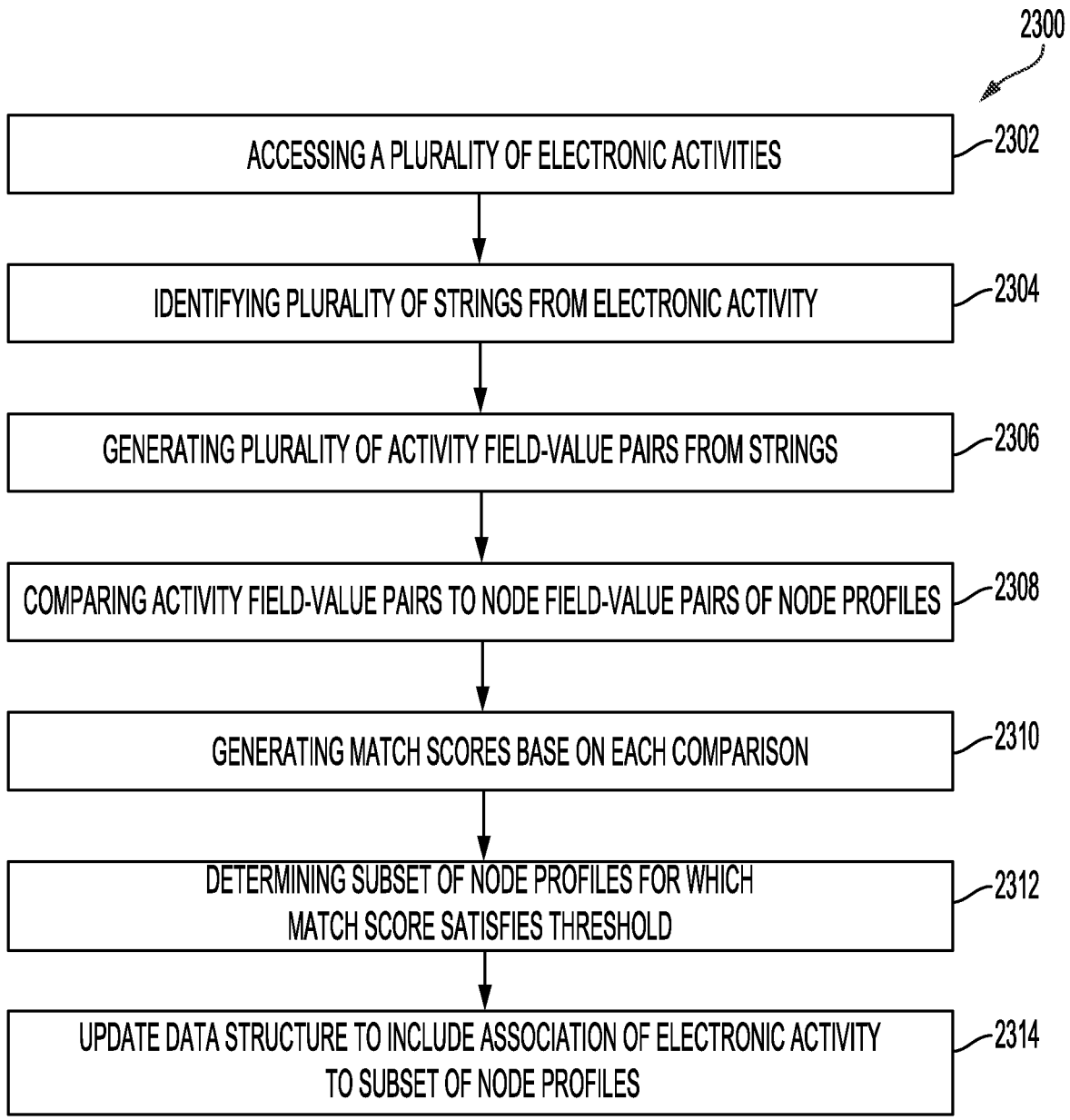
FIG. 23 illustrates a block diagram of an example method to match electronic activities with node profiles according to embodiments of the present disclosure.

Referring now to FIG. 23, FIG. 23 illustrates a method 2300 of linking electronic activities to node profiles. The method 2300 can include accessing a plurality of electronic activities (BLOCK 2302). With reference to FIGS. 16-18, among others, the data processing system 9300 can access a plurality of electronic activities. The electronic activities can be transmitted to the data processing system 9300 from data source providers. The data processing system 9300 can retrieve the electronic activities from the data source providers. For example, the data source provider can include or be an email server. The data processing system 9300 can have the authority to access the emails stored on the email server through an API or an HTTP method (e.g., a GET method). The plurality of electronic activities can be received via electronic accounts associated with a plurality of data source providers.

The data processing system 9300 maintains a plurality of node profiles. Each node profile can include information such as first name, last name, company, and job title, each of which are represented by fields having one or more values, each value having a confidence score assigned to the value. The data processing system 9300 is configured to update the plurality of node profiles using the plurality of electronic activities.

The method 2300 can include identifying a plurality of strings from data included in an electronic activity of the plurality of electronic activities, such as to link the electronic activity to one or more node profiles (BLOCK 2304). For example, the data processing system 9300 can execute the electronic activity parser 210 to identify the plurality of strings. The plurality of strings can correspond to fields including a first name field, a last name field, an email address field, a phone number field, a title field, and a company field.

The method 2300 can include generating a plurality of activity field-value pairs from the plurality of strings (BLOCK 2306). For example, the data processing system 9300 can use an electronic activity parsing policy to generate the plurality of activity field-value pairs. Each activity field-value pair can include a data structure that associates a value extracted from a string of the plurality of strings to a particular field represented by the electronic activity. For example, the data processing system 9300 can identify a value of a first name from the electronic activity (e.g., "John"), and associate the identified value to a first name field, to generate an activity field-value pair such as First Name:John. The data processing system 9300 can use the electronic activity parser 210 to execute the electronic activity parsing policy, such as to identify strings from metadata as well as non-metadata of the electronic activity. For example, the data processing system 9300 can identify a first string from a portion of the electronic activity, and determine a confidence score that the first string is a first name by at least one of (i) comparing the first string to a plurality of values of a first name field of the plurality of node profiles or (ii) a portion of the electronic activity from which the first string was identified.

The method 2300 can include comparing the plurality of activity field-value pairs to respective node field-value pairs of one or more node profiles (BLOCK 2308). For example, the data processing system 9300 can compare each activity field-value pair to respective field-value pairs of each of the one or more node profiles to identify a subset of activity field-value pairs that match respective node field-value pairs of the one or more node profiles. The data processing system 9300 can identify a field of the activity field-value pair, retrieve the value associated to the identified field, identify a corresponding field of the node field-value pairs, and compare the value retrieved from the activity field-value pair to each value associated to the corresponding field each node field-value pair. The data processing system 9300 can identify a string type of the string corresponds to a field type of the activity field or the node field in order to retrieve the values that are compared.

The method 2300 can include generating a match score of the node profile indicating a likelihood that the electronic activity is transmitted or received by an account corresponding to the node profile based on the comparison (BLOCK 2310). The data processing system 9300 can generate the match scores using the comparisons of respective values of activity field-value pairs and node field-value pairs. For example, the data processing system 9300 can compare characters of the value (e.g., of the string from which the value is extracted) to values of the corresponding field of the activity-field-value pairs. In some embodiments, the data processing system 9300 determines a weighted average of a plurality of match scores for a plurality of values of the electronic activity (e.g., each value of each activity field-value pair). The data processing system 9300 can determine the weighted average by assigning a uniqueness score as a weight to each value used to determine the weighted average. For example, the data processing system 9300 can assign a uniqueness score based on the field to which the value is associated (e.g., a value of a first name field has a lesser uniqueness score than a value of a last name field, which has a lesser uniqueness score than a value of a phone number field). The data processing system 9300 can assign a uniqueness score based on a rarity of the value (e.g., some first names may be more rare than other first names); the data processing system 9300 can assign the uniqueness score of each value based on how many node profiles include the same value for the given field relative to the total number of node profiles.

The method 2300 can include determining a subset of the plurality of node profiles to which to link the electronic activity, responsive to determining that the match score of each node profile of the subset of the plurality of node profiles satisfies a threshold (BLOCK 2312). For example, the data processing system 9300 can compare each match score of each electronic activity (which may be a weighted average) to the threshold, and select the subset of the plurality of node profiles for which the comparison satisfies the threshold.

The method 2300 can include updating a data structure to include an association between the electronic activity and each node profile of the subset of the plurality of node profiles (BLOCK 2314). For example, the data processing system 9300 can generate a data structure that includes a link indicating a connection between the electronic activity and the node profiles of the subset of the plurality of node profiles. In some embodiments, the data processing system 9300 adds entries to the node profiles of the subset of the plurality of node profiles to identify the electronic activity responsive to determining the electronic to match the node profiles. For example, the data processing system 9300 can add an entry to a value data structure of the value of the field of the node profile that is used to match the electronic activity to the node profile. For example, the data processing system 9300 can determine that the string used to match the electronic activity to the node profile is a string of a first name, such as the string having the value "John," and in response can add an entry to a value data structure that includes the value John assigned to the first name field of the node profile to identify the electronic activity. The data processing system 9300 can determine that a second string used to match the electronic activity is a string of a second field type, such as a last name field type corresponding to the string having the value "Smith," and in response can add a second entry to a value data structure that includes the value Smith assigned to the last name field of the node profile to identify the electronic activity. In some embodiments, the node profile may not have an existing value data structure corresponding to each value retrieved from the electronic activity. For example, the data processing system 9300 can determine that the node profile has a value data structure that matches the value John for the first name field, but does not have a value data structure that matches the value Smith (retrieved from the same electronic activity as the value John) for the last name field, and the data processing system 9300 can generate a value data structure that includes the value Smith for the last name field.

In some embodiments, the data processing system 9300 determines a contribution score of the entry that is added to identify the electronic activity. The data processing system 9300 can determine the contribution score based on a trust score of a source of the electronic activity. The contribution score can be indicative of the data point's contribution towards the confidence score of the value. The contribution score of a data point can decay over time as the data point becomes staler. For example, the contribution score can be based on a time at which the data point (e.g., the value) was generated or last updated. The data processing system 9300 can use the contribution score to determine a confidence score of the value. The data processing system 9300 can use each contribution score associated with each entry that indicates the value to calculate the confidence score of the value. For example, for the value "John" of a first name field, the data processing system 9300 can determine a weighted average of contribution scores of each electronic activity from which the value "John" is identified to determine the confidence score. By linking electronic activities to node profiles, and using contribution scores to determine the confidence score of each value, the data processing system 9300 can use the electronic activities as data points that support the value associated with the field, such as to enable an objective an accurate indication of the value that should correspond to the electronic account that the node profile represents.

In some embodiments, the method 2300 includes selecting a first node profile of the subset of the plurality of node profiles based on the match score of the first node profile, and linking the electronic activity with the first node profile. For example, the data processing system 9300 can rank each node profile of the subset of the plurality of node profiles based on each respective match score, and select the first node profile as the node profile having a greatest match score in order to link the node profile having the greatest match score to the electronic activity.

18. Linking Record Objects to Node Profiles

The present solution can enable real-time or near real-time linking of record objects to node profiles, with increased accuracy. In some systems that maintain data regarding entities, such as individuals or enterprises, including systems of record, the data may be self-reported, such as in response to specific queries to provide data for fields such as first name, last name, title, or email. As such, this data may be inaccurate. For example, when the data was provided, the data may have been inaccurate due to the data being self-reported. At a particular instant in time after the data was provided, due to changes to the data that may have occurred subsequent to when the data was provided and before the data has been updated, the data even if it was previously correct at the time the data was provided, may also eventually become obsolete, stale or inaccurate.

The present solution described herein can match record objects of systems of record to node profiles maintained by a node graph generation system, that can use the data included in the record objects to update node profiles and the values of fields of these node profiles unobtrusively and without requiring any direct human input. As such, the present disclosure describes solutions for maintaining node profiles that remain accurate as the node profiles do not rely directly on self-reported information submitted by a user to update the node profile and because the node profiles are automatically updated as record objects are ingested and processed by the system without requiring any human activity. In this way, the present solution can enable dynamic updates to node profiles and a node graph including such node profiles, rather than manual/self-reported updates. Even if the underlying record objects include self-reported information, the present solution can maintain contribution scores of each data source of record objects, update the contribution scores based on verification of the data extracted from the data source, and determine confidence scores of each value of a field of the node profile based on the contribution scores of the record objects that support that value.

By linking record objects to node profiles, the present solution can increase the accuracy and validity of the node profiles, such as by increasing a likelihood that each node profile represents the true state of the world. For example, when node profiles are used to generate a node graph indicative of a hierarchy or other relationships amongst node profiles, the present solution can more accurately represent values of fields such as job titles that are used to generate the node graph. The present solution can more accurately rank each value of each field (each value representing a potential true state of the world) by dynamically updating the confidence score corresponding to each value responsive to extracting data from record objects, so that the present solution outputs an evidence-based estimation of which value is the true value with improved accuracy. As an example, a node profile can include a first email address corresponding to a first job and a second email corresponding to a subsequent job. Each of the two email addresses are at respective points in time, accurate and valid. As the person switches jobs, the first email address is no longer valid but the confidence score associated with the email address can in some embodiments, remain high indicating that the first email address belongs to the node profile. Similarly, the second email address also belongs to the node profile and therefore also has a high confidence score. After the system determines that the second email address is active and functioning, the system can assign a higher confidence score to the second email address relative to the first email address since the contribution scores provided by recent data points (for example, recent record objects identifying the second email address) can contribute towards the higher confidence score. The present solution can thus respond to changes in the true state of the world represented by the node profile using the second email, rather than relying on self-reported information which may be inaccurate and/or delayed.

Referring further to FIG. 2, among others, the node graph generation system 200 can ingest record objects to generate or update node profiles that are maintained by the node graph generation system 200 using data from the record objects. For example, as illustrated in FIG. 10, the node graph generation system 200 can process record objects or data records of a system of record, such as a customer relationship management (CRM) system. The node graph generation system 200 can process record objects of systems of records such as Applicant Tracking Systems (ATS), such as Lever, located in San Francisco, Calif. or Talend by Talend Inc., located in Redwood City, Calif., enterprise resource planning (ERP) systems, customer success systems, such as Gainsight located in Redwood City, Calif., Document Management Systems, among others. As illustrated in FIG. 10, the record objects can include a lead record object 1000, an account record object 1002, an opportunity record object 1004, or a contact record object 1006.

The node graph generation system 200 can process the record objects to identify a plurality of object fields of the record objects. For example, each record object can have one or more object field-value pairs. The node graph generation system 200 can process the record object to identify values from structured data fields of the record objects. In some embodiments, the node graph generation system 200 can execute a record object parsing policy to identify values from unstructured data of the record objects, such as by executing functions of the record data extractor 230. The node graph generation system 200 can generate a plurality of object field-value pairs that associate the identified values to the corresponding fields. Because each record object may include multiple strings having data that corresponds to a particular field, the node graph generation system 200 can generate multiple object field-value pairs from each electronic activity (e.g., multiple first name-value field pairs based on multiple record entries of the record object).

Referring further to FIG. 6A, the node graph generation system 200 can maintain a plurality of node profiles 600. Each node profile 600 includes a plurality of node field-value pairs corresponding to attributes 610 and value data structures 615. For example, the node graph generation system 200 can maintain a first node field-value pair associating a first value 620 (e.g., Va) to field 610(1), a second node field-value pair associating a second value 620 (e.g., Vb) to the field 610(1), and so on for each value. As shown for the node profile illustrated in the table above, the node graph generation system 200 can generate a first field-value pair associating a value of John to the first name field, and a second field-value pair associating a value of Johnathan to the first name field.

The node graph generation system 200 can compare the object field-value pairs of a record object to be matched to respective node field-value pairs of one or more candidate node profiles with which to match the record object. The node graph generation system 200 can compare one or more object field-value pairs of the record object to corresponding node field-value pairs of a candidate node profile to determine a match score between the record object and the candidate node profile. The node graph generation system 200 can identify a node profile with which to match the record object based on the match score. Node profiles having a match score below a predetermined threshold can be determined not to be matched.

To compute the match score, the node graph generation system 200 can iterate through each object field-value pair, identify the field of the node field-value pair, and identify a corresponding field of a node field-value pair of the node profile. For example, the node graph generation system 200 can identify the field of the object field-value pair to be first name, and based on the identification, select the field of the node field-value pairs that will be used for the comparison to be the first name field of the node field-value pairs. The node graph generation system 200 can retrieve the value from the object field-value pair, retrieve a corresponding value that is associated to the identified field of the node field-value pair, and compare the values. For example, the node graph generation system 200 can select the first name field of a first object field-value pair, identify a corresponding first name field of a first node field-value pair, retrieve the value of the first name from the first object field-value pair, retrieve the corresponding value of the first name from the first node field-value pair, and compare the retrieved values.

With reference to the account record object 1002 of FIG. 10 and node profile NPID-12 of FIG. 6B, the node graph generation system can generate an object field-value pair of Field 1:XYZ (e.g., "John"), identify the field to be first name, identify the corresponding first name field of each node field-value pair of the node profile NPID-12, retrieve the first name John from the object field-value pair, and retrieve the first name John from the node field-value pair (or the first name Johnathan from the second value that is assigned to the first name field of the node profile NPID-12). The node graph generation system 200 can compare the first name John of the object field-value pair to the first name John of the node field-value pair, and calculate a match score based on the comparison. The node graph generation system can then match object field-value pairs of the record object with remaining field-value pairs of the node profile and based on the comparison of these object field-value pairs and field-value pairs, determine a match score between the record object and the node profile based on a number of pairs that matched. In some embodiments, the match score can be based on which node field-value pairs matched. For instance, node field-value pairs that are more unique to node profiles in the node graph generation system can contribute more to the match score than node field-value pairs that are less unique. For example, the field-value pair for a very large company, such as Google may not be as unique as a cell phone number of a particular person. Moreover, node field-value pairs that have values with a higher confidence score can contribute more to the match score than field-value pairs that have values with a lower confidence score to improve the accuracy of linking or matching record objects to node profiles. The node graph generation system 200 can calculate match scores for each comparison of the record object and respective candidate node profiles.

The node graph generation system 200 can compare each match score between the record object and the node profile to a match score threshold to determine whether the record object is to be matched to the node profile. The node graph generation system 200 can calculate an average (e.g., weighted average) of each match score determined for each comparison for the record object, and compare the weighted average to the match score threshold to determine whether the record object matches the node profile.

The node graph generation system 200 can apply various rules to determine how to calculate the weighted average. In some embodiments, the node graph generation system 200 calculates the weighted average based on a measure of uniqueness of the field of the value used to calculate the match score. The node graph generation system 200 can apply different weights to different fields based on the rarity score of the field. The rarity score of the field can be determined by generating a count of each value of the field across all node profiles maintained by the node graph generation system. If a predetermined number or threshold of values have a frequency count that satisfies a predetermined threshold, the field can have a lower rarity score than another field in which none of the values have a frequency count that exceeds the predetermined threshold. For example, the field FirstName can have a low rarity score because there are a lot of common first names, such as John, Chris, Tom, Ben, Dave, Alex, etc. In contrast, the field Email can have a higher rarity score because email addresses are generally unique to individuals. In some embodiments, the system may determine certain emails that may not be personal to an individual but rather belong to a group and the system can discount the influence those emails that belong to a group In some embodiments, info@example.com or help@example.com may be indicative of an email address that does not belong to an individual node profile. In this way, the node graph generation system 200 can assign a first rarity score to the first name field, a second rarity score greater than the first rarity score to the last name field, and a third rarity score greater than the second value to the phone number field.

In some embodiments, the node graph generation system 200 calculates the weighted average based on a measure of uniqueness of the value in addition to or in contrast to the rarity score of the field. For example, certain names may be more unique (e.g., rare) than other names. The node graph generation system 200 can maintain a uniqueness data structure mapping each value of each field of each of the plurality of node profiles to a corresponding uniqueness or frequency count, and retrieve the uniqueness using the value. The node graph generation system 200 can generate the uniqueness data structure using the plurality of node profiles, and update the uniqueness data structure responsive to receiving node profile data. For example, the node graph generation system 200 can count a number of each unique value of the node profiles, and calculate the uniqueness for each unique value based on the count. The node graph generation system 200 can thus rely more heavily on data extracted from the record object that has a higher likelihood of specifically corresponding to the node profile (e.g., rather than matching the record object from which the first name value of John was extracted to every node profile having the first name John).

Responsive to the match score satisfying the match score threshold, the node graph generation system 200 can link the electronic activity to the node profile. For example, the node graph generation system 200 can maintain an association in a data structure. The association can indicate that the electronic activity is linked to the node profile. The node graph generation system 200 can update a confidence score of each value of the node profile that matches corresponding value(s) extracted from the electronic activity.

Referring further to FIG. 10, the node graph generation system 200 can use relationship information amongst record objects to more precisely determine the subset of node profiles that match the record objects. For example, the node graph generation system 200 can identify that two record objects are linked based on data such as opportunity contact role (OCR) objects, a conversion of a lead record object 100 into a contact record object 1006, an account record object 1002, and an opportunity record object 1004, or other links between record objects, including explicit or implicit linking of record objects. Responsive to identifying a link between two record objects, the node graph generation system 200 can use the node profiles that are determined to match one of the record objects to update the matches to the other record object. For example, responsive to determining that the lead record object 1000 is linked to the account record object 1002, the node graph generation system 200 can increase a match score between the lead record object and node profiles that are matched to the account record object 1002. This can be useful in the event where a few node profiles have a high match score with a first node profile but there are many node profiles that are candidate matches to a second record object linked to the first record object. In such an event, the system can identify the node profiles linked to the first record object to identify the same node profiles from the many node profiles that are candidate matches to the second record object.

For example, the node graph generation system 200 can identify the lead record object 1000, and determine a first subset of node profiles that match the lead record object as described herein, such as by comparing object field-value pairs of the lead record object to node field-value pairs of the node profiles of the first subset and evaluating match scores of the comparison relating to a match score threshold. The node graph generation system 200 can determine that the lead record object 1000 is linked to the account record object 1002 from information included in the record objects or the system of record. The node graph generation system 200 can determine a second subset of node profiles that match the account record object 1002 as described herein, such as by comparing object field-value pairs of the account record object 1002 to node field-value pairs of the node profiles and evaluating match scores of the comparison relative to a match score threshold. In some embodiments, responsive to determining that the account record object 1002 is linked to the lead record object 1000, the node graph generation system 200 can add the node profiles of the second subset to the node profiles of the first subset. In some embodiments, responsive to determining that the account record object 1002 is linked to the lead record object 1000, the node graph generation system 200 increases a match score of the comparison of the node field-value pairs of the node profiles of the second subset to the object field-value pairs of the lead record object 1000. As such, even if certain record objects have incomplete information that may result in inaccurately low match scores, by using the linking between record objects, the node graph generation system 200 can more accurately identify the node profiles that match the record objects (and thus the node profiles to which to link the record objects). This improves the accuracy of the matches made between record objects and node profiles and further improves the accuracy of the values of the fields of the node profile, thereby improving the accuracy of the node graph and the insights and analytics derived from the node profiles and the node graph.

Figure 24:
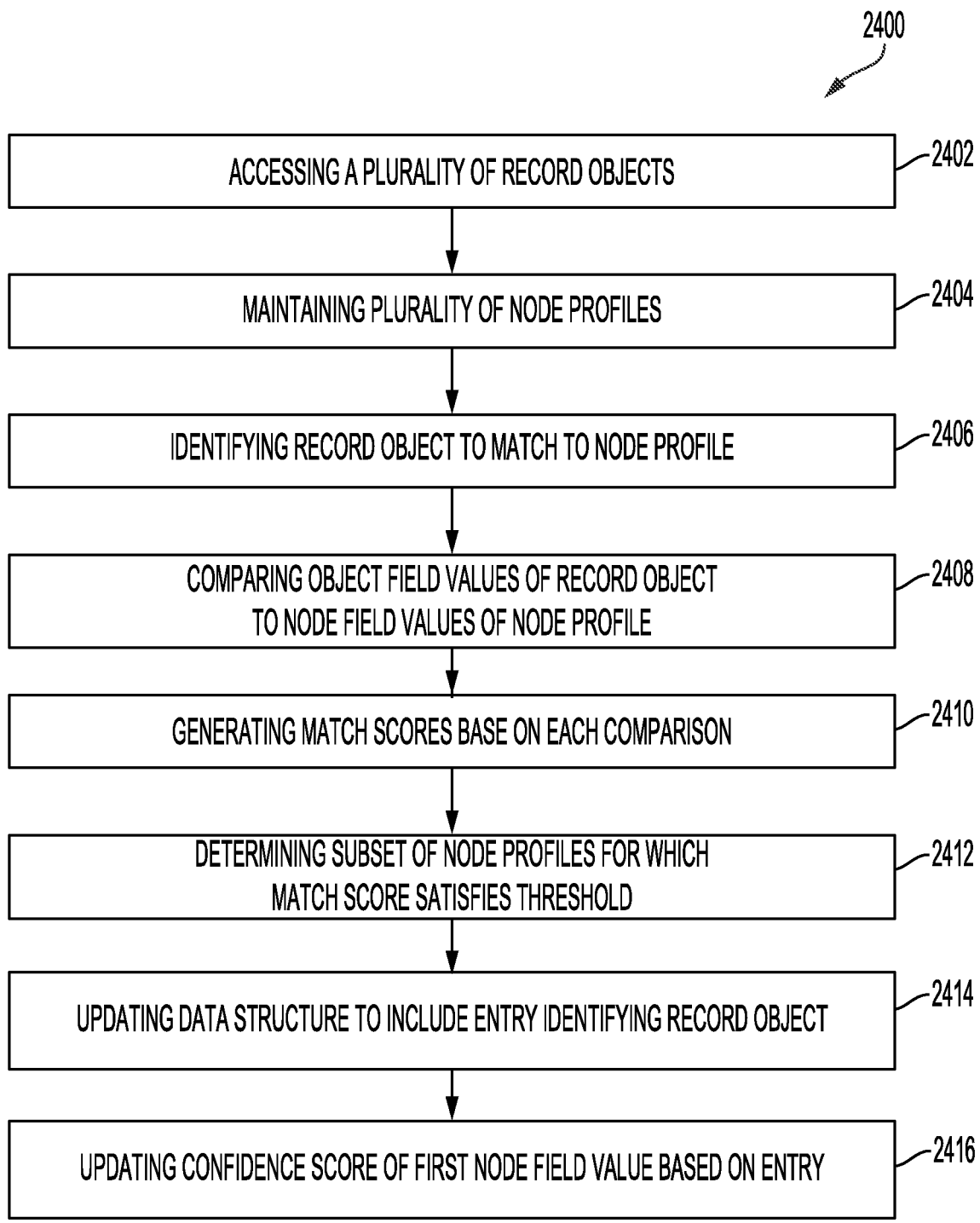
FIG. 24 illustrates a block diagram of an example method to match electronic objects with node profiles according to embodiments of the present disclosure.

Referring now to FIG. 24, FIG. 24 illustrates a method 2400 of linking record objects to node profiles. The method 2400 can include accessing a plurality of record objects of one or more systems of record (BLOCK 2402). Each record object corresponds to a record object type (e.g., lead record object, account record object, among others) and includes one or more object field-value pairs associating an object field value to a corresponding field of the record object. The systems of record correspond to one or more data source providers. The data processing system 9300 can retrieve the record objects from the systems of record.

The method 2400 can include maintaining a plurality of node profiles corresponding to a plurality of unique entities (BLOCK 2404). Each node profile includes one or more field-value pairs associating a node field value to a corresponding field of the node profile. For example, the data processing system 9300 can maintain a plurality of node profiles that can include information such as first name, last name, company, and job title, each of which are represented by fields having one or more values, each value having a confidence score assigned to the value. The data processing system 9300 is configured to update the plurality of node profiles using the plurality of record objects.

The method 2400 can include identifying a record object to match to at least one node profile of the plurality of node profiles (BLOCK 2406). For example, the data processing system 9300 can parse the system of record of the record object to identify the record object periodically, or responsive to detecting or receiving an indication of an update to the system of record. The data processing system 9300 can identify from each record object a plurality of object field-value pairs that associate a value of an object field to the object field. For example, the data processing system 9300 can identify a first name field of the record object, extract the first name from the first name field, and generate the object field-value pair to associate the first name to the first name field.

The method 2400 can include comparing the object field values of the one or more object field-value pairs of the record object to corresponding node field values of the corresponding fields of the node profile (BLOCK 2408). For example, the data processing system 9300 can compare each object field-value pair to respective field-value pairs of each of the one or more node profiles to identify a subset of object field-value pairs that match respective node field-value pairs of the one or more node profiles. The data processing system 9300 can identify a field of the object field-value pair, retrieve the value associated to the identified field, identify a corresponding field of the node field-value pairs, and compare the value retrieved from the object field-value pair to each value associated to the corresponding field each node field-value pair.

The method 2400 can include generating a match score based on the comparison that indicates a likelihood that the record object corresponds to the node profile (BLOCK 2410). The data processing system 9300 can generate the match scores using the comparisons of respective values of object field-value pairs and node field-value pairs. For example, the data processing system 9300 can compare characters of the value (e.g., of the string from which the value is extracted) to values of the corresponding field of the object field-value pairs. In some embodiments, the data processing system 9300 determines a weighted average of a plurality of match scores for a plurality of values of the record object (e.g., each value of each object field-value pair). The data processing system 9300 can determine the weighted average by assigning a uniqueness score as a weight to each value used to determine the weighted average. For example, the data processing system 9300 can assign a uniqueness score based on the field to which the value is associated (e.g., a value of a first name field has a lesser uniqueness score than a value of a last name field, which has a lesser uniqueness score than a value of a phone number field). The data processing system 9300 can assign a uniqueness score based on a rarity of the value (e.g., some first names may be more rare than other first names); the data processing system 9300 can assign the uniqueness score of each value based on how many node profiles include the same value for the given field relative to the total number of node profiles.

The method 2400 can include determining a subset of the plurality of node profiles with which to link the record object responsive to determining that the match score of each node profile of the subset satisfies a threshold (BLOCK 2412). For example, the data processing system 9300 can compare each match score of each record object (which may be a weighted average) to the threshold, and select the subset of the plurality of node profiles for which the comparison satisfies the threshold.

The method 2400 can include updating a first value data structure of the first node field value by adding an entry identifying the record object (BLOCK 2414). For example, the data processing system 9300 can generate a data structure that includes a link indicating a connection between the record object and the node profiles of the subset of the plurality of node profiles. In some embodiments, the data processing system 9300 adds entries to the node profiles of the subset of the plurality of node profiles to identify the record object responsive to determining the record object to match the node profiles. For example, the data processing system 9300 can add an entry to a value data structure of the value of the field of the node profile that is used to match the record object to the node profile. For example, the data processing system 9300 can determine that the data used to match the record object to the node profile is of a first name field, such as a string having the value "John," and in response can add an entry identifying the record object to a value data structure that includes the value John assigned to the first name field of the node profile. The data processing system 9300 can determine that a second string used to match the record object is of a second field type, such as a last name field type corresponding to the string having the value "Smith," and in response can add a second entry identifying the record object to a value data structure that includes the value Smith assigned to the last name field of the node profile. In some embodiments, the node profile may not have an existing value data structure corresponding to each value retrieved from the record object. For example, the data processing system 9300 can determine that the node profile has a value data structure that matches the value John for the first name field, but does not have a value data structure that matches the value Smith (retrieved from the same record object as the value John) for the last name field, and the data processing system 9300 can generate a value data structure that includes the value Smith for the last name field.

The method 2400 can include updating a confidence score of the first node field value based on the entry identifying the record object (BLOCK 2416). For example, the data processing system 9300 can increase the confidence score responsive to adding the entry, as the entry will further support an expectation that the value is a true, accurate value for that field. The data processing system 9300 can update the confidence score based on a contribution score of the entry. The contribution score can indicate a trustworthiness of the source of the entry, and can be updated over time by periodically comparing values of record objects retrieved from particular data sources (e.g., systems of record) to known values (or values having high confidence). For example, the data processing system 9300 can generate the contribution score based on a trust score assigned to the system of record that is associated with the record object. In some embodiments, the data processing system 9300 determines the confidence score for the first node field value based on the contribution scores of the entries used to provide the values to the first node field value. For example, the data processing system 9300 can determine the confidence score based on an average of the contribution scores. The contribution score can be based on a time at which the record object was last updated or modified relative to a time at which the contribution score is calculated, such as to decrease the contribution score based on a difference between the two times.

In some embodiments, the record object includes multiple object field-value pairs. The data processing system 9300 can match a first object field value to a first node field value, and a second object field value to a second node field value. The data processing system 9300 can generate a first confidence score for the first node field value based on the entry that identifies the record object, and can generate a second confidence score for the second node field value based on the entry that identifies the record object.

In some embodiments, the data processing system 9300 maintains a shadow record object corresponding to the record object. Responsive to matching the record object to the subset of node profiles, the data processing system 9300 can add values from the node profile(s) of the subset to the shadow record object, which can facilitate completing or updating the shadow record object. For example, the data processing system 9300 can retrieve one or more values from the node profile(s) of the subset and add the one or more values to one or more shadow object fields of the shadow record object. In some embodiments, the data processing system 9300 provides a notification to a device to update a value of the object field of the record object based on the one or more values added to the one or more shadow object fields of the shadow record object. As such, the data processing system 9300 can increase a completeness of the record object by matching the record object to the subset of node profiles, and then using values from the subset of node profiles to complete the record object. In some embodiments, the data processing system 9300 identifies the values from the subset of node profiles to add to the shadow record object and/or the record object responsive to the confidence scores of the values satisfying a confidence score threshold, which can increase the accuracy of the completion of the shadow record object and/or the record object.

In some embodiments, the data processing system 9300 uses values of the subset of node profiles to update the record object responsive to matching the record object to the subset of node profiles, which can increase the accuracy of the record object, and thus enable features such as more accurate determination of stages associated with the record object. For example, the data processing system 9300 can determine that a particular object field value of a field of the record object is different than a node field value of a corresponding field of the node profile. In response, the data processing system 9300 can retrieve the confidence score of the node field value, and compare the confidence score to a predetermined threshold. Responsive to the confidence score satisfying the predetermined threshold, such as being greater than the predetermined threshold, the data processing system 9300 can generate a request to update the object field value of the record object. The data processing system 9300 can generate the request to include the node field value that has the confidence score that satisfied the predetermined threshold and/or cause the system of record to update the object field value to be the node field value.

19. Generating Confidence Scores of Values of Fields Based on Data Points

The present disclosure relates to systems and methods for generating and updating confidence scores of values of one or more field of node profiles. By generating and updating confidence scores of values, a system can determine, at any point in time, a current state of the node profile while providing a level of confidence for each value. In existing systems that may maintain some form of a node profile, the node profile can include values that are static and only get updated responsive to a change made by a user. In the present disclosure, because the node profiles include value data structures that are continually updated by adding entries identifying new data points that support the value, the system is able to dynamically update the node profile without any user intervention, while at the same time, compute a confidence score of one or more values of the node profile. This allows a user querying the system to determine, at any given point in time, a state of the node profile, including the state of the node profile at any point in the past.

Figure 25:
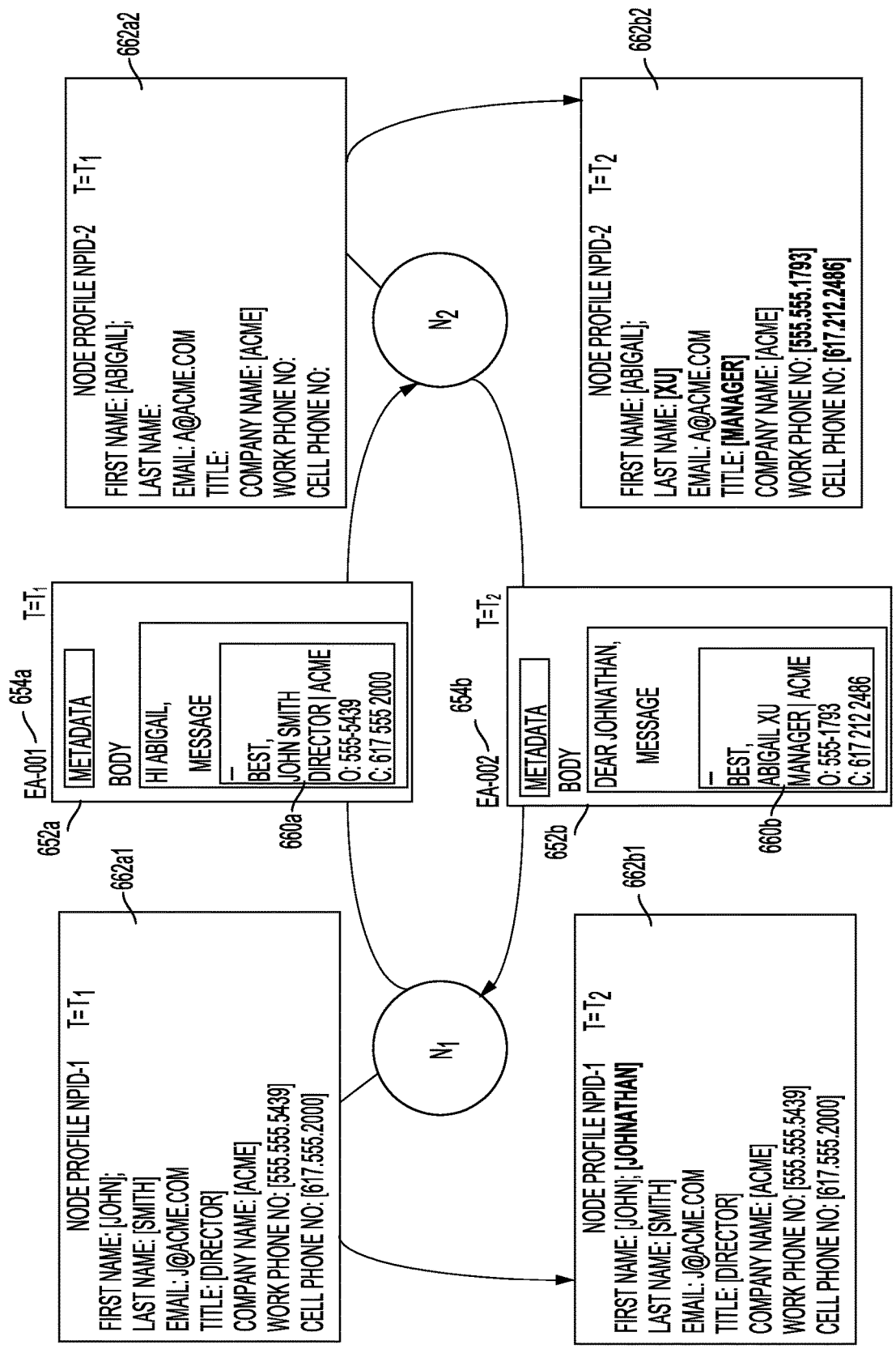
FIG. 25 illustrates a block diagram of a series of electronic activities between two nodes according to embodiments of the present disclosure.

Moreover, the present disclosure can generate and update confidence scores of values of one or more fields of multiple node profiles. In some embodiments, the present disclosure can update node profiles, or more particularly, value data structures of node profiles as the system ingests and processes one or more electronic activities or record objects of systems of record. A single electronic activity or record object can serve as a data point for multiple value data structures of either a single node profile or multiple node profiles. In this way, a single electronic activity can update multiple node profiles simultaneously, accelerating the speed at which the system can generate and update node profiles and construct the node graph based on the node profiles. Based on the present disclosure, confidence scores of values can be generated and updated as more data points are processed, and as a result of dynamically and automatically updating confidence scores by assigning data points to values of fields of node profiles, the system can maintain and update a node graph of node profiles that is updated without human intervention and is more accurate than existing systems as it is dynamically updated, the source of data used to update the node profiles is not centralized and not reported by any one individual or user. Moreover, because electronic activities are constantly being generated, ingested and processed, the node profiles do not remain static. Referring now to FIG. 25, FIG. 25 illustrates a series of electronic activities between two nodes. As described herein, and also referring to FIGS. 6B and 8, a first node N1 and a second node N2 may exchange a series of electronic activities. FIG. 25 also shows a representation of two electronic activities and representations of two node profiles of two nodes at two different states according to embodiments of the present disclosure.

As shown in FIG. 25, a first electronic activity sent at a first time, $T=T_1$, and a second electronic activity sent at a second time, $T=T2$, are shown. The first electronic activity 652a includes or is associated with a first electronic activity identifier 654a ("EA-001"). The second electronic activity 652b includes or is associated with a second electronic activity identifier 654b ("EA-002"). The system 200 can assign the first electronic activity identifier 654a to the first electronic activity 652a and second electronic activity identifier 654b to the second electronic activity 652b. In some embodiments, the system 200 can assign the first and second electronic activities' unique electronic activity identifiers to allow the system to uniquely identify each electronic activity processed by the system 200. Collectively, the first and second electronic activities can be referred to herein as electronic activities 652 or individually as electronic activity 652. Each electronic activity can include corresponding metadata, as described above, a body, and a respective signature 660a and 660b included in the body of the respective electronic activity 652.

The second electronic activity can be sent as a response to the first electronic activity. The system 200 can determine that the second electronic activity is a response to the first electronic activity using one or more response detection techniques based on signals included in the electronic activity including the metadata of the electronic activity, the subject line of the electronic activity, the participants of the electronic activity, and the body of the electronic activity. For instance, the system can determine that the second electronic activity has a timestamp after the first electronic activity. The system 200 can determine that the second electronic activity identifies the sender of the first electronic activity 652a as a recipient of the second electronic activity 652b. The system can determine that the second electronic activity includes a subject line that matches one or more words of the subject line of the first electronic activity. In some embodiments, the system can determine that the second electronic activity includes a subject line that includes the entire string of characters of the subject line of the first electronic activity and the string of characters is preceded by "RE:" or some other predetermined set of characters indicating that the second electronic activity is a reply. In some embodiments, the system can determine that the body of the second electronic activity includes the body of the first electronic activity. The system 200 can also determine that the second electronic activity is a response to the first electronic activity based on the participants included in both the electronic activities. Furthermore, in some embodiments, the system 200 can determine if the second electronic activity is a forward of the first electronic activity or a reply all of the first electronic activity.

FIG. 25 also includes two representations of two node profiles associated with the first node N1 and the second node N2 at two different times, $T=T_1$ and $T=T2$. The node profile NPID-1 corresponds to a first node profile of the first node N1, who is the sender of the electronic activities 652a. The first representation 662a1 of the first node profile was updated after the first electronic activity 652a was ingested by the node graph generation system 200 but before the second electronic activity 652b was ingested by the system 200. The second representation 662b1 of the first node profile was updated after the first and second electronic activities 652a and 652b were ingested by the node graph generation system 200.

The node profile NPID-2 corresponds to a second node profile of one of the recipients of the electronic activity 652a and the sender of the second electronic activity 652b. The first representation 662a2 of the second node profile was updated after the first electronic activity 652a was ingested by the node graph generation system 200 but before the second electronic activity 652b was ingested by the system 200. The second representation 662b2 of the second node profile was updated after the first and second electronic activities 652a and 652b were ingested by the node graph generation system 200.

In some embodiments, as described herein, the node profile manager 220 of the system 200 can maintain, for each value of each field of each node profile, a value data structure that can be stored as a multidimensional array. The multidimensional array can include a list of entries identifying data points that identify electronic activities or systems of record that contribute to the value of the field. Each data point can be associated with a source. For emails or other electronic activities, the source can be a mail server of a data source provider. For record objects, the source of the record object can be a system of record of the data source provider. Each source of a respective data point can have an associated trust score that can be used to determine how much weight to assign to the data point from that source. Each data point can also identify a time at which the data point was generated (for instance, in the case of a data point derived from an electronic activity such as an email, the time the data point was generated can be the time the electronic activity was sent or received). In the case of a data point being derived from a system of record, the time the data point was generated can be the time the data point can be entered into the system of record or the time the data point was last accessed, modified, confirmed, or otherwise validated in or by the system of record. The source of the data point and the time the data point was generated, last accessed, updated or modified, can be used to determine a contribution score of the data point, which can be used to determine the confidence score of the value. In some embodiments, the node profile manager 220 can generate, compute or assign a contribution score to each data point. The contribution score can be indicative of the data point's contribution towards the confidence score of the value. The contribution score of a data point can decay over time as the data point becomes staler. The contribution scores of each of the data points derived from electronic activities and systems of record can be used to compute the confidence score of the value of a field of the node profile.

Each of the representations 662 of the first and second node profiles can include fields and corresponding values. For example, in the first representation 662a1, the field "First Name" is associated with the value John. The first representation 662a1 of the first node profile also includes the field "Title" which is associated with the value "Director." The values of the last name and cell phone number remain the same in both the representations 662a1 and 662b1 of the first node profile. In another example, in the first representation 662a2 of the second node profile, the field "First Name" is associated with the value Abigail. The first representation 662a2 of the second node profile does not include the field "Title" as that information may not have been available to the system 200. It should be appreciated that in the event the value was already associated with the field, the system 200 can update the value data structure of the value by adding an entry identifying the electronic activity. In this way, the electronic activity serves as a data point that supports the value and can increase the confidence score of the value, which can further improve the accuracy of the information included in the node profile.

In the representation 662b2 of the second node profile NPID-2, the second node profile was updated after the first and second electronic activities 652a and 652b were ingested. The field "Title" is now associated with the value "Manager." The values of the "Work Phone No" and "Cell Phone No" fields have new values associated with them. In the representation 662b1 of the first node profile NPID-1, the first node profile was updated after the first and second electronic activities 652a and 652b were ingested. The field "First Name" is now associated with 2 different values, John and Johnathan. In the representative node profiles of NPID-1 and NPID-2, the same electronic activity can update different node profiles.

It should be appreciated that the value data structure of the value J@acme.com corresponding to the email field of the first node profile can be updated to include an entry identifying the second electronic activity 652b. It should further be appreciated that the system 200 is configured to updated the field-value pair of the first node profile corresponding to email: J@acme.com, even though Macme.com is a value previously associated with the email field of the first node profile. The system can use the second electronic activity to update the node profile by not only adding new values, such as the name "Johnathan" but also by updating the value data structures of existing values of the first node profile to include entries identifying the second electronic activity 654b. By doing so, the system 200 can continuously maintain the accuracy of the data included in the node profiles and identify which values are still current and which values are now stale based on the last time a data point supported the particular value. As described herein, the system 200 can be configured to generate respective contribution scores to each entry included in the value data structure of a value and use the respective contribution scores of each entry of the value data structure to determine a confidence score of the value of the field of the node profile. The system can further be configured to dynamically update the contribution scores and the confidence score based on a current time as the contribution scores of data points can change with time. In some embodiments, the contribution scores of data points can decrease with time as the data point becomes older.

Figure 26:
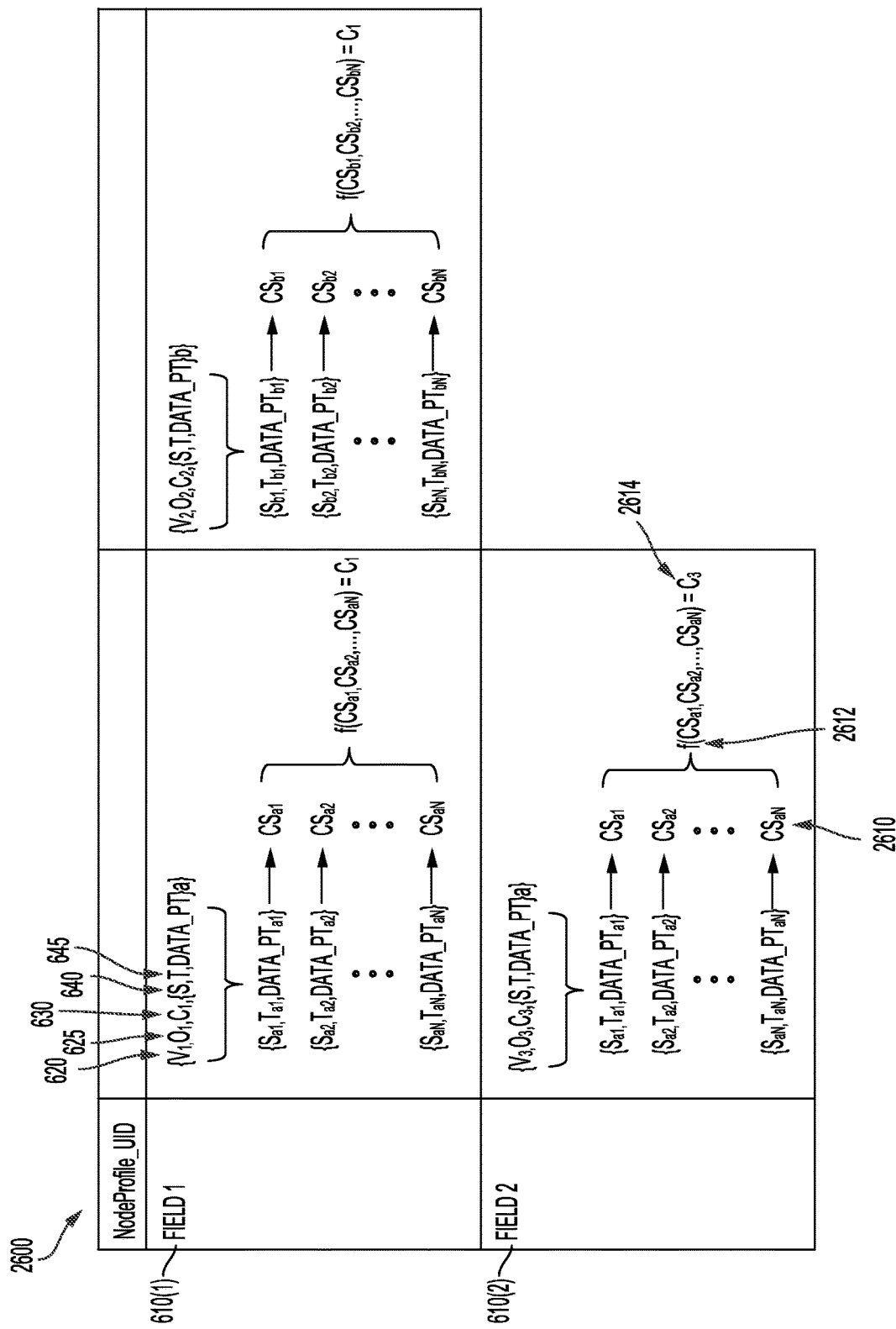
FIG. 26 illustrates a representation of a node profile of a node according to embodiments of the present disclosure.

Referring now to FIG. 26, FIG. 26 illustrates a representation of a node profile 2600 of a node. As described herein, and also referring to FIG. 6A, the node profile can include one or more fields associated with one or more values. Each value can include a corresponding value data structure. The value data structure can include one or more entries. Each entry of the value data structure can identify a data point 2602 representing an electronic activity or a record object. In some embodiments, the node profile manager 220 can generate and assign a contribution score 2610 to each data point 2602 for the value to which the data point serves as evidence. The contribution score 2610 can be indicative of the data point's contribution towards the confidence score 2614 of the value. The contribution score 2610 of a data point 2602 can decay over time as the data point 2602 becomes staler. The contribution scores 2610 of each of the data points 2602 derived from electronic activities and systems of record can be used to compute the confidence score 2614 of the value of a field of the node profile.

As described herein, each of the values included in the node profile can be supported by one or more data points 2602. Data points 2602 can be pieces of information or evidence that can be used to support the existence of values of fields of node profiles. A data point 2602 can be an electronic activity, a record object of a system of record or other information that is accessible and processable by the system 200. In some embodiments, a data point 2602 can identify an electronic activity, a record object of a system of record, or other information that is accessible and processable by the system 200 that serves as a basis for supporting a value in a node profile. Each data point 2602 can be assigned its own unique identifier. Each data point 2602 can be associated with a source of the data point 2602 identifying an origin of the data point 2602. The source of the data point 2602 can be a mail server, a system of record, among others. Each of these data points 2602 can also include a timestamp. The timestamp of a data point 2602 can identify when the data point 2602 was either generated (in the case of an electronic activity such as an email) or the record object that serves as a source of the data point 2602 was last updated (in the case when the data point 2602 is extracted from a system of record). Each data point 2602 can further be associated with a trust score of the source of the data point 2602. The trust score of the source can be used to indicate how trustworthy or reliable the data point 2602 is. The data point 2602 can also be associated with a contribution score that can indicate how much the data point 2602 contributes towards a confidence score 2614 of the value associated with the data point 2602. The contribution score 2610 can be based on the trust score of the source (which is based in part on a health score of the source) and a time at which the data point 2602 was generated or last updated.

In some embodiments, a confidence score 2614 of the value can indicate a level of certainty that the value of the field is a current value of the field. The higher the confidence score 2614, the more certain the value of the field is the current value. The confidence score 2614 can be based on the contribution scores 2610 of individual data points 2602 associated with the value. The confidence score 2614 of the value can also depend on the corresponding contribution scores 2610 of other values of the field, or the contribution scores of data points 2602 associated with other values of the field.

Below is a reproduced portion of Table 1. The table illustrates various values for various fields and includes an array of data points that contribute to the respective value. As shown in the table, the same electronic activity can serve as different data points for different values. Further, the table illustrates a simplified form for the same of convenience and understanding.

| | Data Point # | DP ID | TimeStamp | Activity ID | Source | Trust Score | Contribution Score |
|---|---|---|---|---|---|---|---|
| Field: First Name | | | Value: John [Confidence score] = 0.8 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID343 | Mar. 1, 2018 1 pm ET | EA-017 | Email | 100 | 0.7 |
| | Data Point 4: | DP ID458 | Jul. 1, 2018 3 pm ET | EA-098 | Email | 100 | 0.8 |
| | Data Point 5: | DP ID576 | Sep. 12, 2015 3 pm ET | SOR-145 | Talend | 20 | 0.2 |
| Field: First Name | | | Value: Johnathan [Confidence score] = 0.78 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID343 | Mar. 1, 2018 1 pm ET | EA-017 | Email | 100 | 0.7 |
| | Data Point 4: | DP ID458 | Jul. 1, 2018 3 pm ET | EA-098 | Email | 100 | 0.8 |
| | Data Point 5: | DP ID576 | Sep. 12, 2015 3 pm ET | SOR-145 | Talend | 20 | 0.2 |
| Field: Title | | | Value: Director [Confidence score] = 0.5 | | | | |
| | Data Point 1: | DP ID101 | Feb. 1, 2016 4 pm ET | EA-003 | Email | 100 | 0.6 |
| | Data Point 2: | DP ID225 | Feb. 18, 2017 2 pm ET | SOR-012 | CRM | 70 | 0.4 |
| | Data Point 3: | DP ID243 | Mar. 1, 2017 1 pm ET | EA-117 | Email | 100 | 0.65 |
| | Data Point 4: | DP ID243 | Mar. 1, 2018 1 pm ET | SOR-087 | CRM | 5 | 0.05 |
| Field: Title | | | Value: CEO [Confidence score] = 0.9 | | | | |
| | Data Point 1: | DP ID343 | Mar. 1, 2018 1 pm ET | EA-017 | Email | 100 | 0.7 |
| | Data Point 2: | DP ID458 | Jul. 1, 2018 3 pm ET | EA-098 | Email | 100 | 0.8 |
| | Data Point 3: | DP ID225 | Mar. 18, 2018 2 pm ET | SOR-015 | CRM | 65 | 0.54 |

As a result of populating values of fields of node profiles using electronic activities, the node profile manager 220 can generate a node profile that is unobtrusively generated from electronic activities that traverse networks. In some embodiments, the node profile manager 220 can generate a node profile that is unobtrusively generated from electronic activities and systems of record.

As described herein, the present disclosure relates to methods and systems for assigning contribution scores to each data point (for example, electronic activity) that contributes to a value of a field such that the same electronic activity can assign different contribution scores to different values of a single node profile and of multiple node profiles. The contribution score can be based on a number of different electronic activities contributing to a given value of a field of a node profile, a recency of the electronic activity, among others. In some embodiments, a system of record of an enterprise accessible to the node graph generation system 200 can include data that can also contribute to a value of a field of a node profile. The contribution score can be based on a trust score or health score of the system of record. In some embodiments, the contribution score can be based on a number of different electronic activities or systems of record contributing to the value of the field of the node profile. In some embodiments, the contribution score can be based on a number of different electronic activities or systems of record contributing to other values of the field of the node profile. In some embodiments, the contribution score can be based on when the value was last updated or modified within the system of record, among others.

Referring back to Table 1, various factors can affect the contribution score of a given data point 2602. For example, a high trust score of a source of the data point can promote a higher contribution score. Data points corresponding to electronic activities generally have a higher contribution score while data points corresponding to systems of record with lower trust scores can have a lower contribution score. This may be because systems of record generally include data that is manually input by a user and remains static until it is modified. In contrast, the data in electronic activities, such as emails, are generated by multiple senders and include signatures that are updated by the creator of the signature i.e., the sender of the email. Although it is possible that an individual user may include incorrect information in their signature, they have more opportunities to correct such information and it can be confirmed or refuted based on other signals or electronic activities processed by the node graph generation system 200. Furthermore, the contribution score of a data point decreases as the data point gets older or the date associated with the last update of the data points gets older as can be seen by the contribution scores of the data points shown in the table above.

The system 200 can be configured to compute confidence scores using the contribution scores of individual data points identified by entries in the value data structure of the value for which the confidence score is being generated. The system 200 can compute confidence scores periodically. In some embodiments, the system 200 can update the confidence score of a value when additional data points are added. In some embodiments, the system 200 can compute the confidence score of a value based on a predetermined time schedule. The confidence score of a value can be a function of the contribution scores of various data points supporting the value (i.e. included in the value data structure of the value). The confidence score of the value can also decrease over time if no additional data points support the value. This is because the contribution scores of the data points that support the value will get older and since the contribution score of a data point is based on recency, the contribution scores will decrease resulting in a decrease in the confidence score. As such, to maintain a high confidence score of a value, newer entries need to be added to the value data structure. Via this mechanism of maintaining a dynamically updated value data structure that continually adds entries corresponding to data points that support the value, the node graph generation system 200 can continually compute and update a confidence score of a value based on the data points included in the corresponding value data structure.

By maintaining and periodically updating confidence scores of values, the system 200 can be configured to determine if electronic activities are correctly linked or matched to the right node profiles. For instance, if a given data point contributes to multiple field-value pairs of the node profile and a predetermined number of values of the field-value pairs have a confidence score below a threshold, the system can identify those data points that contribute to those values that have a confidence score below the threshold. The system can determine, for each of those data points, how many values of fields of the node profile does that data point provide support. The system can then identify those data points as candidate data points that were correctly linked or matched to the node profile. The system can then determine that the data point is improperly linked based on the number of values of the fields of the node profiles and the type of fields to which the data point provides support. The system can then unmatch or delink the data point from the node profile by adjusting or recalculating the match score of the data point and the node profile. In this way, using the confidence scores of values, the system 200 can identify data points that were incorrectly linked to the node profile thereby further improving the accuracy of the node profile by removing data points that were previously incorrectly matched.

The systems described herein can also use confidence scores of values to determine a status of a node profile at a given point in time, for instance, 1:55 pm on Jun. 5, 2014. To do so, the node graph generation system 200 can discard all of the data points having a timestamp after 1:55 pm on Jun. 5, 2014 and only use data points before 1:55 pm on Jun. 5, 2014 that are included in the node profile. The node graph generation system 200 can then compute confidence scores of the field-value pairs of the node profile using the remaining or undiscarded data points to determine a state of the node profile on 1:55 pm on Jun. 5, 2014. The node graph generation system 200 can use the confidence score of each field-value pair to determine the state of the node profile at the given time. In this way, confidence state of a node profile can be determined for any point in time. As described herein, the node graph generation system 200 can make a request to determine a status of a node profile at any given point in time. For instance, the node graph generation system 200 can determine the state of a node profile for John Smith on Dec. 20, 2016. Similarly, the node graph generation system 200 can make a query for a particular value of a field of a node profile can be made for any point in time. Entries occurring after the particular time corresponding to the query can be filtered out so a value and its associated confidence score can be calculated using only those data points that have a timestamp before the particular time.

By determining confidence scores of field-value pairs of node profiles, the node graph generation system 200 can be configured to execute various types of requests based on the node profiles maintained by the node graph generation system 200. For instance, the system can be configured to determine a list of node profiles that have a title of Director. The system can be configured to determine a list of node profiles that have a title of Director on Jun. 1, 2015. The system can further be configured to determine a list of node profiles that work in San Francisco and have a title of CEO. Moreover, the system can be configured to determine only those node profiles that have a Company name of "Example-Company, Inc." but with a confidence score for that field-value pair of above 90%. Using confidence scores as a threshold for selecting node profiles to be included in lists responsive to queries and adjusting the confidence score threshold to see changes in the lists can be a useful tool to identify node profiles with different levels of certainty.

In some embodiments, the present disclosure describes systems and methods of updating confidence scores of values of fields based on electronic activity includes associating the electronic activity to a first value of a first field, assigning a first contribution score to the electronic activity indicating a contribution level of the electronic activity to a confidence score of the first value, associating the same electronic activity to a second value of a second field, assigning a second contribution score to the same electronic activity indicating a contribution level of the electronic activity to a confidence score of the second value, and updating the confidence scores of the first value and the second value based on the first contribution score of the electronic activity for the first value and the second contribution score of the electronic activity for the second value.

Figure 27:
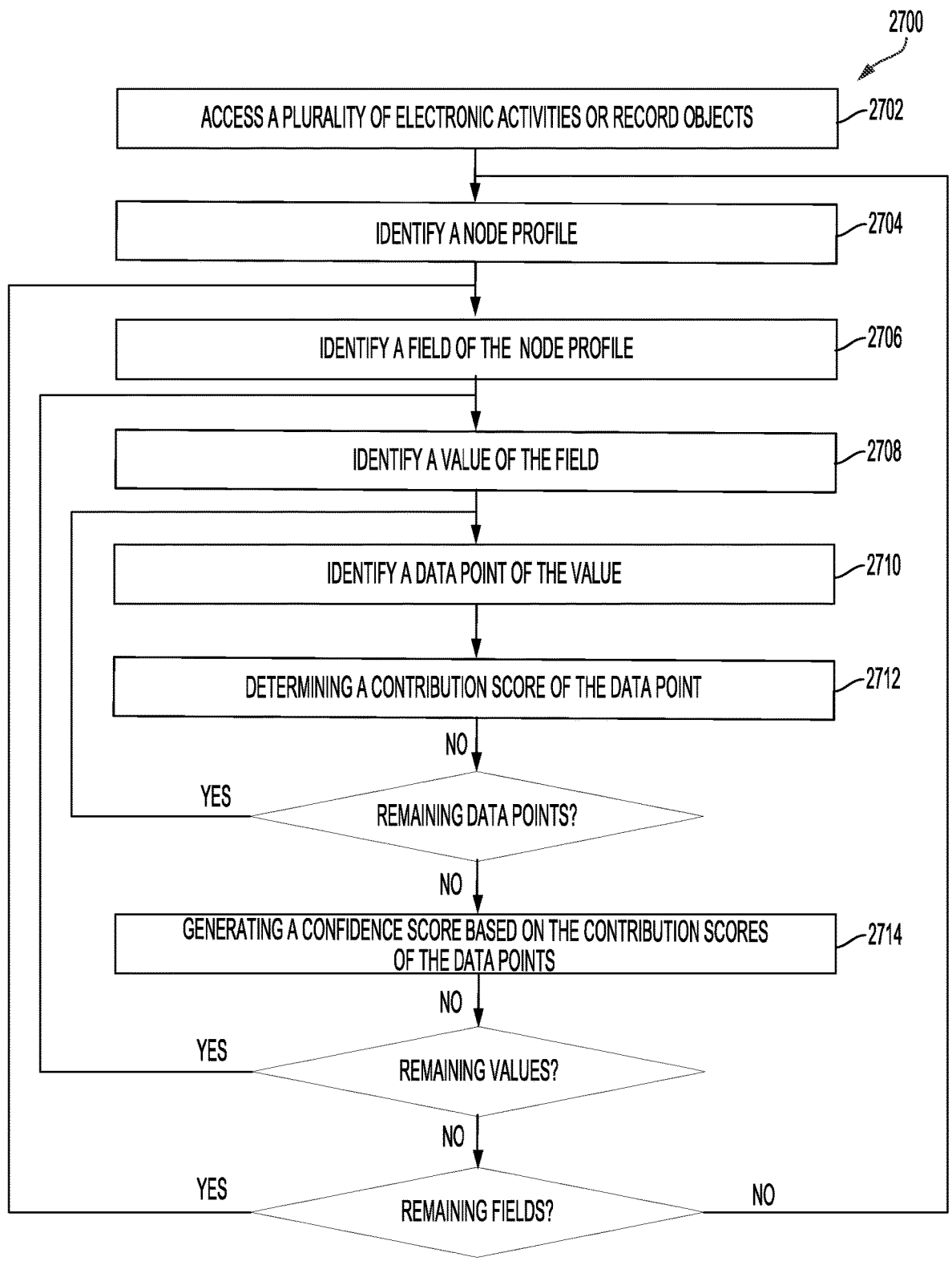
FIG. 27 illustrates a block diagram of an example method to generate confidence scores of values of fields based on data points according to embodiments of the present disclosure.

FIG. 27 illustrates a method 2700 to generate confidence scores of values of fields based on data points. The method 2700 can include accessing a plurality of electronic activities or record objects (BLOCK 2702). The method can identify, from a plurality of node profiles maintained by the data processing system, a first node profile that includes a plurality of fields, each having corresponding one or more values (BLOCK 2704). The method can identify, for a given node profile, a field of the plurality of fields (BLOCK 2706). The method can then identify, for a given field of the plurality of fields of the node profile, a given value of one or more values associated with the field (BLOCK 2708). The method can then identify, for the given value, a data point of one or more data points identified in the value data structure of the value (BLOCK 2710). The method can determine a contribution score of the data point (BLOCK 2712). The method can then determine, if the value data structure of the value includes any other data points that support the value. If additional data points exist in the value data structure, the method can determine the contribution score of the additional data points until the contribution score of each of the data points of the value data structure are determined. If no other data points exist, the method can determine a confidence score of the value based on the contribution scores of one or more of the data points supporting the value (BLOCK 2714). The method can optionally determine if the field of the node profile includes additional values for which a confidence score is to be determined. The method can then repeat the steps from blocks 2708-2714. The method can similarly determine the confidence scores of values of other fields by repeating Blocks 2706-2014. The method can similarly determine the confidence scores of values of other node profiles by repeating Blocks 2704-3014.

In further detail, the data processing system can access a plurality of electronic activities or record objects (BLOCK 2702). The data processing system can access the electronic activities can access a plurality of electronic activities via one or more servers hosting or storing the electronic activities. The servers can store electronic activities transmitted from or received by accounts corresponding to an enterprise. For instance, the servers can be mail servers, phone log servers, calendar servers or any other entity that can store emails, calendar events, phone logs, or other electronic activities of accounts associated with an enterprise, such as a company. The data processing system 9300 can be provided authorization to access the emails stored on one or more email servers through an API or an HTTP method (e.g., a GET method). Similarly, the data processing system can access record objects of one or more systems of record. Each system of record can be managed, owned, maintained or otherwise accessed by an enterprise. The enterprise can provide the data processing system access, permission or other information that enables the data processing system to access data included in the system of record. The data processing system can access the electronic activities and the record objects of one or more data source providers.

The data processing system 9300 accessing the plurality of electronic activities and/or the record objects of the system of record can further maintain a plurality of node profiles. The node profiles can be representations of nodes and includes fields that have values that are generated by data included in the plurality of electronic activities and/or record objects accessible by the system. The system can update the plurality of node profiles using at least one of the plurality of electronic activities or the plurality of record objects. Details regarding node profiles are described herein.

The method 2700 can include identifying a node profile from the plurality of node profiles maintained by the data processing system (BLOCK 2704). The data processing system can identify a node profile of the plurality of node profiles for which the system is to compute one or more confidence scores for one or more values of the node profile. The system can identify a particular node profile or can identify multiple node profiles for which the confidence scores of values of the node profile are to be determined. In some embodiments, the system can be configured to periodically compute confidence scores of node profiles. The system can identify a first node profile responsive to an update to the first node profile or responsive to linking an electronic activity or record object to the first node profile. In some embodiments, the system can identify a first node profile responsive to an update to the first node profile or responsive to adding an entry identifying an electronic activity or record object to a value data structure of a value of a field of the first node profile.

The method 2700 can include identifying a field of the node profile (BLOCK 2706). The system can identify a field of the node profile for which to compute the one or more confidence scores for the one or more values of the field. In some embodiments, the system can identify a first field of a plurality of fields of the identified node profile responsive to an update to the field of the node profile or responsive to adding an entry identifying an electronic activity or record object to a value data structure of a value of the field.

The method 2700 can include identifying a value of the field for which to determine a confidence score for which to compute the confidence score (BLOCK 2708). In some embodiments, the system can identify a value of one or more values associated with the field identified in BLOCK 2706. The system can identify the value responsive to an update to the value of the field or responsive to adding an entry identifying an electronic activity or record object to a value data structure of the identified value.

In some embodiments, the value of the field of the node profile includes a first value of a first field of the node profile. The contribution score of the data point can be a first contribution score of a first data point. The confidence score can be a first confidence score of a first value. The data processing system 9300 can identify a second value data structure of a second field of the node profile. The second value data structure corresponds to a second value of the second field and further includes one or more second entries corresponding to respective one or more second data points that support the second value of the second value data structure. For example, and referring to Table 1, the value data structure corresponding to field-value pair First Name: Johnathan can include the value Johnathan and a first data point DP ID101 and a second data point DP ID225. The data processing system 9300 can determine, for at least one second data point of the one or more second data points of the second value of the second field of the node profile, a second contribution score of the second data point based on a time corresponding to when the second data point was generated or updated. For example, and referring to Table 1, a contribution score of 0.4 can be determined for DP ID225 based on the time corresponding to when the data was generated or updated (Feb. 18, 2017, 2 PM ET). The data processing system 9300 can generate a second confidence score of the second value of the second field of the node profile based on the second contribution score of the at least one second data point. For example, and referring to Table 1, the confidence score of field-value pair First Name: Johnathan can be updated based on the DP ID225.

To determine a confidence score of the value identified in BLOCK 2708, the method 2700 can include identifying a data point that supports the existence of the value (BLOCK 2710). The data processing system can identify a data point of the value by identifying an entry of a value data structure of the value. The entry can identify the data point, a source of the data point, a trust score of a source of the data point and a timestamp associated with the data point. As described herein, for any given value of a field of a node profile, the value is associated with a value data structure that includes one or more entries. Each entry of the one or more entries can correspond to one or more data points that include a string that matches the value of the value data structure. For example, and referring to Table 1, for the field-value pair First Name: John, the entry corresponding to Data Point 1 can include a string in the electronic activity EA-003 that matches the value John. Each data point of the one or more data points can identify a respective electronic activity of the plurality of electronic activities or a respective record object of the plurality of record objects. For example, and referring to Table 1, for the field-value pair Field: Director, Data Point 1 (DP ID101) can be associated with electronic activity EA-003, Data Point 2 (DP ID2265) can be associated with system of record SOR-012, and Data Point 3 (DP ID243) can be associated with electronic activity EA-117. The data point identifies an electronic activity of the plurality of electronic activities or a record object of a system of record previously linked by the data processing system to the node profile associated with the value The method 2700 can include determining a contribution score of the data point (BLOCK 2712). The data processing system can determine for at least one data point of the one or more data points included in a respective value data structure of the value (determined in BLOCK 2708) of the field (determined in BLOCK 2706) of the node profile (determined in BLOCK 2704), a contribution score of the data point based on a time corresponding to when the data point was most recently generated or updated. For example, and as illustrated in FIG. 26, the contribution score $CS_{a1}$ can be based on the time $T_{a1}$ when the data point $DATA\_PT_{a1}$ was generated or updated.

In some embodiments, the data processing system 9300 can determine for the at least one data point of the one or more data points, the contribution score of the data point includes determining, for the at least one data point, a contribution score of the data point based on a trust score assigned to a source of the data point, the trust score determined based on a type of source of the data point. For example, and with reference to Table 1, the contribution score of DP ID101 corresponding to field-value pair First Name: John is 0.6 and is based on the trust score of 100. In some embodiments in which the data point is a record object, the trust score assigned to the data point is based on a health of the system of record from which the record object was accessed. In some embodiments, the health of the system of record from which the record object was accessed is determined based on comparing field values of object fields included in record objects of the system of record to node profile field values of fields of one or more node profiles having respective confidence scores above a predetermined threshold.

The method 2700 can include generating a confidence score based on the contribution scores of the data points (BLOCK 2714). The data processing system 9300 can generate a confidence score of the value of the field of the node profile based on the contribution score of the at least one data point. In some embodiments, the data processing system can generate the confidence score of the value based on the contribution score of each of the data points identified in entries of the value data structure of the value. For example, and as illustrated in FIG. 26, the confidence score C1 is a function of the contribution scores $CS_{a1}$, $CS_{a2}$, . . . , $CS_{aN}$. The confidence score C2 can be based on the contribution scores $CS_{b1}$, $CS_{b2}$, . . . , $CS_{bN}$. The confidence score C3 can be based on the contribution scores $CS_{a1}$, $CS_{a2}$, . . . , $CS_{aN}$.

In some embodiments, a data point identifies an electronic activity is an automatically generated bounce back electronic activity. Examples of bounce back electronic activity can include emails indicating that the destination email address is invalid or incorrect, the person is no longer with company, among others. In some embodiments, the node profile includes a first field having a first value data structure identifying a first value. The first value can be assigned to the first field by linking a first electronic activity to the node profile In some embodiments the data processing system can receive a second electronic activity. The data processing system can determine that the second electronic activity includes or supports the value of the field of the node profile. For example, and with reference to Table 1, an electronic activity EA-098 can include a value John of the field First Name. The data processing system can match the electronic activity to the node profile and add an entry in one or more value data structures corresponding to field-value pairs of the node profile that are supported by the electronic activity. The system can determine which field-value pairs of the node profile are supported by the electronic activity as this information is used for matching electronic activities to node profiles. The system can then determine a contribution score of the second electronic activity for each field-value pair of the node profile that the second electronic activity supports. The data processing system can generate a second contribution score of the second electronic activity for the value of the field of the node profile as described herein. For example, and with reference to Table 1, a contribution score for DP ID458 associated with electronic activity EA-098 and field-value pair First Name: John can be generated. The data processing system can update the confidence score of the value based on the contribution score of the second electronic activity. The confidence score for field-value pair First Name: John can be updated based on the contribution score of DP ID458 that identifies the electronic activity EA-098.

In some embodiments, the data processing system can identify the first electronic activity. The first electronic activity can be linked to the first node profile by identifying from data included in the first electronic activity, a plurality of strings. For example, and as illustrated in FIG. 25, data included in electronic activity 652*a* can be identified. The strings that can be identified from the data can include "John Smith", "Director", "ACME", "555-5439", "617.555.2000", "j@acme", "a@acme", and "Abigail." In some embodiments, the electronic activity includes a signature block in the electronic activity and linking the electronic activity to the node profile includes the data processing system 9300 extracting a plurality of strings from the signature block of the electronic activity.

The data processing system can identify a plurality of candidate node profiles to which to link the electronic activity by comparing one or more strings of the plurality of strings to values of fields of respective candidate node profiles. For example, the data processing system can identify that node profile NPID-1 and node profile NPID-2 are candidate node profiles because they contain field-value pairs associated with the strings identified from the data included in electronic activity 652*a*. The data processing system can generate, for each candidate node profile, a match score indicating a likelihood that the electronic activity is transmitted or received by an account corresponding to the candidate node profile based on comparing the plurality of strings included in the electronic activity to values of fields included in the candidate node profile. The match score can be based on a number of fields of the node profile including a value that matches a value or string in the electronic activity. The match score can also be based on different weights applied to different fields. The weights may be based on the uniqueness of values of the field, as mentioned above. The data processing system can be configured to match the electronic activity to the node with the greatest match score. In some embodiments, the data processing system can match the electronic activity to each candidate node that has a match score that exceeds a predetermined threshold. Further, the data processing system can maintain a match score for each electronic activity to that particular node profile, or to each value of the node profile to which the electronic activity matched. By doing so, the data processing system can use the match score to determine how much weight to assign to that particular electronic activity. The data processing system 9300 can link the first electronic activity to the first node profile based on the match score of the first node profile. For example, the strings "John Smith", "Director", "ACME", "555-5439", "617.555.2000", and "j@acme" can have a high match score to node profile NPID-1 and be linked to node profile NPID-1. The strings "a@acme" and "Abigail" can have a high match score to node profile NPID-2 and can be linked to node profile NPID-2.

In some embodiments the data processing system 9300 can identify a record object of a system of record previously not matched to the value of the field of the node profile. The data processing system 9300 can determine that the record object includes the value of the field of the node profile. The data processing system can then add an entry identifying the record object to a value data structure of the value. The data processing system 9300 can generate a contribution score of the record object. The contribution score of the record object indicates a level of contribution of the record object to the value of the field. For instance, if the value is the name "John" for the field "First Name" of a particular node profile, the record object can be identified in an entry of the value data structure of the field-value pair "First Name: John" for the particular node profile if the record object includes a corresponding name-value pair that supports the field-value pair "First Name: John" for the particular node profile. To do so, the data processing system will first have to match the record object to the particular node profile and then add an entry to a value data structure of the field-value pair "First Name: John." The data processing system can compute a new confidence score for the value based on the contribution score of the record object.

In some embodiments the data processing system 9300 can receive a subsequent electronic activity. The data processing system 9300 can link the electronic activity to the node profile by including one or more entries identifying the electronic activity to one or more value data structures corresponding to one or more values of one or more fields. The data processing system can generate for each entry identifying the electronic activity, a contribution score of the electronic activity, the entry corresponding to a respective value data structure of a respective value of a respective field. The data processing system can generate respective confidence scores for the values based on the respective contribution scores of the electronic activity.

20. Systems and Methods for Determining the Shareability of Values of Node Profiles The present disclosure relates to systems and methods for determining the shareability of values of node profiles of a node profile database. A system of record can maintain record objects each corresponding to different entities and record types. The record objects can be generated using data provided by a data source provider. Each record object can include one or more fields. Each field of each record object can be attributed with one or more values. Concurrently, a node graph generation system can maintain node profiles each corresponding to different entities and generated using electronic activities among different entities or record objects of one or more systems of record. Each node profile can include one or more fields. Each field can be attributed with or include one or more values. Each value can be attributed with a value data structure. Each value data structure can include entries identifying data source providers that are associated with the value of the value data structure. For example, a data source provider can be associated with a value if the data source provider provided the value to the node graph generation system with a record object of an electronic activity.

The entries in the value data structures of the values can be used to determine whether information about a node can be shared with other systems of record of other data source providers or other users corresponding to other data source providers. The node graph generation system can identify particular types of fields of node field-value pairs as having a predetermined type. The predetermined types can be selected by an administrator, and may correspond to types of information that may be subject to sharing restrictions. In some embodiments, the predetermined types can be defined by the node graph generation system. A value data structure of a field can have a number of values or a number of data source providers who contributed to the value of the field, and this number may be compared with a threshold. The threshold can be associated with a number of data source providers needed for a value of a node field-value pair to be shareable with other systems of record and/or data source providers. If the number of data source providers associated with a value satisfies (e.g., meets or exceeds) the predetermined threshold, the node graph generation system 200 can share the value with other data source providers and/or node profiles. Otherwise, sharing of the value with other data source providers or node profiles may be subject to restriction.

With reference to the node graph generation system 200 of FIG. 4, if a value is determined not to be shareable by the node graph generation system 200 (e.g., if the number of data source providers associated with the value does not satisfy a threshold), the node graph generation system 200 can generate a restriction tag associated with the value. In some implementations, the node graph generation system 200 can generate a restriction tag if a value of a node field-value pair is only associated with one entry in an associated value data structure. The node graph generation system 200 can store the restriction tag in a data structure within the node graph generation system 200. The node graph generation system 200 can use the restriction tag to restrict populating other node profiles of a plurality of node profiles or systems of record with the value associated with the restriction tag. The node graph generation system 200 can restrict access by ignoring requests for the restricted value or by sending a signal to a requesting data source provider of a system of record indicating the value is unavailable.

In some implementations, the node graph generation system 200 can also remove a restriction tag that was previously associated with a value from the data structure within the node graph generation system 200. For example, the node graph generation system 200 can extract more field value pairs from a record object or an electronic activity of a data source provider unique from other data source providers associated with a restricted value. The node graph generation system 200 can update the value data structure of the restricted value to include an entry including an identifier of the unique data source provider and compare a new number of data source providers identified in entries of the value to a threshold. If the new number of data source providers satisfies the predetermined threshold, the node graph generation system 200 can remove the restriction tag associated with the value from the data structure of the node graph generation system 200 and share the value with other node profiles and/or data source providers.

Figure 28:
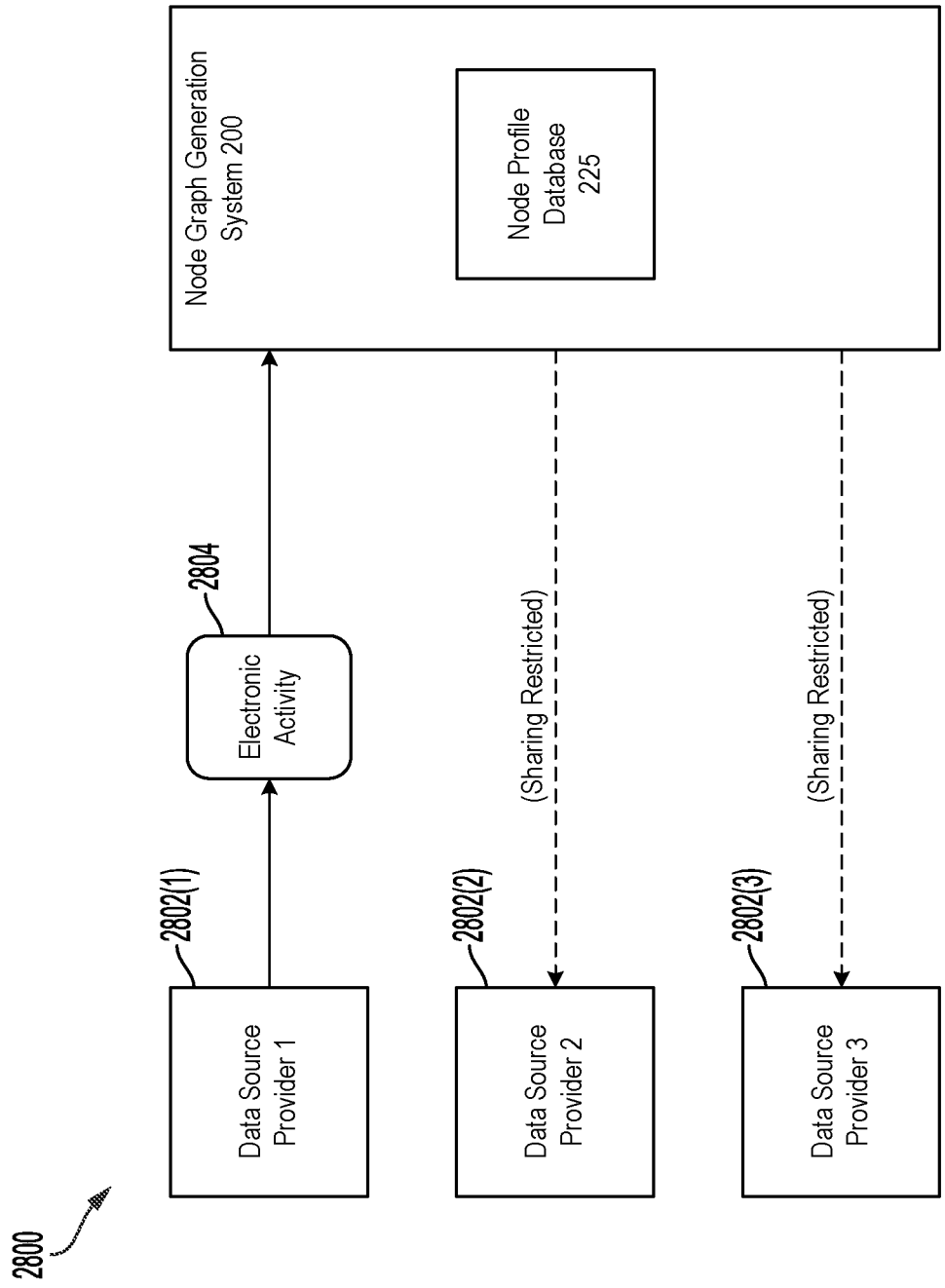
FIG. 28 illustrates a block diagram of an example system for determining the shareability of values of node profiles, according to embodiments of the present disclosure.

Referring now to FIG. 28, illustrated is a block diagram of a system 2800 for determining the shareability of values of node profiles, according to embodiments of the present disclosure. Some of the components of the system 2800 may correspond to components of the data processing system 9300 of FIG. 3 or the node graph generation system 200 of FIG. 4. Thus, FIG. 3, FIG. 4 and FIG. 28 are described together below.

The system 2800 can include a plurality of data source providers 2802(1)-2802(3) (generally referred to as data source providers 2802). For example, in the system 2800, a data source provider 2802(1) can transmit or provide an electronic activity 2804 to the node graph generation system 200, in some implementations. The node graph generation system 200 can receive the electronic activity 2804 and determine whether to share node field-value pairs gathered from the electronic activity 2804 with the other data source providers 2802(2) and 2802(3). In some implementations, the node graph generation system 200 can determine whether to share the node field-value pairs of the electronic activity 2804 based on a number of data source providers that have node field-value pairs that correspond with the gathered node field-value pairs (e.g., based on whether the number exceeds a threshold). If the node graph generation system 200 determines that the number of data source providers having the node field-value pairs does not exceed a threshold, the node graph generation system 200 can place a restriction tag in a data structure of the node field-value pair and restrict sharing the node field-value pair with other data source providers (e.g., data source providers 2802(2) and 2802(3)). However, if the node graph generation system 200 determines that the number of data source providers having the node field-value pairs exceeds the threshold, the node graph generation system 200 can share the node field-value pairs with other data source providers. In some embodiments, the restriction tag can be an identifier, label or other marker that the node graph generation system 200 or the system 2800 can use to restrict the value of the node field-value pair from being shared with other data source providers, their systems of record or nodes corresponding to the other data source providers, for instance, employees of companies that correspond to as the data source providers.

The node graph generation system 200 is shown to include a node profile database 225. The node profile database 225 can be a database configured to maintain node profiles and data (e.g., node field-value pairs) associated with the node profiles. Each node profile of the node profiles can correspond to a unique entity. For example, one node profile may correspond to a person named "John Smith," another node profile may correspond to a person named "Abagail Xu," and another node may correspond to a company with the name "NewCo." In some embodiments, at least one node profile can be generated using an electronic activity (e.g., electronic activity 2804). The electronic activity 2804 can be provided by data source provider 2802(1) or any other data source providers. The node profiles stored in the node profile database 225 can be generated based on any number of electronic activities.

Each node profile can have a set of fields each associated with one or more values. The set of fields can vary based on the type of entity of the node profile. For example, a set of fields of a node profile for a person can include, among others: a field for a first name of the entity; a field for a last name of the entity; a field for a company entity associated with the entity; a field for a phone number of the entity; and a field for an e-mail address of the entity. Each field of the node profiles can be assigned or associated with one or more values. For example, the field for the first name of an entity in a node profile can be associated with the values "John" or "Jonathan." Each field and the associated one or more values can form a node field-value pair. The fields of each node profile corresponding to a company can include, among others: a field for company name; a field for an email address; a field for a phone number; and a field for a location of the entity.

In some embodiments, node profiles and/or node field-value pairs of the node profiles can be generated based on record objects and/or electronic activities of systems of record of data source providers that the node graph generation system 200 accesses. The node graph generation system 200 can access the systems of record associated with the data source provider and analyze record objects of the systems of record to identify values of object field-value pairs of the record objects. The values of the object field value pairs can correspond to values of node field-value pairs of node profiles of the node graph generation system 200. The node graph generation system 200 can identify and add the values of the object field-value pairs to a data structure of a corresponding node field-value pair. In some embodiments, at least one node profile or node field-value pair of the node graph generation system 200 can be aggregated from multiple systems of record.

In some embodiments, the record data extractor 230 of the node graph generation system 200 can extract values of field value pairs included in a record object of a system of record that are also included in a corresponding node profile (e.g., a node profile associated with the same entity as the record object) maintained by the node graph generation system 200. The record data extractor 230 can match the node profile to the record object by comparing one or more node field-value pairs of the node profile to one or more corresponding object field-value pairs of the record object. Object field-value pairs can correspond to node field-value pairs if the object field-value pairs and node field-value pairs are associated with the same type of field. For example, the record data extractor 230 can compare first name and last name field-value pairs of a node profile for John Smith with first name and last name field-value pairs of record objects in a system of record of data source provider 2802(1). If the record data extractor 230 can find a record object with the same field-value pair values (e.g., John for the first name field and Smith for the last name field) in the system of record, the record data extractor 230 can match the record object with the same field-value pairs as the node profile. In some embodiments, the record data extractor 230 can extract object field-value pair values from the matching record object and add the values to corresponding data structures of the node field-value pair values. The node profile manager 220 can update the corresponding value data structures of the matched node profile with an entry corresponding to the extracted object field-value pairs.

In some embodiments, values of node field-value pairs of node profiles can include or be associated with a value data structure that stores at least one entry comprising an identifier identifying an electronic activity or record object. The entry can include a source of the electronic activity or the record object identified by the identifier. The entry can include a timestamp of the electronic activity or the record object identified by the identifier. Thus, each entry can include information, identified with an identifier, about the record objects and electronic activities the node graph generation system 200 used to identify or extract the value of the value data structure. The information can include, but is not limited to, the value, the record object or electronic activity that the value was extracted from, the data source associated with the record object or electronic activity that the value was extracted from, the time that the node graph generation system 200 accessed the record object or electronic activity and a trust score of the data source. The information can include any amount or type of information. The value data structure can include any number of entries.

For example, the record data extractor 230 may identify a record object of a system of record as a matching record object to a node profile of node graph generation system 200. The record data extractor 230 can extract values of object field-value pairs of the matching record object. The node profile manager 220 of node graph generation system 200 can update value data structures of corresponding node field-value pairs of the node profile based on the extracted values and information about the matching record object (e.g., the data source provider associated with the matching record object, etc.). In some embodiments, electronic activity parser 210 of node graph generation system 200 can perform a similar process to extract data from electronic activities. The node profile manager 220 can use the data extracted from electronic activities to update value data structures in a similar manner. Details of matching electronic activities to node profiles are described above at least with respect to Section 17. Details of matching record objects to node profiles are described above at least with respect to Section 18.

In some embodiments, the node profile manager 220 can update value data structures with new entries. The node profile manager 220 can extract electronic activity field-value pairs and/or object field value pairs from electronic activities and/or record objects and update value data structures that correspond to the extracted field-value pairs. The node profile manager 220 can add an entry to each value data structure being updated. In some embodiments, the value data structure can include a counter indicating a number of entries that have been used to update the value data structure. The node profile manager 220 can increment the counter for each entry of the value. In some embodiments, the node profile manager 220 can increment the counter for each data source provider associated with the data structure.

In some embodiments, the node profile manager 220 can identify, for a node profile, a value of a node field-value pair corresponding to a predetermined type of field that is included in one or more electronic activities or record objects accessed from a set of data source providers. The number of data source providers of the set of data source providers may include fewer than a predetermined threshold number of data source providers. The predetermined type of field may be selected by an administrator. In some embodiments, the predetermined type of field may be selected based on whether the administrator determines the type of field to include private information. For example, an administrator may determine a mailing address field to be private information that should not be shared with other systems of record or users that may not be entitled to have access to the mailing address. Consequently, the administrator may associate a predetermined threshold of data source providers with mailing address fields of node profiles. The administrator may associate a predetermined threshold with any type of field such as, but not limited to, mailing address, phone number, email, first name, last name, company of employment, etc. In some embodiments, the administrator may select the predetermined type of fields to be the fields that identify how to contact the entity associated with the node profiles (e.g., the phone number, email, mailing address etc.). The administrator may not associate predetermined thresholds with fields that may be more publicly known (e.g. first name, last name, company of employment, etc.).

The predetermined threshold of data source providers may be a number of data source providers that the administrator deems to be sufficient to consider a predetermined type of field public information, non-sensitive information, or otherwise shareable information. For instance, the administrator may determine phone numbers to be a type of field that should remain private or subject to sharing restrictions when a phone number is not known by a threshold number of entities (e.g., data source providers). As a result, the administrator can associate a predetermined threshold with phone number fields of node profiles. For example, the administrator may determine that the phone number of a person is private unless five other companies, or data source providers, have the phone number of the person. The administrator may then set the predetermined threshold associated with phone numbers to be five. In some implementations, the administrator may set the predetermined threshold of data source providers to be any number (e.g., one, two, three, four, five, six, seven, eight, nine, ten, or more than ten, etc.). The administrator can set predetermined thresholds for any number of predetermined types of fields, each predetermined threshold can be unique to each predetermined type of field.

The node profile manager 220 can determine the threshold to be met for a value in a predetermined type of field of a node profile if the node profile manager 220 determines the value was generated based on data extracted from record objects and/or electronic activities of enough data source providers to satisfy or exceed the predetermined threshold. The node profile manager 220 can determine the number of data source providers that are associated with a value of a node field value pair based on the counter the node profile manager 220 increments and maintains for each unique data source that is associated with a value data structure of the value. A unique data source may be a data source different from the other data sources that were used to support information included in the value data structure.

In some embodiments, the node profile manager 220 can generate a restriction tag that can be used to restrict the node graph generation system 200 from populating other node profiles of the plurality of node profiles or systems of record with a value of a node field-value pair of a node profile that is not associated with a number of data source providers that exceeds the predetermined threshold. Thus, the restriction tag can indicate that a particular value is not associated with enough systems of record to exceed a predetermined threshold associated with the value. For example, a node profile of the node profile database 225 may have a value of a field-value pair for a phone number. An administrator may have selected phone number fields of the node profiles to be subject to sharing restrictions based on a predetermined threshold, which may indicate that the value of the phone number field of the node profile must be associated with at least four data sources. If the value of the phone number field of the node profile is associated with only three data sources, the node profile manager 220 may generate a restriction tag and tag the value of the phone number field of the node profile with the restriction tag. The restriction tag may restrict the node profile manager 220 from provisioning, or populating, the value of the phone number of the node profile to other node profiles or systems of record.

In some embodiments, the node profile manager 220 can store generated restriction tags in one or more data structures associated with the values determined to be below a predetermined threshold and the node profiles with which the values are associated. The one or more data structures can be associated with the node graph generation system 200 and can store any number of restriction tags. The restriction tags can indicate which node profiles include field-value pairs and/or the field-value pairs the restriction tags apply to. For example, if node profile manager 220 generates a restriction tag for the mailing address field of a first node profile, the restriction tag can be stored in a data structure within the node graph generation system 200 indicating that the node profile and/or the mailing address field-value pair of the first node profile is subject to a sharing restriction.

In some embodiments, the node profile manager 220 can update a value data structure with a new entry including data extracted from a new electronic activity from a data source provider unique to the data source providers that are associated with entries in the value data structure. The value data structure may be associated with a restriction tag in a data structure. In some instances, by updating the value data structure with an entry from the unique data source provider, the node profile manager 220 can determine that the number of data source providers associated with entries of the value data structure satisfy a predetermined threshold and remove the restriction tag from the data structure.

To update the data structure to remove a restriction tag, the node profile manager 220 can access a new electronic activity associated with a data source provider. The node profile manager 220 can access the new electronic activity from a data source provider. For example, a company can provide to the node graph generation system 200 an email sent or received by an electronic account associated with the company. The electronic activity parser 210 can analyze the newly received electronic activity and identify an electronic activity field-value pair that matches a node field-value pair of a node profile stored in the node profile database 225.

The electronic activity parser 210 can identify electronic activity field-value pairs that match node field-value pairs to identify a matching node profile. The electronic activity parser 230 can match the electronic activity field-value pairs with node field-value pairs in a manner similar that used by the node profile manager 220 to match object field-value pairs of record objects with node field-value pairs of node profiles. In some implementations, the electronic activity parser 210 can use natural language processing techniques to identify electronic activity field-value pairs of the electronic activity. For example, electronic activity parser 210 can access an email from a data source provider and determine values for a first name field, a last name field, a phone number field, and a company field based on a signature on the bottom of the email. The electronic activity parser 210 can use key word cues to identify the values for the fields. The electronic activity parser 210 can compare the extracted electronic activity field-value pairs with node field-value pairs of node profiles to identify which node profile the electronic activity is associated with. Further, the electronic activity parser 210 can identify electronic field-value pairs that match (e.g., have the same value and the same field) as a node field-value pair of the identified node profile.

The node profile manager 220 can identify the extracted and matched values of the electronic activity field-value pairs and add an entry to the value data structures of the corresponding node field-value pairs of the matching node profile. The node profile manager 220 can include information about the electronic activity in the value data structure including which data source provider the electronic activity is associated with in the entry in the value data structure. If the data source provider associated with the value of the node field-value pair is unique from the data source providers already associated with the value. The node profile manager 220 can increment the counter indicating the number of unique data source providers associated with the value. If the additional entry results in the number of unique data source providers of the value satisfying a threshold, node profile manager can update the data structure storing a restriction tag associated with the value and/or node field-value pair to remove the restriction tag.

Continuing with the example above, the node profile manager 220 can identify electronic field-value pairs of the email matching node field-value pairs of the node profile. The node profile manager 220 can add an entry to a value data structure associated with a value associated with a matching node field-value pair (e.g., a field-value pair having a phone number type). The entry may be the second entry and may be associated with a data source provider different from the data source provider of the first entry. An administrator may have set a predetermined threshold that is associated with phone numbers to be satisfied if at least two data source providers are associated with entries of the value data structure associated with a phone number value. Continuing with this example, there may have been a restriction tag associated with the phone number value of the node profile in a data structure of the node graph generation system 200, because previously the value came only from one data source provider. After the additional entry is added, the number of data source providers of the value data structure of the phone number value satisfies the predetermined threshold associated with the value of the phone number. As a result, the node profile manager 220 can remove the restriction tag of the phone number from the data structure.

In some embodiments, values of node field-value pairs of node profiles that do not have a restriction tag associated with them can be shared to a system of record having a record object that is matched to a node field-value pair. For example, if a node profile has a first name field-value pair with a value of "John" and there is no predetermined threshold for shareability of this field, or if there are a number of data sources that provided electronic activities or record objects that support the value "John" of the node profile to satisfy the predetermined threshold, the node graph generation system 200 can share the first name field of the node profile for John with another system of record that has a record object associated with John or that requests information about the node profile of John. The node graph generation system 200 can also share the node profile of John with other node profiles stored in the node profile database 225.

Continuing with the example above, if the node profile for John has a phone number field value and there are not enough data source providers that provided electronic activities or record objects that support the phone number field value of John to satisfy a predetermined threshold, the node graph generation system 200 may restrict sharing the phone number field-value with another system of record because of a restriction tag associated with the phone number field of John. If an entry gets added to the phone number field-value pair value of John so the number of data source providers that are associated with John exceeds a threshold, node graph generation system 200 can remove the restriction tag and share the value of the phone number field of John with another system of record or with another user of the node graph generation system.

In some embodiments, the node profile manager 220 can generate a restriction tag for a particular node field-value pair based on a request received from a computing device. For example, an administrator of one of the data source providers 2800 can make the request from the computing device. The request can be transmitted over a network and can identify a particular node field-value pair of a node profile. The node profile manager 220 can receive the request and generate a restriction tag for the identified node field-value pair, similar to the process that the node profile manager 220 uses generate a restriction tag for node field-value pairs as described above. The node profile manager 220 can store the generated restriction tag in a data structure within the node graph generation system 200.

For example, an administrator of Company X can send a request, via a computing device of the administrator, to the node graph generation system 200 requesting for the node graph generation system 200 to restrict access to the mailing address of an employee, John Smith, of Company X. The node graph generation system 200 can receive the request and identify the node profile and the node field-value pair associated with the mailing address of John Smith. The node profile manager 220 can generate a restriction tag associated with the identified field-value pair indicating that the mailing address of John Smith may not be shared with systems of record that John Smith is not already associated with. The node profile manager 220 can store the restriction tag in a data structure within the node graph generation system 200.

In some embodiments, the node profile manager 220 can generate node field-value pairs based on there being only one entry in a value data structure associated with a value of a node field-value pair. The node profile manager 220 can receive a new electronic activity including field-value pairs and match the electronic activity field-value pairs to a node profile using the methods described above. In some instances, an electronic activity field-value pair may not have a corresponding node field-value pair in the matched node profile. Consequently, the node profile manager 220 can generate the missing node field-value pair with the value and field of the corresponding field-value pairs of an electronic activity field-value pair. For example, if the node profile manager 220 extracts electronic field-value pairs associated with a phone number, a mailing address, a first name, and a last name of a company employee from an email of the employee, the node profile manager 220 may match the electronic field-value pairs with a node profile of the employee within the node profile database 225 based on the first name and last name electronic activity field-value pairs matching first name and last name node field-value pairs of the node profile. The node profile manager 220 can update each entry of the value data structures of the values of the matched node profile to include the matched electronic field-value pairs. In some instances, a phone number value or field-value pair of the employee may not be included in the node profile of the employee. The node profile manager 220 can determine the phone number node field-value pair is not present in the node profile of the employee and generate a phone number field-value pair including the phone number electronic field-value pair extracted from the email.

In some embodiments, the node profile manager 220 can determine whether the generated field-value pair is a predetermined type of field that may be subject to restriction if a value of the field-value pair is not supported by a number of data source providers meeting or exceeding a predetermined threshold (e.g., one). The node profile manager 220 can identify the updated field-value pair and identify the type of field of the field-value pair. The node profile manager 220 can compare the type with the predetermined types set by the administrator. If the types match, then the node profile manager 220 can determine the type is of the predetermined type of field. If the field of the generated node field-value pair is of the predetermined type, the node profile manager 220 can generate a restriction tag and store the restriction tag in a data structure within the node graph generation system 200.

Continuing with the example above, the node profile manager 220 can determine if the phone number type of the node field-value pair is a predetermined type as set by an administrator of the node graph generation system 200. If the phone number type is of the predetermined type, the node profile manager 220 can generate a restriction tag associated with the phone number and store the restriction tag in a data structure within the node graph generation system 200. As a result of the restriction tag, provisioning or sharing of the value associated with the tag with other systems of record may be restricted.

Figure 29:
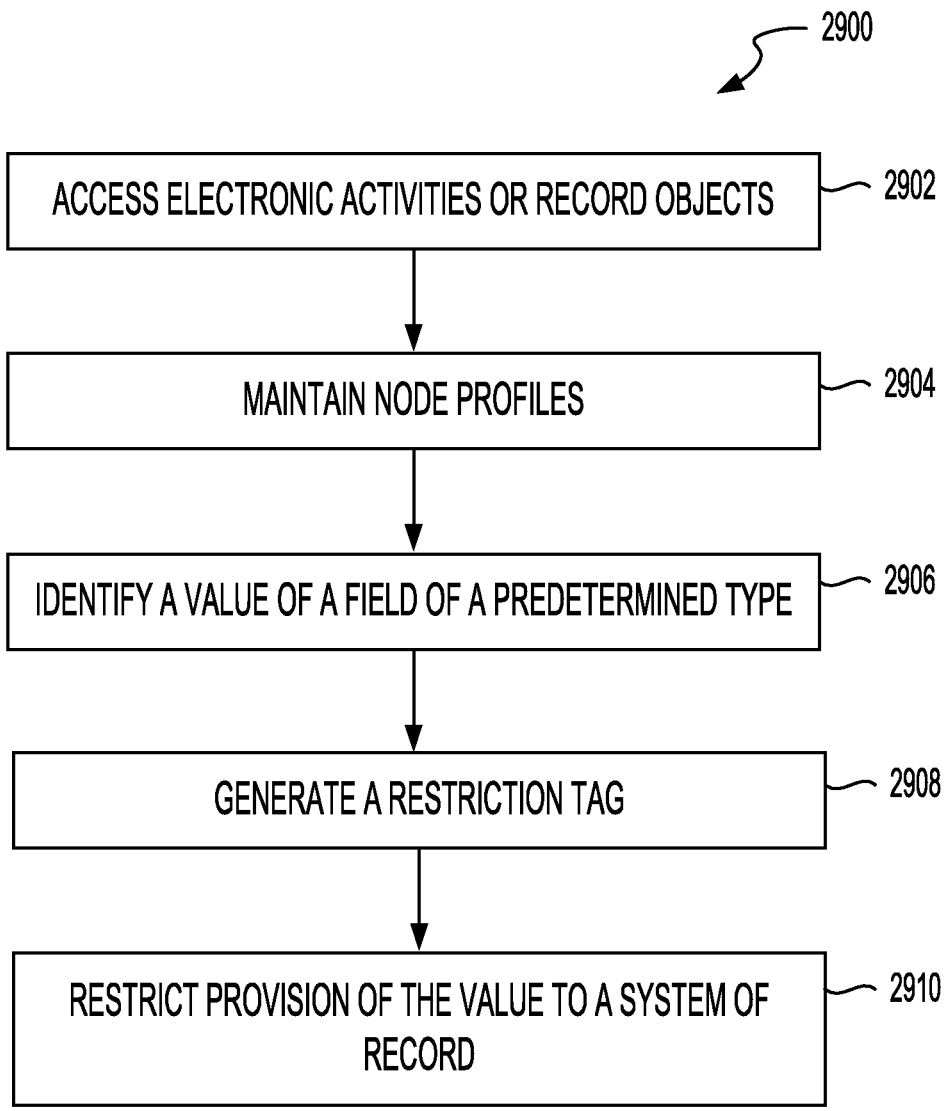
FIG. 29 illustrates a flow diagram of an example method for determining the shareability of values of node profiles, according to embodiments of the present disclosure.

FIG. 29 illustrates a flow diagram of an example method 2900 for determining the shareability of values of node profiles, according to embodiments of the present disclosure. The method 2900 can be implemented or performed using any of the components described above in conjunction with FIGS. 1-28 (e.g., the node graph generation system 200) or the server system 3000 detailed below in conjunction with FIG. 30. In brief overview, a data processing system can access electronic activities or record objects (BLOCK 2902). The data processing system can maintain node profiles (BLOCK 2904). The data processing system can identify a value of a field of a predetermined type (BLOCK 2906). The data processing system can generate a restriction tag (BLOCK 2908). The data processing system can restrict provision of the value to a system of record (BLOCK 2910). Each of the acts 2902-2910 can be conducted by components of the node graph generation system 200 as discussed with reference to FIG. 28.

In further detail, a data processing system (e.g., the node graph generation system 200) can access electronic activities or record objects (2902). Each record object can correspond to a record object type and can be associated with a unique entity. Each record object can have one or more fields. Each field of the record object can be attributed with one or more values. Each field and one of the attributed values can form an object field-value pair. The data processing system can also access electronic activities received from data source providers. Each electronic activity can be associated with the data source provider and with a unique entity. The data processing system can extract electronic activity field-value pairs from the electronic activities.

The data processing system can maintain node profiles (2904). Each node profile can be generated from electronic activities of a data source provider or from record objects from systems of record of the data source providers. Each node profile can be associated with a unique entity. Each node profile can have one or more fields. Each field of the node profile can be attributed with one or more values. Each field and one of the attributed values can form a node field-value pair. Each value of the node field-value pairs can be associated with a value data structure with entries identifying data sources that have provided electronic activities or record objects associated with the node field-value pair to the data processing system.

The data processing system can identify a value of a field of a predetermined type (2906). The predetermined type can be set by an administrator to keep the privacy of entities of the node profiles. Any field can be a predetermined type. The predetermined types can be associated with a predetermined threshold set by an administrator. The predetermined threshold can be a number of data source providers that have provided record objects and/or electronic activities to the data processing system. Each predetermined threshold can be associated with a type of field. In some embodiments, the predetermined type can be associated with types of field that can be used to contact an entity associated with the node profile (e.g., email address, mailing address, phone number, etc.).

The data processing system can determine whether the number of data source providers associated with a value of a node field-value pair exceeds a predetermined threshold. The data processing system can identify the number of unique data source providers that are associated with entries in a value structure database of a value of field having a predetermined type. The data processing system can identify the number of unique data source providers based on a counter incremented and maintained by the data processing system based on the unique data source providers of value data structures. If the data processing system determines the number of data source providers does not exceed the predetermined threshold of a value, the data processing system can generate a restriction tag to restrict populating other node profiles of the data processing system or record objects of systems of record based on the restricted value (2908). The data processing system can store the restriction tag in a data structure within the data processing system. In some embodiments, the data processing can receive a request to restrict access to a particular node field-value pair and generate and store a restriction tag associated with the requested node field-value pair.

The data processing system can restrict provision of the value to at least one system of record of a data source provider different from a data source provider that provided the value if the value is associated with a restriction tag (2910). The data processing system can identify the restriction tag associated with value and restrict systems of record from retrieving the value based on the restriction tag.

The data processing system can update a value data structure with new entries upon extracting object field-value pairs or electronic field-value pairs from new record objects and/or electronic activities. The data processing system can match the field-value pairs with a node profile by matching field-value pairs to node field-value pairs of the node profile. The node profile can be associated with the value data structure. The data processing system can identify the extracted field-value pairs and update the value data structures associated with the corresponding values of the field-value pairs. If the data source provider associated with the electronic activities or record objects is unique from the field-value pairs of previous entries in the value data structure, the data source provider can increment a counter indicating another data source is associated with value. If the incremented value satisfies a threshold, the data processing system can remove the restriction tag from the data structure of the data processing system. With the restriction tag removed, the data processing system can communicate the value of the previously restricted node field-value pair to a system of record having a record object that matches (e.g., that is associated with the same entity) as the node profile of the node field-value pair.

In some instances, a node profile matched with an electronic activity or record object may not have a corresponding node field-value pair to an electronic activity field-value pair or object field-value pair of the electronic activity or record object. The data processing system can generate a node field-value pair that corresponds to the electronic activity field-value pair or object field-value pair. The data processing system can generate and store a restriction tag associated with the generated node field-value pair.

In some embodiments, the node graph generation system 200 can be configured to provide information to one or more users of the node graph generation system. Users of the node graph generation system can be employees of companies that serve as data source providers. The node graph generation system 200 can generate one or more notifications identifying actions that an employee of a company can perform to increase the likelihood of one or more record objects advancing from a first stage to a second stage or to change a status of an opportunity corresponding to the record object. In some embodiments, the node graph generation system 200 can provide information to the employee that may be used to contact other individuals. As described herein, the node graph generation system 200 can restrict the information that may be used to contact another individual if the information is associated with a restriction tag. The node graph generation system 200 however can share the information if the restriction tag does not apply or has been removed.

21. Computer System

Figure 30:
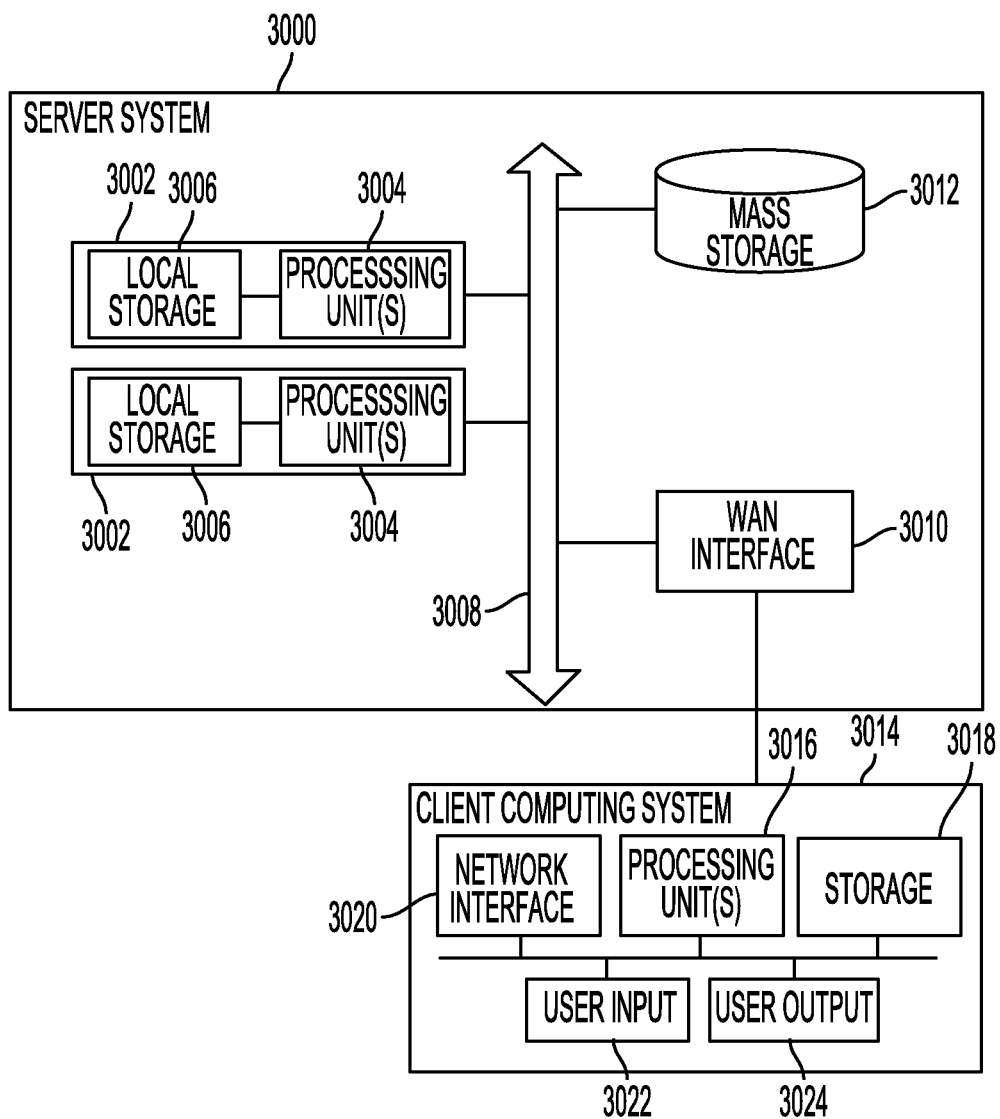
FIG. 30 illustrates a simplified block diagram of a representative server system and client computer system according to embodiments of the present disclosure.

Various operations described herein can be implemented on computer systems, which can be of generally conventional design. FIG. 30 shows a simplified block diagram of a representative server system 3000 and client computer system 3014 usable to implement certain embodiments of the present disclosure. In various embodiments, server system 3000 or similar systems can implement services or servers described herein or portions thereof. Client computer system 3014 or similar systems can implement clients described herein. Each of the systems 9300, 200 and others described herein can be similar to the server system 3000.

Server system 3000 can have a modular design that incorporates a number of modules 3002 (e.g., blades in a blade server embodiment); while two modules 3002 are shown, any number can be provided. Each module 3002 can include processing unit(s) 3004 and local storage 3006.

Processing unit(s) 3004 can include a single processor, which can have one or more cores, or multiple processors. In some embodiments, processing unit(s) 3004 can include a general-purpose primary processor as well as one or more special-purpose co-processors such as graphics processors, digital signal processors, or the like. In some embodiments, some or all processing units 3004 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 3004 can execute instructions stored in local storage 3006. Any type of processors in any combination can be included in processing unit(s) 3004.

Local storage 3006 can include volatile storage media (e.g., conventional DRAM, SRAM, SDRAM, or the like) and/or non-volatile storage media (e.g., magnetic or optical disk, flash memory, or the like). Storage media incorporated in local storage 3006 can be fixed, removable or upgradeable as desired. Local storage 3006 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 3004 need at runtime. The ROM can store static data and instructions that are needed by processing unit(s) 3004. The permanent storage device can be a non-volatile read-and-write memory device that can store instructions and data even when module 3002 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 3006 can store one or more software programs to be executed by processing unit(s) 3004, such as an operating system and/or programs implementing various server functions such as functions of the data processing system 9300 of FIG. 2, the node graph generation system 300, or any other system described herein, or any other server(s) associated with data processing system 9300 of FIG. 2 or the node graph generation system 300 or any other system described herein.

"Software" refers generally to sequences of instructions that, when executed by processing unit(s) 3004 cause server system 3000 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 3004. Software can be implemented as a single program or a collection of separate programs or program modules that interact as desired. From local storage 3006 (or non-local storage described below), processing unit(s) 3004 can retrieve program instructions to execute and data to process in order to execute various operations described above.

In some server systems 3000, multiple modules 3002 can be interconnected via a bus or other interconnect 3008, forming a local area network that supports communication between modules 3002 and other components of server system 3000. Interconnect 3008 can be implemented using various technologies including server racks, hubs, routers, etc.

A wide area network (WAN) interface 3010 can provide data communication capability between the local area network (interconnect 3008) and a larger network, such as the Internet. Conventional or other activities technologies can be used, including wired (e.g., Ethernet, IEEE 802.3 standards) and/or wireless technologies (e.g., Wi-Fi, IEEE 802.11 standards).

In some embodiments, local storage 3006 is intended to provide working memory for processing unit(s) 3004, providing fast access to programs and/or data to be processed while reducing traffic on interconnect 3008. Storage for larger quantities of data can be provided on the local area network by one or more mass storage subsystems 3012 that can be connected to interconnect 3008. Mass storage subsystem 3012 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 3012. In some embodiments, additional data storage resources may be accessible via WAN interface 3010 (potentially with increased latency).

Server system 3000 can operate in response to requests received via WAN interface 3010. For example, one of modules 3002 can implement a supervisory function and assign discrete tasks to other modules 3002 in response to received requests. Conventional work allocation techniques can be used. As requests are processed, results can be returned to the requester via WAN interface 3010. Such operation can generally be automated. Further, in some embodiments, WAN interface 3010 can connect multiple server systems 3000 to each other, providing scalable systems capable of managing high volumes of activity. Conventional or other techniques for managing server systems and server farms (collections of server systems that cooperate) can be used, including dynamic resource allocation and reallocation.

Server system 3000 can interact with various user-owned or user-operated devices via a wide-area network such as the Internet. An example of a user-operated device is shown in FIG. 30 as client computing system 3014. Client computing system 3014 can be implemented, for example, as a consumer device such as a smartphone, other mobile phone, tablet computer, wearable computing device (e.g., smart watch, eyeglasses), desktop computer, laptop computer, and so on.

For example, client computing system 3014 can communicate via WAN interface 3010. Client computing system 3014 can include conventional computer components such as processing unit(s) 3016, storage device 3018, network interface 3020, user input device 3022, and user output device 3024. Client computing system 3014 can be a computing device implemented in a variety of form factors, such as a desktop computer, laptop computer, tablet computer, smartphone, other mobile computing device, wearable computing device, or the like.

Processor 3016 and storage device 3018 can be similar to processing unit(s) 3004 and local storage 3006 described above. Suitable devices can be selected based on the demands to be placed on client computing system 3014; for example, client computing system 3014 can be implemented as a "thin" client with limited processing capability or as a high-powered computing device. Client computing system 3014 can be provisioned with program code executable by processing unit(s) 3016 to enable various interactions with server system 3000 of a message management service such as accessing messages, performing actions on messages, and other interactions described above. Some client computing systems 3014 can also interact with a messaging service independently of the message management service.

Network interface 3020 can provide a connection to a wide area network (e.g., the Internet) to which WAN interface 3010 of server system 3000 is also connected. In various embodiments, network interface 3020 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 3022 can include any device (or devices) via which a user can provide signals to client computing system 3014; client computing system 3014 can interpret the signals as indicative of particular user requests or information. In various embodiments, user input device 3022 can include any or all of a keyboard, touch pad, touch screen, mouse or other pointing device, scroll wheel, click wheel, dial, button, switch, keypad, microphone, and so on.

User output device 3024 can include any device via which client computing system 3014 can provide information to a user. For example, user output device 3024 can include a display to display images generated by or delivered to client computing system 3014. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 3024 can be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 3004 and 3016 can provide various functionality for server system 3000 and client computing system 3014, including any of the functionality described herein as being performed by a server or client, or other functionality associated with message management services.

It will be appreciated that server system 3000 and client computing system 3014 are illustrative and that variations and modifications are possible. Computer systems used in connection with embodiments of the present disclosure can have other capabilities not specifically described here. Further, while server system 3000 and client computing system 3014 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. For instance, although specific examples of rules (including triggering conditions and/or resulting actions) and processes for generating suggested rules are described, other rules and processes can be implemented. Embodiments of the disclosure can be realized using a variety of computer systems and communication technologies including but not limited to specific examples described herein.

Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method comprising:
   accessing, by one or more processors, data of i) a plurality of electronic activities transmitted or received via electronic accounts associated with a plurality of data source providers or ii) a plurality of record objects of a plurality of systems of record associated with the plurality of data source providers;
   identifying, by the one or more processors, from a first system of record of a first data source provider, an object field-value pair of a first record object of the first system of record;
   determining, by the one or more processors, that the object field-value pair is associated with a restriction tag used to restrict sharing a value of the object field-value pair with one or more second systems of record of the plurality of systems of record;
   identifying, by the one or more processors, the object field-value pair from at least one electronic activity of the plurality of electronic activities that are accessible via a second data source provider of the plurality of data source providers or at least one second record object of a second system of record of the one or more second systems of record that corresponds to the second data source provider;
   determining, by the one or more processors, responsive to identifying the object field-value pair from the at least one electronic activity or the at least one second record object, that the object field-value pair satisfies a shareability condition defined by a restriction policy associated with the first data source provider; and
   providing, by the one or more processors, the value of the object field-value pair to at least one third system of record of a third data source provider of the plurality of data source providers responsive to determining that the shareability condition is satisfied.

2. The method of claim 1, further comprising updating, by the one or more processors, in one or more data structures, an association between the object field-value pair and a shareability setting responsive to determining that the object field-value pair satisfies the shareability condition.

3. The method of claim 1, wherein identifying the object field-value pair of the first record object of the first system of record comprises determining that the object field-value pair corresponds to a predetermined type of object field with which restriction tags can be associated.

4. The method of claim 3, wherein identifying the object field-value pair of the first record object of the first system of record comprises:
   identifying, by the one or more processors, an electronic activity of the plurality of electronic activities;
   determining, by the one or more processors, from the electronic activity, an activity field-value pair identifying the value; and
   transmitting, by the one or more processors, instructions to update the first record object of the first system of record by generating the object field-value pair using the value of the activity field-value pair.

5. The method of claim 4, further comprising maintaining, by the one or more processors, in one or more data structures, an association between the object field-value pair and the restriction tag.

6. The method of claim 1, further comprising:
receiving, by the one or more processors, a request to restrict sharing the object field-value pair of the first record object;
generating, by the one or more processors, the restriction tag to restrict sharing the value with the one or more second systems of record; and
storing, by the one or more processors, in one or more data structures, an association between the restriction tag and the object field-value pair.

7. The method of claim 1, wherein determining that the object field-value pair satisfies the shareability condition comprises:
maintaining, by the one or more processors, for the object field-value pair, a value data structure that identifies one or more data points corresponding to the object field-value pair, each data point of the one or more data points identifying an electronic activity or a record object including the value of the object field-value pair; and
determining, by the one or more processors, that a count of the one or more data points satisfies a threshold corresponding to the shareability condition.

8. The method of claim 1, wherein determining that the object field-value pair satisfies the shareability condition comprises:
maintaining, by the one or more processors, for the object field-value pair, a value data structure that identifies one or more data points corresponding to the object field-value pair, each data point of the one or more data points identifying an electronic activity or a record object including the value of the object field-value pair and a data source provider of the plurality of data source providers; and
determining, by the one or more processors, a number of data source providers that provide the one or more data points included in the value data structure corresponding to the object field-value pair; and
determining, by the one or more processors, that the number of data source providers satisfies a threshold corresponding to the shareability condition.

9. A system comprising:
one or more processors configured by machine-readable instructions to:
access data of i) a plurality of electronic activities transmitted or received via electronic accounts associated with a plurality of data source providers or ii) a plurality of record objects of a plurality of systems of record associated with the plurality of data source providers;
identify from a first system of record of a first data source provider, an object field-value pair of a first record object of the first system of record;
determine that the object field-value pair is associated with a restriction tag used to restrict sharing a value of the object field-value pair with one or more second systems of record of the plurality of systems of record;
identify the object field-value pair from at least one electronic activity of the plurality of electronic activities that are accessible via a second data source provider of the plurality of data source providers or at least one second record object of a second system of record of the one or more second systems of record that corresponds to the second data source provider;
determine responsive to identifying the object field-value pair from the at least one electronic activity or the at least one second record object, that the object field-value pair satisfies a shareability condition defined by a restriction policy associated with the first data source provider; and
provide the value of the object field-value pair to at least one third system of record of a third data source provider of the plurality of data source providers responsive to determining that the shareability condition is satisfied.

10. The system of claim 9, wherein the one or more processors are further configured to update in one or more data structures, an association between the object field-value pair and a shareability setting responsive to determining that the object field-value pair satisfies the shareability condition.

11. The system of claim 9, wherein to identify the object field-value pair of the first record object of the first system of record, the one or more processors are configured to determine that the object field-value pair corresponds to a predetermined type of object field with which restriction tags can be associated.

12. The system of claim 11, wherein to identify the object field-value pair of the first record object of the first system of record, the one or more processors are configured to:
identify an electronic activity of the plurality of electronic activities;
determine from the electronic activity, an activity field-value pair identifying the value; and
transmit a request to update the first record object of the first system of record by generating the object field-value pair using the value of the activity field-value pair.

13. The system of claim 12, wherein the one or more processors are further configured to maintain in one or more data structures, an association between the object field-value pair and the restriction tag.

14. The system of claim 9, wherein the one or more processors are further configured to:
receive a request to restrict sharing the object field-value pair of the first record object;
generate the restriction tag to restrict sharing the value with the one or more second systems of record; and
store in one or more data structures, an association between the restriction tag and the object field-value pair.

15. The system of claim 9, wherein to determine that the object field-value pair satisfies the shareability condition, the one or more processors are configured to:
maintain for the object field-value pair, a value data structure that identifies one or more data points corresponding to the object field-value pair, each data point of the one or more data points identifying an electronic activity or a record object including the value of the object field-value pair; and
determine that a count of the one or more data points satisfies a threshold corresponding to the shareability condition.

16. The system of claim 9, wherein to determine that the object field-value pair satisfies the shareability condition, the one or more processors are configured to:
maintain for the object field-value pair, a value data structure that identifies one or more data points corresponding to the object field-value pair, each data point of the one or more data points identifying an electronic activity or a record object including the value of the object field-value pair and a data source provider of the plurality of data source providers; and determine a number of data source providers that provide the one or more data points included in the value data structure corresponding to the object field-value pair; and determine that the number of data source providers satisfies a threshold corresponding to the shareability condition.

17. A non-transitory computer-readable storage medium having instructions embodied thereon, the instructions being executable by one or more processors to:

access data of i) a plurality of electronic activities transmitted or received via electronic accounts associated with a plurality of data source providers or ii) a plurality of record objects of a plurality of systems of record associated with the plurality of data source providers;

identify from a first system of record of a first data source provider, an object field-value pair of a first record object of the first system of record;

determine that the object field-value pair is associated with a restriction tag used to restrict sharing a value of the object field-value pair with one or more second systems of record of the plurality of systems of record;

identify the object field-value pair from at least one electronic activity of the plurality of electronic activities that are accessible via a second data source provider of the plurality of data source providers or at least one second record object of a second system of record of the one or more second systems of record that corresponds to the second data source provider;

determine responsive to identifying the object field-value pair from the at least one electronic activity or the at least one second record object, that the object field-value pair satisfies a shareability condition defined by a restriction policy associated with the first data source provider; and provide the value of the object field-value pair to at least one third system of record of a third data source provider of the plurality of data source providers responsive to determining that the shareability condition is satisfied.

18. The non-transitory computer-readable storage medium of claim 17, wherein the one or more processors are configured to update, in one or more data structures, an association between the object field-value pair and a shareability setting responsive to determining that the object field-value pair satisfies the shareability condition.

19. The non-transitory computer-readable storage medium of claim 17, wherein to identify the object field-value pair of the first record object of the first system of record, the one or more processors are configured to determine that the object field-value pair corresponds to a predetermined type of object field with which restriction tags can be associated.

20. The non-transitory computer-readable storage medium of claim 19, wherein to identify the object field-value pair of the first record object of the first system of record, the one or more processors are configured to:

identify an electronic activity of the plurality of electronic activities;

determine from the electronic activity, an activity field-value pair identifying the value; and transmit a request to update the first record object of the first system of record by generating the object field-value pair using the value of the activity field-value pair.

\* \* \* \* \*